(12) United States Patent
Zhang et al.

(10) Patent No.: US 12,083,142 B2
(45) Date of Patent: *Sep. 10, 2024

(54) NUCLEIC ACID, COMPOSITION AND CONJUGATE COMPRISING THE SAME, AND PREPARATION METHOD AND USE THEREOF

(71) Applicant: SUZHOU RIBO LIFE SCIENCE CO., LTD., Kunshan (CN)

(72) Inventors: Hongyan Zhang, Kunshan (CN); Shan Gao, Kunshan (CN); Daiwu Kang, Kunshan (CN)

(73) Assignee: SUZHOU RIBO LIFE SCIENCE CO., LTD., Jiangsu (CN)

(*) Notice: Subject to any disclaimer, the term of this patent is extended or adjusted under 35 U.S.C. 154(b) by 839 days.

This patent is subject to a terminal disclaimer.

(21) Appl. No.: 16/765,799

(22) PCT Filed: Nov. 29, 2018

(86) PCT No.: PCT/CN2018/118303
§ 371 (c)(1),
(2) Date: May 20, 2020

(87) PCT Pub. No.: WO2019/105437
PCT Pub. Date: Jun. 6, 2019

(65) Prior Publication Data
US 2022/0395526 A1    Dec. 15, 2022

(30) Foreign Application Priority Data

Dec. 1, 2017  (CN) .......................... 201711249333.8
Dec. 29, 2017 (CN) .......................... 201711482970.X

(51) Int. Cl.
*A61K 31/713* (2006.01)
*A61K 47/54* (2017.01)
*A61P 31/20* (2006.01)

(52) U.S. Cl.
CPC .......... *A61K 31/713* (2013.01); *A61K 47/549* (2017.08); *A61P 31/20* (2018.01)

(58) Field of Classification Search
CPC .............. C12N 15/113; C12N 15/1131; C12N 2310/14; C12N 2310/315;
(Continued)

(56) References Cited

U.S. PATENT DOCUMENTS 8,030,474 B2   10/2011   Khvorova et al.
8,106,022 B2    1/2012   Manoharan et al.
(Continued)

FOREIGN PATENT DOCUMENTS

AU    2014208251 A1    8/2014
CA    2930393 A1       6/2009
(Continued)

OTHER PUBLICATIONS

Durnov, et al., "Children's Oncology", Paediatric Oncology, Second Edition, Moscow Publishing House Medicine, 2002, p. 139 and its English translation. Cited in Office Action issued on Oct. 10, 2022 in Russian Application No. 2020121741). (4 pages).

(Continued)

*Primary Examiner* — Terra C Gibbs
(74) *Attorney, Agent, or Firm* — Panitch Schwarze Belisario & Nadel LLP

(57) ABSTRACT

Provided are a siRNA for inhibiting the expression of hepatitis B virus gene, and a pharmaceutical composition and conjugate containing the siRNA. Each nucleotide in the siRNA is independently a modified nucleotide. The siRNA comprises a sense strand and an antisense strand. The sense strand of the siRNA comprises a nucleotide sequence 1 having the same length and no more than three nucleotides different from the nucleotide sequence shown in SEQ ID NO: 155, and the antisense strand of the siRNA comprises (Continued)

a nucleotide sequence 2 having the same length and no more than three nucleotides different from the nucleotide sequence shown in SEQ ID NO: 156.

26 Claims, 16 Drawing Sheets

Specification includes a Sequence Listing.

(58) Field of Classification Search
 CPC ........ C12N 2310/321; C12N 2310/322; C12N 2310/346; C12N 2310/351; A61K 31/713
 See application file for complete search history.

(56) References Cited

U.S. PATENT DOCUMENTS

| | | | |
|---|---|---|---|
| 8,334,372 | B2 | 12/2012 | Freier et al. |
| 8,344,125 | B2 | 1/2013 | Manoharan et al. |
| 9,428,751 | B2 | 8/2016 | Macdonald et al. |
| 9,670,492 | B2 | 6/2017 | Freier et al. |
| 10,130,651 | B2 | 11/2018 | Wooddell et al. |
| 10,246,708 | B2 | 4/2019 | Kasperkovitz et al. |
| 10,294,477 | B2 | 5/2019 | Swayze |
| 10,370,453 | B2 | 8/2019 | Sexton et al. |
| 10,934,544 | B2 | 3/2021 | Akinc et al. |
| 11,084,884 | B2 | 8/2021 | Sexton et al. |
| 11,414,661 | B2 | 8/2022 | Zhang et al. |
| 11,414,665 | B2 | 8/2022 | Zhang et al. |
| 11,492,620 | B2 | 11/2022 | Zhang et al. |
| 11,633,482 | B2 * | 4/2023 | Zhang ................. C12Q 1/6886 514/25 |
| 2003/0206887 | A1 | 11/2003 | Morrissey et al. |
| 2005/0245475 | A1 | 11/2005 | Khvorova et al. |
| 2005/0246794 | A1 | 11/2005 | Khvorova et al. |
| 2005/0255487 | A1 | 11/2005 | Khvorova et al. |
| 2008/0113351 | A1 | 5/2008 | Naito et al. |
| 2008/0146788 | A1 | 6/2008 | Bhat et al. |
| 2010/0063132 | A1 | 3/2010 | Kim et al. |
| 2010/0137414 | A1 | 6/2010 | Freier et al. |
| 2011/0015252 | A1 | 1/2011 | Fitzgerald et al. |
| 2011/0039914 | A1 | 2/2011 | Pavco et al. |
| 2011/0054005 | A1 | 3/2011 | Naito et al. |
| 2012/0052487 | A9 | 3/2012 | Khvorova et al. |
| 2012/0108803 | A1 | 5/2012 | Han et al. |
| 2012/0172412 | A1 | 7/2012 | Rozema et al. |
| 2012/0184595 | A1 | 7/2012 | MacDonald et al. |
| 2012/0201756 | A1 | 8/2012 | Sexton |
| 2013/0005793 | A1 | 1/2013 | Chin et al. |
| 2013/0023579 | A1 | 1/2013 | Crooke et al. |
| 2013/0041133 | A1 | 2/2013 | Aaronson et al. |
| 2013/0096288 | A1 | 4/2013 | Han et al. |
| 2013/0123482 | A1 | 5/2013 | Xi et al. |
| 2013/0158021 | A1 | 6/2013 | Dong et al. |
| 2014/0099666 | A1 | 4/2014 | Rossomando et al. |
| 2014/0128453 | A1 | 5/2014 | Mullick et al. |
| 2014/0179768 | A1 | 6/2014 | Bettencourt et al. |
| 2014/0194489 | A1 | 7/2014 | Bumcrot et al. |
| 2014/0343123 | A1 | 11/2014 | Prakash et al. |
| 2015/0093444 | A1 | 4/2015 | Zhang et al. |
| 2015/0152436 | A1 | 6/2015 | Musunuru et al. |
| 2015/0174260 | A1 | 6/2015 | Yang et al. |
| 2015/0191726 | A1 | 7/2015 | Manoharan et al. |
| 2015/0247143 | A1 | 9/2015 | Fitzgerald et al. |
| 2015/0291958 | A1 | 10/2015 | Albaek et al. |
| 2015/0315584 | A1 | 11/2015 | MacDonald et al. |
| 2015/0315594 | A1 | 11/2015 | Prakash et al. |
| 2016/0017335 | A1 | 1/2016 | Borodovsky et al. |
| 2016/0186180 | A1 | 6/2016 | Bettencourt et al. |
| 2016/0237438 | A1 | 8/2016 | Brown et al. |
| 2016/0283653 | A1 | 9/2016 | Staudt et al. |
| 2016/0354404 | A1 | 12/2016 | Hinkle et al. |
| 2017/0000815 | A1 | 1/2017 | Fitzgerald et al. |
| 2017/0002094 | A1 | 1/2017 | Sexton et al. |
| 2017/0114341 | A1 | 4/2017 | Bradshaw et al. |
| 2018/0087054 | A1 | 3/2018 | Querbes et al. |
| 2018/0148722 | A1 | 5/2018 | Fitzgerald et al. |
| 2018/0216114 | A1 | 8/2018 | Fitzgerald et al. |
| 2018/0245077 | A1 | 8/2018 | Chiu et al. |
| 2019/0062749 | A1 | 2/2019 | Zhang |
| 2019/0202855 | A1 | 7/2019 | Sakamuri et al. |
| 2019/0255091 | A1 | 8/2019 | Li et al. |
| 2019/0292547 | A1 | 9/2019 | Li et al. |
| 2020/0199591 | A1 | 6/2020 | Fitzgerald et al. |
| 2020/0338201 | A1 | 10/2020 | Zhang et al. |
| 2020/0350346 | A1 | 11/2020 | Ohura et al. |
| 2020/0360522 | A1 | 11/2020 | Zhang et al. |
| 2021/0032623 | A1 | 2/2021 | Zhang et al. |
| 2021/0275564 | A1 | 9/2021 | Zhang et al. |
| 2021/0277400 | A1 | 9/2021 | Zhang et al. |
| 2021/0401994 | A1 | 12/2021 | Zhang et al. |
| 2022/0049249 | A1 | 2/2022 | Zhang et al. |
| 2022/0356474 | A1 | 11/2022 | Zhang et al. |
| 2022/0389428 | A1 | 12/2022 | Zhang et al. |

FOREIGN PATENT DOCUMENTS

| | | |
|---|---|---|
| CA | 2 677 068 A1 | 3/2011 |
| CN | 102006890 A | 4/2011 |
| CN | 102016036 A | 4/2011 |
| CN | 102124107 A | 7/2011 |
| CN | 102140459 A | 8/2011 |
| CN | 102140460 A | 8/2011 |
| CN | 102344477 A | 2/2012 |
| CN | 102439148 A | 5/2012 |
| CN | 102719434 A | 10/2012 |
| CN | 102753186 A | 10/2012 |
| CN | 102140461 B | 12/2012 |
| CN | 102869774 A | 1/2013 |
| CN | 101603042 B | 5/2013 |
| CN | 102140458 B | 5/2013 |
| CN | 103380113 A | 10/2013 |
| CN | 102083983 B | 4/2014 |
| CN | 103890000 A | 6/2014 |
| CN | 104107437 A | 10/2014 |
| CN | 104232644 A | 12/2014 |
| CN | 104328121 A | 2/2015 |
| CN | 102344477 B | 4/2015 |
| CN | 104717982 A | 6/2015 |
| CN | 104854242 A | 8/2015 |
| CN | 104922141 A | 9/2015 |
| CN | 105324485 A | 2/2016 |
| CN | 105378082 A | 3/2016 |
| CN | 105392488 A | 3/2016 |
| CN | 105452465 A | 3/2016 |
| CN | 105517556 A | 4/2016 |
| CN | 105713092 A | 6/2016 |
| CN | 105814204 A | 7/2016 |
| CN | 106132442 A | 11/2016 |
| CN | 106146591 A | 11/2016 |
| CN | 106232831 A | 12/2016 |
| CN | 106255755 A | 12/2016 |
| CN | 106460025 A | 2/2017 |
| CN | 107075516 A | 8/2017 |
| CN | 107109405 A | 8/2017 |
| CN | 107250362 A | 10/2017 |
| CN | 107854478 A | 3/2018 |
| CN | 108064294 A | 5/2018 |
| CN | 108064313 A | 5/2018 |
| CN | 108220293 A | 6/2018 |
| CN | 108239644 A | 7/2018 |
| CN | 108265052 A | 7/2018 |
| CN | 108271386 A | 7/2018 |
| CN | 108348541 A | 7/2018 |
| CN | 110945131 A | 3/2020 |
| CN | 110959011 A | 4/2020 |
| CN | 111050807 A | 4/2020 |
| CN | 111973617 A | 11/2020 |
| CN | 111973618 A | 11/2020 |
| CN | 111973619 A | 11/2020 |
| CN | 111979237 A | 11/2020 |
| CN | 112423795 A | 2/2021 |
| CN | 113330117 A | 8/2021 |
| EP | 1 752 536 A1 | 2/2007 |
| EP | 2194128 A1 | 6/2010 |

(56) References Cited

FOREIGN PATENT DOCUMENTS

| | | |
|---|---|---|
| EP | 2213738 A2 | 8/2010 |
| EP | 2376641 A1 | 10/2011 |
| EP | 2213738 B1 | 10/2012 |
| EP | 2669377 A2 | 12/2013 |
| EP | 2990410 A1 | 3/2016 |
| EP | 3312281 A2 | 4/2018 |
| EP | 3315608 A1 | 5/2018 |
| EP | 3335715 A2 | 6/2018 |
| EP | 3409780 A1 | 12/2018 |
| EP | 3719128 A1 | 10/2020 |
| EP | 3862024 A1 | 8/2021 |
| JP | 2013523149 A | 6/2013 |
| JP | 2013537423 A | 10/2013 |
| JP | 2016501195 A | 1/2016 |
| JP | 2016523087 A | 8/2016 |
| JP | 2017521045 A | 8/2017 |
| JP | 2017534290 A | 11/2017 |
| RU | 2013134745 A | 2/2015 |
| RU | 2558258 C2 | 7/2015 |
| TW | 201925471 A | 7/2019 |
| TW | 201929905 A | 8/2019 |
| WO | WO-0027795 A1 | 5/2000 |
| WO | 2004/045543 A2 | 6/2004 |
| WO | WO-2004078181 A1 | 9/2004 |
| WO | WO-2005116204 A1 | 12/2005 |
| WO | WO-2006006948 A2 | 1/2006 |
| WO | WO-2006096018 A1 | 9/2006 |
| WO | WO-2007134161 A2 | 11/2007 |
| WO | WO-2008011431 A2 | 1/2008 |
| WO | WO-2008109472 A2 | 9/2008 |
| WO | WO-2009073809 A2 | 6/2009 |
| WO | WO-2009082607 A2 | 7/2009 |
| WO | WO-2009134487 A2 | 11/2009 |
| WO | WO-2010012244 A1 | 2/2010 |
| WO | WO-2010045509 A2 | 4/2010 |
| WO | WO-2010068978 A1 | 6/2010 |
| WO | WO-2010083615 A1 | 7/2010 |
| WO | WO-2010101951 A1 | 9/2010 |
| WO | WO-2010121074 A1 | 10/2010 |
| WO | WO-2010131916 A2 | 11/2010 |
| WO | WO-2010147992 A1 | 12/2010 |
| WO | 2011/028938 A1 | 3/2011 |
| WO | WO-2011085271 A2 | 7/2011 |
| WO | WO-2011104169 A1 | 9/2011 |
| WO | 2011126974 A1 | 10/2011 |
| WO | WO-2011139702 A2 | 11/2011 |
| WO | WO-2011154331 A1 | 12/2011 |
| WO | 2012024170 A2 | 2/2012 |
| WO | WO-2012013127 A1 | 2/2012 |
| WO | WO-2012037254 A1 | 3/2012 |
| WO | WO-2012068176 A1 | 5/2012 |
| WO | WO-2012083185 A2 | 6/2012 |
| WO | WO-2012089352 A1 | 7/2012 |
| WO | 2012/139081 A2 | 10/2012 |
| WO | WO-2012130086 A1 | 10/2012 |
| WO | WO-2012139469 A1 | 10/2012 |
| WO | WO-2012177784 A2 | 12/2012 |
| WO | WO-2013060261 A1 | 5/2013 |
| WO | WO-2013070771 A1 | 5/2013 |
| WO | WO-2013166155 A1 | 11/2013 |
| WO | WO-2014025805 A1 | 2/2014 |
| WO | 2014076195 A1 | 5/2014 |
| WO | WO-2014089313 A1 | 6/2014 |
| WO | WO-2014118267 A1 | 8/2014 |
| WO | WO-2014179626 A2 | 11/2014 |
| WO | WO-2014179627 A2 | 11/2014 |
| WO | WO-2014179629 A2 | 11/2014 |
| WO | 2014205451 A1 | 12/2014 |
| WO | WO-2015006498 A2 | 1/2015 |
| WO | WO-2015006740 A2 | 1/2015 |
| WO | WO-2015015496 A1 | 2/2015 |
| WO | WO-2015031679 A2 | 3/2015 |
| WO | 2015/051366 A2 | 4/2015 |
| WO | WO-2015100394 A1 | 7/2015 |
| WO | WO-2015113922 A1 | 8/2015 |
| WO | WO-2015148580 A2 | 10/2015 |
| WO | 2015168589 A1 | 11/2015 |
| WO | WO-2015168532 A2 | 11/2015 |
| WO | 2015188194 A1 | 12/2015 |
| WO | WO-2015188197 A2 | 12/2015 |
| WO | WO-2016011123 A1 | 1/2016 |
| WO | WO-2016028649 A1 | 2/2016 |
| WO | 2016/040589 A1 | 3/2016 |
| WO | 2016077349 A1 | 5/2016 |
| WO | WO-2016077321 A1 | 5/2016 |
| WO | WO-2016081444 A1 | 5/2016 |
| WO | WO-2016099982 A2 | 6/2016 |
| WO | WO-2016149331 A2 | 9/2016 |
| WO | WO-2016154127 A2 | 9/2016 |
| WO | WO-2016168286 A1 | 10/2016 |
| WO | WO-2016179342 A2 | 11/2016 |
| WO | 2016/201301 A1 | 12/2016 |
| WO | WO-2016188473 A1 | 12/2016 |
| WO | WO-2016206626 A1 | 12/2016 |
| WO | WO-2017015175 A1 | 1/2017 |
| WO | WO-2017019660 A1 | 2/2017 |
| WO | WO-2017019891 A2 | 2/2017 |
| WO | WO-2017035340 A1 | 3/2017 |
| WO | WO-2017055627 A1 | 4/2017 |
| WO | WO-2017100542 A1 | 6/2017 |
| WO | WO-2017120397 A1 | 7/2017 |
| WO | 2017131236 A1 | 8/2017 |
| WO | WO-2017184689 A1 | 10/2017 |
| WO | WO-2017189813 A1 | 11/2017 |
| WO | 2018/035380 A1 | 2/2018 |
| WO | WO-2018027106 A2 | 2/2018 |
| WO | WO-2018044350 A1 | 3/2018 |
| WO | WO-2018075658 A1 | 4/2018 |
| WO | WO-2018140920 A1 | 8/2018 |
| WO | WO-2018191278 A2 | 10/2018 |
| WO | WO-2018209848 A1 | 11/2018 |
| WO | WO-2018223073 A1 | 12/2018 |
| WO | 2019/105418 A1 | 6/2019 |
| WO | WO-2019105403 A1 | 6/2019 |
| WO | WO-2019105404 A1 | 6/2019 |
| WO | WO-2019105414 A1 | 6/2019 |
| WO | WO-2019105419 A1 | 6/2019 |
| WO | WO-2019105435 A1 | 6/2019 |
| WO | WO-2019105437 A1 | 6/2019 |
| WO | WO-2019128611 A1 | 7/2019 |
| WO | WO-2020038377 A1 | 2/2020 |
| WO | 2020/063198 A | 4/2020 |
| WO | WO-2020093053 A1 | 5/2020 |
| WO | WO-2020135581 A1 | 7/2020 |
| WO | WO-2020147847 A1 | 7/2020 |

OTHER PUBLICATIONS

Dysop, "Chemistry of Synthetic Drugs", Publishing House MIR, 1964, pp. 12-19 and its English translation. Cited in Office Action issued on Oct. 10, 2022 in Russian Application No. 2020121741). (18 pages).

Belikov, V.G., "Pharmaceutical Chemistry", textbook, Moscow, 11th Edition, MEDpress-inform, 2007, pp. 27-29 and its English translation. (Cited in Office Action issued on Oct. 10, 2022 in Russian Application No. 2020121741). (8 pages).

Nakamoto, et al., "Enhanced Intercellular Delivery of cRGD-siRNA Conjugates by an Additional Oligospermine Modification", ACS Omega, vol. 3, No. 7, 2018, pp. 8226-8232.

Nothisen, et al., "Cationic siRNAs Provide Carrier-Free Gene Silencing in Animal Cells", Journal of the American Chemical Society, vol. 131, No. 49, 2009, pp. 17730-17731.

Examination Report No. 2 issued on Feb. 3, 2023, by the Australian Government IP Australia in Australian Patent Application No. 2018394875 (4 pages).

Ren et al., "Synthesis of Galactosyl Compounds for Targeted Gene Delivery", Bioorganic & Medicinal Chemistry, 2001, 9(11), pp. 2969-2978.

Extended European Search Report issued on Mar. 27, 2023, by the European Patent Office in European Patent Application No. 19902173.4 (11 pages).

(56) References Cited

OTHER PUBLICATIONS

Li et al., "The silencing of ApoC3 suppresses oxidative stress and inflammatory responses in placenta cells from mice with preeclampsia via inhibition of the NF-B signaling pathway", Biomedicine & Pharmacotherapy, Aug. 31, 2018, vol. 107, pp. 1377-1384.
Notice of Reasons for Refusal issued on Jun. 1, 2023, by the Japanese Patent Office in Japanese Patent Application No. 2021-537877, with an English translation of the Notice (6 pages).
Kanasty et al., "Delivery materials for siRNA therapeutics", Nature Materials, Nov. 2023, vol. 12, pp. 967-977.
Notice of Reasons for Refusal issued on Jun. 6, 2023, by the Japanese Patent Office in Japanese Patent Application No. 2021-509880, with an English translation of the Notice (6 pages).
Behlke, M. A. "Chemical Modification of siRNAs for In Vivo Use," Oligonucleotides, Nov. 29, 2008, vol. 18, No. 4, , pp. 305-320, XP002546697.
Chen, Y. et al., "Research Progress on Factor XI as a Novel Target for Antithrombotic Therapy", Chinese Pharmacological Bulletin, Apr. 15, 2015, vol. 31, No. 5, pp. 619-622 (with English abstract).
Dai, R., et al., "A vital role for Angptl3 in the PAN-induced podocyte loss by affecting detachment and apoptosis in vitro", BMC. Nephrology, 2015, pp. 1-10.
Dar, S.A. et al. "siRNAmod: A database of experimentally validated chemically modified siRNAs," Scientific Reports, Jan. 28, 2016, vol. 6, No. 1, XP055674735, pp. 1-8.
Ding, C. et al., "Limited role of kininogen in the host response during gram-negative pneumonia derived sepsis", Am J Physiol Lung Cell Mol Physiol., .Nov. 9, 2017, pp. 1-33, doi:10.1152/ajplung.00288.2017.
Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).
Foster, D.J. et al., "Advanced siRNA Designs Further Improve In Vivo Performance of GalNac-siRNA Conjugates", Molecular Therapy, vol. 26, No. 3, Mar. 2018, pp. 708-717.
Khaitmetova, S.B. et al., "Synthesis and Study of the Properties of Polymer Complexes of Ethacizin with Carboxymethylcellulose", Chemistry of Plant Raw Materials, 2017, vol. 4, pp. 23-30.
Khan, M.M. et al., "High-Molecular-Weight Kininogen Fragments Stimulate the Secretion of Cytokines and Chemokines Through uPAR, Mac-1, and gC1qR in Monocytes", Arterioscler Thromb Vasc Biol., 2006;26:2260-2266, DOI: 10.1161/01.ATV.0000240290.70852.c0.
Khvorova et al., "The chemical evolution of oligonucleotide therapies of clinical utility", Nature Biotechnology, 2017, vol. 35, No. 3, pp. 238-248; doi:10.1038/nbt.3765.
"Kim, K S, et al., "Bifunctional compounds for targeted heptatic gene delivery", Gene Therapy, Nature Publishing Group (2007) vol. 14, No. 8, pp. 704-708".
Liu, W., et al., "Coagulation factor XI induces Ca2+ response and accelerates cell migration in vascular smooth muscle cells via proteinase-activated receptor 1", Am J Physiol Cell Physiol, Dec. 19, 2018, vol. 316, No. 3, C377-C392 https://doi.org/10.1152/ajpcell.00426.2018.
Liu, Z. et al."Determination of Human Plasma Pre-Kallikrein", Journal of China Medical University. 1988, vol. 17, No. 6, ISSN: 0238-4646, pp. 432-436, with English Abstract.
Love et al., "Lipid-like materials for low-dose, in vivo gene silencing", Proceedings of the National Academy of Sciences, Feb. 2, 2010, vol. 107, No. 5 with correction. (7 pages).
Montagne, A. et al., "Pericyte degeneration causes white matter dysfunction in the mouse CNS", Nat Med., Mar. 2018; 24(3): 326-337.
Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961. (4 pages).
Nakagawa, A. et al., "The RNAi-Mediated Silencing of Xanthine Dehydrogenase Impairs Growth and Fertility and Accelerates Leaf Senescence in Transgenic Arabidopsis Plants", Plant Cell Physiol., Dec. 31, 2007, vol. 48, No. 10, , pp. 1484-1495.
No Author, "Experiment 21 RNA interference technology", retrieved from internet https://img.duxiu.com/n/jpgfs/book/base/12143891/af4f71d173f4fb48deb54aaf0ef2adcd/9ce955611111536dd3aefc5607ec2ae7.sthmil?uf=1&t=2&ti . . . retrieved online Oct. 15, 2021, pp. 5 pages. [English translation included].
Norata, G.D. et al., "Gene silencing approaches for the management of dyslipidaemia", Trends in Pharmacological Sciences, 2013, vol. 34, No. 4, pp. 198-205.
Nordestgaard, B., et al., "Advances in lipid-lowering therapy through gene-silencing technologies," Nature Reviews Cardiology, May 2018, published online Feb. 8, 2018, vol. 15, pp. 261-272.
Papulov, Y.G., "Relationship of the Properties of Substances with the Structure of Molecules: Math Modeling", Advances in Modern Natural Sciences, 2006, vol. 2, pp. 75-76. [English translation included].
Pena-Altamira, L.E. et al., "Release of soluble and vesicular purine nucleoside phosphorylase from rat astrocytes and microglia induced by pro-inflammatory stimulation with extracellular ATP via P2X7 receptors", Neurochemistry International, May 31, 2018, vol. 115, ISSN: 0197-0186, pp. 37-49.
Pessentheiner, A.R., et al., "ANGPTL3 targeting: The power of versatile lipid-lowering", Atherosclerosis, 2018, vol. 268, pp. 185-187.
"Prakash, T.P., et al., "Comprehensive Structure-Activity Relationship of Triantennary N-Acetylgalactosamine Conjugated Antisense Oligonucleotides for Targeted Delivery to Hepatocytes" Journal of Medicinal Chemistry, vol. 59, No. 6 (2016) pp. 2718-2733".
Ren, T. et al., "Synthesis of bifunctional cationic compound for gene delivery", Tetrahedron Letters, 2001, vol. 42, No. 6, pp. 1007-1010.
Springer, A. D. et al., "GalNac-siRNA Conjugates: Leading the Way for Delivery of RNAi Therapeutics", Nucleic Acid Therapeutics, May 24, 2018, vol. 28, No. 3, , pp. 109-118.
Su, L., et al., "Progress on Inhibition of Hepatitis B Virus by siRNA Strategy", China Biotechnology, Sep. 15, 2014, vol. 34, No. 9, pp. 102-105 , English abstract.
Tangkijvanich, P. et al., "Low pretreatment serum HBsAg level and viral mutations as predictors of response to PEG-interferon alpha-2b therapy in chronic hepatitis B", Journal of Clinical Virology, Aug. 3, 2009, vol. 46, Issue 2, pp. 117-123.
Watts et al., "Chemically modified siRNA: tools and applications", Drug Discovery Today, Oct. 2008, vol. 13, Nos. 19/20, pp. 842-855. (14 pages).
Wu, Y., et al., "Cleaved high molecular weight kininogen inhibits tube formation of endothelial progenitor cells via suppression of matrix metalloproteinase 2", J Thromb Haemost. 2010, vol. 8, pp. 185-193, DOI: 10.1111/j.1538-7836.2009.03662.x.
Wu, Y. et al., "Contact pathway of coagulation and inflammation", Thrombosis Journal. 2015, vol. 13, No. 17, pp. 1-9, DOI 10.1186/s12959-015-0048-y.
Xu, Y.X., et al., "Role of angiopoietin-like 3 (ANGPTL3) in regulating plasma level of low-density lipoprotein cholesterol", Atherosclerosis, 2018, vol. 268, pp. 196-206.
Yang, A., et al., "A critical role for plasma kallikrein in the pathogenesis of autoantibody-induced arthritis", The FASEB Journal, 2017, vol. 31, No. 12, pp. 5419-5431, doi: 10.1096/fj.201700018R.
Yang, A., et al., "An essential role of high-molecular-weight kininogen in endotoxemia", J. Exp. Med., 2017, vol. 214, No. 9, pp. 2649-2670, https://doi.org/10.1084/jem.20161900.
Chen et al., "Proof-of-concept Studies for siRNA-mediated Gene Silencing for Coagulation Factors in Rat and Rabbit", Molecular Therapy—Nucleic Acids, Jan. 27, 2015, vol. 4, No. 1, p. e224.
Ferrone et al., "IONIS-PKK Rx a Novel Antisense Inhibitor of Prekallikrein and Bradykinin Production", Nucleic Acid Therapeutics, Apr. 1, 2019, vol. 29, No. 2, pp. 82-91.
Ghosh et al., "Effectiveness and Safety of Inclisiran, A Novel Long-Acting RNA Therapeutic Inhibitor of Proprotein Convertase Subtilisin/Kexin 9", American Journal of Cardiology, Cahners Publishing Co., Newton, MA, US, Jul. 3, 2018, vol. 122, No. 7, pp. 1272-1277.

(56) References Cited

OTHER PUBLICATIONS

Joshi et al., " siRNA: novel therapeutics from functional genomics", Biotechnology and Genetic Engineering Reviews, Jan. 2, 2014, vol. 30, No. 1, pp. 1-30.
Pawluczyk et al., "Kallikrein gene 'knock-down' by small interfering RNA transfection induces a profibrotic phenotype in rat mesangial cells", Journal of Hypertension, Lippincott Williams & Wilkens, Ltd., Jan. 1, 2008, vol. 26, No. 1, pp. 93-101.
Revenko et al., "Selective depletion of plasma prekallikrein or coagulation factor XII inhibits thrombosis in mice without increased risk of bleeding", Blood, American Society of Hematology, Nov. 10, 2011, vol. 118, No. 19, pp. 5302-5311.
Yamasaki et al., "Novel molecular targets regulated by tumor suppressors microRNA-1 and microRNA-133a in bladder cancer", International Journal of Oncology, Feb. 29, 2012, vol. 40, pp. 1821-1830.
Supplementary European Search Report issued on Jun. 14, 2023, by the European Patent Office in European Patent Application No. 20809702.2 (12 pages).
Supplementary European Search Report issued on Jun. 16, 2023, by the European Patent Office in European Patent Application No. 20814338.8 (10 pages).
Partial Supplementary European Search Report issued on Jul. 5, 2023, by the European Patent Office in European Patent Application No. 20810635.1 (13 pages).
Partial Supplementary European Search Report issued on Jul. 10, 2023, by the European Patent Office in European Patent Application No. 20815633.1 (17 pages).
Beaucage et al., "Tetrahedron Report No. 309: Advances in Synthesis of Oligonucleotides by the Phosphoramidite Approach", Tetrahedron, 1992, vol. 48, No. 12, pp. 2223-2311.
Dong et al., "A novel packaging system of recombinant AAV5/5 vector", Chinese Journal of Biotechnology, May 25, 2010, vol. 26, No. 5, pp. 679-686.
Dong et al., "Lipopeptide nanoparticles for potent and selective siRNA delivery in rodents and nonhuman primates", PNAS Early Edition, 2014, vol. 111, No. 11, pp. 1-6 doi:10.1073/pnas.1322937111.
International Search Report and Written Opinion for corresponding PCT Application PCT/CN2018/118224 which issued Jul. 4, 2019.
International Search Report and Written Opinion for corresponding PCT Application PCT/CN2018/118303 which issued Mar. 7, 2019.
Khvorova et al., "The chemical evolution of oligonucleotide therapies of clinical utility", Nature Biotechnology, 2017, vol. 35, pp. 1-11.
Love et al., "Lipid-like materials for low-dose in vivo gene silencing", PNAS, Feb. 2, 2010, vol. 107, No. 5, pp. 1864-1869. (Correction included May 25, 2010, vol. 107, No. 21, p. 9915).
Matsuda et al., "siRNA Conjugates Carrying Sequentially Assembled Trivalent N-Aceytlgalactosamine Linked Through Nucleosides Elicit Robust Gene Silencing In Vivo in Hepatocytes", ACS Chem Biol., 2015, vol. 10, No. 5, 7 pages.
Nair et al., "Multivalent N-Acetylgalactosamine-Conjugated siRNA Localizes in Hepatocytes and Elicits Robust RNAi-Mediated Gene Silencing", J. Am. Chem. Soc., 2014, vol. 136, pp. 16958-16961.
Protective Groups in Organic Synthesis, by Theodora W. Greene and Wuts Peter G M., Wiley, 1999, Chapter 2, pp. 17-245.
Rajeev et al., "Hepatocyte-Specific Delivery of siRNAs Conjugated to Novel Non-nucleosidic Trivalent N-Aceytlgalactosamine Elicits Robust Gene Slicing in Vivo", ChemBioChem, 2015, vol. 16, pp. 903-908.
Ren et al., "Gene Expression Profile of Transgenic Mouse Kidney Reveals Pathogenesis of Hepatitis B Virus Associated Nephropathy", Journal of Medical Virology, 2006, vol. 78, pp. 551-560.
Ui-Tei et al., "Functional dissection of siRNA sequence by systematic DNA substitution: modified siRNA with a DNA seed arm is a powerful took for mammalian gene silencing with significantly reduced off-target effect", Nucleic Acids Research, 2008, vol. 36, No. 7, pp. 2136-2151.
Watts et al., "Chemically modified siRNA tools and applications", Drug Discovery Today, Oct. 2008, vol. 13, No. 19/20, pp. 842-855.
Woodell et al., "Hepatocyte-targeted RNAi Therapeutics for the Treatment of Chronic Hepatitis B Virus Infection", Molecular Therapy, 2013, vol. 21, No. 15, pp. 1-13, doi: 10.1038/mt.2013.31.
Berthold, et al., "Celluler Delivery and Antisense Effects of Peptide Nucleic Acid Conjugated to Polyethyleneimine via Disulfide Linkers" (2010) Bioconjugate Chemistry, vol. 21, No. 10, p. 1933-1938.
Paris, et al., "Conjugating Phosphospermines to siRNAs for Improved Stability in Serum, Intracelluler Delivery and RNAi-Mediated Gene Silencing" Molecular Pharmaceutics, vol. 9, No. 12, (2012) pp. 3464-3475.
Qui, S. et al., "Dickkopf 3 attenuates xanthine dehydrogenase expression to prevent oxidative stress-induced apoptosis," Genes to Cells, 2017, vol. 22, pp. 406-417. (cited in Extended European Search Report issued on Jan. 30, 2024, in European Patent Application No. 20813863.6).
Yasuda, T. et al., "Anti-Gout Agent Allopurinol Exerts Cytotoxicity to Human Hormone-Refractory Prostate Cancer Cells in Combination with Tumor Necrosis Factor-Related Apoptosis-Inducing Ligand," Mol Cancer Res, Dec. 2008, vol. 6, No. 12, pp. 1852-1860. (cited in Extended European Search Report issued on Jan. 30, 2024, in European Patent Application No. 20813863.6).
Hashimoto, K. et al., "Sulfotransferase-1A1-dependent bioactivation of aristolochic acid I and N-hydroxyaristolactam I in human cells," Carcinogenesis, 2016, vol. 37, No. 7, pp. 647-655. (cited in Extended European Search Report issued on Jan. 30, 2024, in European Patent Application No. 20813863.6).
Fedin A.I. et al., "Review of clinical recommendations for treatment and prevention of ischemic stroke", S. S. Korsakov Journal of Neurology and Psychiatry, 2019, vol. 119, No. 8, pp. 91-96, doi: 10.17116/jnevro201911908291, with English abstract. (Cited in Office Action issued on Mar. 6, 2024, in corresponding Russian Application No. 2021130601) (6 pages).
Meijers J.C. et al., "High levels of coagulation factor XI as a risk factor for venous thrombosis", N. Engl. J. Med., 2000, vol. 342, No. 10, pp. 696-701, doi: 10.1056/NEJM200003093421004. (Cited in Office Action issued on Mar. 6, 2024, in corresponding Russian Application No. 2021130601) (6 pages).
Soodabeh S. et al., "From in vitro Experiments to in vivo and Clinical Studies; Pros and Cons", Curr. Drug Discov. Technol., 2015, vol. 12, No. 4, pp. 218-224. (Cited in Office Action issued on Mar. 6, 2024, in corresponding Russian Application No. 2021130601) (7 pages).
Shafer A.I. et al., "Thrombotic Disorders Diagnosis and Treatment", Am. Soc. Hematol. Educ. Program, 2003, v. 1, pp. 520-539, doi 10.1182asheducation-2003.1.520. (Cited in Office Action issued on Mar. 6, 2024, in corresponding Russian Application No. 2021130601) (20 pages).
Sehgal, Alfica et al., "Liver as a target for oligonucleotide therapeutics", Journal of hepatology, 2013, vol. 59, pp. 1354-1359. (Cited in Office Action issued on Mar. 11, 2024, in corresponding Taiwanese Patent Application No. 109116935) (6 pages).
Diaz-Torné, Cesar et al., "New medications in development for the treatment of hyperuricemia of gout", Current opinion in rheumatology. 2015, vol. 27, No. 2, pp. 164-169. (Cited in Office Action issued on Mar. 11, 2024, in corresponding Taiwanese Patent Application No. 109116934) (6 pages).
Kojima, S. et al., "Tumour suppressors miR-1 and miR-133a target the oncogenic function of purine nucleoside phosphorylase (PNP) in prostate cancer", Br. J. Cancer, 2012, vol. 106(2), pp. 405-413. (Cited in Office Action issued on May 21, 2024, in corresponding Japanese Patent Application No. JP2021-569112) (9 pages).

\* cited by examiner

SEQUENCE LISTING

```
<160> NUMBER OF SEQ ID NOS: 156

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (20)..(20)
<223> OTHER INFORMATION: n is a, c, g, or u

<400> SEQUENCE: 1
wccuugaggc auacuucaan                                                 20

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: n is A, U, G or C

<400> SEQUENCE: 2
nuugaaguau gccucaagg                                                  19

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: n is A, U, G or C

<400> SEQUENCE: 3
nuugaaguau gccucaaggu u                                               21

<210> SEQ ID NO 4
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: n is A, U, G or C

<400> SEQUENCE: 4
nuugaaguau gccucaaggu c                                              21

<210> SEQ ID NO 5
<211> LENGTH: 19
<212> TYPE: RNA
<213> ORGANISM: Artificial Sequence
<220> FEATURE:
<223> OTHER INFORMATION: sense sequence for siHBa1

<400> SEQUENCE: 5
ccuugaggca uacuucaaa                                                 19

<210> SEQ ID NO 6
<211> LENGTH: 21
<212> TYPE: RNA
<213> ORGANISM: Artificial Sequence
<220> FEATURE:
<223> OTHER INFORMATION: antisense sequence for siHBa1

<400> SEQUENCE: 6
uuugaaguau gccucaaggu u                                              21

<210> SEQ ID NO 7
<211> LENGTH: 21
<212> TYPE: RNA
<213> ORGANISM: Artificial Sequence
<220> FEATURE:
<223> OTHER INFORMATION: sense sequence for siHBa2

<400> SEQUENCE: 7
gaccuugagg cauacuucaa a                                              21

<210> SEQ ID NO 8
<211> LENGTH: 23
<212> TYPE: RNA
<213> ORGANISM: Artificial Sequence
<220> FEATURE:
<223> OTHER INFORMATION: antisense sequence for siHBa2

<400> SEQUENCE: 8
uuugaaguau gccucaaggu cgg                                            23

<210> SEQ ID NO 9
<211> LENGTH: 19
<212> TYPE: RNA
<213> ORGANISM: Artificial Sequence
<220> FEATURE:
<223> OTHER INFORMATION: sense sequence for siHBa1M1

<400> SEQUENCE: 9
ccuugaggca uacuucaaa                                                 19

<210> SEQ ID NO 10
<211> LENGTH: 21
<212> TYPE: RNA
<213> ORGANISM: Artificial Sequence
<220> FEATURE:
<223> OTHER INFORMATION: antisense sequence for siHBa1M1
```

<400> SEQUENCE: 10
uuugaaguau gccucaaggu u                                              21

<210> SEQ ID NO 11
<211> LENGTH: 19
<212> TYPE: RNA
<213> ORGANISM: Artificial Sequence
<220> FEATURE:
<223> OTHER INFORMATION: sense sequence for siHBa1M2

<400> SEQUENCE: 11
ccuugaggca uacuucaaa                                                 19

<210> SEQ ID NO 12
<211> LENGTH: 21
<212> TYPE: RNA
<213> ORGANISM: Artificial Sequence
<220> FEATURE:
<223> OTHER INFORMATION: antisense sequence for siHBa1M2

<400> SEQUENCE: 12
uuugaaguau gccucaaggu u                                              21

<210> SEQ ID NO 13
<211> LENGTH: 21
<212> TYPE: RNA
<213> ORGANISM: Artificial Sequence
<220> FEATURE:
<223> OTHER INFORMATION: sense sequence for siHBa2M1

<400> SEQUENCE: 13
gaccuugagg cauacuucaa a                                              21

<210> SEQ ID NO 14
<211> LENGTH: 23
<212> TYPE: RNA
<213> ORGANISM: Artificial Sequence
<220> FEATURE:
<223> OTHER INFORMATION: antisense sequence for siHBa2M1

<400> SEQUENCE: 14
uuugaaguau gccucaaggu cgg                                            23

<210> SEQ ID NO 15
<211> LENGTH: 21
<212> TYPE: RNA
<213> ORGANISM: Artificial Sequence
<220> FEATURE:
<223> OTHER INFORMATION: sense sequence for siHBa2M2

<400> SEQUENCE: 15
gaccuugagg cauacuucaa a                                              21

<210> SEQ ID NO 16
<211> LENGTH: 23
<212> TYPE: RNA
<213> ORGANISM: Artificial Sequence
<220> FEATURE:
<223> OTHER INFORMATION: antisense sequence for siHBa2M2

<400> SEQUENCE: 16
uuugaaguau gccucaaggu cgg                                            23

<210> SEQ ID NO 17
<211> LENGTH: 19

```
<212> TYPE: RNA
<213> ORGANISM: Artificial Sequence
<220> FEATURE:
<223> OTHER INFORMATION: sense sequence for siHBa1M1S

<400> SEQUENCE: 17
ccuugaggca uacuucaaa                                          19

<210> SEQ ID NO 18
<211> LENGTH: 21
<212> TYPE: RNA
<213> ORGANISM: Artificial Sequence
<220> FEATURE:
<223> OTHER INFORMATION: antisense sequence for siHBa1M1S

<400> SEQUENCE: 18
uuugaaguau gccucaaggu u                                       21

<210> SEQ ID NO 19
<211> LENGTH: 19
<212> TYPE: RNA
<213> ORGANISM: Artificial Sequence
<220> FEATURE:
<223> OTHER INFORMATION: sense sequence for siHBa1M2S

<400> SEQUENCE: 19
ccuugaggca uacuucaaa                                          19

<210> SEQ ID NO 20
<211> LENGTH: 21
<212> TYPE: RNA
<213> ORGANISM: Artificial Sequence
<220> FEATURE:
<223> OTHER INFORMATION: antisense sequence for siHBa1M2S

<400> SEQUENCE: 20
uuugaaguau gccucaaggu u                                       21

<210> SEQ ID NO 21
<211> LENGTH: 21
<212> TYPE: RNA
<213> ORGANISM: Artificial Sequence
<220> FEATURE:
<223> OTHER INFORMATION: sense sequence for siHBa2M1S

<400> SEQUENCE: 21
gaccuugagg cauacuucaa a                                       21

<210> SEQ ID NO 22
<211> LENGTH: 23
<212> TYPE: RNA
<213> ORGANISM: Artificial Sequence
<220> FEATURE:
<223> OTHER INFORMATION: antisense sequence for siHBa2M1S

<400> SEQUENCE: 22
uuugaaguau gccucaaggu cgg                                     23

<210> SEQ ID NO 23
<211> LENGTH: 21
<212> TYPE: RNA
<213> ORGANISM: Artificial Sequence
<220> FEATURE:
<223> OTHER INFORMATION: sense sequence for siHBa2M2S

<400> SEQUENCE: 23
```
gaccuugagg cauacuucaa a                                                     21

<210> SEQ ID NO 24
<211> LENGTH: 23
<212> TYPE: RNA
<213> ORGANISM: Artificial Sequence
<220> FEATURE:
<223> OTHER INFORMATION: antisense sequence for siHBa2M2S

<400> SEQUENCE: 24
uuugaaguau gccucaaggu cgg                                                   23

<210> SEQ ID NO 25
<211> LENGTH: 19
<212> TYPE: RNA
<213> ORGANISM: Artificial Sequence
<220> FEATURE:
<223> OTHER INFORMATION: sense sequence for siHBa1M1P1

<400> SEQUENCE: 25
ccuugaggca uacuucaaa                                                        19

<210> SEQ ID NO 26
<211> LENGTH: 21
<212> TYPE: RNA
<213> ORGANISM: Artificial Sequence
<220> FEATURE:
<223> OTHER INFORMATION: antisense sequence for siHBa1M1P1

<400> SEQUENCE: 26
uuugaaguau gccucaaggu u                                                     21

<210> SEQ ID NO 27
<211> LENGTH: 19
<212> TYPE: RNA
<213> ORGANISM: Artificial Sequence
<220> FEATURE:
<223> OTHER INFORMATION: sense sequence for siHBa1M2P1

<400> SEQUENCE: 27
ccuugaggca uacuucaaa                                                        19

<210> SEQ ID NO 28
<211> LENGTH: 21
<212> TYPE: RNA
<213> ORGANISM: Artificial Sequence
<220> FEATURE:
<223> OTHER INFORMATION: antisense sequence for siHBa1M2P1

<400> SEQUENCE: 28
uuugaaguau gccucaaggu u                                                     21

<210> SEQ ID NO 29
<211> LENGTH: 21
<212> TYPE: RNA
<213> ORGANISM: Artificial Sequence
<220> FEATURE:
<223> OTHER INFORMATION: sense sequence for siHBa2M1P1

<400> SEQUENCE: 29
gaccuugagg cauacuucaa a                                                     21

<210> SEQ ID NO 30
<211> LENGTH: 23
<212> TYPE: RNA
<213> ORGANISM: Artificial Sequence

```
<220> FEATURE:
<223> OTHER INFORMATION: antisense sequence for siHBa2M1P1

<400> SEQUENCE: 30
uuugaaguau gccucaaggu cgg                                           23

<210> SEQ ID NO 31
<211> LENGTH: 21
<212> TYPE: RNA
<213> ORGANISM: Artificial Sequence
<220> FEATURE:
<223> OTHER INFORMATION: sense sequence for siHBa2M2P1

<400> SEQUENCE: 31
gaccuugagg cauacuucaa a                                             21

<210> SEQ ID NO 32
<211> LENGTH: 23
<212> TYPE: RNA
<213> ORGANISM: Artificial Sequence
<220> FEATURE:
<223> OTHER INFORMATION: antisense sequence for siHBa2M2P1

<400> SEQUENCE: 32
uuugaaguau gccucaaggu cgg                                           23

<210> SEQ ID NO 33
<211> LENGTH: 19
<212> TYPE: RNA
<213> ORGANISM: Artificial Sequence
<220> FEATURE:
<223> OTHER INFORMATION: sense sequence for siHBa1M1SP1

<400> SEQUENCE: 33
ccuugaggca uacuucaaa                                                19

<210> SEQ ID NO 34
<211> LENGTH: 21
<212> TYPE: RNA
<213> ORGANISM: Artificial Sequence
<220> FEATURE:
<223> OTHER INFORMATION: antisense sequence for siHBa1M1SP1

<400> SEQUENCE: 34
uuugaaguau gccucaaggu u                                             21

<210> SEQ ID NO 35
<211> LENGTH: 19
<212> TYPE: RNA
<213> ORGANISM: Artificial Sequence
<220> FEATURE:
<223> OTHER INFORMATION: sense sequence for siHBa1M2SP1

<400> SEQUENCE: 35
ccuugaggca uacuucaaa                                                19

<210> SEQ ID NO 36
<211> LENGTH: 21
<212> TYPE: RNA
<213> ORGANISM: Artificial Sequence
<220> FEATURE:
<223> OTHER INFORMATION: antisense sequence for siHBa1M2SP1

<400> SEQUENCE: 36
uuugaaguau gccucaaggu u                                             21
```

<210> SEQ ID NO 37
<211> LENGTH: 21
<212> TYPE: RNA
<213> ORGANISM: Artificial Sequence
<220> FEATURE:
<223> OTHER INFORMATION: sense sequence for siHBa2M1SP1

<400> SEQUENCE: 37
gaccuugagg cauacuucaa a                                              21

<210> SEQ ID NO 38
<211> LENGTH: 23
<212> TYPE: RNA
<213> ORGANISM: Artificial Sequence
<220> FEATURE:
<223> OTHER INFORMATION: Antisense sequence for siHBa2M1SP1

<400> SEQUENCE: 38
uuugaaguau gccucaaggu cgg                                            23

<210> SEQ ID NO 39
<211> LENGTH: 21
<212> TYPE: RNA
<213> ORGANISM: Artificial Sequence
<220> FEATURE:
<223> OTHER INFORMATION: sense sequence for siHBa2M2SP1

<400> SEQUENCE: 39
gaccuugagg cauacuucaa a                                              21

<210> SEQ ID NO 40
<211> LENGTH: 23
<212> TYPE: RNA
<213> ORGANISM: Artificial Sequence
<220> FEATURE:
<223> OTHER INFORMATION: Antisense sequence for siHBa2M2SP1

<400> SEQUENCE: 40
uuugaaguau gccucaaggu cgg                                            23

<210> SEQ ID NO 41
<211> LENGTH: 19
<212> TYPE: RNA
<213> ORGANISM: Artificial Sequence
<220> FEATURE:
<223> OTHER INFORMATION: sense sequence for L10-siHBa1M1SVP

<400> SEQUENCE: 41
ccuugaggca uacuucaaa                                                 19

<210> SEQ ID NO 42
<211> LENGTH: 21
<212> TYPE: RNA
<213> ORGANISM: Artificial Sequence
<220> FEATURE:
<223> OTHER INFORMATION: antisense sequence for L10-siHBa1M1SVP

<400> SEQUENCE: 42
uuugaaguau gccucaaggu u                                              21

<210> SEQ ID NO 43
<211> LENGTH: 19
<212> TYPE: RNA
<213> ORGANISM: Artificial Sequence
<220> FEATURE:
<223> OTHER INFORMATION: sense sequence for L10-siHBa1M1SP

```
<400> SEQUENCE: 43
ccuugaggca uacuucaaa                                                    19

<210> SEQ ID NO 44
<211> LENGTH: 21
<212> TYPE: RNA
<213> ORGANISM: Artificial Sequence
<220> FEATURE:
<223> OTHER INFORMATION: antisense sequence for L10-siHBa1M1SP

<400> SEQUENCE: 44
uuugaaguau gccucaaggu u                                                 21

<210> SEQ ID NO 45
<211> LENGTH: 19
<212> TYPE: RNA
<213> ORGANISM: Artificial Sequence
<220> FEATURE:
<223> OTHER INFORMATION: sense sequence for L10-siHBa1M1SPsT

<400> SEQUENCE: 45
ccuugaggca uacuucaaa                                                    19

<210> SEQ ID NO 46
<211> LENGTH: 21
<212> TYPE: DNA
<213> ORGANISM: Artificial Sequence
<220> FEATURE:
<223> OTHER INFORMATION: antisense sequence for L10-siHBa1M1SPsT

<400> SEQUENCE: 46
tuugaaguau gccucaaggu u                                                 21

<210> SEQ ID NO 47
<211> LENGTH: 19
<212> TYPE: RNA
<213> ORGANISM: Artificial Sequence
<220> FEATURE:
<223> OTHER INFORMATION: sense sequence for L10-siHBa1M1SPs

<400> SEQUENCE: 47
ccuugaggca uacuucaaa                                                    19

<210> SEQ ID NO 48
<211> LENGTH: 21
<212> TYPE: RNA
<213> ORGANISM: Artificial Sequence
<220> FEATURE:
<223> OTHER INFORMATION: antisense sequence for L10-siHBa1M1SPs

<400> SEQUENCE: 48
uuugaaguau gccucaaggu u                                                 21

<210> SEQ ID NO 49
<211> LENGTH: 19
<212> TYPE: RNA
<213> ORGANISM: Artificial Sequence
<220> FEATURE:
<223> OTHER INFORMATION: sense sequence for L10-siHBa1M2S

<400> SEQUENCE: 49
ccuugaggca uacuucaaa                                                    19

<210> SEQ ID NO 50
```

<211> LENGTH: 21
<212> TYPE: RNA
<213> ORGANISM: Artificial Sequence
<220> FEATURE:
<223> OTHER INFORMATION: antisense sequence for L10-siHBa1M2S

<400> SEQUENCE: 50
uuugaaguau gccucaaggu u                                                   21

<210> SEQ ID NO 51
<211> LENGTH: 19
<212> TYPE: RNA
<213> ORGANISM: Artificial Sequence
<220> FEATURE:
<223> OTHER INFORMATION: sense sequence for L10-siHBa1M2SVP

<400> SEQUENCE: 51
ccuugaggca uacuucaaa                                                      19

<210> SEQ ID NO 52
<211> LENGTH: 21
<212> TYPE: RNA
<213> ORGANISM: Artificial Sequence
<220> FEATURE:
<223> OTHER INFORMATION: antisense sequence for L10-siHBa1M2SVP

<400> SEQUENCE: 52
uuugaaguau gccucaaggu u                                                   21

<210> SEQ ID NO 53
<211> LENGTH: 21
<212> TYPE: RNA
<213> ORGANISM: Artificial Sequence
<220> FEATURE:
<223> OTHER INFORMATION: sense sequence for L10-siHBa2M1S

<400> SEQUENCE: 53
gaccuugagg cauacuucaa a                                                   21

<210> SEQ ID NO 54
<211> LENGTH: 23
<212> TYPE: RNA
<213> ORGANISM: Artificial Sequence
<220> FEATURE:
<223> OTHER INFORMATION: antisense sequence for L10-siHBa2M1S

<400> SEQUENCE: 54
uuugaaguau gccucaaggu cgg                                                 23

<210> SEQ ID NO 55
<211> LENGTH: 19
<212> TYPE: RNA
<213> ORGANISM: Artificial Sequence
<220> FEATURE:
<223> OTHER INFORMATION: sense sequence for L10-siHBa1M1S

<400> SEQUENCE: 55
ccuugaggca uacuucaaa                                                      19

<210> SEQ ID NO 56
<211> LENGTH: 21
<212> TYPE: RNA
<213> ORGANISM: Artificial Sequence
<220> FEATURE:
<223> OTHER INFORMATION: antisense sequence for L10-siHBa1M1S

<400> SEQUENCE: 56

```
uuugaaguau gccucaaggu u                                              21

<210> SEQ ID NO 57
<211> LENGTH: 19
<212> TYPE: RNA
<213> ORGANISM: Artificial Sequence
<220> FEATURE:
<223> OTHER INFORMATION: sense sequence for L10-siHBa2M2SPs

<400> SEQUENCE: 57
ccuugaggca uacuucaaa                                                 19

<210> SEQ ID NO 58
<211> LENGTH: 21
<212> TYPE: RNA
<213> ORGANISM: Artificial Sequence
<220> FEATURE:
<223> OTHER INFORMATION: antisense sequence for L10-siHBa2M2SPs

<400> SEQUENCE: 58
uuugaaguau gccucaaggu u                                              21

<210> SEQ ID NO 59
<211> LENGTH: 21
<212> TYPE: RNA
<213> ORGANISM: Artificial Sequence
<220> FEATURE:
<223> OTHER INFORMATION: sense sequence for L10-siHBa2M2SP

<400> SEQUENCE: 59
gaccuugagg cauacuucaa a                                              21

<210> SEQ ID NO 60
<211> LENGTH: 23
<212> TYPE: RNA
<213> ORGANISM: Artificial Sequence
<220> FEATURE:
<223> OTHER INFORMATION: antisense sequence for L10-siHBa2M2SP

<400> SEQUENCE: 60
uuugaaguau gccucaaggu cgg                                            23

<210> SEQ ID NO 61
<211> LENGTH: 21
<212> TYPE: RNA
<213> ORGANISM: Artificial Sequence
<220> FEATURE:
<223> OTHER INFORMATION: sense sequence for L10-siHBa2M1SVP

<400> SEQUENCE: 61
gaccuugagg cauacuucaa a                                              21

<210> SEQ ID NO 62
<211> LENGTH: 23
<212> TYPE: RNA
<213> ORGANISM: Artificial Sequence
<220> FEATURE:
<223> OTHER INFORMATION: antisense sequence for L10-siHBa2M1SVP

<400> SEQUENCE: 62
uuugaaguau gccucaaggu cgg                                            23

<210> SEQ ID NO 63
<211> LENGTH: 19
<212> TYPE: RNA
```

```
<213> ORGANISM: Artificial Sequence
<220> FEATURE:
<223> OTHER INFORMATION: sense sequence for L10-siHBa1

<400> SEQUENCE: 63
ccuugaggca uacuucaaa                                                  19

<210> SEQ ID NO 64
<211> LENGTH: 21
<212> TYPE: RNA
<213> ORGANISM: Artificial Sequence
<220> FEATURE:
<223> OTHER INFORMATION: antisense sequence for L10-siHBa1

<400> SEQUENCE: 64
uuugaaguau gccucaaggu u                                               21

<210> SEQ ID NO 65
<211> LENGTH: 21
<212> TYPE: RNA
<213> ORGANISM: Artificial Sequence
<220> FEATURE:
<223> OTHER INFORMATION: sense sequence for L10-siHBa2

<400> SEQUENCE: 65
gaccuugagg cauacuucaa a                                               21

<210> SEQ ID NO 66
<211> LENGTH: 23
<212> TYPE: RNA
<213> ORGANISM: Artificial Sequence
<220> FEATURE:
<223> OTHER INFORMATION: antisense sequence for L10-siHBa2

<400> SEQUENCE: 66
uuugaaguau gccucaaggu cgg                                             23

<210> SEQ ID NO 67
<211> LENGTH: 19
<212> TYPE: RNA
<213> ORGANISM: Artificial Sequence
<220> FEATURE:
<223> OTHER INFORMATION: sense sequence for L10-siHBa1M1

<400> SEQUENCE: 67
ccuugaggca uacuucaaa                                                  19

<210> SEQ ID NO 68
<211> LENGTH: 21
<212> TYPE: RNA
<213> ORGANISM: Artificial Sequence
<220> FEATURE:
<223> OTHER INFORMATION: antisense sequence for L10-siHBa1M1

<400> SEQUENCE: 68
uuugaaguau gccucaaggu u                                               21

<210> SEQ ID NO 69
<211> LENGTH: 19
<212> TYPE: RNA
<213> ORGANISM: Artificial Sequence
<220> FEATURE:
<223> OTHER INFORMATION: sense sequence for L10-siHBa1M2

<400> SEQUENCE: 69
ccuugaggca uacuucaaa                                                  19
```

<210> SEQ ID NO 70
<211> LENGTH: 21
<212> TYPE: RNA
<213> ORGANISM: Artificial Sequence
<220> FEATURE:
<223> OTHER INFORMATION: antisense sequence for L10-siHBa1M2

<400> SEQUENCE: 70
uuugaaguau gccucaaggu u                                        21

<210> SEQ ID NO 71
<211> LENGTH: 21
<212> TYPE: RNA
<213> ORGANISM: Artificial Sequence
<220> FEATURE:
<223> OTHER INFORMATION: sense sequence for L10-siHBa2M1

<400> SEQUENCE: 71
gaccuugagg cauacuucaa a                                        21

<210> SEQ ID NO 72
<211> LENGTH: 23
<212> TYPE: RNA
<213> ORGANISM: Artificial Sequence
<220> FEATURE:
<223> OTHER INFORMATION: antisense sequence for L10-siHBa2M1

<400> SEQUENCE: 72
uuugaaguau gccucaaggu cgg                                      23

<210> SEQ ID NO 73
<211> LENGTH: 21
<212> TYPE: RNA
<213> ORGANISM: Artificial Sequence
<220> FEATURE:
<223> OTHER INFORMATION: sense sequence for L10-siHBa2M2

<400> SEQUENCE: 73
gaccuugagg cauacuucaa a                                        21

<210> SEQ ID NO 74
<211> LENGTH: 23
<212> TYPE: RNA
<213> ORGANISM: Artificial Sequence
<220> FEATURE:
<223> OTHER INFORMATION: antisense sequence for L10-siHBa2M2

<400> SEQUENCE: 74
uuugaaguau gccucaaggu cgg                                      23

<210> SEQ ID NO 75
<211> LENGTH: 21
<212> TYPE: RNA
<213> ORGANISM: Artificial Sequence
<220> FEATURE:
<223> OTHER INFORMATION: sense sequence for L10-siHBa2M2S

<400> SEQUENCE: 75
gaccuugagg cauacuucaa a                                        21

<210> SEQ ID NO 76
<211> LENGTH: 23
<212> TYPE: RNA
<213> ORGANISM: Artificial Sequence
<220> FEATURE:

<223> OTHER INFORMATION: antisense sequence for L10-siHBa2M2S

<400> SEQUENCE: 76
uuugaaguau gccucaaggu cgg                                        23

<210> SEQ ID NO 77
<211> LENGTH: 19
<212> TYPE: RNA
<213> ORGANISM: Artificial Sequence
<220> FEATURE:
<223> OTHER INFORMATION: sense sequence for L10-siHBa1M1VP

<400> SEQUENCE: 77
ccuugaggca uacuucaaa                                             19

<210> SEQ ID NO 78
<211> LENGTH: 21
<212> TYPE: RNA
<213> ORGANISM: Artificial Sequence
<220> FEATURE:
<223> OTHER INFORMATION: antisense sequence for L10-siHBa1M1VP

<400> SEQUENCE: 78
uuugaaguau gccucaaggu u                                          21

<210> SEQ ID NO 79
<211> LENGTH: 19
<212> TYPE: RNA
<213> ORGANISM: Artificial Sequence
<220> FEATURE:
<223> OTHER INFORMATION: sense sequence for L10-siHBa1M2VP

<400> SEQUENCE: 79
ccuugaggca uacuucaaa                                             19

<210> SEQ ID NO 80
<211> LENGTH: 21
<212> TYPE: RNA
<213> ORGANISM: Artificial Sequence
<220> FEATURE:
<223> OTHER INFORMATION: antisense sequence for L10-siHBa1M2VP

<400> SEQUENCE: 80
uuugaaguau gccucaaggu u                                          21

<210> SEQ ID NO 81
<211> LENGTH: 21
<212> TYPE: RNA
<213> ORGANISM: Artificial Sequence
<220> FEATURE:
<223> OTHER INFORMATION: sense sequence for L10-siHBa2M1VP

<400> SEQUENCE: 81
gaccuugagg cauacuucaa a                                          21

<210> SEQ ID NO 82
<211> LENGTH: 23
<212> TYPE: RNA
<213> ORGANISM: Artificial Sequence
<220> FEATURE:
<223> OTHER INFORMATION: antisense sequence for L10-siHBa2M1VP

<400> SEQUENCE: 82
uuugaaguau gccucaaggu cgg                                        23

```
<210> SEQ ID NO 83
<211> LENGTH: 21
<212> TYPE: RNA
<213> ORGANISM: Artificial Sequence
<220> FEATURE:
<223> OTHER INFORMATION: sense sequence for L10-siHBa2M2VP

<400> SEQUENCE: 83
gaccuugagg cauacuucaa a                                              21

<210> SEQ ID NO 84
<211> LENGTH: 23
<212> TYPE: RNA
<213> ORGANISM: Artificial Sequence
<220> FEATURE:
<223> OTHER INFORMATION: antisense sequence for L10-siHBa2M2VP

<400> SEQUENCE: 84
uuugaaguau gccucaaggu cgg                                            23

<210> SEQ ID NO 85
<211> LENGTH: 21
<212> TYPE: RNA
<213> ORGANISM: Artificial Sequence
<220> FEATURE:
<223> OTHER INFORMATION: sense sequence for L10-siHBa2M2SVP

<400> SEQUENCE: 85
gaccuugagg cauacuucaa a                                              21

<210> SEQ ID NO 86
<211> LENGTH: 23
<212> TYPE: RNA
<213> ORGANISM: Artificial Sequence
<220> FEATURE:
<223> OTHER INFORMATION: antisense sequence for L10-siHBa2M2SVP

<400> SEQUENCE: 86
uuugaaguau gccucaaggu cgg                                            23

<210> SEQ ID NO 87
<211> LENGTH: 19
<212> TYPE: RNA
<213> ORGANISM: Artificial Sequence
<220> FEATURE:
<223> OTHER INFORMATION: sense sequence for L10-siHBa1M5SVP

<400> SEQUENCE: 87
ccuugaggca uacuucaaa                                                 19

<210> SEQ ID NO 88
<211> LENGTH: 21
<212> TYPE: RNA
<213> ORGANISM: Artificial Sequence
<220> FEATURE:
<223> OTHER INFORMATION: antisense sequence for L10-siHBa1M5SVP

<400> SEQUENCE: 88
uuugaaguau gccucaaggu u                                              21

<210> SEQ ID NO 89
<211> LENGTH: 19
<212> TYPE: RNA
<213> ORGANISM: Artificial Sequence
<220> FEATURE:
<223> OTHER INFORMATION: sense sequence for L10-siHBa1M3SVP
```

```
<400> SEQUENCE: 89
ccuugaggca uacuucaaa                                                   19

<210> SEQ ID NO 90
<211> LENGTH: 21
<212> TYPE: RNA
<213> ORGANISM: Artificial Sequence
<220> FEATURE:
<223> OTHER INFORMATION: antisense sequence for L10-siHBa1M3SVP

<400> SEQUENCE: 90
uuugaaguau gccucaaggu u                                                21

<210> SEQ ID NO 91
<211> LENGTH: 19
<212> TYPE: RNA
<213> ORGANISM: Artificial Sequence
<220> FEATURE:
<223> OTHER INFORMATION: sense sequence for L10-siHBa1M4SVP

<400> SEQUENCE: 91
ccuugaggca uacuucaaa                                                   19

<210> SEQ ID NO 92
<211> LENGTH: 21
<212> TYPE: RNA
<213> ORGANISM: Artificial Sequence
<220> FEATURE:
<223> OTHER INFORMATION: antisense sequence for L10-siHBa1M4SVP

<400> SEQUENCE: 92
uuugaaguau gccucaaggu u                                                21

<210> SEQ ID NO 93
<211> LENGTH: 19
<212> TYPE: RNA
<213> ORGANISM: Artificial Sequence
<220> FEATURE:
<223> OTHER INFORMATION: sense sequence for P10-siHBa1M1SVP

<400> SEQUENCE: 93
ccuugaggca uacuucaaa                                                   19

<210> SEQ ID NO 94
<211> LENGTH: 21
<212> TYPE: RNA
<213> ORGANISM: Artificial Sequence
<220> FEATURE:
<223> OTHER INFORMATION: antisense sequence for P10-siHBa1M1SVP

<400> SEQUENCE: 94
uuugaaguau gccucaaggu u                                                21

<210> SEQ ID NO 95
<211> LENGTH: 19
<212> TYPE: RNA
<213> ORGANISM: Artificial Sequence
<220> FEATURE:
<223> OTHER INFORMATION: sense sequence for R5-siHBa1M1SVP

<400> SEQUENCE: 95
ccuugaggca uacuucaaa                                                   19

<210> SEQ ID NO 96
<211> LENGTH: 21
```

```
<212> TYPE: RNA
<213> ORGANISM: Artificial Sequence
<220> FEATURE:
<223> OTHER INFORMATION: antisense sequence for R5-siHBa1M1SVP

<400> SEQUENCE: 96
uuugaaguau gccucaaggu u                                              21

<210> SEQ ID NO 97
<211> LENGTH: 19
<212> TYPE: RNA
<213> ORGANISM: Artificial Sequence
<220> FEATURE:
<223> OTHER INFORMATION: sense sequence for LA5-siHBa1M1SVP

<400> SEQUENCE: 97
ccuugaggca uacuucaaa                                                 19

<210> SEQ ID NO 98
<211> LENGTH: 21
<212> TYPE: RNA
<213> ORGANISM: Artificial Sequence
<220> FEATURE:
<223> OTHER INFORMATION: antisense sequence for LA5-siHBa1M1SVP

<400> SEQUENCE: 98
uuugaaguau gccucaaggu u                                              21

<210> SEQ ID NO 99
<211> LENGTH: 19
<212> TYPE: RNA
<213> ORGANISM: Artificial Sequence
<220> FEATURE:
<223> OTHER INFORMATION: sense sequence for LB5-siHBa1M1SVP

<400> SEQUENCE: 99
ccuugaggca uacuucaaa                                                 19

<210> SEQ ID NO 100
<211> LENGTH: 21
<212> TYPE: RNA
<213> ORGANISM: Artificial Sequence
<220> FEATURE:
<223> OTHER INFORMATION: antisense sequence for LB5-siHBa1M1SVP

<400> SEQUENCE: 100
uuugaaguau gccucaaggu u                                              21

<210> SEQ ID NO 101
<211> LENGTH: 19
<212> TYPE: RNA
<213> ORGANISM: Artificial Sequence
<220> FEATURE:
<223> OTHER INFORMATION: sense sequence for V8-siHBa1M1SVP

<400> SEQUENCE: 101
ccuugaggca uacuucaaa                                                 19

<210> SEQ ID NO 102
<211> LENGTH: 21
<212> TYPE: RNA
<213> ORGANISM: Artificial Sequence
<220> FEATURE:
<223> OTHER INFORMATION: antisense sequence for V8-siHBa1M1SVP

<400> SEQUENCE: 102
```
uuugaaguau gccucaaggu u                                              21

<210

```
<220> FEATURE:
<223> OTHER INFORMATION: sense sequence for FIN-siHBa2

<400> SEQUENCE: 109
gaccuugagg cauacuucaa a                                              21

<210> SEQ ID NO 110
<211> LENGTH: 23
<212> TYPE: RNA
<213> ORGANISM: Artificial Sequence
<220> FEATURE:
<223> OTHER INFORMATION: antisense sequence for FIN-siHBa2

<400> SEQUENCE: 110
uuugaaguau gccucaaggu cgg                                            23

<210> SEQ ID NO 111
<211> LENGTH: 21
<212> TYPE: RNA
<213> ORGANISM: Artificial Sequence
<220> FEATURE:
<223> OTHER INFORMATION: sense sequence for FIN-siHBa2M5SVP

<400> SEQUENCE: 111
gaccuugagg cauacuucaa a                                              21

<210> SEQ ID NO 112
<211> LENGTH: 23
<212> TYPE: RNA
<213> ORGANISM: Artificial Sequence
<220> FEATURE:
<223> OTHER INFORMATION: antisense sequence for FIN-siHBa2M5SVP

<400> SEQUENCE: 112
uuugaaguau gccucaaggu cgg                                            23

<210> SEQ ID NO 113
<211> LENGTH: 21
<212> TYPE: RNA
<213> ORGANISM: Artificial Sequence
<220> FEATURE:
<223> OTHER INFORMATION: sense sequence for FIN-siHBa2M3SVP

<400> SEQUENCE: 113
gaccuugagg cauacuucaa a                                              21

<210> SEQ ID NO 114
<211> LENGTH: 23
<212> TYPE: RNA
<213> ORGANISM: Artificial Sequence
<220> FEATURE:
<223> OTHER INFORMATION: antisense sequence for FIN-siHBa2M3SVP

<400> SEQUENCE: 114
uuugaaguau gccucaaggu cgg                                            23

<210> SEQ ID NO 115
<211> LENGTH: 21
<212> TYPE: RNA
<213> ORGANISM: Artificial Sequence
<220> FEATURE:
<223> OTHER INFORMATION: sense sequence for FIN-siHBa2M4SVP

<400> SEQUENCE: 115
gaccuugagg cauacuucaa a                                              21
```

```
<210> SEQ ID NO 116
<211> LENGTH: 23
<212> TYPE: RNA
<213> ORGANISM: Artificial Sequence
<220> FEATURE:
<223> OTHER INFORMATION: antisense sequence for FIN-siHBa2M4SVP

<400> SEQUENCE: 116
uuugaaguau gccucaaggu cgg                                               23

<210> SEQ ID NO 117
<211> LENGTH: 21
<212> TYPE: RNA
<213> ORGANISM: Artificial Sequence
<220> FEATURE:
<223> OTHER INFORMATION: sense sequence for FIN-siHBa2M1SVP

<400> SEQUENCE: 117
gaccuugagg cauacuucaa a                                                 21

<210> SEQ ID NO 118
<211> LENGTH: 23
<212> TYPE: RNA
<213> ORGANISM: Artificial Sequence
<220> FEATURE:
<223> OTHER INFORMATION: antisense sequence for FIN-siHBa2M1SVP

<400> SEQUENCE: 118
uuugaaguau gccucaaggu cgg                                               23

<210> SEQ ID NO 119
<211> LENGTH: 21
<212> TYPE: RNA
<213> ORGANISM: Artificial Sequence
<220> FEATURE:
<223> OTHER INFORMATION: sense sequence for FIN-siHBa2M2SVP

<400> SEQUENCE: 119
gaccuugagg cauacuucaa a                                                 21

<210> SEQ ID NO 120
<211> LENGTH: 23
<212> TYPE: RNA
<213> ORGANISM: Artificial Sequence
<220> FEATURE:
<223> OTHER INFORMATION: antisense sequence for FIN-siHBa2M2SVP

<400> SEQUENCE: 120
uuugaaguau gccucaaggu cgg                                               23

<210> SEQ ID NO 121
<211> LENGTH: 19
<212> TYPE: RNA
<213> ORGANISM: Artificial Sequence
<220> FEATURE:
<223> OTHER INFORMATION: sense sequence for FIN-siHBa3M2SVP

<400> SEQUENCE: 121
ccuugaggca uacuucaaa                                                    19

<210> SEQ ID NO 122
<211> LENGTH: 21
<212> TYPE: RNA
<213> ORGANISM: Artificial Sequence
<220> FEATURE:
<223> OTHER INFORMATION: antisense sequence for FIN-siHBa3M2SVP
```

```
<400> SEQUENCE: 122
uuugaaguau gccucaaggu c                                              21

<210> SEQ ID NO 123
<211> LENGTH: 19
<212> TYPE: RNA
<213> ORGANISM: Artificial Sequence
<220> FEATURE:
<223> OTHER INFORMATION: sense sequence for FIN-siHBa3M2S

<400> SEQUENCE: 123
ccuugaggca uacuucaaa                                                 19

<210> SEQ ID NO 124
<211> LENGTH: 21
<212> TYPE: RNA
<213> ORGANISM: Artificial Sequence
<220> FEATURE:
<223> OTHER INFORMATION: antisense sequence for FIN-siHBa3M2S

<400> SEQUENCE: 124
uuugaaguau gccucaaggu c                                              21

<210> SEQ ID NO 125
<211> LENGTH: 19
<212> TYPE: RNA
<213> ORGANISM: Artificial Sequence
<220> FEATURE:
<223> OTHER INFORMATION: sense sequence for FIN-siHBa1

<400> SEQUENCE: 125
ccuugaggca uacuucaaa                                                 19

<210> SEQ ID NO 126
<211> LENGTH: 21
<212> TYPE: RNA
<213> ORGANISM: Artificial Sequence
<220> FEATURE:
<223> OTHER INFORMATION: antisense sequence for FIN-siHBa1

<400> SEQUENCE: 126
uuugaaguau gccucaaggu u                                              21

<210> SEQ ID NO 127
<211> LENGTH: 19
<212> TYPE: RNA
<213> ORGANISM: Artificial Sequence
<220> FEATURE:
<223> OTHER INFORMATION: sense sequence for FIN-siHBa1M2SVP

<400> SEQUENCE: 127
ccuugaggca uacuucaaa                                                 19

<210> SEQ ID NO 128
<211> LENGTH: 21
<212> TYPE: RNA
<213> ORGANISM: Artificial Sequence
<220> FEATURE:
<223> OTHER INFORMATION: antisense sequence for FIN-siHBa1M2SVP

<400> SEQUENCE: 128
uuugaaguau gccucaaggu u                                              21

<210> SEQ ID NO 129
```

-continued

```
<211> LENGTH: 19
<212> TYPE: RNA
<213> ORGANISM: Artificial Sequence
<220> FEATURE:
<223> OTHER INFORMATION: sense sequence for FIN-siHBa1M2S

<400> SEQUENCE: 129
ccuugaggca uacuucaaa                                                  19

<210> SEQ ID NO 130
<211> LENGTH: 21
<212> TYPE: RNA
<213> ORGANISM: Artificial Sequence
<220> FEATURE:
<223> OTHER INFORMATION: antisense sequence for FIN-siHBa1M2S

<400> SEQUENCE: 130
uuugaaguau gccucaaggu u                                               21

<210> SEQ ID NO 131
<211> LENGTH: 19
<212> TYPE: RNA
<213> ORGANISM: Artificial Sequence
<220> FEATURE:
<223> OTHER INFORMATION: sense sequence for FIN-siHBa1M1SVP

<400> SEQUENCE: 131
ccuugaggca uacuucaaa                                                  19

<210> SEQ ID NO 132
<211> LENGTH: 21
<212> TYPE: RNA
<213> ORGANISM: Artificial Sequence
<220> FEATURE:
<223> OTHER INFORMATION: antisense sequence for FIN-siHBa1M1SVP

<400> SEQUENCE: 132
uuugaaguau gccucaaggu u                                               21

<210> SEQ ID NO 133
<211> LENGTH: 21
<212> TYPE: RNA
<213> ORGANISM: Artificial Sequence
<220> FEATURE:
<223> OTHER INFORMATION: sense sequence for FIN-siHBa2M1S

<400> SEQUENCE: 133
gaccuugagg cauacuucaa a                                               21

<210> SEQ ID NO 134
<211> LENGTH: 23
<212> TYPE: RNA
<213> ORGANISM: Artificial Sequence
<220> FEATURE:
<223> OTHER INFORMATION: antisense sequence for FIN-siHBa2M1S

<400> SEQUENCE: 134
uuugaaguau gccucaaggu cgg                                             23

<210> SEQ ID NO 135
<211> LENGTH: 19
<212> TYPE: RNA
<213> ORGANISM: Artificial Sequence
<220> FEATURE:
<223> OTHER INFORMATION: sense sequence for FIN-siHBa1M1S

<400> SEQUENCE: 135
```
ccuugaggca uacuucaaa                                          19

<210> SEQ ID NO 136
<211> LENGTH: 21
<212> TYPE: RNA
<213> ORGANISM: Artificial Sequence
<220> FEATURE:
<223> OTHER INFORMATION: antisense sequence for FIN-siHBa1M1S

<400> SEQUENCE: 136
uuugaaguau gccucaaggu u                                       21

<210> SEQ ID NO 137
<211> LENGTH: 21
<212> TYPE: DNA
<213> ORGANISM: Artificial Sequence
<220> FEATURE:
<223> OTHER INFORMATION: sense sequence for FIN-X2M2

<400> SEQUENCE: 137
ccuugaggca uacuucaaat t                                       21

<210> SEQ ID NO 138
<211> LENGTH: 21
<212> TYPE: DNA
<213> ORGANISM: Artificial Sequence
<220> FEATURE:
<223> OTHER INFORMATION: antisense sequence for FIN-X2M2

<400> SEQUENCE: 138
uuugaaguau gccucaaggt t                                       21

<210> SEQ ID NO 139
<211> LENGTH: 19
<212> TYPE: RNA
<213> ORGANISM: Artificial Sequence
<220> FEATURE:
<223> OTHER INFORMATION: sense sequence for L10-NC

<400> SEQUENCE: 139
uucuccgaac gugucacgu                                          19

<210> SEQ ID NO 140
<211> LENGTH: 21
<212> TYPE: RNA
<213> ORGANISM: Artificial Sequence
<220> FEATURE:
<223> OTHER INFORMATION: antisense sequence for L10-NC

<400> SEQUENCE: 140
acgugacacg uucggagaau u                                       21

<210> SEQ ID NO 141
<211> LENGTH: 19
<212> TYPE: RNA
<213> ORGANISM: Artificial Sequence
<220> FEATURE:
<223> OTHER INFORMATION: sense sequence for AD-66810

<400> SEQUENCE: 141
gugugcacuu cgcuucaca                                          19

<210> SEQ ID NO 142
<211> LENGTH: 21
<212> TYPE: RNA

```
<213> ORGANISM: Artificial Sequence
<220> FEATURE:
<223> OTHER INFORMATION: antisense sequence for AD-66810

<400> SEQUENCE: 142
ugugaagcga agugcacacu u                                              21

<210> SEQ ID NO 143
<211> LENGTH: 19
<212> TYPE: RNA
<213> ORGANISM: Artificial Sequence
<220> FEATURE:
<223> OTHER INFORMATION: sense sequence for Sequence 1

<400> SEQUENCE: 143
ccuugaggca uacuucaaa                                                 19

<210> SEQ ID NO 144
<211> LENGTH: 21
<212> TYPE: RNA
<213> ORGANISM: Artificial Sequence
<220> FEATURE:
<223> OTHER INFORMATION: antisense sequence for Sequence 1

<400> SEQUENCE: 144
uuugaaguau gccucaaggu c                                              21

<210> SEQ ID NO 145
<211> LENGTH: 19
<212> TYPE: RNA
<213> ORGANISM: Artificial Sequence
<220> FEATURE:
<223> OTHER INFORMATION: sense sequence for Sequence 2

<400> SEQUENCE: 145
ccuugaggca uacuucaaa                                                 19

<210> SEQ ID NO 146
<211> LENGTH: 21
<212> TYPE: RNA
<213> ORGANISM: Artificial Sequence
<220> FEATURE:
<223> OTHER INFORMATION: antisense sequence for Sequence 2

<400> SEQUENCE: 146
uuugaaguau gccucaaggu c                                              21

<210> SEQ ID NO 147
<211> LENGTH: 19
<212> TYPE: RNA
<213> ORGANISM: Artificial Sequence
<220> FEATURE:
<223> OTHER INFORMATION: sense sequence for Sequence 3

<400> SEQUENCE: 147
ccuugaggca uacuucaaa                                                 19

<210> SEQ ID NO 148
<211> LENGTH: 21
<212> TYPE: RNA
<213> ORGANISM: Artificial Sequence
<220> FEATURE:
<223> OTHER INFORMATION: antisense sequence for Sequence 3

<400> SEQUENCE: 148
uuugaaguau gccucaaggu u                                              21
```

```
<210> SEQ ID NO 149
<211> LENGTH: 21
<212> TYPE: DNA
<213> ORGANISM: Artificial Sequence
<220> FEATURE:
<223> OTHER INFORMATION: sense sequence for X2M2

<400> SEQUENCE: 149
ccuugaggca uacuucaaat t                                              21

<210> SEQ ID NO 150
<211> LENGTH: 21
<212> TYPE: DNA
<213> ORGANISM: Artificial Sequence
<220> FEATURE:
<223> OTHER INFORMATION: antisense sequence for X2M2

<400> SEQUENCE: 150
uuugaaguau gccucaaggt t                                              21

<210> SEQ ID NO 151
<211> LENGTH: 20
<212> TYPE: DNA
<213> ORGANISM: Artificial Sequence
<220> FEATURE:
<223> OTHER INFORMATION: upstream primer for HBV

<400> SEQUENCE: 151
ccgtctgtgc cttctcatct                                                20

<210> SEQ ID NO 152
<211> LENGTH: 20
<212> TYPE: DNA
<213> ORGANISM: Artificial Sequence
<220> FEATURE:
<223> OTHER INFORMATION: downstream primer for HBV

<400> SEQUENCE: 152
taatctcctc ccccaactcc                                                20

<210> SEQ ID NO 153
<211> LENGTH: 24
<212> TYPE: DNA
<213> ORGANISM: Artificial Sequence
<220> FEATURE:
<223> OTHER INFORMATION: upstream primer for -actin

<400> SEQUENCE: 153
agcttctttg cagctccttc gttg                                           24

<210> SEQ ID NO 154
<211> LENGTH: 24
<212> TYPE: DNA
<213> ORGANISM: Artificial Sequence
<220> FEATURE:
<223> OTHER INFORMATION: downstream primer for -actin

<400> SEQUENCE: 154
ttctgaccca ttcccaccat caca                                           24

<210> SEQ ID NO 155
<211> LENGTH: 19
<212> TYPE: RNA
<213> ORGANISM: Artificial Sequence
<220> FEATURE:
```

```
<223> OTHER INFORMATION: sense strand for the sequence
<220> FEATURE:
<221> NAME/KEY: misc_feature
<222> LOCATION: (19)..(19)
<223> OTHER INFORMATION: nA

<400> SEQUENCE: 155
ccuugaggca uacuucaan                                              19

<210> SEQ ID NO 156
<211> LENGTH: 19
<212> TYPE: RNA
<213> ORGANISM: Artificial Sequence
<220> FEATURE:
<223> OTHER INFORMATION: antisense strand for the sequece
<220> FEATURE:
<221> NAME/KEY: misc_feature
<222> LOCATION: (1)..(1)
<223> OTHER INFORMATION: nU

<400> SEQUENCE: 156
nuugaaguau gccucaagg                                              19
```

NUCLEIC ACID, COMPOSITION AND CONJUGATE COMPRISING THE SAME, AND PREPARATION METHOD AND USE THEREOF

CROSS REFERENCE TO RELATED APPLICATIONS

This application is a national phase entry under 35 U.S.C. 371 of International Application No. PCT/CN2018/118303, filed on Nov. 29, 2018, which claims priority to Chinese patent application No. 201711249333.8, filed on Dec. 1, 2017, and Chinese patent application No. 201711482970.X, filed on Dec. 29, 2017, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 2, 2020, is named 55246-703_831_SL.txt and is 33,233 bytes in size.

BACKGROUND OF THE INVENTION

Viral hepatitis type B (also known as hepatitis type B or hepatitis B) is a class of infectious diseases, which is a serious threat to the world, especially China. At present, interferons and nucleoside analogs are two main kinds of globally recognized drugs for the prevention/treatment of hepatitis B; however, such drugs have various drawbacks (e.g., being prone to development of drug resistance after use or having limited usefulness). For example, interferons are susceptible to cause adverse reactions; and nucleoside analogs have the problems of drug resistance and disease recurrence after drug withdrawal. Therefore, if the gene expression of the virus can be silenced at gene level to block the generation and replication of HBV, thereby fundamentally reducing the virus metabolism and the infection to liver cells, this will undoubtedly be the most ideal means for the treatment of hepatitis B. Small interfering RNA (siRNA) can inhibit or block the expression of any target gene of interest, e.g., a gene triggering a disease such as cancer, in a sequence-specific manner based on the mechanism of RNA interference (RNAi), thereby achieving the purpose of treating diseases.

Stabilized modification of siRNA and its delivery system are two key technologies in the development of small RNA drugs.

SUMMARY OF THE INVENTION

In some embodiments, provided herein is a siRNA conjugate having a structure as shown by Formula (1):

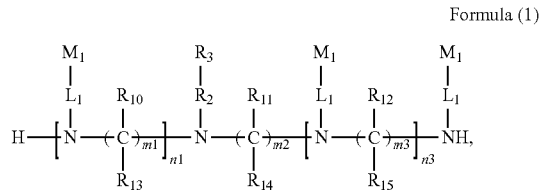

Formula (1)

wherein,
n1 is an integer of 1-3, and n3 is an integer of 0-4;
each of m1, m2, and m3 is independently an integer of 2-10;
each of $R_{10}$, $R_{11}$, $R_{12}$, $R_{13}$, $R_{14}$ and $R_{15}$ is independently H or selected from the group consisting of $C_1$-$C_{10}$ alkyl, $C_1$-$C_{10}$ haloalkyl and $C_1$-$C_{10}$ alkoxy;
$R_3$ is a group having a structure as shown by Formula A59:

(A59)

wherein $E_1$ is OH, SH or $BH_2$; and
Nu is siRNA.

Each nucleotide in the siRNA is independently a modified or unmodified nucleotide. The siRNA comprises a sense strand and an antisense strand, wherein the sense strand comprises a nucleotide sequence 1, and the antisense strand comprises a nucleotide sequence 2; the nucleotide sequence 1 and the nucleotide sequence 2 are at least partly reverse complementary to form a double-stranded region; the nucleotide sequence 1 has the same length and no more than 3 nucleotides different from the nucleotide sequence shown in SEQ ID NO:155; and the nucleotide sequence 2 has the same length and no more than 3 nucleotides different from the nucleotide sequence shown in SEQ ID NO: 156:

```
                            (SEQ ID NO: 155)
5'-CCUUGAGGCAUACUUCAAZ-3';

(SEQ ID NO: 156)
5'-Z'UUGAAGUAUGCCUCAAGG-3';
``` wherein,
Z is A; Z' is U;
the nucleotide sequence 1 comprises nucleotide $Z_A$ at the corresponding site to Z;
the nucleotide sequence 2 comprises nucleotide $Z'_B$ at the corresponding site to Z'; the nucleotide $Z'_B$ is the first nucleotide from 5' terminal of the antisense strand;
$R_2$ is a linear alkylene of 1 to 20 carbon atoms in length, wherein one or more carbon atoms are optionally replaced with any one or more of the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O$C_1$-$C_{10}$ alkyl, —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-

C$_{10}$ alkyl), —SO$_2$NH(phenyl), —NHSO$_2$(C$_1$-C$_{10}$ alkyl), —NHSO$_2$(phenyl), and —NHSO$_2$(C$_1$-C$_{10}$ haloalkyl);

each L$_1$ is independently a linear alkylene of 1 to 70 carbon atoms in length, wherein one or more carbon atoms are optionally replaced with any one or more of the group consisting of: C(O), NH, O, S, CH=N, S(O)$_2$, C$_2$-C$_{10}$ alkeylene, C$_2$-C$_{10}$ alkynylene, C$_6$-C$_{10}$ arylene, C$_3$-C$_{18}$ heterocyclylene, and C$_5$-C$_{10}$ heteroarylene, and wherein L$_1$ is optionally substituted by any one or more of the group consisting of: C$_1$-C$_{10}$ alkyl, C$_6$-C$_{10}$ aryl, C$_5$-C$_{10}$ heteroaryl, C$_1$-C$_{10}$ haloalkyl, —OC$_1$-C$_{10}$ alkyl, —OC$_1$-C$_{10}$ alkylphenyl, —C$_1$-C$_{10}$ alkyl-OH, —OC$_1$-C$_{10}$ haloalkyl, —SC$_1$-C$_{10}$ alkyl, —SC$_1$-C$_{10}$ alkylphenyl, —C$_1$-C$_{10}$ alkyl-SH, —SC$_1$-C$_{10}$ haloalkyl, halo, —OH, —SH, —NH$_2$, —C$_1$-C$_{10}$ alkyl-NH$_2$, —N(C$_1$-C$_{10}$ alkyl)(C$_1$-C$_{10}$ alkyl), —NH(C$_1$-C$_{10}$ alkyl), cyano, nitro, —CO$_2$H, —C(O)OC$_1$-C$_{10}$ alkyl, —CON(C$_1$-C$_{10}$ alkyl)(C$_1$-C$_{10}$ alkyl), —CONH(C$_1$-C$_{10}$ alkyl), —CONH$_2$, —NHC(O)(C$_1$-C$_{10}$ alkyl), —NHC(O)(phenyl), —N(C$_1$-C$_{10}$ alkyl)C(O)(C$_1$-C$_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O)C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH(phenyl), —NHSO$_2$(C$_1$-C$_{10}$ alkyl), —NHSO$_2$(phenyl), and —NHSO$_2$(C$_1$-C$_{10}$ haloalkyl);

〜〜〜 represents a site where a group is attached to the rest of the molecule;

M$_1$ represents a targeting group.

In some embodiments, provided herein is a method for preparing a conjugate, comprising successively linking nucleoside monomers in 3' to 5' direction according to the nucleotide type and sequence of the sense strand and antisense strand of siRNA respectively, under a condition of phosphoramidite solid phase synthesis, wherein the linking of each nucleoside monomer includes a four-step reaction of deprotection, coupling, capping, and oxidation or sulfurization; isolating the sense strand and the antisense strand of siRNA; and annealing; wherein, each nucleotide in the siRNA is independently a modified or unmodified nucleotide; the siRNA comprises a sense strand and an antisense strand, wherein the sense strand comprises a nucleotide sequence 1, and the antisense strand comprises a nucleotide sequence 2; the nucleotide sequence 1 and the nucleotide sequence 2 are at least partly reverse complementary to form a double-stranded region; the nucleotide sequence 1 has the same length and no more than 3 nucleotides different from the nucleotide sequence shown in SEQ ID NO:155; and the nucleotide sequence 2 has the same length and no more than 3 nucleotides different from the nucleotide sequence shown in SEQ ID NO:156:

```
                          (SEQ ID NO: 155)
  5'- CCUUGAGGCAUACUUCAAZ -3';

(SEQ ID NO: 156)
  5'- Z'UUGAAGUAUGCCUCAAGG -3';
``` wherein,

Z is A; Z' is U;

the nucleotide sequence 1 comprises nucleotide Z$_A$ at the corresponding site to Z; the nucleotide sequence 2 comprises nucleotide Z'$_B$ at the corresponding site to Z'; the nucleotide Z'$_B$ is the first nucleotide from 5' terminal of the antisense strand;

Moreover, the method further comprises contacting a compound as shown by Formula (321) with a nucleoside monomer or the nucleotide sequence linked to a solid phase support under a coupling reaction condition in the presence of a coupling reagent, thereby linking the compound as shown by Formula (321) to the nucleotide sequence by coupling reaction. Hereinafter, the compound as shown by Formula (321) is also referred to as conjugating molecule.

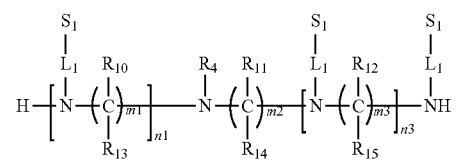

Formula (321)

wherein,

R$_4$ is a moiety capable of binding to the siRNA represented by Nu; in some embodiments, R$_4$ is a moiety capable of binding to the siRNA represented by Nu via a covalent bond; in some embodiments, R$_4$ is a moiety comprising any functional group that may be conjugated to the siRNA represented by Nu via a phosphodiester bond by reaction;

each S$_1$ is independently a group in M$_1$ formed by substituting all active hydroxyl with the group represented by the formula YCOO—, wherein each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl;

the definitions and options of n1, n3, m1, m2, m3, R$_{10}$, R$_{11}$, R$_{12}$, R$_{13}$, R$_{14}$, R$_{15}$, L$_1$, and M$_1$ are respectively as described above.

In some embodiments, provided herein is a siRNA capable of inhibiting the expression of hepatitis B virus (HBV) gene, the siRNA comprising a sense strand and an antisense strand, both of which comprise fluoro modified nucleotides and non-fluoro modified nucleotides; wherein, the sense strand comprises a segment of nucleotide sequence I; the antisense strand comprises a segment of nucleotide sequence II; the nucleotide sequence I and the nucleotide sequence II are at least partly reverse complementary to form a double-stranded region; wherein, the nucleotide sequence I comprises nucleotide sequence A, which has the same length and no more than 3 nucleotides different from the nucleotide sequence shown in SEQ ID NO:155; and the nucleotide sequence II comprises nucleotide sequence B, which has the same length and no more than 3 nucleotides different from the nucleotide sequence shown in SEQ ID NO:156:

```
                          (SEQ ID NO: 155)
  5'-CCUUGAGGCAUACUUCAAZ-3';

(SEQ ID NO: 156)
  5'-Z'UUGAAGUAUGCCUCAAGG-3';
``` wherein,

Z is A; Z' is U;

the nucleotide sequence A comprises nucleotide Z$_A$ at the corresponding site to Z; the nucleotide sequence B comprises nucleotide Z'$_B$ at the corresponding site to Z';

the nucleotide $Z'_B$ is the first nucleotide from 5' terminal of the antisense strand; and the fluoro modified nucleotides are located within the nucleotide sequences A and B; in the direction from 5' terminal to 3' terminal, the nucleotides at positions 7, 8 and 9 of the nucleotide sequence A are fluoro modified nucleotides; and in the direction from 5' terminal to 3' terminal, the nucleotides at positions 2, 6, 14 and 16 of the nucleotide sequence B are fluoro modified nucleotides.

In some embodiments, provided herein is a pharmaceutical composition, comprising the siRNA disclosed herein and a pharmaceutically acceptable carrier.

In some embodiments, provided herein is a siRNA conjugate, which comprises the siRNA disclosed herein and a conjugating group conjugatively linked to the siRNA; the siRNA comprises a sense strand and an antisense strand, both of which comprise fluoro modified nucleotides and non-fluoro modified nucleotides; wherein, the sense strand comprises a segment of nucleotide sequence I; the antisense strand comprises a segment of nucleotide sequence II; the nucleotide sequence I and the nucleotide sequence II are at least partly reverse complementary to form a double-stranded region; wherein, the nucleotide sequence I comprises nucleotide sequence A, which has the same length and no more than 3 nucleotides different from the nucleotide sequence shown in SEQ ID NO: 155; and the nucleotide sequence II comprises nucleotide sequence B, which has the same length and no more than 3 nucleotides different from the nucleotide sequence shown in SEQ ID NO: 156:

```
                                          (SEQ ID NO: 155)
    5'-CCUUGAGGCAUACUUCAAZ-3';

(SEQ ID NO: 156)
    5'-Z'UUGAAGUAUGCCUCAAGG-3';
``` wherein,

Z is A; Z' is U;

the nucleotide sequence A comprises nucleotide $Z_A$ at the corresponding site to Z; the nucleotide sequence B comprises nucleotide $Z'_B$ at the corresponding site to Z'; the nucleotide $Z'_B$ is the first nucleotide from 5' terminal of the antisense strand; and the fluoro modified nucleotides are located within the nucleotide sequences A and B; in the direction from 5' terminal to 3' terminal, the nucleotides at positions 7, 8 and 9 of the nucleotide sequence A are fluoro modified nucleotides; and in the direction from 5' terminal to 3' terminal, the nucleotides at positions 2, 6, 14 and 16 of the nucleotide sequence B are fluoro modified nucleotides.

In some embodiments, provided herein is use of the siRNA, and/or pharmaceutical composition and/or siRNA conjugate of the present disclosure in the manufacture of a medicament for treating and/or preventing pathological conditions or diseases caused by hepatitis B virus (HBV) infection.

In some embodiments, provided herein is a method for treating and/or preventing pathological conditions or diseases caused by hepatitis B virus (HBV) infection, comprising administering an effective amount of the siRNA, and/or pharmaceutical composition and/or siRNA conjugate of the present disclosure to a patient in need thereof.

In some embodiments, provided herein is a method for inhibiting the expression of HBV genes, comprising contacting an effective amount of the modified siRNA, and/or pharmaceutical composition and/or siRNA conjugate of the present disclosure with hepatitis cells infected with HBV.

In some embodiments, provided herein is a kit comprising the siRNA, and/or pharmaceutical composition and/or siRNA conjugate of the present disclosure.

INCORPORATION BY REFERENCE

All publications, patents, and patent applications mentioned in this description are herein incorporated by reference to the same extent as if each individual publication, patent, or patent application was specifically and individually indicated to be incorporated by reference.

DETAILED DESCRIPTION OF THE INVENTION

Figure 1:
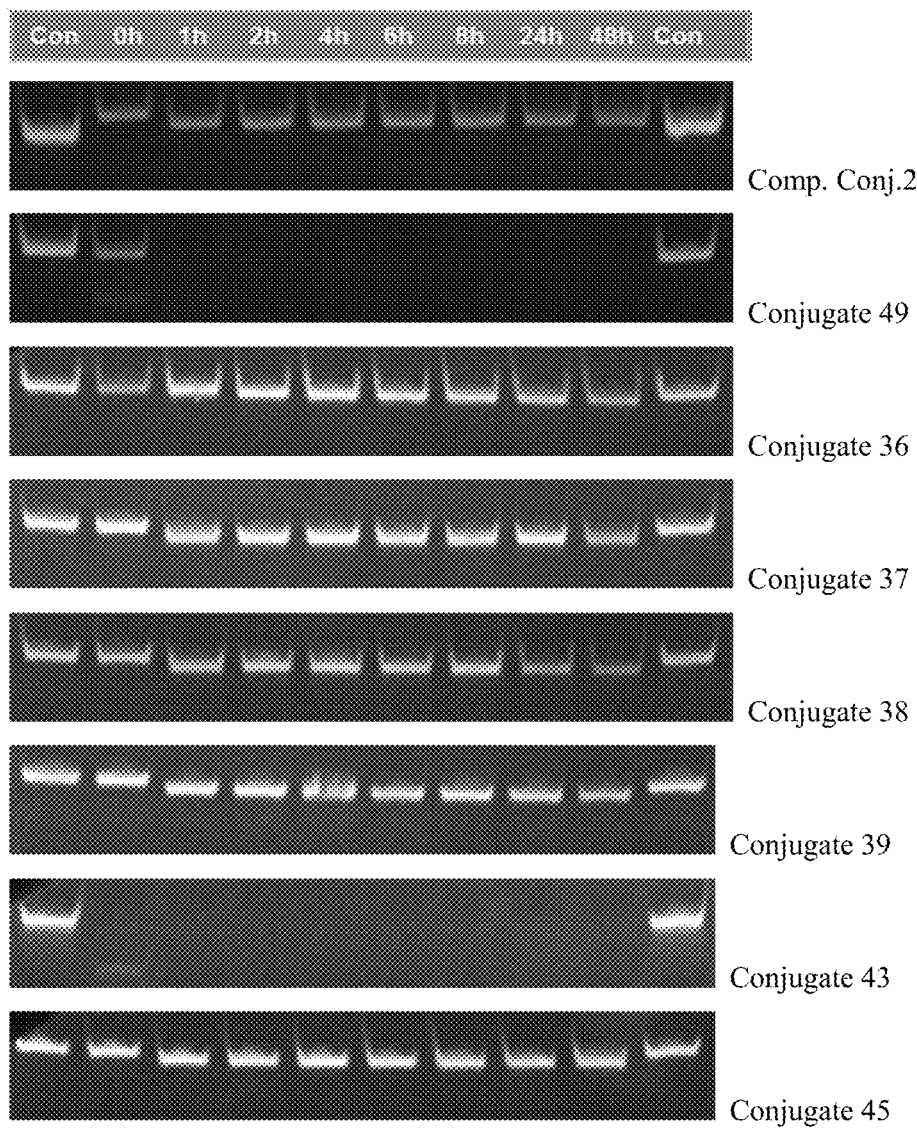
FIG. 1 shows the semiquantitative result of the stability test of the tested siRNA conjugates in the Tritosome in vitro.

The specific embodiments of the present disclosure are described in detail as below. It should be understood that the specific embodiments described herein are only for the purpose of illustration and explanation of the present disclosure and are not intended to limit the present disclosure in any respect.

Definitions

In the context of the present disclosure, HBV gene refers to a gene having a DNA sequence as shown in Genbank Accession No. NC_003977.1.

In the context of the present disclosure, unless otherwise specified, C, G, U, A, and T indicate the base composition of the nucleotides; d indicates that the one nucleotide on the right side of the letter d is a deoxyribonucleotide; letter m indicates that the nucleotide adjacent to the left side of the letter m is a methoxy modified nucleotide; f indicates that the nucleotide adjacent to the left side of the letter f is a fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analog modified nucleotide, especially a vinyl phosphate modified nucleotide (expressed as VP in the Examples below), a 5'-phosphate nucleotide (expressed as P in the Examples below) or a 5'-thiophosphate modified nucleotide (expressed as Ps in the Examples below).

In the context of the present disclosure, a "fluoro modified nucleotide" refers to a nucleotide formed by substituting the 2'-hydroxy of the ribose group of the nucleotide with a fluoro. A "non-fluoro modified nucleotide" refers to a nucleotide formed by substituting the 2'-hydroxy of the ribose group of the nucleotide with a non-fluoro group, or a nucleotide analogue. A "nucleotide analogue" refers to a group that can replace a nucleotide in the nucleic acid, while structurally differs from an adenine ribonucleotide, a guanine ribonucleotide, a cytosine ribonucleotide, a uracil ribonucleotide or thymine deoxyribonucleotide, such as an isonucleotide, a bridged nucleic acid (BNA) nucleotide or an acyclic nucleotide. The methoxy modified nucleotide refers to a nucleotide formed by substituting the 2'-hydroxy of the ribose group with a methoxy group.

In the context of the present disclosure, expressions "complementary" and "reverse complementary" can be interchangeably used, and have a well-known meaning in the art, namely, the bases in one strand are complementarily paired with those in the other strand of a double-stranded nucleic acid molecule. In DNA, a purine base adenine (A) is always paired with a pyrimidine base thymine (T) (or uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines are always paired with cytosines, these two strands are considered as being complementary each other; and the sequence of a strand may be deduced from the sequence of its complementary strand. Correspondingly, a "mispairing" means that in a double-stranded nucleic acid, the bases at corresponding sites are not presented in a manner of being complementarily paired.

In the context of the present disclosure, unless otherwise specified, "basically reverse complementary" means that there are no more than 3 base mispairings between two nucleotide sequences. "Substantially reverse complementary" means that there is no more than 1 base mispairing between two nucleotide sequences. "Completely complementary" means that there is no based mispairing between two nucleotide sequences.

In the context of the present disclosure, when a nucleotide sequence has "nucleotide difference" from another nucleotide sequence, the bases of the nucleotides at the same position therebetween are changed. For example, if a nucleotide base in the second sequence is A and the nucleotide base at the same position in the first sequence is U, C, G or T, these two nucleotide sequences are considered as having a nucleotide difference at this position. In some embodiments, if a nucleotide at a position is replaced with an abasic nucleotide or a nucleotide analogue, it is also considered that there is a nucleotide difference at the position.

In the context of the present disclosure, particularly in the description of the method for preparing the conjugating molecule or the siRNA conjugate of the present disclosure, unless otherwise specified, the "nucleoside monomer" refers to, according to the kind and sequence of the nucleotides in the siRNA or siRNA conjugate to be prepared, "unmodified or modified RNA phosphoramidites used in a solid phase phosphoramidite synthesis" (the RNA phosphoramidites are also called as Nucleoside phosphoramidites elsewhere). Solid phase phosphoramidite synthesis is a well-known method RNA synthesis to those skilled in the art. Nucleoside monomers used in the present disclosure can all be commercially available.

In the context of the present disclosure, unless otherwise stated, "conjugating" refers to two or more chemical moieties each with specific function being linked to each other via a covalent linkage. Correspondingly, a "conjugate" refers to the compound formed by covalent linkage of individual chemical moieties. Further, a "siRNA conjugate" represents a compound formed by covalently attaching siRNA and one or more chemical moieties each with specific functions. In this context, the siRNA conjugate disclosed herein is sometimes abbreviated as "conjugate". The siRNA conjugate should be understood according to the context as the generic term of siRNA conjugates, the first siRNA conjugate or the second siRNA conjugate. In the context of the present disclosure, a "conjugating molecule" should be understood as a specific compound capable of being conjugated to a siRNA via reactions, thus finally forming the siRNA conjugate of the present disclosure.

As used herein, a dash ("-") that is not positioned between two letters or symbols is used to indicate the attachment position of a substituent. For example, —$C_1$-$C_{10}$ alkyl-$NH_2$ is attached through $C_1$-$C_{10}$ alkyl.

As used herein, "optional" or "optionally" means that the subsequently described event or condition may or may not occur, and that the description includes instances wherein the event or condition may or may not occur. For example, "optionally substituted alkyl" encompasses both "alkyl" and "substituted alkyl" as defined below. Those skilled in the art would understand, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain having the indicated number of carbon atoms, usually 1 to 20 carbon atoms, for example 1 to 10 carbon atoms, such as 1 to 8 or 1 to 6 carbon atoms. For example, $C_1$-$C_6$ alkyl encompasses both straight and branched chain alkyl of 1 to 6 carbon atoms. When naming an alkyl residue having a specific number of carbon atoms, all branched and straight chain forms having that number of carbon atoms are intended to be encompassed; thus, for example, "butyl" is meant to include n-butyl, sec-butyl, isobutyl and t-butyl; "propyl" includes n-propyl and isopropyl. Alkylene is a subset of alkyl, referring to the same residues as alkyl, but having two attachment positions.

As used herein, "alkenyl" refers to an unsaturated branched or straight-chain alkyl group having at least one carbon-carbon double bond which is obtained by respectively removing one hydrogen molecule from two adjacent carbon atoms of the parent alkyl. The group may be in either cis or trans configuration of the double bond. Typical alkenyl groups include, but not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl; and the like. In certain embodiments, an alkenyl group has 2 to 20 carbon atoms, and in other embodiments, 2 to 10, 2 to 8, or 2 to 6 carbon atoms. Alkenylene is a subset of alkenyl, referring to the same residues as alkenyl, but having two attachment positions.

As used herein, "alkynyl" refers to an unsaturated branched or straight-chain alkyl group having at least one carbon-carbon triple bond which is obtained by respectively removing two hydrogen molecules from two adjacent carbon atoms of the parent alkyl. Typical alkynyl groups include, but not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has 2 to 20 carbon atoms, and in other embodiments, 2 to 10, 2 to 8, or 2 to 6 carbon atoms. Alkynylene is a subset of alkynyl, referring to the same residues as alkynyl, but having two attachment positions.

As used herein, "alkoxy" refers to an alkyl group of the indicated number of carbon atoms attached through an oxygen bridge, such as, for example, methoxy, ethoxy, propoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have 1 to 10, 1 to 8, 1 to 6, or 1 to 4 carbon atoms attached through oxygen bridge.

As used herein, "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon, including six to eighteen carbon atoms, wherein at least one ring in the ring system is fully unsaturated, i.e., it contains a cyclic, delocalized (4n+2) π-electron system in accordance with the Hückel theory. Aryl groups include, but not limited to, phenyl, fluorenyl, naphthyl and the like. Arylene is a subset of aryl, referring to the same residues as aryl, but having two attachment positions.

As used herein, "cycloalkyl" refers to a non-aromatic carbon ring, usually having 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "halo substituent" or "halo" refers to fluoro, chloro, bromo, and iodo, and the term "halogen" includes fluorine, chlorine, bromine, and iodine.

As used herein, "haloalkyl" refers to alkyl as defined above with the specified number of carbon atoms being substituted with one or more halogen atoms, up to the maximum allowable number of halogen atoms. Examples of haloalkyl include, but not limited to, trifluoromethyl, difluoromethyl, 2-fluoroethyl, and penta-fluoroethyl.

"Heterocyclyl" refers to a stable 3- to 18-membered non-aromatic ring radical that comprises two to twelve carbon atoms and one to six heteroatoms selected from nitrogen, oxygen and sulfur. Unless stated otherwise in the description, heterocyclyl is a monocyclic, bicyclic, tricyclic, or tetracyclic ring system, which may include fused or bridged ring systems. The heteroatoms in the heterocyclyl radical may be optionally oxidized. One or more nitrogen atoms, if present, are optionally quaternized. The heterocyclyl is partially or fully saturated. Heterocyclyl may be linked to the rest of the molecule through any atom of the ring. Examples of such heterocyclyl include, but not limited to, dioxanyl, thienyl[1,3]disulfonyl, decahydroisoquinolyl, imidazolinyl, imidazolidinyl, isothiazolidinyl, isoxazolidinyl, morpholinyl, octahydroindolyl, octahydroisoindolyl, 2-oxapiperazinyl, 2-oxapiperidinyl, 2-oxapyrimidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, trisulfonyl, tetrahydropyranyl, thiomorpholinyl, thiamorpholinyl, 1-oxa-thiomorpholinyl, and 1,1-dioxa-thiomorpholinyl.

"Heteroaryl" refers to a radical derived from a 3- to 18-membered aromatic ring radical that comprises two to seventeen carbon atoms and one to six heteroatoms selected from nitrogen, oxygen and sulfur. As used herein, heteroaryl may be a monocyclic, bicyclic, tricyclic or tetracyclic ring system, wherein at least one ring in the ring system is fully unsaturated, i.e., it contains a cyclic, delocalized (4n+2) π-electron system in accordance with the Hückel theory. Heteroaryl includes fused or bridged ring systems. The heteroatom in the heteroaryl radical is optionally oxidized. One or more nitrogen atoms, if present, are optionally quaternized. The heteroaryl is linked to the rest of the molecule through any atom of the ring. Examples of such heteroaryls include, but not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxazolyl, benzo[b][1,4]oxazolyl, 1,4-benzodioxazolyl, benzonaphthofuranyl, benzodiazolyl, benzodioxaphenyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothienyl, furanyl, furanonyl, furo[3,2-c]pyridinyl, 5,6,7,8,9,10-hexahydrocyclohepta[d]pyrimidinyl, 5,6,7,8,9, 10-hexahydrocycloocta[d]pyridazinyl, 5,6,7,8,9,10-hexahydrocycloocta[d]pyridinyl, isothiazolyl, indazolyl, imidazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinonyl, 1,6-naphthyridinonyl, oxadiazolyl, 2-oxoazepinyl, oxazolyl, oxalyl, 5,6,6a,7,8,9,10,10a-octahydrobenzo[h]quinazolinyl, 1-phenyl-1H-pyrrolyl, phenazinyl, phenothiazinyl, phenoxazinyl, phthalyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta [4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thienyl.

Various hydroxyl protecting groups can be used in the present disclosure. In general, protecting groups render chemical functionalities inert to specific reaction conditions, and can be attached to and removed from such functionalities in a molecule without substantially damaging the remainder of the molecule. Representative hydroxylprotecting groups are disclosed in Beaucage, et al., *Tetrahedron* 1992, 48, 2223-2311, and also in Greene and Wuts, Protective Groups in Organic Synthesis, Chapter 2, 2d ed, John Wiley & Sons, New York, 1991, each of which is hereby incorporated by reference in their entirety. In some embodiments, the protecting group is stable under basic conditions but can be removed under acidic conditions. In some embodiments, non-exclusive examples of hydroxyl protecting groups used herein include dimethoxytrityl (DMT), monomethoxytrityl, 9-phenylxanthen-9-yl (Pixyl), and 9-(p-methoxyphenyl)xanthen-9-yl (Mox). In some embodiments, non-exclusive examples of hydroxyl protecting groups used herein comprise Tr (trityl), MMTr (4-methoxytrityl), DMTr (4,4'-dimethoxytrityl), and TMTr (4,4',4"-trimethoxytrityl).

The term "subject", as used herein, refers to any animal, e.g., mammal or marsupial. Subject of the present disclosure includes, but not limited to, human, non-human primate (e.g., rhesus or other kinds of macaque), mouse, pig, horse, donkey, cow, sheep, rat and any kind of poultry.

As used herein, "treatment" or "treating" or "ameliorating" or "improving" are used interchangeably herein. These terms refer to a method for obtaining advantageous or desired result, including but not limited to, therapeutic benefit. "Therapeutic benefit" means eradication or improvement of potential disorder to be treated. Also, therapeutic benefit is achieved by eradicating or ameliorating one or more of physiological symptoms associated with the potential disorder such that an improvement is observed in the patient, notwithstanding that the patient may still be afflicted with the potential disorder.

As used herein, "prevention" and "preventing" are used interchangeably. These terms refer to a method for obtaining advantageous or desired result, including but not limited to, prophylactic benefit. For obtaining "prophylactic benefit", the conjugate or composition may be administered to the patient at risk of developing a particular disease, or to the patient reporting one or more physiological symptoms of the disease, even though the diagnosis of this disease may not have been made.

Modified siRNA

The siRNA of the present disclosure comprises nucleotides as basic structural units. It is well-known to those skilled in the art that the nucleotide comprises a phosphate group, a ribose group and a base. Detailed illustrations relating to such groups are omitted herein.

CN102140458B has disclosed a siRNA that specifically inhibits HBV gene and studied various chemical modification strategies of the siRNA. This study found that different modification strategies have completely different effects on the parameters of the siRNA, such as stability, biological activity and cytotoxicity. In this study, seven effective modification manners were proved. Comparing with unmodified siRNA, the siRNA obtained by one of the seven modification manners showed increased stability in blood, while maintaining substantially equal inhibitory activity as that of the unmodified siRNA.

Provided herein is a modified siRNA capable of inhibiting the expression of HBV gene, which comprises a sense strand and an antisense strand, each nucleotide in the siRNA being a modified nucleotide, wherein, the sense strand and antisense strand both comprise fluoro modified nucleotides and non-fluoro modified nucleotides; the sense strand comprises nucleotide sequence I; the antisense strand comprises nucleotide sequence II; the nucleotide sequence I and the nucleotide sequence II are at least partly reverse complementary to form a double-stranded region; wherein, the nucleotide sequence I comprises nucleotide sequence A, which has the same length and no more than 3 nucleotides different from the nucleotide sequence shown in SEQ ID NO: 155; and the nucleotide sequence II comprises nucleotide sequence B, which has the same length and no more than 3 nucleotides different from the nucleotide sequence shown in SEQ ID NO:156:

```
                                    (SEQ ID NO: 155)
5'-CCUUGAGGCAUACUUCAAZ-3';

(SEQ ID NO: 156)
5'-Z'UUGAAGUAUGCCUCAAGG-3';
``` wherein,

Z is A; Z' is U;

the nucleotide sequence A comprises nucleotide $Z_A$ at the corresponding site to Z; the nucleotide sequence B comprises nucleotide $Z'_B$ at the corresponding site to Z'; the nucleotide $Z'_B$ is the first nucleotide from 5' terminal of the antisense strand; the fluoro modified nucleotides are located within the nucleotide sequences A and B; in the direction from 5' terminal to 3' terminal, the nucleotides at positions 7, 8 and 9 of the nucleotide sequence A are fluoro modified nucleotides; and in the direction from 5' terminal to 3' terminal, the nucleotides at positions 2, 6, 14 and 16 of the nucleotide sequence B are fluoro modified nucleotides. In some embodiments, no more than 5 fluoro modified nucleotides are present in the nucleotide sequence A; and no more than 7 fluoro modified nucleotides are present in the nucleotide sequence B.

In this context, the term "corresponding site" means being at the same site in the nucleotide sequence by counting from the same terminal of the nucleotide sequence. For example, the first nucleotide at the 3' terminal of the nucleotide sequence A is a nucleotide at the corresponding site to the first nucleotide at the 3' terminal of SEQ ID NO: 155.

In some embodiments, the sense strand is exclusively composed of nucleotide sequence I, and the antisense strand is exclusively composed of nucleotide sequence II.

In some embodiments, the nucleotide sequence A has no more than 1 nucleotide different from the nucleotide sequence shown in SEQ ID NO:155; and/or the nucleotide sequence B has no more than 1 nucleotide different from the nucleotide sequence shown in SEQ ID NO:156.

In some embodiments, the nucleotide difference between the nucleotide sequence B and the nucleotide sequence shown in SEQ ID NO:156 includes a difference at the site of $Z'_B$, where $Z'_B$ is selected from A, C or G. In some embodiments, the nucleotide difference is a difference at the site of $Z'_B$, where $Z'_B$ is selected from A, C or G. In some embodiments, $Z_A$ is a nucleotide complementary to $Z'_B$. These nucleotide differences will not significantly reduce the ability of the siRNAs to inhibit the target gene, and such siRNAs comprising nucleotide differences are also within the scope of the present disclosure.

In some embodiments, the nucleotide sequence A is basically reverse complementary, substantially reverse complementary, or completely reverse complementary to the nucleotide sequence B. "basically reverse complementary" refers to no more than 3 base mispairings in two nucleotide sequences. "Substantially reverse complementary" refers to no more than 1 base mispairings in two nucleotide sequences. "Completely reverse complementary" refers to no mispairing in two nucleotide sequences.

In some embodiments, the nucleotide sequence A is a nucleotide sequence shown in SEQ ID NO: 1; and the nucleotide sequence B is a nucleotide sequence shown in SEQ ID NO: 2:

```
                                      (SEQ ID NO: 1)
5'-CCUUGAGGCAUACUUCAAZ_a-3';

(SEQ ID NO: 2)
5'-Z'_bUUGAAGUAUGCCUCAAGG-3';
``` wherein, the $Z'_B$ is the first nucleotide from 5' terminal of the antisense strand; $Z_A$ is selected from A, U, G or C; and $Z'_B$ is a nucleotide complementary to $Z_A$; and in the direction from 5' terminal to 3' terminal, the nucleotides at positions 7, 8 and 9 of the nucleotide sequence A are fluoro modified nucleotides; and in the direction from 5' terminal to 3' terminal, the nucleotides at positions 2, 6, 14 and 16 of the nucleotide sequence B are fluoro modified nucleotides.

In some embodiments, the siRNA comprises a sense strand and an antisense strand; wherein the sense strand comprises a segment of nucleotide sequence I, and the antisense strand comprises a segment of nucleotide sequence II; the nucleotide sequence I and the nucleotide sequence II are reverse complementary to form a double-stranded region; the nucleotide sequence I comprises a nucleotide sequence shown in SEQ ID NO:1; and the nucleotide sequence II comprises a nucleotide sequence shown in SEQ ID NO:2:

```
                                      (SEQ ID NO: 1)
5'-CCUUGAGGCAUACUUCAAZ_A-3';

(SEQ ID NO: 2)
5'-Z'_BUUGAAGUAUGCCUCAAGG-3';
``` wherein, the $Z'_B$ is the first nucleotide from 5' terminal of the antisense strand; $Z_A$ is selected from A, U, G or C; and $Z'_B$ is a nucleotide complementary to $Z_A$; in some embodiments, $Z_A$ is A; and $Z'_B$ is U; and in the direction from 5' terminal to 3' terminal, the nucleotides at positions 7, 8 and 9 of SEQ ID NO: 1 in the sense strand of the siRNA are fluoro modified nucleotides, and the nucleotides at the rest of positions in the sense strand of the siRNA are non-fluoro modified nucleotides; and in the direction from 5' terminal to 3' terminal, the nucleotides at positions 2, 6, 14 and 16 of SEQ ID NO: 2 in the antisense strand of the siRNA are fluoro modified nucleotides, and the nucleotides at the rest of positions in the antisense strand of the siRNA are non-fluoro modified nucleotides.

The sense strand and antisense strand have the same or different lengths. The sense strand has a length of 19-23 nucleotides, and the antisense strand has a length of 20-26 nucleotides. As such, the length ratio of the sense strand to the antisense strand in the siRNA of the present disclosure may be 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25 or 23/26. In some embodiments, the length ratio of the sense strand to the antisense strand in the siRNA of the present disclosure is 19/21, 21/23 or 23/25.

According to one embodiment of the present disclosure, the sense strand and antisense strand have the same length. The nucleotide sequence I further comprises a nucleotide sequence III; and the nucleotide sequence II further comprises a nucleotide sequence IV. The nucleotide sequence III and the nucleotide sequence IV each independently have a length of 1-4 nucleotides; the nucleotide sequence III is linked to the 5' terminal of nucleotide sequence A; the nucleotide sequence IV is linked to the 3' terminal of nucleotide sequence B; and the nucleotide sequence III and the nucleotide sequence IV have the same length.

The nucleotide sequence III may be complementary or not complementary to the nucleotide sequence IV. In order to enhance the stability of siRNA, in some embodiments, the nucleotide sequence III is at least partly complementary to the nucleotide sequence IV; in some embodiments, the nucleotide sequence III is complementary to more than 80% or 90% of the bases in the nucleotide sequence IV; in some embodiments, the nucleotide sequence III is substantially reverse complementary or completely reverse complementary to the nucleotide sequence IV; the "substantially reverse complementary" refers to no more than 1 base mispairing in two nucleotide sequences; "completely reverse complementary" refers to no mispairing in two nucleotide sequences; and in some embodiments, the nucleotide sequence III is completely reverse complementary to the nucleotide sequence IV. As such, the sense strand and antisense strand of the siRNA have the same length, and the length ratio thereof is 20/20, 21/21, 22/22, or 23/23. In some embodiments, the length ratio of the sense strand to the antisense strand in the siRNA is 21/21 or 23/23.

In some embodiments, the nucleotide sequence III and the nucleotide sequence IV both have a length of 1 nucleotide. The base of the nucleotide sequence III is A, and the base of the nucleotide sequence IV is U; in this case, the length ratio of the sense strand to the antisense strand is 20/20; alternatively, the nucleotide sequence III and the nucleotide sequence IV both have a length of 2 nucleotides; in the direction from 5' terminal to 3' terminal, the base composition of the nucleotide sequence III is GA, and the base composition of the nucleotide sequence IV is UC; in this case, the length ratio of the sense strand to the antisense strand is 21/21; alternatively, the nucleotide sequence III and the nucleotide sequence IV both have a length of 3 nucleotides; in the direction from 5' terminal to 3' terminal, the base composition of the nucleotide sequence III is CGA, and the base composition of the nucleotide sequence IV is UCG; in this case, the length ratio of the sense strand to the antisense strand is 22/22; alternatively, the nucleotide sequence III and the nucleotide sequence IV both have a length of 4 nucleotides; in the direction from 5' terminal to 3' terminal, the base composition of the nucleotide sequence III is CCGA, and the base composition of the nucleotide sequence IV is UCGG; in this case, the length ratio of the sense strand to the antisense strand is 23/23. In some embodiments, the nucleotide sequence III and the nucleotide sequence IV both have a length of 2 nucleotides; in the direction from 5' terminal to 3' terminal, the base composition of the nucleotide sequence III is GA, and the base composition of the nucleotide sequence IV is UC; in this case, the length ratio of the sense strand to the antisense strand is 21/21.

In some embodiments, the nucleotide sequence III has the same length and is completely reverse complementary to the nucleotide sequence IV. Thus, if the base of the nucleotide sequence III is provided, the base of the nucleotide sequence IV is also determined.

In some embodiments, the sense strand and antisense strand have different lengths. The nucleotide sequence II further comprises a nucleotide sequence V, which has a length of 1-3 nucleotides and is linked to 3' terminal of the antisense strand, thereby constituting a 3' overhang of the antisense strand. As such, the length ratio of the sense strand to the antisense strand in the siRNA of the present disclosure may be 19/20, 19/21, 19/22, 20/21, 20/22, 20/23, 21/22, 21/23, 21/24, 22/23, 22/24, 22/25, 23/24, 23/25, or 23/26. In some embodiments, the nucleotide sequence V has a length of 2 nucleotides. As such, the length ratio of the sense strand to the antisense strand in the siRNA of the present disclosure may be 19/21, 21/23 or 23/25.

Each nucleotide in the nucleotide sequence V may be any nucleotide. In some embodiments, the nucleotide sequence V is 2 continuous thymidine deoxyribonucleotides (TT) or 2 continuous uridine ribonucleotides (UU); in some embodiments, the nucleotide sequence V is complementary to the nucleotides at the corresponding sites of the target mRNA.

In some embodiments, the sense strand of the siRNA comprises the nucleotide sequence shown in SEQ ID NO:1, and the antisense strand of the siRNA comprises the nucleotide sequence shown in SEQ ID NO:3:

```
                                       (SEQ ID NO: 1)
5'-CCUUGAGGCAUACUUCAAZ_A-3';

(SEQ ID NO: 3)
5'-Z'_BUUGAAGUAUGCCUCAAGGUU-3';
``` alternatively, the sense strand of the siRNA comprises the nucleotide sequence shown in SEQ ID NO:1, and the antisense strand of the siRNA comprises the nucleotide sequence shown in SEQ ID NO:4:

```
                                       (SEQ ID NO: 1)
5'-CCUUGAGGCAUACUUCAAZ_A-3';

(SEQ ID NO: 4)
5'-Z'_BUUGAAGUAUGCCUCAAGGUC-3';
``` wherein, the nucleotide $Z'_B$ is the first nucleotide from 5' terminal of the antisense strand; $Z_A$ is selected from A, U, G or C; and $Z'_B$ is a nucleotide complementary to $Z_A$.

According to some embodiments of the present disclosure, the siRNA disclosed herein is siHBa1 or siHBa2:

```
siHBa1
Sense strand:
                                       (SEQ ID NO: 5)
5'-CCUUGAGGCAUACUUCAAA-3', Antisense strand:
                                       (SEQ ID NO: 6)
5'-UUUGAAGUAUGCCUCAAGGUU-3', siHBa2
Sense strand:
                                       (SEQ ID NO: 7)
5'-GACCUUGAGGCAUACUUCAAA-3', Antisense strand:
                                       (SEQ ID NO: 8)
5'-UUUGAAGUAUGCCUCAAGGUCGG-3'.
```

As described above, all the nucleotides in the siRNA of the present disclosure are modified nucleotides. Such modifications on the nucleotides would not cause significant decrease or loss of the function of the siRNA conjugate of the present disclosure to inhibit the expression of HBV genes. For example, the modified nucleotides disclosed by J. K. Watts, G. F. Deleavey and M. J. Damha, Chemically Modified siRNA: tools and applications. Drug Discov Today, 2008.13(19-20): p. 842-55 may be selected.

In some embodiments, in the direction from 5' terminal to 3' terminal, the nucleotides at positions 7, 8 and 9 or 5, 7, 8 and 9 of the nucleotide sequence A in the sense strand are fluoro modified nucleotides, and the nucleotides at the rest of positions in the sense strand are non-fluoro modified nucleotides; and the nucleotides at positions 2, 6, 14 and 16 or 2, 6, 8, 9, 14 and 16 of the nucleotide sequence B in the antisense strand are fluoro modified nucleotides, and the nucleotides at the rest of positions in the antisense strand are non-fluoro modified nucleotides.

In the context of the present disclosure, the fluoro modified nucleotide refers to a nucleotide formed by substituting the 2'-hydroxy of the ribose group thereof with a fluoro group, which has a structure as shown by Formula (107). The non-fluoro modified nucleotide refers to a nucleotide formed by substituting the 2'-hydroxy of the ribose group with a non-fluoro group, or a nucleotide analogue. In some embodiments, each non-fluoro modified nucleotide is independently selected from the group consisting of a nucleotide formed by substituting the 2'-hydroxy of the ribose group thereof with a non-fluoro group, and a nucleotide analogue.

A nucleotide formed by substituting the 2'-hydroxy of the ribose group with a non-fluoro group is well-known to those skilled in the art, and can be selected from one of 2'-alkoxy modified nucleotide, 2'-substituted alkoxy modified nucleotide, 2'-alkyl modified nucleotide, 2'-substituted alkyl modified nucleotide, 2'-amino modified nucleotide, 2'-substituted amino modified nucleotide and 2'-deoxy nucleotide.

In some embodiments, the 2'-alkoxy modified nucleotide is a methoxy modified nucleotide (2'-OMe), as shown by Formula (108). In some embodiments, the 2'-substituted alkoxy modified nucleotide is, for example, a 2'-O-methoxyethoxy modified nucleotide (2'-MOE) as shown by Formula (109). In some embodiments, the 2'-amino modified nucleotide (2'-NH$_2$) is as shown by Formula (110). In some embodiments, the 2'-deoxy nucleotide (DNA) is as shown by Formula (111).

nucleotide. In some embodiments, the BNA may be LNA, ENA and cET BNA, which are as shown by Formula (112), (113) and (114), respectively.

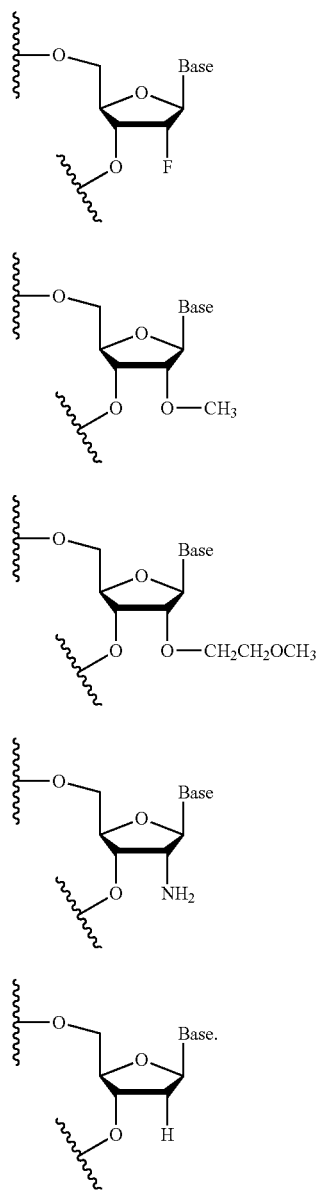

Formula (107)

Formula (108)

Formula (109)

Formula (110)

Formula (111)

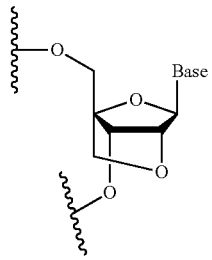

Formula (112)

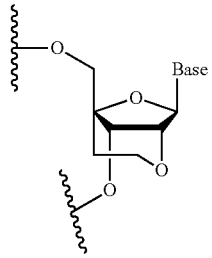

Formula (113)

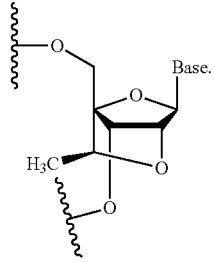

Formula (114)

An acyclic nucleotide is a nucleotide in which the ribose ring is opened. In some embodiments, the acyclic nucleotide may be an unlocked nucleic acid (UNA) nucleotide and a glycerol nucleic acid (GNA) nucleotide, which are as shown by Formula (115) and (116), respectively.

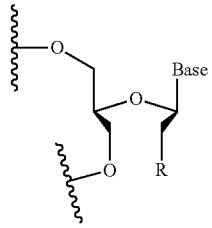

Formula (115)

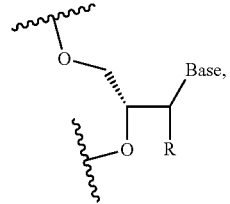

Formula (116)

A "nucleotide analogue" refers to a group that can replace a nucleotide in the nucleic acid, while structurally differs from an adenine ribonucleotide, a guanine ribonucleotide, a cytosine ribonucleotide, a uracil ribonucleotide or thymine deoxyribonucleotide. In some embodiments, the nucleotide analogue may be an isonucleotide, a bridged nucleic acid (BNA) nucleotide or an acyclic nucleotide.

A BNA is a nucleotide that is constrained or is not accessible. BNA can contain a 5-, 6-membered or even a 7-membered ring bridged structure with a "fixed" C3'-endo sugar puckering. The bridge is typically incorporated at the 2'- and 4'-position of the ribose to afford a 2', 4'-BNA wherein R is H, OH or alkoxy (O-alkyl).

An isonucleotide is a nucleotide in which the position of the base on the ribose ring alters. In some embodiments, the isonucleotide may be a compound in which the base is transposed from position-1' to position-2' or -3' on the ribose ring, as shown by Formula (117) or (118) respectively.

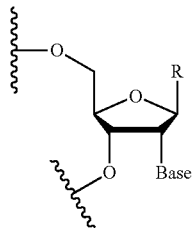

Formula (117)

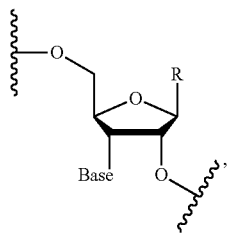

Formula (118)

wherein "Base" represents a base, such as A, U, G, C or T; R is H, OH, F or a non-fluoro group described above.

In some embodiments, a nucleotide analogue is selected from the group consisting of an isonucleotide, LNA, ENA, cET, UNA, and GNA. In some embodiments, each non-fluoro modified nucleotide is a methoxy modified nucleotide. In the context of the present disclosure, the methoxy modified nucleotide refers to a nucleotide formed by substituting the 2'-hydroxy of the ribose group with a methoxy group.

In the context of the present disclosure, a "fluoro modified nucleotide", a "2'-fluoro modified nucleotide", a "nucleotide in which 2'-hydroxy of the ribose group is substituted with fluoro" and a "2'-fluororibosyl" have the same meaning, referring to the nucleotide formed by substituting the 2'-hydroxy of the ribose group with fluoro, having a structure as shown by Formula (107). A "methoxy modified nucleotide", a "2'-methoxy modified nucleotide", a "nucleotide in which 2'-hydroxy of a ribose group is substituted with methoxy" and a "2'-methoxyribosyl" have the same meaning, referring to the nucleotide that 2'-hydroxy of the ribose group in the nucleotide is substituted with methoxy, having a structure as shown by Formula (108).

In some embodiments, the fluoro modified nucleotides are located within the nucleotide sequences A and B; no more than 5 fluoro modified nucleotides are present in the nucleotide sequence A, and in the direction from 5' terminal to 3' terminal, the nucleotides at positions 7, 8 and 9 in the nucleotide sequence A are fluoro modified nucleotides; no more than 7 fluoro modified nucleotides are present in the nucleotide sequence B, and the nucleotides at positions 2, 6, 14 and 16 in the nucleotide sequence B are fluoro modified nucleotides.

In some embodiments, in the direction from 5' terminal to 3' terminal, the nucleotides at positions 7, 8 and 9 or 5, 7, 8 and 9 of the nucleotide sequence A in the sense strand are fluoro modified nucleotides, and the nucleotides at the rest of positions in the sense strand are non-fluoro modified nucleotides; and in the direction from 5' terminal to 3' terminal, the nucleotides at positions 2, 6, 14 and 16 or 2, 6, 8, 9, 14 and 16 of the nucleotide sequence B in the antisense strand are fluoro modified nucleotides, and the nucleotides at the rest of positions in the antisense strand are non-fluoro modified nucleotides.

In some embodiments, the siRNA of the present disclosure is a siRNA with the following modifications: in the direction from 5' terminal to 3' terminal, the nucleotides at positions 7, 8 and 9 or 5, 7, 8 and 9 of the nucleotide sequence A in the sense strand of the siRNA are fluoro modified nucleotides, and the nucleotides at the rest of positions in the sense strand of the siRNA are methoxy modified nucleotides; and the nucleotides at positions 2, 6, 14 and 16 or 2, 6, 8, 9, 14 and 16 of the nucleotide sequence B in the antisense strand are fluoro modified nucleotides, and the nucleotides at the rest of positions in the antisense strand of the siRNA are methoxy modified nucleotides.

In some embodiments, the siRNA of the present disclosure is a siRNA with the following modifications: in the direction from 5' terminal to 3' terminal, the nucleotides at positions 5, 7, 8 and 9 of the nucleotide sequence A in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 8, 9, 14 and 16 of the nucleotide sequence B in the antisense strand of the siRNA are fluoro modified nucleotides, and the nucleotides at the rest of positions in the antisense strand of the siRNA are methoxy modified nucleotides;

alternatively, in the direction from 5' terminal to 3' terminal, the nucleotides at positions 5, 7, 8 and 9 of the nucleotide sequence A in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 14 and 16 of the nucleotide sequence B in the antisense strand of the siRNA are fluoro modified nucleotides, and the nucleotides at the rest of positions in the antisense strand of the siRNA are methoxy modified nucleotides;

alternatively, in the direction from 5' terminal to 3' terminal, the nucleotides at positions 7, 8 and 9 of the nucleotide sequence A in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 14 and 16 of the nucleotide sequence B in the antisense strand of the siRNA are fluoro modified nucleotides, and the nucleotides at the rest of positions in the antisense strand of the siRNA are methoxy modified nucleotides.

In other words, the ribose groups in phosphate-ribose backbone of the siRNA respectively have the following modifying groups: in the direction from 5' terminal to 3' terminal, the ribose groups of the nucleotides at positions 5, 7, 8 and 9 of the nucleotide sequence A in the sense strand of the siRNA are 2'-fluororibosyl, and the ribose groups of the nucleotides at the rest of positions in the sense strand of the siRNA are 2'-methoxyribosyl; and, in the direction from 5' terminal to 3' terminal, the ribose groups of the nucleotides at positions 2, 6, 8, 9, 14 and 16 of the nucleotide sequence B in the antisense strand of the siRNA are 2'-fluororibosyl, and the ribose groups of the nucleotides at the rest of positions in the antisense strand of the siRNA are 2'-methoxyribosyl;

alternatively, in the direction from 5' terminal to 3' terminal, the ribose groups of the nucleotides at positions 5, 7, 8 and 9 of the nucleotide sequence A in the sense strand of the siRNA are 2'-fluororibosyl, and the ribose groups of the nucleotides at the rest of positions in the sense strand of the siRNA are 2'-methoxyribosyl; and in the direction from 5' terminal to 3' terminal, the ribose groups of the nucleotides at positions 2, 6, 14 and 16 of the nucleotide sequence B in the antisense strand of the siRNA are 2'-fluororibosyl, and the ribose groups of the nucleotides at the rest of positions in the antisense strand of the siRNA are 2'-methoxyribosyl;

alternatively, in the direction from 5' terminal to 3' terminal, the ribose groups of the nucleotides at positions 7, 8 and 9 of the nucleotide sequence A in the sense strand of the siRNA are 2'-fluororibosyl, and the ribose groups of the nucleotides at the rest of positions in the sense strand of the siRNA are 2'-methoxyribosyl; and, in the direction from 5' terminal to 3' terminal, the ribose groups of the nucleotides at positions 2, 6, 14 and 16 of the nucleotide sequence B in the antisense strand of the siRNA are 2'-fluororibosyl, and the ribose groups of the nucleotides at the rest of positions in the antisense strand of the siRNA are 2'-methoxyribosyl.

In some embodiments, the siRNA provided herein is siHBa1M1, siHBa1M2, siHBa2M1 or siHBa2M2:

siHBa1M1
Sense strand:
(SEQ ID NO: 9)
5'-CmCmUmUmGmAmGfGfCfAmUmAmCmUmUmCmAmAmAm-3', Antisense strand:
(SEQ ID NO: 10)
5'-UmUfUmGmAmAfGmUmAmUmGmCmCmUfCmAfAmGmGmUmUm-3', siHBa1M2
Sense strand:
(SEQ ID NO: 11)
5'-CmCmUmUmGfAmGfGfCfAmUmAmCmUmUmCmAmAmAm-3', Antisense strand:
(SEQ ID NO: 12)
5'-UmUfUmGmAmAfGmUfAfUmGmCmCmUfCmAfAmGmGmUmUm-3', siHBa2M1
Sense strand:
(SEQ ID NO: 13)
5'-GmAmCmCmUmUmGmAmGfGfCfAmUmAmCmUmUmCmAmAmAm-3', Antisense strand:
(SEQ ID NO: 14)
5'-UmUfUmGmAmAfGmUmAmUmGmCmCmUfCmAfAmGmGmUmCmGm-3', siHBa2M2
Sense strand:
(SEQ ID NO: 15)
5'-GmAmCmCmUmUmGfAmGfGfCfAmUmAmCmUmUmCmAmAmAm-3', Antisense strand:
(SEQ ID NO: 16)
5'-UmUfUmGmAmAfGmUfAfUmGmCmCmUfCmAfAmGmGmUmCmGm-3', wherein, C, G, U, and A indicate the base composition of the nucleotides; m indicates that the nucleotide adjacent to the left side of the letter m is a 2'-methoxy modified nucleotide; f indicates that the nucleotide adjacent to the left side of the letter f is a 2'-fluoro modified nucleotide. The siRNAs with said modifications can not only be afforded at lower costs, but also allow the ribonucleases in the blood to be less liable to cleaving the nucleic acid so as to increase the stability of the nucleic acid and enable the nucleic acid to have stronger resistance against nuclease hydrolysis.

In some embodiments, at least a portion of the phosphate groups in phosphate-ribose backbone of at least one single strand in the sense strand and the antisense strand of the siRNA provided by the present disclosure are phosphate groups with modified groups. In some embodiments, the phosphate groups with modified groups are phosphorothioate groups formed by substituting at least one oxygen atom in a phosphodiester bond in the phosphate groups with a sulfur atom; and in some embodiments the phosphate groups with modified groups are phosphorothioate groups having a structure as shown by Formula (101):

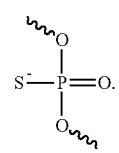

Formula (101)

This modification stabilizes the double-stranded structure of the siRNA, thereby maintaining high specificity and high affinity for base pairing.

In some embodiments, in the siRNA provided by the present disclosure, a phosphorothioate linkage exists in at least one of the following positions: the position between the first and the second nucleotides at either terminal of the sense or antisense strand, the position between the second and the third nucleotides at either terminal of the sense or antisense strand, or any combination thereof. In some embodiments, a phosphorothioate linkage exists at all the above positions except for 5' terminal of the sense strand. In some embodiments, a phosphorothioate linkage exists at all the above positions except for 3' terminal of the sense strand. In some embodiments, a phosphorothioate linkage exists in at least one of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

In some embodiments, the siRNA provided by the present disclosure is siHBa1M1S, siHBa1M2S, siHBa2M1S, or siHBa2M2S:

```
siHBa1M1S
Sense strand:
                                   (SEQ ID NO: 17)
5'-CmsCmsUmUmGmAmGfGfCfAmUmAmCmUmUmCmAmAmAm-3', Antisense strand:
                                   (SEQ ID NO: 18)
5'-UmsUfsUmGmAmAfGmUmAmUmGmCmCmUfCmAfAmGmGmsUmsU m-3', siHBa1M2S
Sense strand:
                                   (SEQ ID NO: 19)
5'-CmsCmsUmUmGfAjnGfGfCfAmUmAmCmUmUmCmAmAmAm-3', Antisense strand:
                                   (SEQ ID NO: 20)
5'-UmsUfsUmGmAmAfGmUfAfUmGmCmCmUfCmAfAmGmGmsUmsU m-3', siHBa2M1S
Sense strand:
                                   (SEQ ID NO: 21)
5'-GmsAmsCmCmUmUmGmAmGfGfCfAmUmAmCmUmUmCmAmAmA m-3', Antisense strand:
                                   (SEQ ID NO: 22)
5'-UmsUfsUmGmAmAfGmUmAmUmGmCmCmUfCmAfAmGmGmUmCms GmsGm-3', siHBa2M2S
Sense strand:
                                   (SEQ ID NO: 23)
5'-GmsAmsCmCmUmUmGfAmGfGfCfAmUmAmCmUmUmCmAmAmA m-3', Antisense strand:
                                   (SEQ ID NO: 24)
5'-UmsUfsUmGmAmAfGmUfAfUmGmCmCmUfCmAfAmGmGmUmCms GmsGm-3',
``` wherein, C, G, U, and A indicate the base composition of the nucleotides; m indicates that the nucleotide adjacent to the left side of the letter m is a methoxy modified nucleotide; f indicates that the nucleotide adjacent to the left side of the letter f is a fluoro modified nucleotide; s indicates the phosphorothioate linkage between the two nucleotides adjacent to both sides of the letter.

In some embodiments, the 5'-terminal nucleotide in the antisense strand of the siRNA is a 5'-phosphate nucleotide or a 5'-phosphate analogue modified nucleotide.

Common types of the 5'-phosphate nucleotides or 5'-phosphate analogue modified nucleotides are well known to those skilled in the art; for example, the 5'-phosphate nucleotides may have the following structure:

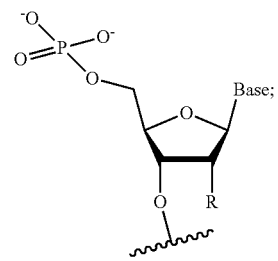

Formula (102)

for another example, as disclosed in Anastasia Khvorova and Jonathan K. Watts, The chemical evolution of oligonucleotide therapies of clinical utility. Nature Biotechnology, 2017, 35(3): 238-48, the following four 5'-phosphate analogue modified nucleotides:

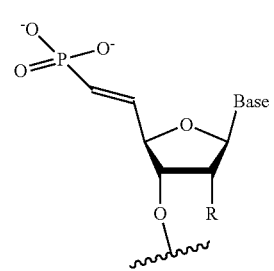

Formula (103)

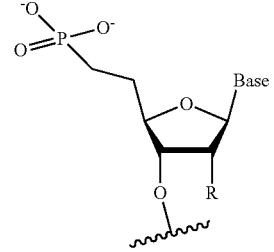

Formula (104)

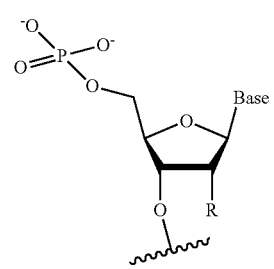

Formula (105)

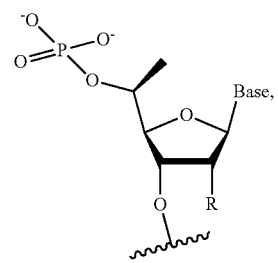

Formula (106)

wherein,
R represents a group selected from the group consisting of H, OH, methoxy and F;
"Base" represents a base selected from A, U, C, G, or T.

In some embodiments, the 5'-phosphate nucleotide is a nucleotide with 5'-phosphate modification as shown by Formula (102); the 5'-phosphate analogue modified nucleotide is a nucleotide with 5'-(E)-vinylphosphonat (E-VP) modification as shown by Formula (103) or a phosphorothioate modified nucleotide as shown by Formula (105).

In some embodiments, the siRNA provided by the present disclosure is any one selected from the group consisting of siHBa1M1P1, siHBa1M2P1, siHBa2M1P1, siHBa2M2P1, siHBa1M1SP1, siHBa1M2SP1, siHBa2M1SP1, and siHBa2M2SP1:

siHBa1M1P1
Sense strand:
(SEQ ID NO: 25)
5'-CmCmUmUmGmAmGfGfCfAmUmAmCmUmUmCmAmAmAm-3', Antisense strand:
(SEQ ID NO: 26)
5'-P1-UmUfUmGmAmAfGmUmAmUmGmCmCmUfCmAfAmGmGmUmUm-3', siHBa1M2P1
Sense strand:
(SEQ ID NO: 27)
5'-CmCmUmUmGfAmGfGfCfAmUmAmCmUmUmCmAmAmAm-3', Antisense strand:
(SEQ ID NO: 28)
5'-P1-UmUfUmGmAmAfGmUfAfUmGmCmCmUfCmAfAmGmGmUmUm-3', siHBa2M1P1
Sense strand:
(SEQ ID NO: 29)
5'-GmAmCmCmUmUmGmAmGfGfCfAmUmAmCmUmUmCmAmAmAm-3', Antisense strand:
(SEQ ID NO: 30)
5'-P1-UmUfUmGmAmAfGmAmUmGmCmCmUfCmAfAmGmGmUmCmGmGm-3', siHBa2M2P1
Sense strand:
(SEQ ID NO: 31)
5'-GmAmCmCmUmUmGfAmGfGfCfAmUmAmCmUmUmCmAmAmAm-3', Antisense strand:
(SEQ ID NO: 32)
5'-P1-UmUfUmGmAmAfGmUfAfUmGmCmCmUfCmAfAmGmGmUmCmGmGm-3', siHBa1M1SP1
Sense strand:,
(SEQ ID NO: 33)
5'-CmsCmsUmUmGmAmGfGfCfAmUmAmCmUmUmCmAmAmAm-3'

Antisense strand:
(SEQ ID NO: 34)
5'-P1-UmsUfsUmGmAmAfGmUmAmUmGmCmCmUfCmAfAmGmGms UmsUm-3', siHBa1M2SP1
Sense strand:
(SEQ ID NO: 35)
5'-CmsCmsUmUmGfAjnGfGfCfAmUmAmCmUmUmCmAmAmAm-3', Antisense strand:
(SEQ ID NO: 36)
5'-P1-UmsUfsUmGmAmAfGmUfAfUmGmCmCmUfCmAfAmGmGms UmsUm-3', siHBa2M1SP1
Sense strand:
(SEQ ID NO: 37)
5'-GmsAmsCmCmUmUmGmAmGfGfCfAmUmAmCmUmUmCmAmAmAm-3', Antisense strand:
(SEQ ID NO: 38)
5'-P1-UmsUfsUmGmAmAfGmUmAmUmGmCmCmUfCmAfAmGmGm UmCmsGmsGm-3', siHBa2M2SP1
Sense strand:
(SEQ ID NO: 39)
5'-GmsAmsCmCmUmUmGfAmGfGfCfAmUmAmCmUmUmCmAmAmAm-3', Antisense strand:
(SEQ ID NO: 40)
5'-P1-UmsUfsUmGmAmAfGmUfAfUmGmCmCmUfCmAfAmGmGmUm CmsGmsGm-3', wherein, C, G, U, and A indicate the base composition of the nucleotides; m indicates that the nucleotide adjacent to the left side of the letter m is a 2'-methoxy modified nucleotide; f indicates that the nucleotide adjacent to the left side of the letter f is a 2'-fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analog modified nucleotide.

The inventors of the present disclosure have surprisingly found that the siRNAs provided herein have significantly enhanced plasma and lysosomal stability, reduced off-target effects, while maintaining higher gene-suppressing activity.

The siRNAs provided herein can be obtained by conventional methods for preparing siRNAs in the art, e.g., solid phase synthesis and liquid phase synthesis methods. Therein, commercial customization services have already been available for solid phase synthesis. Modified nucleotides can be introduced into the siRNAs of the present disclosure by using a nucleotide monomer having a corresponding modification, wherein the methods for preparing a nucleotide monomer having a corresponding modification and the methods for introducing a modified nucleotide into a siRNA are also well-known to those skilled in the art.

Pharmaceutical Composition

Provided herein is a pharmaceutical composition, comprising the siRNA described above as an active ingredient, and a pharmaceutically acceptable carrier.

The pharmaceutically acceptable carrier may be a carrier conventionally used in the field of siRNA administration, for example, but not limited to, one or more of magnetic nanoparticles (such as $Fe_3O_4$ and $Fe_2O_3$-based nanoparticle), carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly(D&L-lactic/glycolic acid) copolymer (PLGA), poly(2-aminoethyl ethylene phosphate) (PPEEA), poly(2-dimethylaminoethyl methacrylate) (PDMAEMA), and derivatives thereof.

According to some embodiments, in the pharmaceutical composition of the present invention, there are no special requirements for the contents of the siRNA and the pharmaceutically acceptable carrier. In some embodiments, the weight ratio of the siRNA to the pharmaceutically acceptable carrier is 1:(1-500), and in some embodiments 1:(1-50).

In some embodiments, the pharmaceutical composition of the present invention may also contain other pharmaceutically acceptable excipients, which may be one or more of various conventional formulations or compounds in the art. For example, said other pharmaceutically acceptable excipients may comprise at least one of a pH buffer, a protective agent and an osmotic pressure regulator.

The pH buffer may be a tris(hydroxymethyl) aminomethane hydrochloride buffer solution with a pH of 7.5-8.5, and/or a phosphate buffer solution with a pH of 5.5-8.5, preferably a phosphate buffer solution with a pH of 5.5-8.5.

The protective agent may be at least one of inositol, sorbitol, sucrose, trehalose, mannose, maltose, lactose, and glucose. The content of the protective agent may be from 0.01 wt % to 30 wt % on the basis of the total weight of the pharmaceutical composition.

The osmotic pressure regulator may be sodium chloride and/or potassium chloride. The content of the osmotic pressure regulator allows the osmotic pressure of the pharmaceutical composition to be 200-700 milliosmol/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation upon administration. The liquid formulation may be administered by, but not limited to, subcutaneous, intramuscular or intravenous injection routes, and also may be administered to, but not limited to, lung by spray, or other organs (such as liver) via lung by spray. In some embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a PEGylated lipid. Therein, the organic amine, the helper lipid and the PEGylated lipid may be respectively selected from one or more of the amine-containing transfection compounds or the pharmaceutically acceptable salts or derivatives thereof, the helper lipids and the PEGylated lipids as described in CN103380113A, which is incorporated herein by reference in its entirety.

In some embodiments, the organic amine may be a compound as shown by Formula (201) as described in CN103380113A or a pharmaceutically acceptable salt thereof:

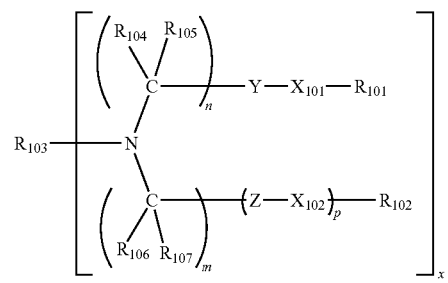

Formula (201)

wherein:
$X_{101}$ and $X_{102}$ independently of one another are selected from O, S, N-A and C-A, wherein A is hydrogen or a $C_1$-$C_{20}$ hydrocarbon chain;
Y and Z independently of one another are selected from C=O, C=S, S=O, CH—OH and $SO_2$;
$R_{101}$, $R_{102}$, $R_{103}$, $R_{104}$, $R_{105}$, $R_{106}$ and $R_{107}$ independently of one another are selected from hydrogen; a cyclic or an acyclic, substituted or unsubstituted, branched or linear aliphatic group; a cyclic or an acyclic, substituted or unsubstituted, branched or linear heteroaliphatic group; a substituted or unsubstituted, branched or linear acyl group; a substituted or unsubstituted, branched or linear aryl group, or a substituted or unsubstituted, branched or linear heteroaryl group;
x is an integer of 1-10;
n is an integer of 1-3, m is an integer of 0-20, p is 0 or 1; wherein if m and p are both 0, then
$R_{102}$ is hydrogen, and
if at least one of n or m has is 2, then $R_{103}$ and nitrogen in Formula (201) form a structure as shown by Formula (202) or (203):

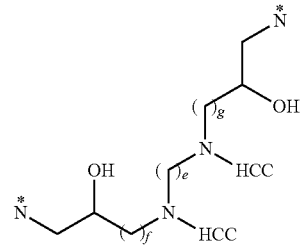

Formula (202)

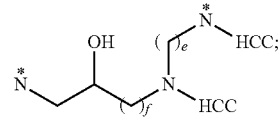

Formula (203)

wherein g, e and f independently of one another are an integer of 1-6, "HCC" represents a hydrocarbon chain, and each *N represents a nitrogen atom shown in Formula (201).

In some embodiments, $R_{103}$ is a polyamine. In other embodiments, $R_{103}$ is a ketal. In some embodiments, $R_{101}$ and $R_{102}$ in the Formula (201) independently of one another are any of substituted or unsubstituted, branched or linear alkyl or alkenyl groups which have 3-20 carbon atoms (such as 8-18 carbon atoms) and 0-4 double bonds (such as 0-2 double bonds).

In some embodiments, if n and m independently of one another are 1-3, $R_{103}$ represents any of the following Formulae (204)-(213):

Formula (204)
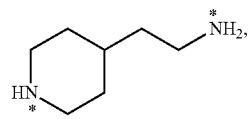

Formula (205)
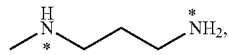

Formula (206)
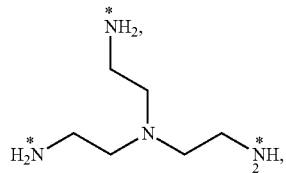

Formula (207)
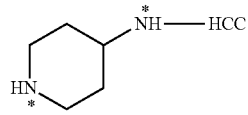

Formula (208)
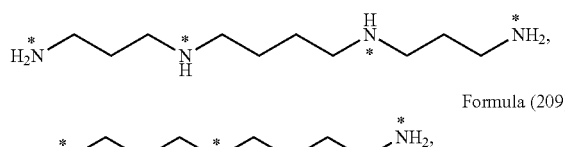

Formula (209)
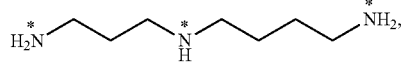

Formula (210)
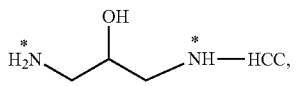

Formula (211)
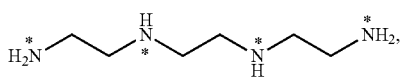

Formula (212)

and

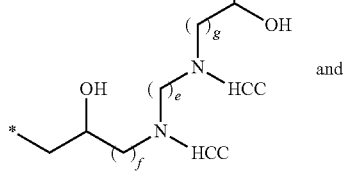

Formula (213)
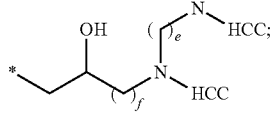

wherein, each of g, e and f is independently an integer of between 1 and 6; each "HCC" represents a hydrocarbon chain, and each * represents a potential attachment point of $R_{103}$ to the nitrogen atom in Formula (201), where each H at any * position can be replaced to realize the attachment to the nitrogen atom in Formula (201).

The compound as shown by (201) may be prepared as described in CN103380113A.

In some embodiments, the organic amine may be an organic amine as shown by Formula (214) and/or an organic amine as shown by Formula (215):

Formula (214)
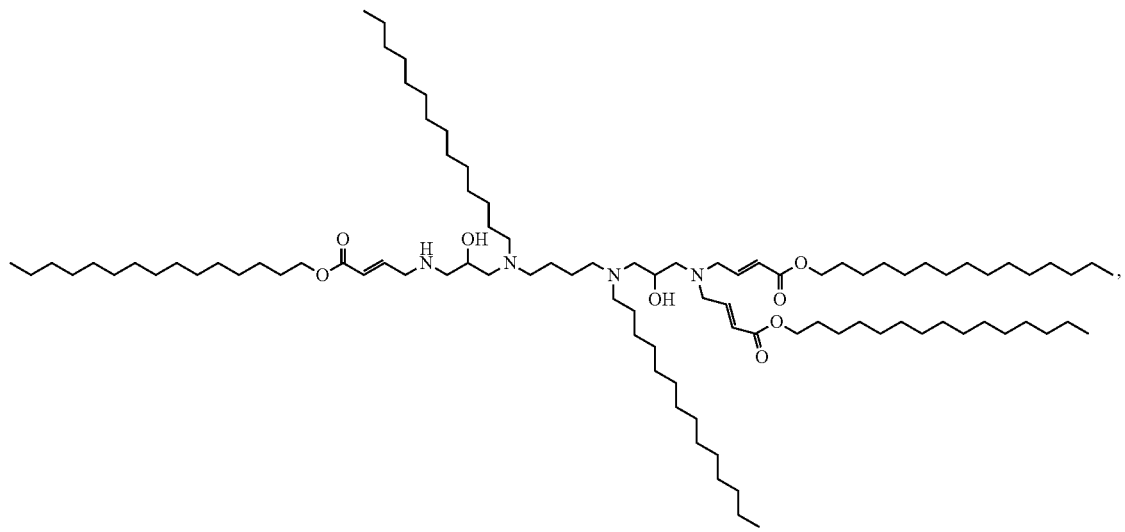

Formula (215)

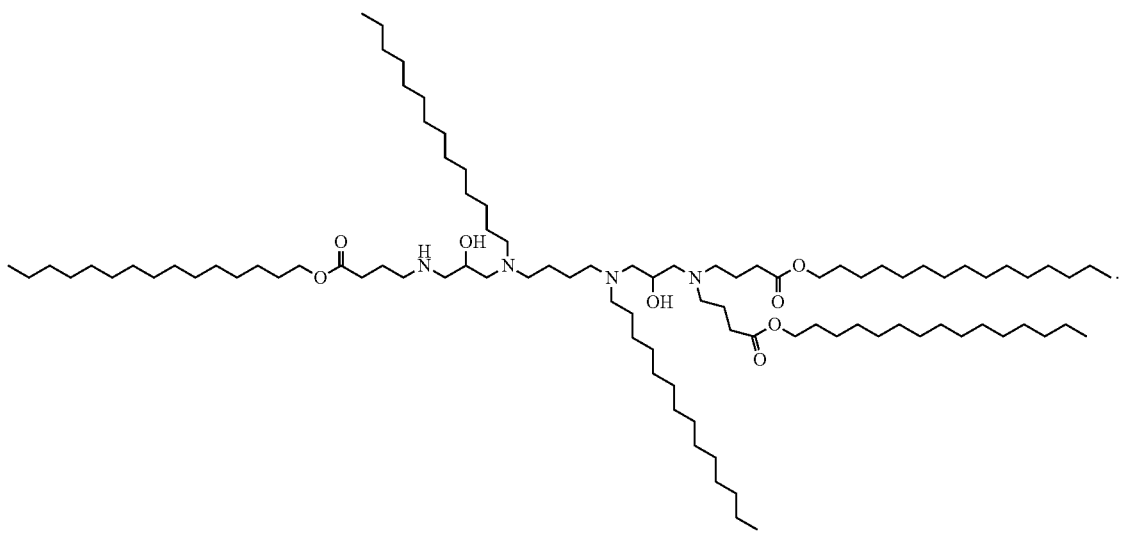

The helper lipid is cholesterol, cholesterol analogue and/or cholesterol derivatives.

The PEGylated lipid is 1,2-dipalmitoyl-sn-glycero-3-phosphatidylethanolamine-N-[methoxy(polyethylene glycol)]-2000.

In some embodiments, the molar ratio among the organic amine, the helper lipid, and the PEGylated lipid in the pharmaceutical composition is (19.7-80):(19.7-80):(0.3-50); for example, the molar ratio may be (50-70):(20-40):(3-20).

In some embodiments, the pharmaceutical compositions formed by the siRNA of the present disclosure and the above amine-containing transfection agents have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm, for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection agents, the ratio (weight/weight ratio) of the siRNA to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10. For example, the ratio of the siRNA of the present disclosure to total lipids is about 1:5, 1:6, 1:7, 1:8, 1:9, 1:10, 1:11, 1:12, 1:13, 1:14, 1:15, 1:16, 1:17 or 1:18 by weight.

In some embodiments, the pharmaceutical composition may be marketed with each component being separate, and used in the form of a liquid formulation. In some embodiments, the pharmaceutical composition formed by the siRNA of the present disclosure and the above pharmaceutically acceptable carrier may be prepared by various known processes, except replacing the existing double-stranded oligonucleotide with the siRNA of the present disclosure. In some embodiments, the pharmaceutical composition may be prepared according to the following process.

The organic amines, helper lipids and PEGylated lipids are suspended in alcohol at a molar ratio as described above and mixed homogeneously to yield a lipid solution; the alcohol is used in an amount such that the resultant lipid solution is present at a total mass concentration of 2 to 25 mg/mL (e.g., 8 to 18 mg/mL). The alcohol is a pharmaceutically acceptable alcohol, such as an alcohol that is in liquid form at about room temperature, for example, one or more of ethanol, propylene glycol, benzyl alcohol, glycerol, PEG 200, PEG 300, PEG 400, preferably ethanol.

The siRNA of the present disclosure is dissolved in a buffered salt solution to produce an aqueous solution of the siRNA. The buffered salt solution has a concentration of 0.05 to 0.5 M, such as 0.1 to 0.2 M. The pH of the buffered salt solution is adjusted to 4.0 to 5.5, such as 5.0 to 5.2. The buffered salt solution is used in an amount such that the siRNA is present at a concentration of less than 0.6 mg/ml, such as 0.2 to 0.4 mg/mL. The buffered salt may be one or more selected from the group consisting of soluble acetate and soluble citrate, such as sodium acetate and/or potassium acetate.

The lipid solution and the aqueous solution of the siRNA are mixed. The product obtained after mixing is incubated at a temperature of 40 to 60° C. for at least 2 minutes (e.g., 5 to 30 minutes) to produce an incubated lipid formulation. The volume ratio of the lipid solution to the aqueous solution of the siRNA is 1:(2-5), such as 1:4.

The incubated lipid formulation is concentrated or diluted, purified to remove impurities, and then sterilized to obtain the pharmaceutical composition of the present disclosure, which has physicochemical parameters as follows: a pH of 6.5 to 8, an encapsulation percentage of more than 80%, a particle size of 40 to 200 nm, a polydispersity index of less than 0.30, and an osmotic pressure of 250 to 400 mOsm/kg; for example, the physicochemical parameters may be as follows: a pH of 7.2 to 7.6, an encapsulation percentage of more than 90%, a particle size of 60 to 100 nm, a polydispersity index of less than 0.20, and an osmotic pressure of 300 to 400 mOsm/kg.

Therein, the concentration or dilution step may be performed before, after or simultaneously with the step of impurity removal. The method for removing impurities may be any of various existing methods, for example, ultrafiltration using 100 kDa hollow fiber column, PBS at pH 7.4 as ultrafiltration exchange solution and the tangential flow system. The method for sterilization may be any of various existing methods, such as filtration sterilization on a 0.22 μm filter.

A First siRNA Conjugate

In one aspect, provided herein is a first siRNA conjugate, which comprises the siRNA described above and a conjugating group attached thereto.

The conjugation group typically comprises at least one pharmaceutically acceptable targeting group and an optional linker. Moreover, the siRNA, the linker and the targeting group are linked in succession. In some embodiments, there are 1 to 6 targeting groups. In some embodiments, there are 2 to 4 targeting groups. The siRNA molecule may be non-covalently or covalently conjugated to the conjugating group, for example, the siRNA molecule is covalently conjugated to the conjugating group. The conjugating site between the siRNA and the conjugating group can be at 3'-terminal or 5'-terminal of the sense strand of the siRNA, or at 5'-terminal of the antisense strand, or within the internal sequence of the siRNA. In some embodiments, the conjugating site between the siRNA and the conjugating group is at 3'-terminal of the sense strand of the siRNA.

In some embodiments, the conjugation group is linked to the phosphate group, the 2'-hydroxy group or the base of a nucleotide. In some embodiments, the conjugation group may be linked to a 3'-hydroxy group when the nucleotides are linked via a 2'-5'-phosphodiester bond. When the conjugation group is linked to a terminal of the siRNA, the conjugation group is typically linked to a phosphate group of a nucleotide; when the conjugation group is linked to an internal sequence of the siRNA, the conjugation group is typically linked to a ribose ring or a base. For specific linking modes, reference may be made to: Muthiah Manoharan et. al. siRNA conjugates carrying sequentially assembled trivalent N-acetylgalactosamine linked through nucleosides elicit robust gene silencing in vivo in hepatocytes. ACS Chemical biology, 2015,10(5):1181-7.

In some embodiments, the siRNA and the conjugation group can be linked by an acid-labile or reducible chemical bond, and these chemical bonds can be degraded under the acidic environment of cell endosomes, thereby rendering the siRNA to be in free state. For non-degradable conjugation modes, the conjugation group can be linked to the sense strand of the siRNA, thereby minimizing the effect of conjugation on the activity of the double-stranded oligonucleotide.

In some embodiments, the pharmaceutically acceptable targeting group may be a conventional ligand in the field of double-stranded oligonucleotide administration, for example, the various ligands as described in WO2009082607A2, which is incorporated herein by reference in its entirety.

In some embodiments, the pharmaceutically acceptable targeting group may be selected from one or more of the ligands formed by the following targeting molecules or derivatives thereof: lipophilic molecules, such as cholesterol, bile acids, vitamins (such as vitamin E), lipid molecules of different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein), glucagon, neurotransmitters (such as adrenaline), growth factors, transferrin and the like.

In some embodiments, each ligand is independently a ligand capable of binding to a cell surface receptor. In some embodiments, at least one ligand is a ligand capable of binding to a hepatocyte surface receptor. In some embodiments, at least one ligand is a ligand capable of binding to a mammalian hepatocyte surface receptor. In some embodiments, at least one ligand is a ligand capable of binding to a human hepatocyte surface receptor. In some embodiments, at least one ligand is a ligand capable of binding to a hepatic surface asialoglycoprotein receptor (ASGP-R). The types of these ligands are well-known to those skilled in the art and they typically serve the function of binding to specific receptors on the surface of the target cell, thereby mediating delivery of the double-stranded oligonucleotide linked to the ligand into the target cell.

In some embodiments, the pharmaceutically acceptable targeting group may be any ligand that binds to asialoglycoprotein receptors (ASGP-R) on the surface of mammalian hepatocytes. In one embodiment, each ligand is independently selected from asialoglycoprotein, such as asialoorosomucoid (ASOR) or asialofetuin (ASF). In some embodiments, the ligand is a saccharide or its derivatives.

In some embodiments, at least one ligand is a saccharide. In some embodiments, each ligand is a saccharide. In some embodiments, at least one ligand is a monosaccharide, polysaccharide, modified monosaccharide, modified polysaccharide, or derivatives thereof. In some embodiments, at least one ligand may be a monosaccharide, disaccharide or trisaccharide. In some embodiments, at least one ligand is a modified saccharide. In some embodiments, each ligand is a modified saccharide. In some embodiments, each ligand is independently selected from the group consisting of polysaccharides, modified polysaccharides, monosaccharides modified monosaccharides, polysaccharide derivatives and monosaccharide derivatives. In some embodiments, each ligand or at least one ligand may be independently selected from the group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid.

In some embodiments, each ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O-[(R)-1-carboxyethyl]-2-deoxy-α-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-α-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, L-4-thioribose. Other ligand selections may be found, for example, in the disclosure of CN105378082A, which is incorporated herein by reference in its entirety.

In some embodiments, the pharmaceutically acceptable targeting group in the first siRNA conjugate may be galactose or N-acetylgalactosamine, wherein the galactose or N-acetylgalactosamine molecules can be mono-, bi-, tri-, or tetra-valent. It should be understood that the terms mono-, bi-, tri-, or tetra-valent described herein respectively mean that the molar ratio of the double-stranded oligonucleotide molecule to the galactose or N-acetylgalactosamine molecule in the oligonucleotide conjugate is 1:1, 1:2, 1:3 or 1:4, wherein the oligonucleotide conjugate is formed from the double-stranded oligonucleotide molecule and the conjugation group containing galactose or N-acetylgalactosamine molecule as the targeting group. In some embodiments, the pharmaceutically acceptable targeting group is N-acetylgalactosamine. In some embodiments, when the double-stranded oligonucleotide of the present disclosure is conjugated to a conjugation group comprising N-acetylgalactosamine, the N-acetylgalactosamine molecule is trivalent or tetravalent. In some embodiments, when the double-stranded oligonucleotide of the present disclosure is conjugated to a conjugation group containing N-acetylgalactosamine, the N-acetylgalactosamine molecule is trivalent.

The targeting group can be linked to the siRNA molecule via an appropriate linker, and the appropriate linker can be selected by the skilled in the art according to the specific type of the targeting group. The types of these linkers and targeting groups and the linking modes with the siRNA may be found in the disclosure of WO2015006740A2, which is incorporated herein by reference in its entirety.

In some embodiments, when the targeting group is N-acetylgalactosamine, a suitable linker may be of the following structure as shown by Formula (301):

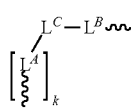

Formula (301)

wherein,
wherein k is an integer of 1-3;

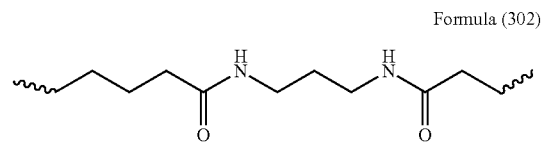

Formula (302)

$L^B$ is an N-acylpyrrolidine-comprising chain moiety that has a structure as shown by Formula (303), the chain moiety having a carbonyl group at one terminal and being linked to the $L^C$ moiety through an amide bond, and having an oxy-group at the other terminal and being linked to the siRNA via a phosphoester bond:

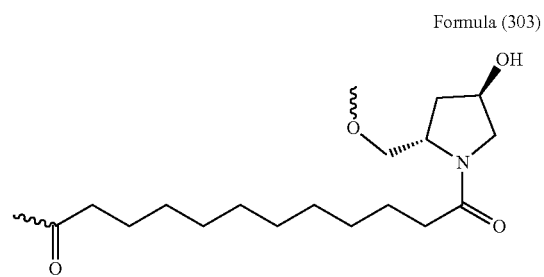

Formula (303)

$L^C$ is a bivalent to tetravalent linking group based on hydroxymethyl aminomethane, dihydroxymethyl aminomethane or trihydroxymethyl aminomethane, $L^C$ being linked to each of the $L^A$ moieties through an ether bond via oxygen atom, and being linked to $L^B$ moiety through amide bond via nitrogen atom.

In some embodiments, when n=3 and $L^C$ is a tetravalent linking group based on trihydroxymethyl aminomethane, the first siRNA conjugate formed by linking N-acetylgalactosamine molecules with a siRNA molecule via -$(L^A)_3$-trihydroxymethyl aminomethane-$L^B$- as a linker has a structure as shown by Formula (304):

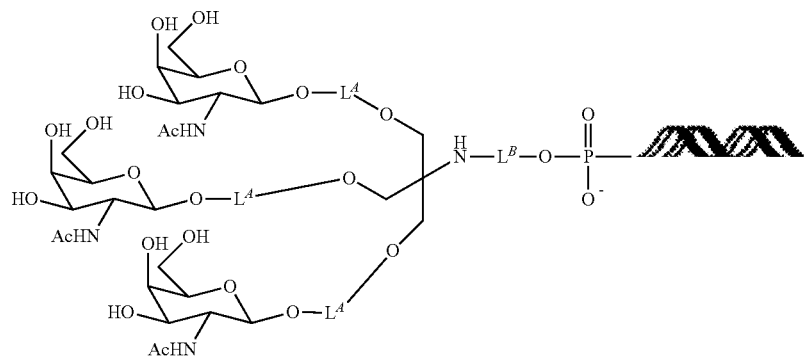

Formula (304)

$L^A$ is a amide bond-comprising chain moiety that has a structure as shown by Formula (302), each $L^A$ being respectively linked to the targeting group and the $L^C$ moiety through ether bond at its two terminals:

wherein the double helix structure represents a siRNA.

Likewise, the conjugating site between the siRNA and the conjugating group can be at the 3'-terminal or 5'-terminal of the sense strand of the siRNA, or at the 5'-terminal of the antisense strand, or within the internal sequence of the siRNA.

In some embodiments, the 3'-terminal of the sense strand of the siRNA of the present disclosure is covalently conjugated to three N-acetylgalactosamine (GalNAc) molecules via a linker -(L$^A$)$_3$-trihydroxymethyl aminomethane-L$^B$- to obtain a first siRNA conjugate in which the molar ratio of the siRNA molecule to the GalNAc molecule is 1:3 (hereinafter referred to as (GalNAc)$_3$-siRNA), and this conjugate has a structure as shown by Formula (305):

wherein,
l is an integer of between 0 and 3;
\* represents a site linked to the targeting group via an ether bond on the linker; and
\# represents a site linked to the siRNA via a phosphoester bond on the linker.

In some specific embodiments, when l=2, the siRNA conjugate has a structure as shown by Formula (307):

Formula (305)

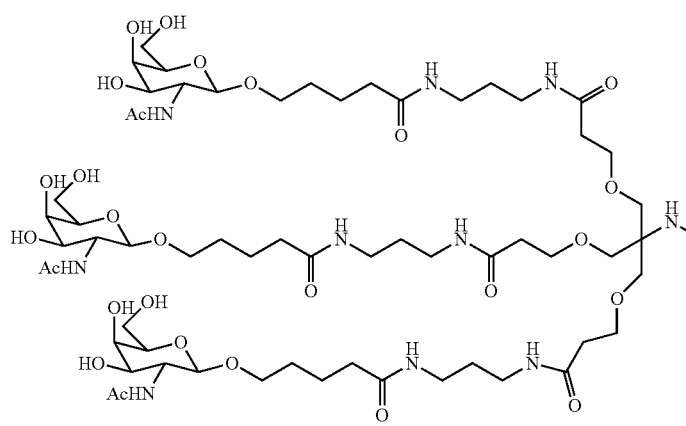

wherein the double helix structure represents the siRNA; and the linker is linked to the 3'-terminal of the sense strand of the siRNA.

In some embodiments, when the targeting group is N-acetylgalactosamine, a suitable linker may have a structure as shown by Formula (306):

Formula (306)

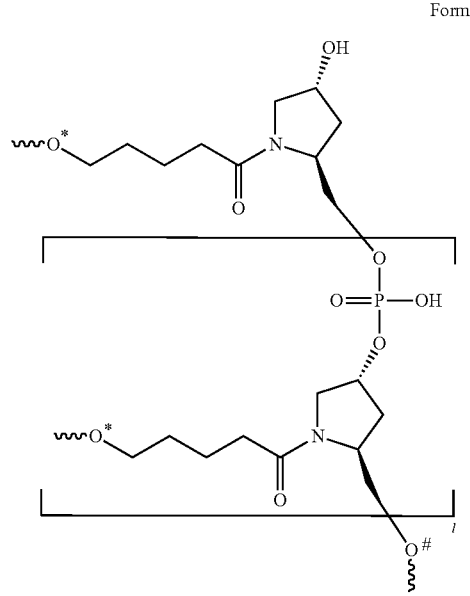

Formula (307)

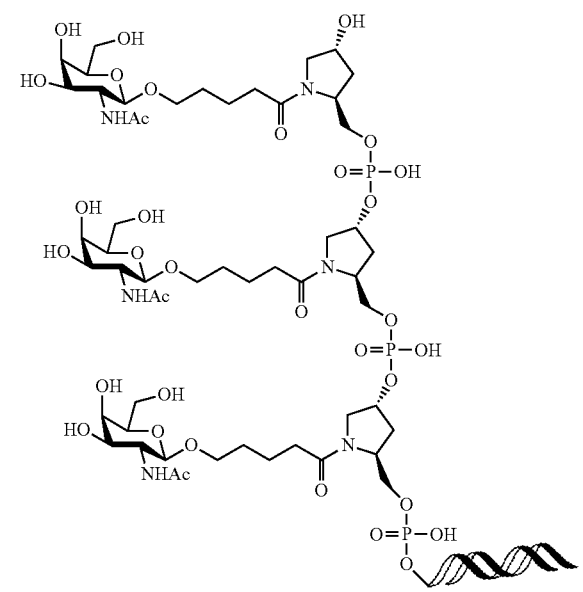

wherein, the double helix structure denotes the siRNA; and the linker is linked to the 3'-terminal of the sense strand of the siRNA.

The above conjugates can be synthesized according to the method described in detail in the prior art. For example, WO2015006740 A2 described in detail the preparation of various conjugates. The first siRNA conjugate of the present disclosure may be obtained by methods well known to those skilled in the art. As another example, WO2014025805A1 described the preparation method of the conjugate having the structure as shown by Formula (305). As a further example, Rajeev er al., Chem Bio Chem 2015, 16, 903-908, described the preparation method of the conjugate having the structure as shown by Formula (307).

A Second siRNA Conjugate

In some embodiments, provided herein is a second siRNA conjugate, which has a structure as shown by Formula (1):

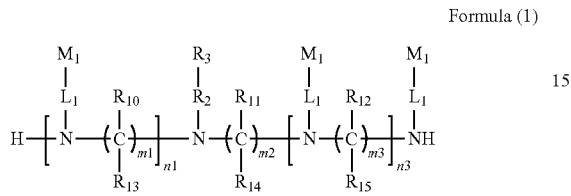

Formula (1)

wherein, n1 is an integer of 1-3, and n3 is an integer of 0-4;

each of m1, m2, and m3 is independently an integer of 2-10;

each of $R_{10}$, $R_{11}$, $R_{12}$, $R_{13}$, $R_{14}$ and $R_{15}$ is independently H, or selected from the group consisting of $C_1$-$C_{10}$ alkyl, $C_1$-$C_{10}$ haloalkyl, and $C_1$-$C_{10}$ alkoxy; $R_3$ is a group having a structure as shown by Formula (A59):

Formula (A59)

wherein, $E_1$ is OH, SH or $BH_2$;

Nu is a siRNA;

each nucleotide in the siRNA represented by Nu is independently a modified or unmodified nucleotide. The siRNA represented by Nu comprises a sense strand and an antisense strand, wherein the sense strand comprises a nucleotide sequence 1, and the antisense strand comprises a nucleotide sequence 2; the nucleotide sequence 1 and the nucleotide sequence 2 are at least partly reverse complementary to form a double-stranded region; the nucleotide sequence 1 has the same length and no more than 3 nucleotides different from the nucleotide sequence shown in SEQ ID NO:155; and the nucleotide sequence 2 has the same length and no more than 3 nucleotides different from the nucleotide sequence shown in SEQ ID NO: 156:

```
                                          (SEQ ID NO: 155)
5'-CCUUGAGGCAUACUUCAAZ-3';

(SEQ ID NO: 156)
5'-Z'UUGAAGUAUGCCUCAAGG-3';
``` wherein,

Z is A; Z' is U;

the nucleotide sequence 1 comprises nucleotide $Z_A$ at the corresponding site to Z; the nucleotide sequence 2 comprises nucleotide $Z'_B$ at the corresponding site to Z'; the nucleotide $Z'_B$ is the first nucleotide at 5' terminal of the antisense strand;

$R_2$ is a linear alkylene of 1 to 20 carbon atoms in length, wherein one or more carbon atoms are optionally replaced with one or more groups selected from the group consisting of: C(O), NH, O, S, CH=N, $S(O)_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —$N(C_1$-$C_{10}$ alkyl)($C_1$-$C_{10}$ alkyl), —NH ($C_1$-$C_{10}$ alkyl), cyano, nitro, —$CO_2H$, —C(O)$OC_1$-$C_{10}$ alkyl, —CON($C_1$-$C_{10}$ alkyl)($C_1$-$C_{10}$ alkyl), —CONH ($C_1$-$C_{10}$ alkyl), —$CONH_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH(C_1$-$C_{10}$alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl);

each $L_1$ is independently a linear alkylene of 1 to 70 carbon atoms in length, wherein one or more carbon atoms are optionally replaced with one or more groups selected from the group consisting of: C(O), NH, O, S, CH=N, $S(O)_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ optionally has one or more substituents selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —$OC_1$-$C_{10}$ alkyl, —$OC_1$-$C_{10}$ alkylphenyl, —$C_1$-$C_{10}$ alkyl-OH, —$OC_1$-$C_{10}$ haloalkyl, —$SC_1$-$C_{10}$ alkyl, —$SC_1$-$C_{10}$ alkylphenyl, —$C_1$-$C_{10}$ alkyl-SH, —$SC_1$-$C_{10}$ haloalkyl, halo, —OH, —SH, —$NH_2$, —$C_1$-$C_{10}$ alkyl-$NH_2$, —$N(C_1$-$C_{10}$ alkyl)($C_1$-$C_{10}$ alkyl), —NH($C_1$-$C_{10}$ alkyl), cyano, nitro, —$CO_2H$, —C(O)$OC_1$-$C_{10}$ alkyl, —CON($C_1$-$C_{10}$ alkyl)($C_1$-$C_{10}$ alkyl), —CONH($C_1$-$C_{10}$ alkyl), —$CONH_2$, —NHC(O) ($C_1$-$C_{10}$ alkyl), —NHC(O)(phenyl), —N($C_1$-$C_{10}$ alkyl) C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH(C_1$-$C_{10}$ alkyl), —$SO_2$NH(phenyl), —$NHSO_2$($C_1$-$C_{10}$ alkyl), —$NHSO_2$(phenyl), and —$NHSO_2$($C_1$-$C_{10}$ haloalkyl).

In some embodiments, $L_1$ may be selected from the group consisting of groups A1-A26 and any combination thereof, wherein the structures and definitions of A1-A26 are as follows:

(A1)

(A2)

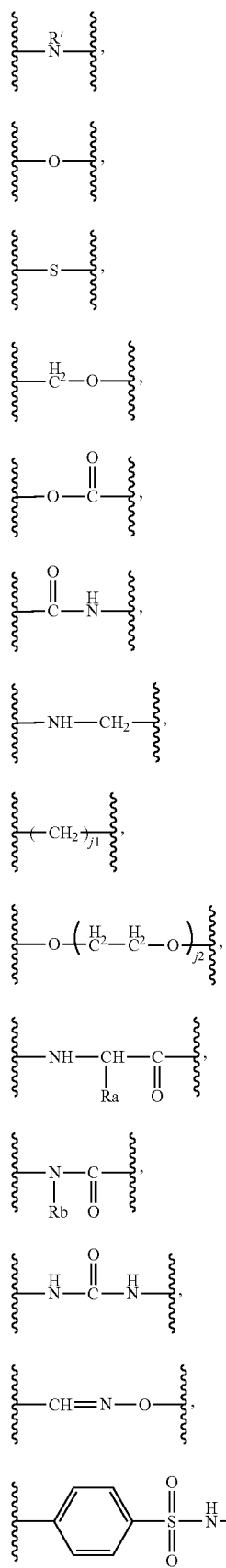
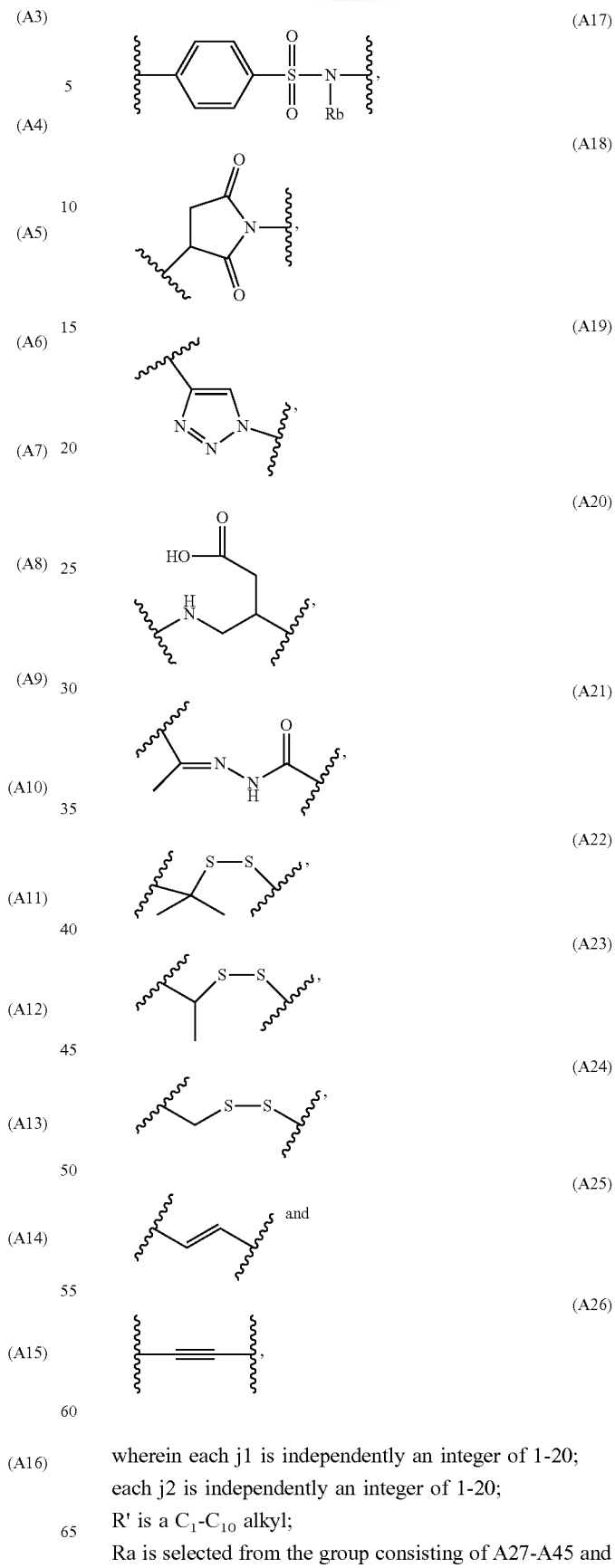
wherein each j1 is independently an integer of 1-20;
each j2 is independently an integer of 1-20;
R' is a $C_1$-$C_{10}$ alkyl;
Ra is selected from the group consisting of A27-A45 and any combination thereof:

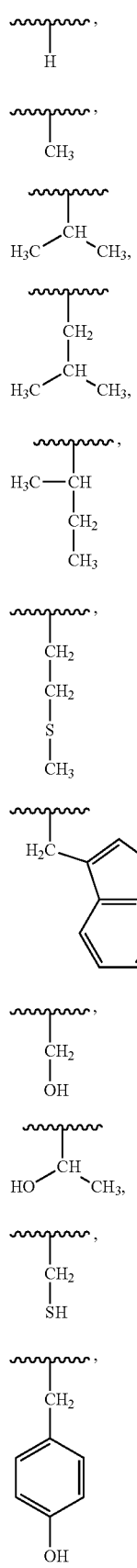
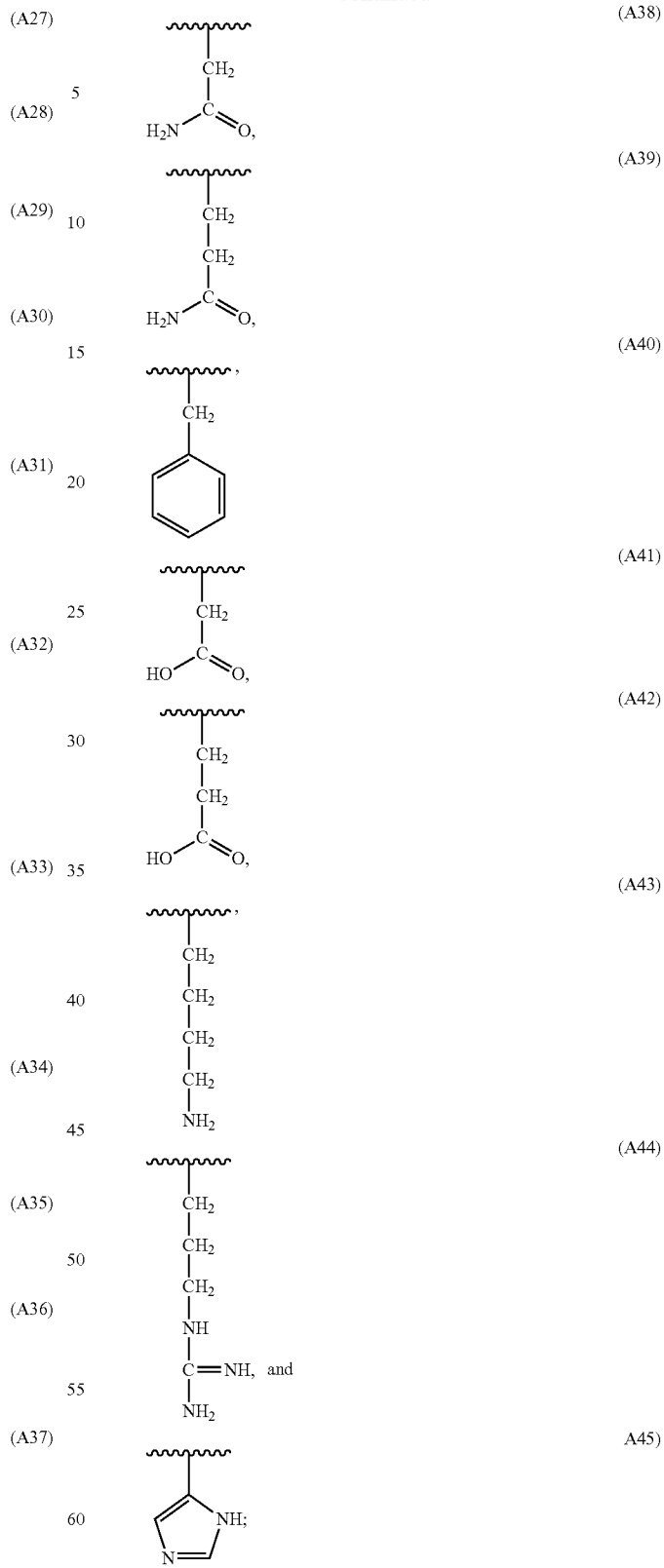
Rb is a $C_1$-$C_{10}$ alkyl; and
⁓⁓⁓ represents a site where a group is linked to the rest of the molecule.

Those skilled in the art would understand that, though $L_1$ is defined as a linear alkyl for convenience, but it may not be a linear group or be named differently, such as an amine or alkenyl produced by the above replacement and/or substitution. For the purpose of the present disclosure, the length of $L_1$ is the number of the atoms in the chain connecting the two attaching points. For this purpose, a ring obtained by replacement of a carbon atom of the linear alkylene, such as a heterocyclylene or heteroarylene, is counted as one atom.

$M_1$ represents a targeting group, of which the definitions and options are the same as those described above. In some embodiments, each $M_1$ is independently selected from one of the ligands that have affinity to the asialoglycoprotein receptor on the surface of mammalian hepatocytes.

When $M_1$ is a ligand that has affinity to the asialoglycoprotein receptor (ASGP-R) on the surface of mammalian hepatocyte, in some embodiments, n1 may be an integer of 1-3, and n3 may be an integer of 0-4 to ensure that the number of the $M_1$ ligand in the conjugate may be at least 2. In some embodiments, n1+n3≥, 2, such that the number of the $M_1$ ligand in the conjugate may be at least 3, thereby allowing the $M_1$ ligand to more conveniently bind to the asialoglycoprotein receptor on the surface of hepatocytes, which may facilitates the endocytosis of the conjugate into cells. Experiments have shown that when the number of the $M_1$ ligand is greater than 3, the ease of binding the $M_1$ ligand to the asialoglycoprotein receptor on the surface of hepatocytes is not significantly increased. Therefore, in view of various aspects such as synthesis convenience, structure/process costs and delivery efficiency, in some embodiments, n1 is an integer of 1-2, n3 is an integer of 0-1, and n1+n3=2-3.

In some embodiments, when m1, m2, and m3 independently of one another are selected from an integer of 2-10, the steric mutual positions among many $M_1$ ligands may be fit for binding the $M_1$ ligands to the asialoglycoprotein receptor on the surface of hepatocytes. In order to make the conjugate of the present disclosure have simpler structure, easier synthesis and/or reduced cost, in some embodiments, m1, m2 and m3 independently of one another are an integer of 2-5, in some embodiments, m1=m2=m3.

Those skilled in the art would understand that when $R_{10}$, $R_{11}$, $R_{12}$, $R_{13}$, $R_{14}$, and $R_{15}$ independently of one another is one of H, $C_1$-$C_{10}$ alkyl, $C_1$-$C_{10}$ haloalkyl, and $C_1$-$C_{10}$ alkoxy, they would not change the properties of the conjugate of the present disclosure and could all achieve the purpose of the present disclosure. In some embodiments, $R_{10}$, $R_{11}$, $R_{12}$, $R_{13}$, $R_{14}$, and $R_{15}$ independently of one another are selected from H, methyl and ethyl. In some embodiments, $R_{10}$, $R_{11}$, $R_{12}$, $R_{13}$, $R_{14}$, and $R_{15}$ are H.

$R_3$ is a group having the structure as shown by Formula A59, wherein $E_1$ is OH, SH or $BH_2$, and considering the availability of starting materials, in some embodiments, $E_1$ is OH or SH.

In some embodiments, $R_2$ is selected to achieve the linkage between the group as shown by Formula (A59) and the N atom on a nitrogenous backbone. In the context of the present disclosure, a "nitrogenous backbone" refers to a chain structure in which the carbon atom attached to $R_{10}$, $R_{11}$, $R_{12}$, $R_{13}$, $R_{14}$, and $R_{15}$ and the N atoms are linked to each other. In some embodiments, $R_2$ may be any linking group capable of attaching the group as shown by Formula (A59) to the N atom on a nitrogenous backbone by suitable means. In some embodiments, in the case where the siRNA conjugate of the present disclosure is prepared by a solid phase synthesis process, $R_2$ group needs to have both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ is B5, B6, B5' or B6':

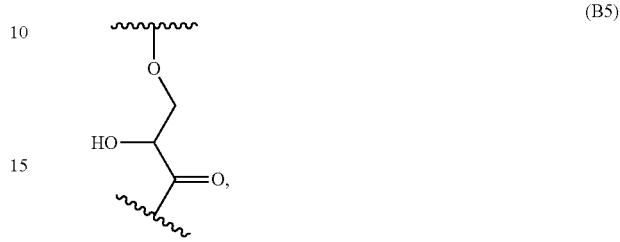

(B5)

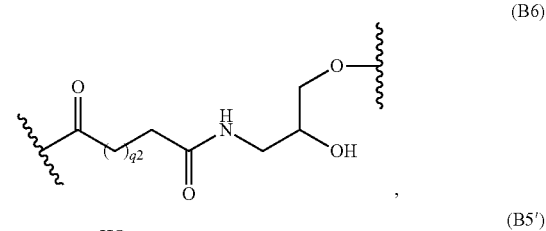

(B6)

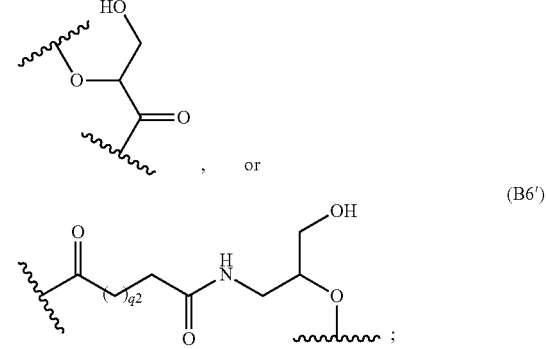

(B5')

, or

(B6')

;

wherein ⌇⌇⌇ represents the site where the group is covalently linked;

$q_2$ is an integer of 1-10; in some embodiments, $q_2$ is an integer of 1-5.

$L_1$ is used to link the $M_1$ ligand to the N atom on the nitrogenous backbone, thereby providing liver targeting function for the second siRNA conjugate of the present disclosure. In some embodiments, $L_1$ is selected from the connection combinations of one or more of Formulae A1-A26. In some embodiments, $L_1$ is selected from the connection combinations of one or more of Formulae A1, A4, A5, A6, A8, A10, A11, and A13. In some embodiments, $L_1$ is selected from the connection combinations of at least two of Formula A1, A4, A8, A10, and A11. In some embodiments, $L_1$ is selected from the connection combinations of at least two of Formula A1, A8, and A10.

In some embodiments, the length of $L_1$ may be 3 to 25, 3 to 20, 4 to 15 or 5 to 12 atoms. In some embodiments, $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms in length.

In some embodiments, j1 is an integer of 2-10, and in some embodiments, is an integer of 3-5. j2 is an integer of 2-10, and in some embodiments, is an integer of 3-5. R' is a $C_1$-$C_4$ alkyl, and in some embodiments, is one of methyl, ethyl, and isopropyl. Ra is one of A27, A28, A29, A30, and A31, and in some embodiments, is A27 or A28. Rb is a $C_1$-$C_5$ alkyl, and in some embodiments, is one of methyl, ethyl, isopropyl, and butyl. In some embodiments, j1, j2, R', Ra, and Rb of Formulae A1-A26 are respectively selected to achieve the linkage between the $M_1$ ligands and the N atom on the nitrogenous backbone, and to make the steric mutual position among the $M_1$ ligands more suitable for binding the $M_1$ ligands to the asialoglycoprotein receptor on the surface of hepatocytes.

In some embodiments, the second siRNA conjugate of the present disclosure has a structure as shown by Formula (3), (4), (5), (6), (7), (8), (9), (10), (11), (12), (13), (14), (15), (16), (17), (18), (19), (20), (21) or (22):

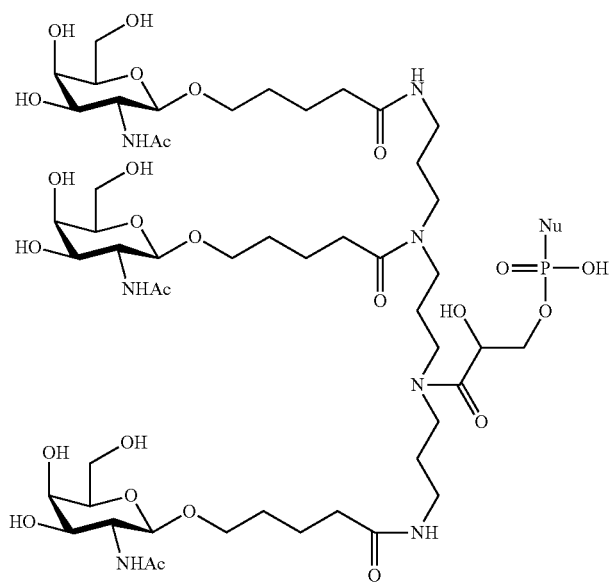

Formula (3)

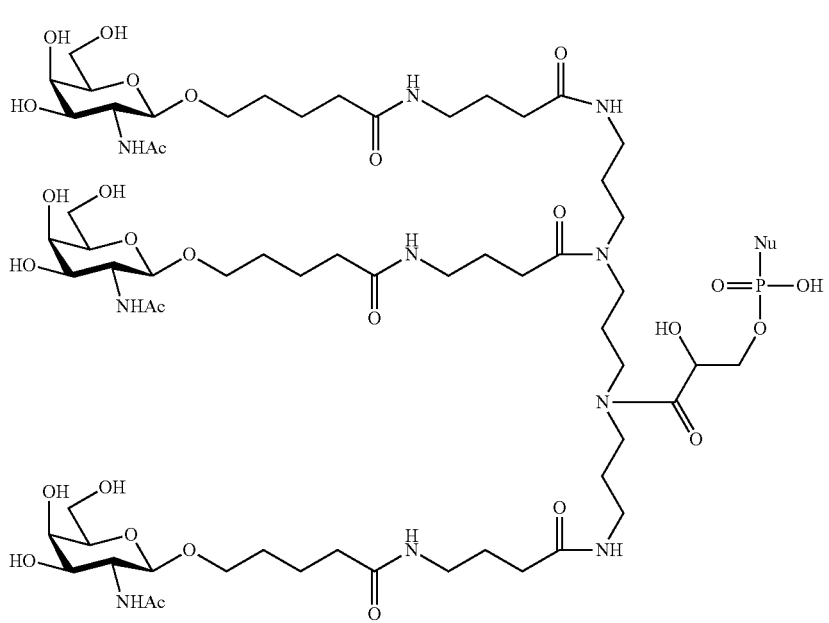

Formula (4)

-continued
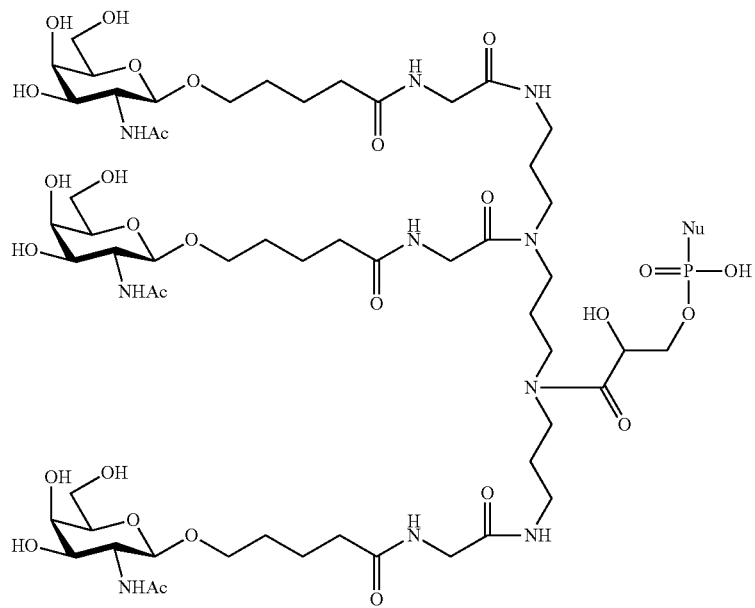
Formula (5)
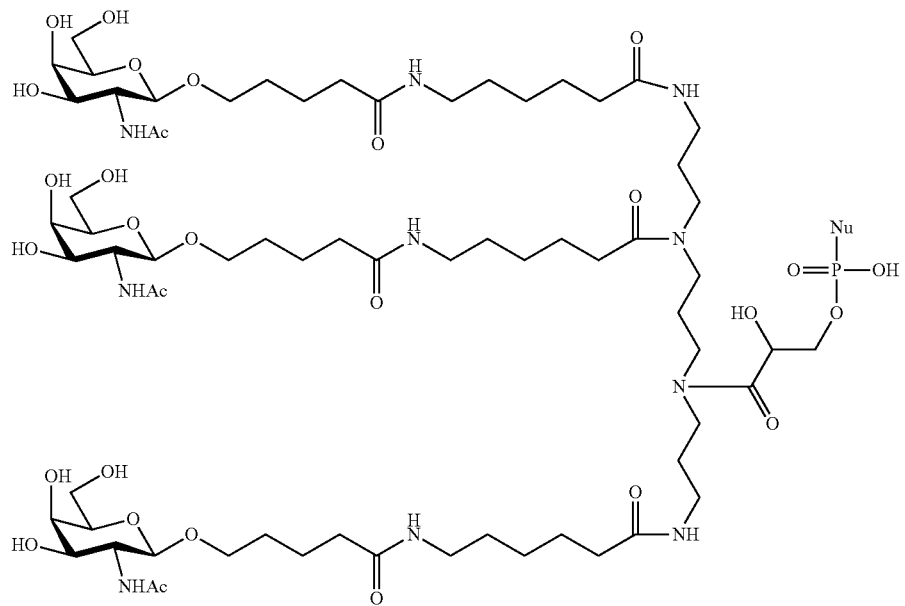
Formula (6)

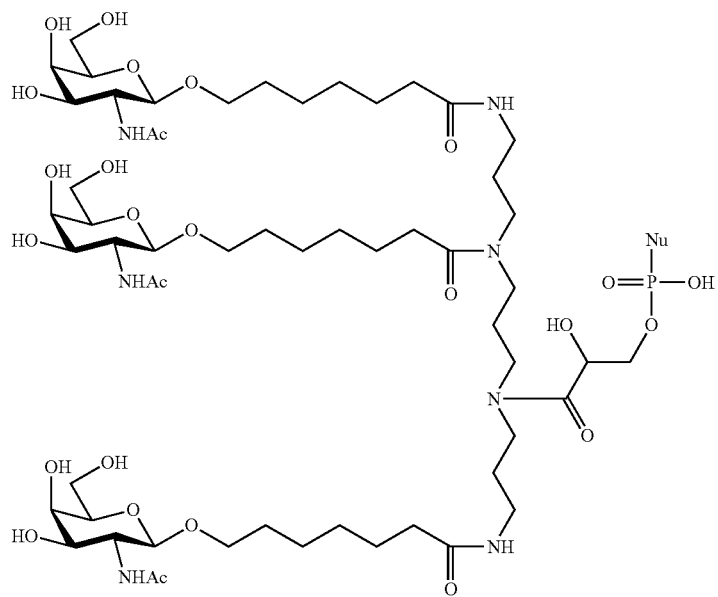
Formula (7)
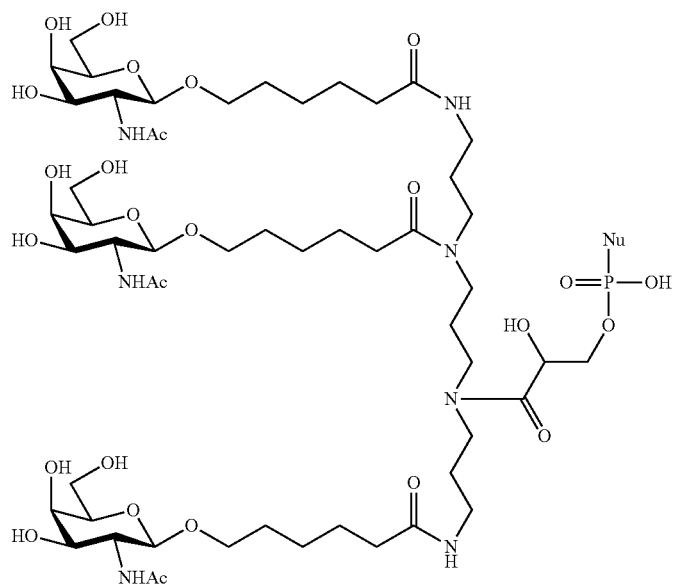
Formula (8)

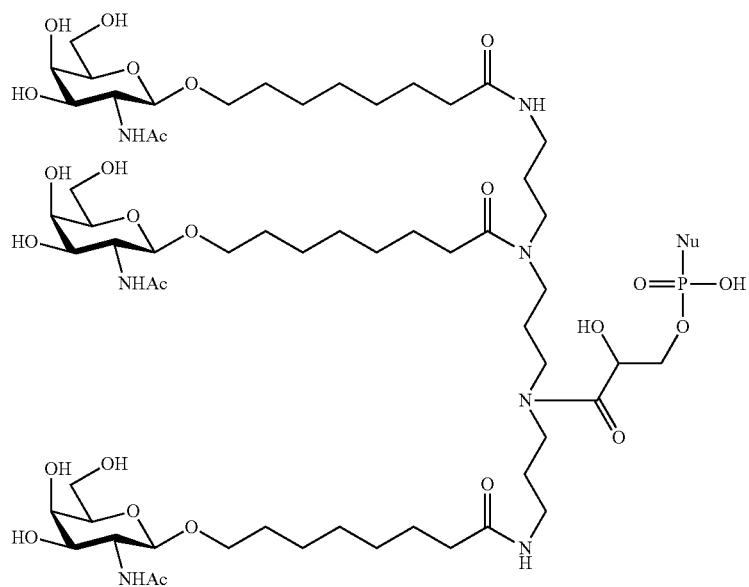
Formula (9)
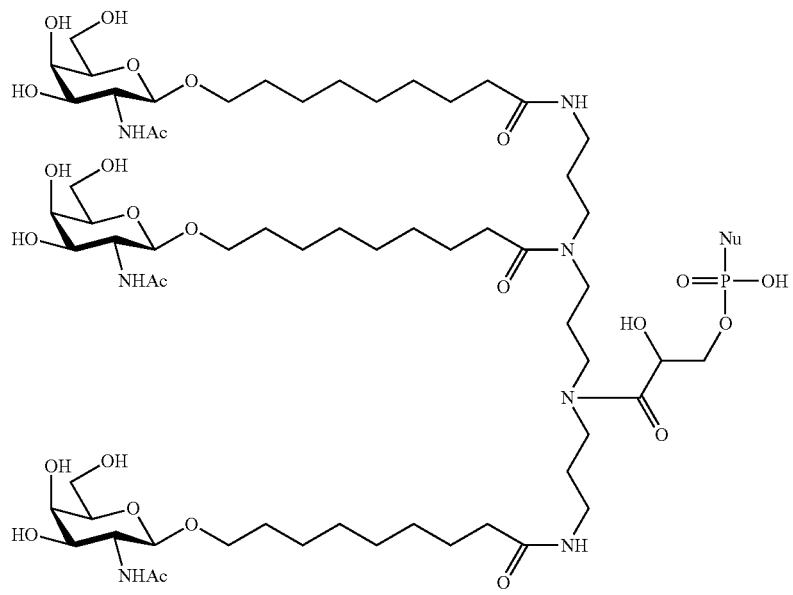
Formula (10)

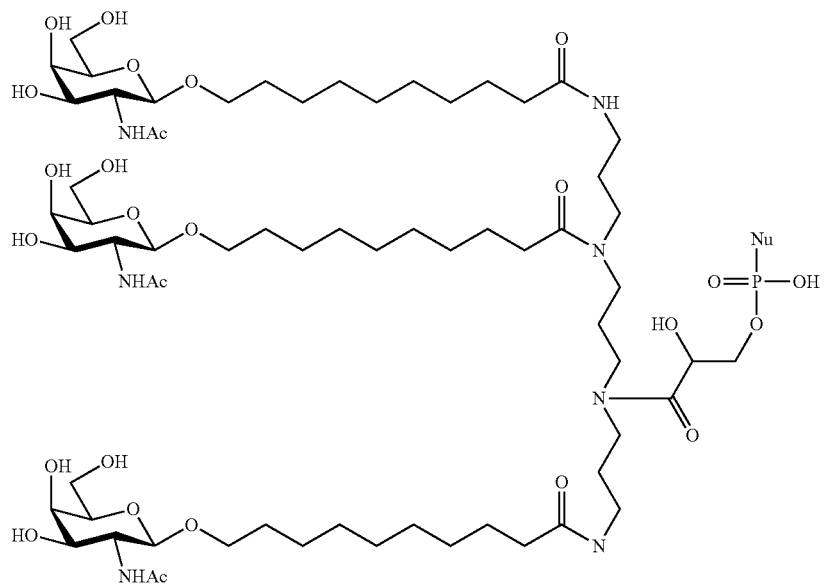
Formula (11)
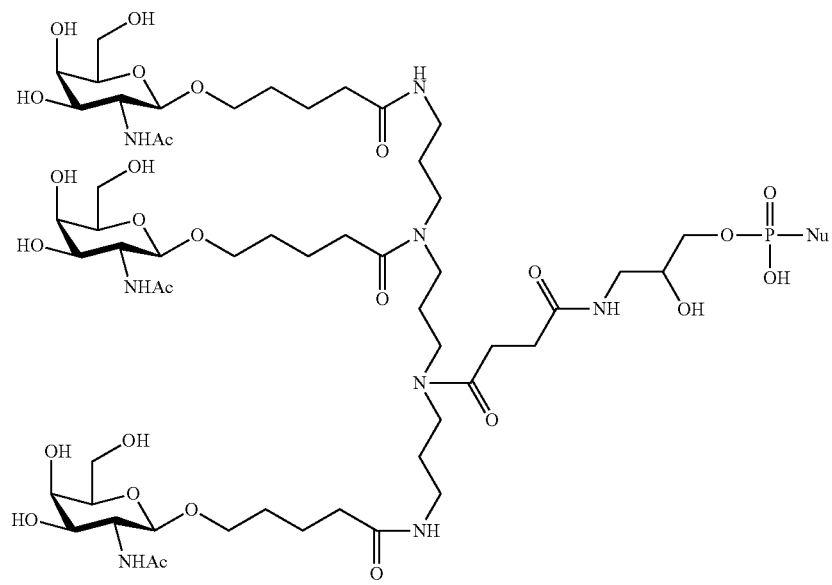
Formula (12)

Formula (13)
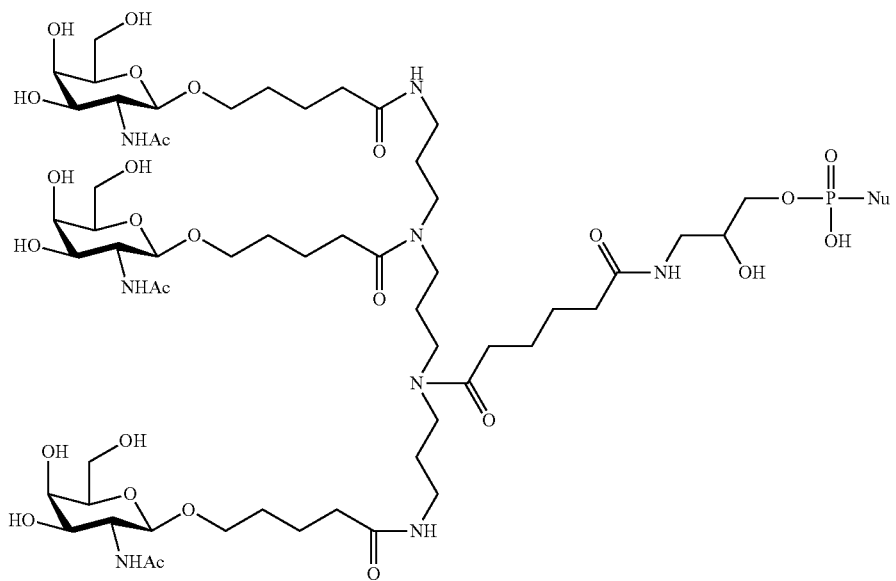
Formula (14)
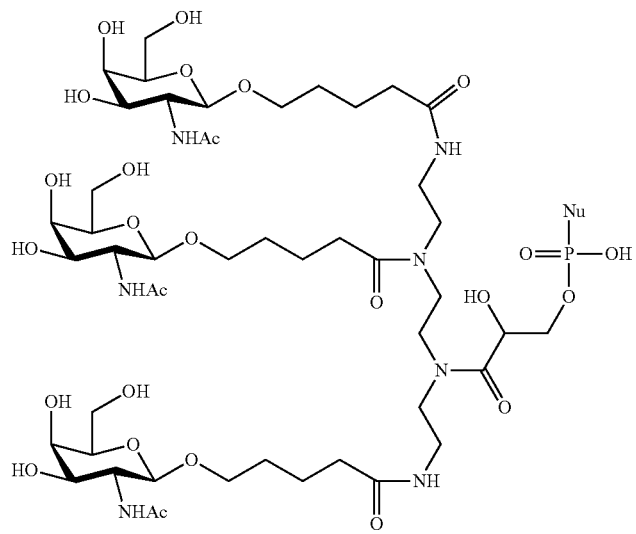

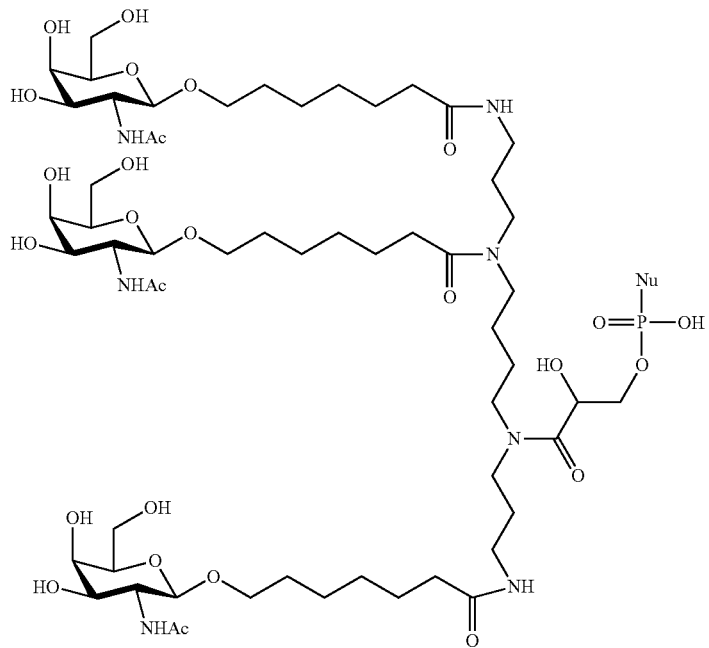
Formula (15)
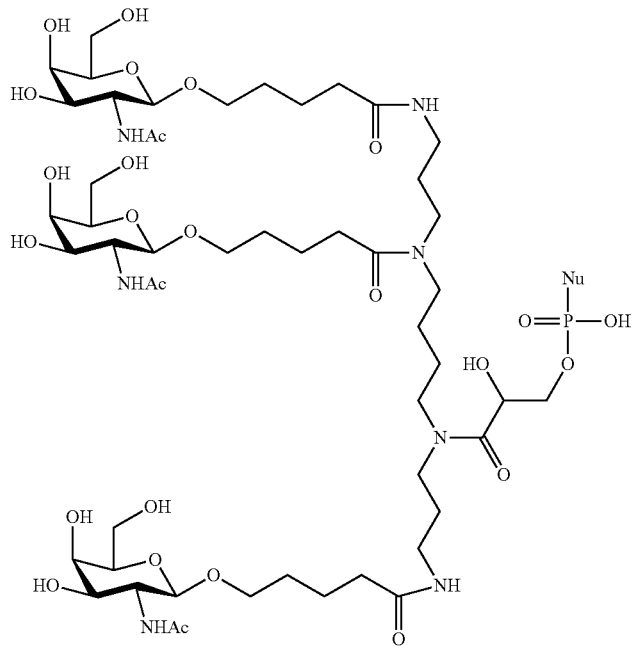
Formula (16)

Formula (17)
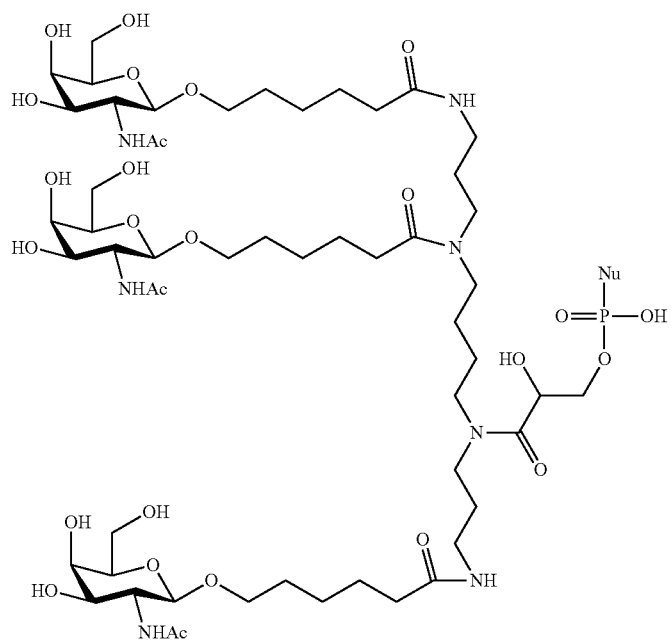
Formula (18)
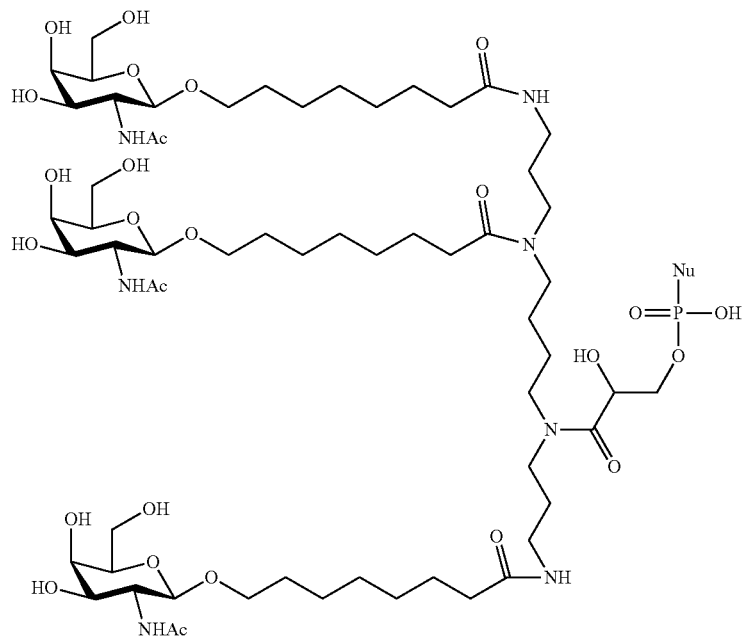

Formula (19)
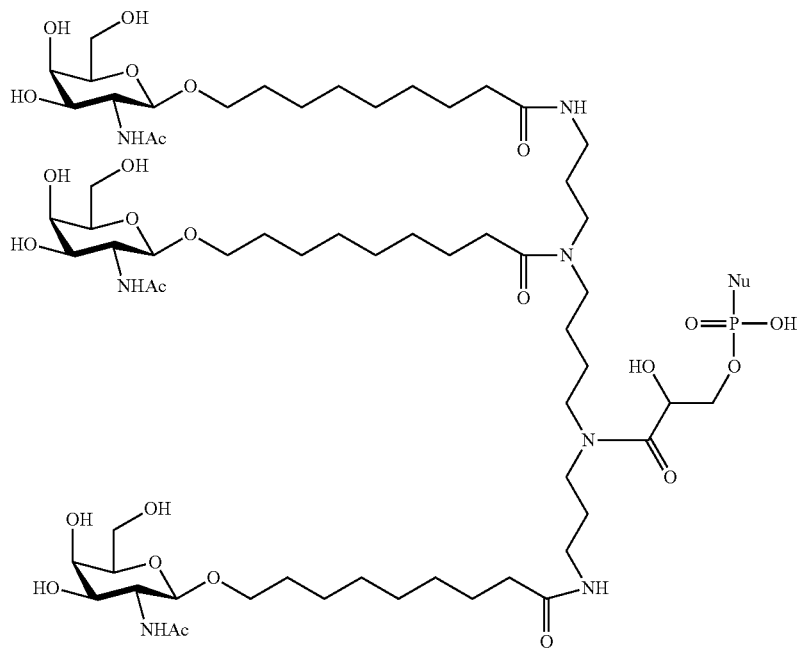
Formula (20)
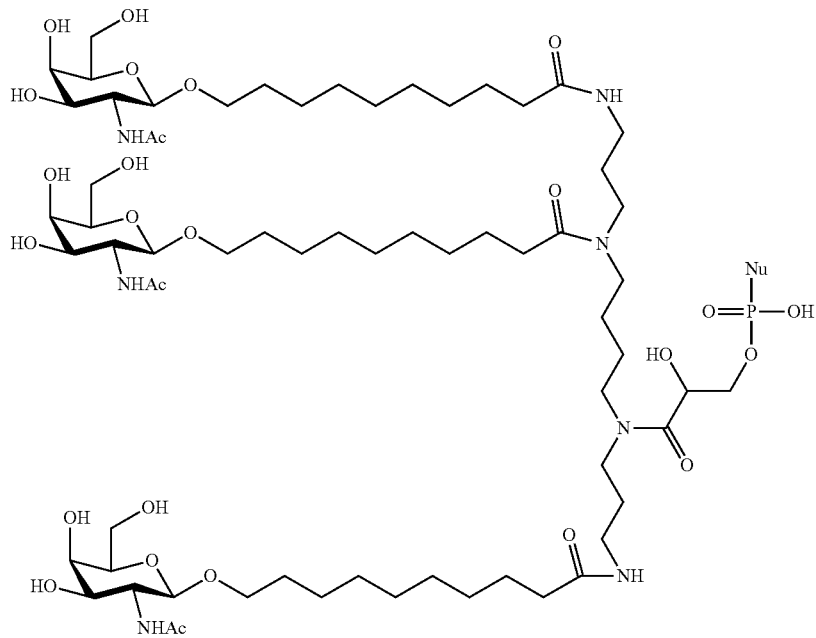

Formula (21)
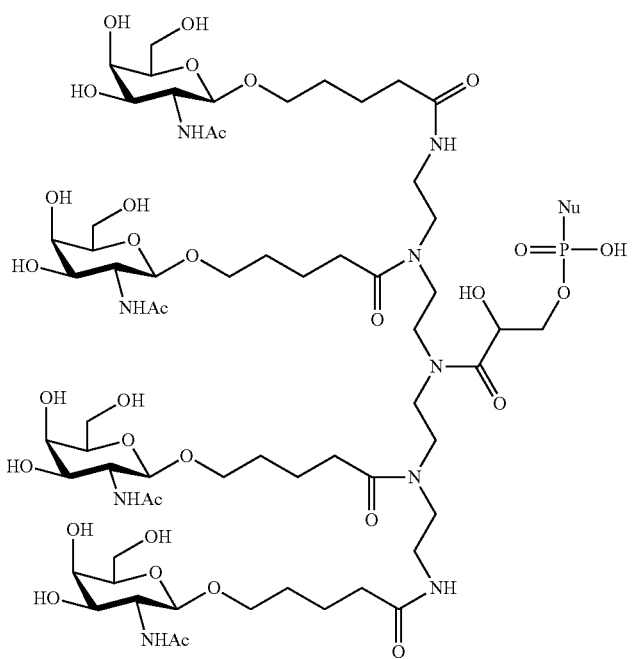
Formula (22)
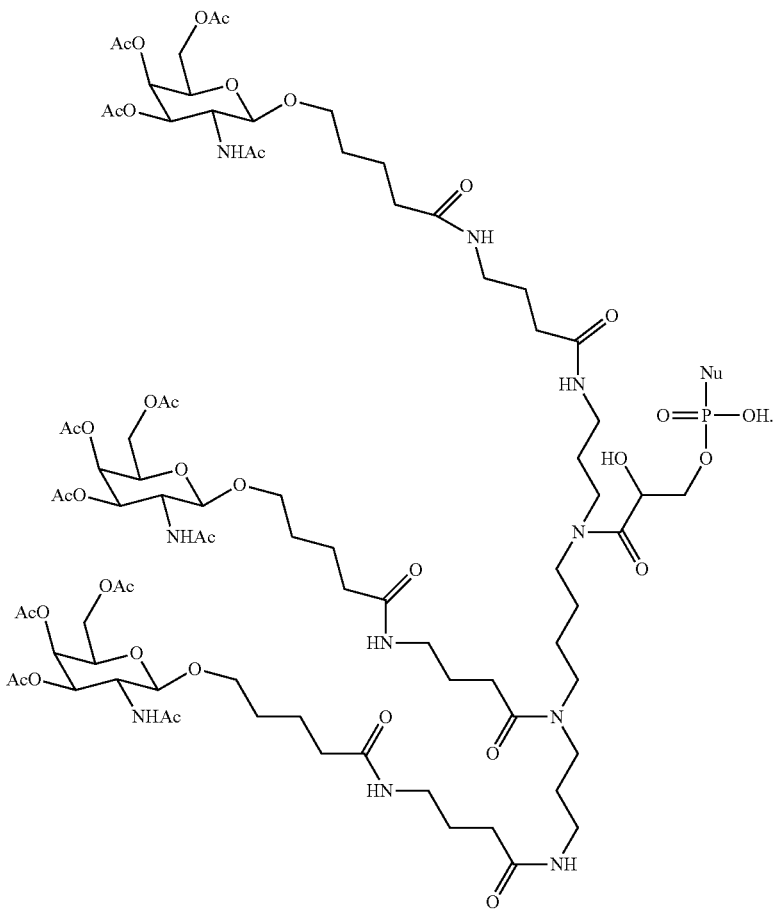

In some embodiments, the P atom in Formula A59 may be linked to any possible position in the siRNA (represented by Nu in the above formulae) sequence, for example, the P atom in Formula A59 may be linked to any nucleotide in the sense or antisense strand of the siRNA. In some embodiments, the P atom in Formula A59 is linked to any nucleotide in the sense strand of the siRNA. In some embodiments, the P atom in Formula A59 may be linked to a terminal of the sense or antisense strand of the siRNA. In some embodiments, the P atom in Formula A59 is linked to a terminal of the sense strand of the siRNA. Said terminal refers to the first 4 nucleotides counted from one terminal of the sense or antisense strand. In some embodiments, the P atom in Formula A59 is linked to either terminal of the sense or antisense strand of the siRNA. In some embodiments, the P atom in Formula A59 is linked to 3' terminal of the sense strand of the siRNA. In the case where the P atom in Formula A59 is linked to the above position in the sense strand of the siRNA, after entering into cells, the conjugate provided by the present disclosure can release a separate antisense strand of the siRNA during unwinding, thereby blocking the translation of the HBV mRNA into protein and inhibiting the expression of hepatitis B virus (HBV) gene.

The P atom in Formula A59 may be linked to any possible position of a nucleotide in the siRNA represented by Nu, for example, to position 5', 2' or 3', or to the base of the nucleotide. In some embodiments, the P atom in Formula A59 may be linked to position 2', 3', or 5' of a nucleotide in the siRNA by forming a phosphodiester bond. In some embodiments, the P atom in Formula A59 is linked to an oxygen atom formed by deprotonation of 3'-hydroxy of the nucleotide at 3' terminal of the sense strand in the siRNA, or the P atom in Formula A59 is linked to a nucleotide by substituting a hydrogen atom in 2'-hydroxy of a nucleotide of the sense strand in the siRNA, or the P atom in Formula A59 is linked to a nucleotide by substituting a hydrogen atom in 5'-hydroxy of the nucleotide at 5' terminal of the sense strand in the siRNA.

In some embodiments, the nucleotide sequence 1 has no more than 1 nucleotide different from the nucleotide sequence shown in SEQ ID NO: 1; and/or the nucleotide sequence 2 has no more than 1 nucleotide different from the nucleotide sequence shown in SEQ ID NO:2.

In some embodiments, the nucleotide differences between the nucleotide sequence 2 and the nucleotide sequence shown in SEQ ID NO:2 include a difference at the site of the nucleotide $Z'_B$, and $Z'_B$ is selected from A, C or G; in some embodiments, the nucleotide difference is a difference at the site of the nucleotide $Z'_B$, and $Z'_B$ is selected from A, C or G; in some embodiments, $Z_A$ is a nucleotide complementary to $Z'_B$. These special nucleotide differences will not significantly reduce the ability of the second siRNA conjugate to inhibit the target gene, and thus the second siRNA conjugates comprising specific nucleotide differences are also within the scope of the present disclosure.

In some embodiments, the nucleotide sequence 1 is basically reverse complementary, substantially reverse complementary, or completely reverse complementary to the nucleotide sequence 2. "Basically reverse complementary" refers to no more than 3 mispairings in two nucleotide sequences. "Substantially reverse complementary" refers to no more than 1 mispairing in two nucleotide sequences. "Completely reverse complementary" refers to no mispairing in two nucleotide sequences.

In some embodiments, the sense strand also comprises a nucleotide sequence 3, and the antisense strand further comprises a nucleotide sequence 4. The nucleotide sequences 3 and 4 each independently have a length of 1-4 nucleotides. The nucleotides in the nucleotide sequence 3 correspond to those at the corresponding sites in the nucleotide sequence 4. In some embodiments, the nucleotide sequence 4 is at least partly complementary to the nucleotides at the corresponding sites in the target mRNA. In some embodiments, the nucleotide sequence 4 is completely complementary to the nucleotides at the corresponding sites in the target mRNA.

In some embodiments, the nucleotide sequence 3 is linked to the 5' terminal of the nucleotide sequence 1, and the nucleotide sequence 4 is linked to the 3' terminal of the nucleotide sequence 2. In some embodiments, the nucleotide sequence 3 has the same length and is reverse complementary to the nucleotide sequence 4. Therefore, in some embodiments, the sense strand and the antisense strand may have a length of 19-23 nucleotides.

In some embodiments, the nucleotide sequence 3 and the nucleotide sequence 4 both have a length of 1 nucleotide. The base of the nucleotide sequence 3 is A; in this case, the double-stranded region may have a length of 20 nucleotides, i.e., the length ratio of the sense strand to the antisense strand is 20/20; alternatively, the nucleotide sequence 3 and the nucleotide sequence 4 both have a length of 2 nucleotides; in the direction from 5' terminal to 3' terminal, the bases of the nucleotide sequence 3 are G and A in succession; in this case, the double-stranded region may have a length of 21 nucleotides, i.e., the length ratio of the sense strand to the antisense strand is 21/21; alternatively, the nucleotide sequence 3 and the nucleotide sequence 4 both have a length of 3 nucleotides; in the direction from 5' terminal to 3' terminal, the bases of the nucleotide sequence 3 are C, G and A in succession; in this case, the double-stranded region may have a length of 22 nucleotides, i.e., the length ratio of the sense strand to the antisense strand is 22/22; alternatively, the nucleotide sequence 3 and the nucleotide sequence 4 both have a length of 4 nucleotides; in the direction from 5' terminal to 3' terminal, the bases of the nucleotide sequence 3 are C, C, G and A in succession; in this case, the double-stranded region may have a length of 23 nucleotides, i.e., the length ratio of the sense strand to the antisense strand is 23/23.

In some embodiments, the nucleotide sequence 3 has a length of 2 nucleotides; in the direction from 5' terminal to 3' terminal, the bases of the nucleotide sequence 3 are G and G in succession.

It should be understood that the nucleotide sequence 3 and the nucleotide sequence 4 have the same length and are complementary to each other. Thus, once the bases of the nucleotide sequence 3 are provided, the bases of the nucleotide sequence 4 are also determined.

In some embodiments, the siRNA represented by Nu in the Formula (1) further comprises a nucleotide sequence 5, which has a length of 1-3 nucleotides and is linked to 3' terminal of the antisense strand, thereby constituting a 3' overhang of the antisense strand. In some embodiments, the nucleotide sequence 5 has a length of 1 or 2 nucleotides. As such, the length ratio of the sense strand to the antisense strand in the siRNA represented by Nu may be 19/20, 19/21, 20/21, 20/22, 21/22, 21/23, 22/23, 22/24, 23/24, or 23/25.

In some embodiments, the nucleotide sequence 5 has a length of 2 nucleotides. Moreover, in the direction from 5' terminal to 3' terminal, the nucleotide sequence 5 is 2 continuous thymidine deoxyribonucleotides, 2 continuous uridine ribonucleotidesor 2 nucleotides complementary to the target mRNA. Thus, in some embodiments, the length ratio of the sense strand to the antisense strand in the siRNA represented by Nu is 19/21 or 21/23. Here, a conjugate comprising the siRNA exhibits better silencing activity against APOC3 mRNA.

In some embodiments, the sense strand comprises the nucleotide sequence shown in SEQ ID NO:1, and the antisense strand comprises the nucleotide sequence shown in SEQ ID NO:3 or SEQ ID NO:4:

```
                                        (SEQ ID NO: 1)
        5'-CCUUGAGGCAUACUUCAAZ_A-3', (SEQ ID NO: 3)
        5'-Z'_BUUGAAGUAUGCCUCAAGGUU-3', (SEQ ID NO: 4)
        5'-Z'_BUUGAAGUAUGCCUCAAGGUC-3',
``` wherein, the nucleotide $Z'_B$ is the first nucleotide from 5' terminal of the antisense strand; $Z_A$ is selected from A, U, G or C; and $Z'_B$ is a nucleotide complementary to $Z_A$.

In some embodiments, the siRNA represented by Nu is siHBa1 or siHBa2:

```
siHBa1
                                        (SEQ ID NO: 5)
Sense strand: 5'-CCUUGAGGCAUACUUCAAA -3', (SEQ ID NO: 6)
Antisense strand: 5'-UUUGAAGUAUGCCUCAAGGUU -3', siHBa2
                                        (SEQ ID NO: 7)
Sense strand: 5'-GACCUUGAGGCAUACUUCAAA -3', (SEQ ID NO: 8)
Antisense strand: 5'-UUUGAAGUAUGCCUCAAGGUCGG -3'.
```

As described above, the nucleotides in the siRNA represented by Nu in Formula (1) are each independently modified or unmodified nucleotides. In some embodiments, the nucleotides in the siRNA represented by Nu are unmodified nucleotides; in some embodiments, some or all nucleotides in the siRNA represented by Nu are modified nucleotides. Such modifications on the nucleotides would not cause significant decrease or loss of the function of the second siRNA conjugate of the present disclosure to inhibit the expression of HBV genes.

In some embodiments, the siRNA in the conjugate comprises at least one modified nucleotide. In the context of the present disclosure, the term "modified nucleotide" employed herein refers to a nucleotide formed by substituting the 2'-hydroxy of the ribose group with other groups, a nucleotide analogue, or a nucleotide with modified base. Such modified nucleotides would not cause significant decrease or loss of the function of the siRNA conjugate to inhibit the expression of genes. For example, the modified nucleotides disclosed by J. K. Watts, G. F. Deleavey and M. J. Damha, Chemically Modified siRNA: tools and applications. Drug Discov Today, 2008.13(19-20): p. 842-55 may be selected.

In some embodiments, at least one nucleotide in the sense or antisense strand is a modified nucleotide, and/or at least one phosphate is a phosphate group with modified groups. In other words, at least a portion of the phosphate and/or ribose groups in phosphate-ribose backbone of at least one single strand in the sense strand and the antisense strand are phosphate and/or ribose groups with modified groups.

In some embodiments, all nucleotides in the sense strand and/or the antisense strand are modified nucleotides. In some embodiments, each nucleotide in the sense strand and the antisense strand is independently a fluoro modified nucleotide or a non-fluoro modified nucleotide.

The inventors of the present disclosure have surprisingly found that the second siRNA conjugate disclosed herein has achieved a high degree of balance between the stability in serum and the gene silencing efficiency in animal experiments.

In some embodiments, the fluoro modified nucleotides are located within the nucleotide sequences 1 and 2; and in the direction from 5' terminal to 3' terminal, the nucleotides at positions 7, 8 and 9 of the nucleotide sequence 1 are fluoro modified nucleotides; and in the direction from 5' terminal to 3' terminal, the nucleotides at positions 2, 6, 14 and 16 of the nucleotide sequence 2 are fluoro modified nucleotides.

In some embodiments, no more than 5 fluoro modified nucleotides are present in the nucleotide sequence 1; in some embodiments, no more than 7 fluoro modified nucleotides are present in the nucleotide sequence 2.

In some embodiments, in the direction from 5' terminal to 3' terminal, the nucleotides at positions 7, 8 and 9 or 5, 7, 8 and 9 of the nucleotide sequence 1 in the sense strand are fluoro modified nucleotides, and the nucleotides at the rest of positions in the sense strand are non-fluoro modified nucleotides; in the direction from 5' terminal to 3' terminal, the nucleotides at positions 2, 6, 14 and 16 or 2, 6, 8, 9, 14 and 16 of the nucleotide sequence 2 in the antisense strand are fluoro modified nucleotides, and the nucleotides at the rest of positions in the antisense strand are non-fluoro modified nucleotides.

The definitions and options of the fluoro modified nucleotides and non-fluoro modified nucleotides are respectively as described above.

In some embodiments, in the direction from 5' terminal to 3' terminal, the nucleotides at positions 5, 7, 8 and 9 of the nucleotide sequence 1 in the sense strand of the siRNA represented by Nu are fluoro modified nucleotides, and the nucleotides at the rest of positions in the sense strand of the siRNA are methoxy modified nucleotides; and in the direction from 5' terminal to 3' terminal, the nucleotides at positions 2, 6, 8, 9, 14 and 16 of the nucleotide sequence 2 in the antisense strand of the siRNA represented by Nu are fluoro modified nucleotides, and the nucleotides at the rest of positions in the antisense strand of the siRNA are methoxy modified nucleotides;

alternatively, in the direction from 5' terminal to 3' terminal, the nucleotides at positions 7, 8 and 9 of the nucleotide sequence 1 in the sense strand of the siRNA represented by Nu are fluoro modified nucleotides, and the nucleotides at the rest of positions in the sense strand of the siRNA are methoxy modified nucleotides; and in the direction from 5' terminal to 3' terminal, the nucleotides at positions 2, 6, 14 and 16 of the nucleotide sequence 2 in the antisense strand of the siRNA represented by Nu are fluoro modified nucleotides, and the nucleotides at the rest of positions in the antisense strand of the siRNA are methoxy modified nucleotides;

alternatively, in the direction from 5' terminal to 3' terminal, the nucleotides at positions 5, 7, 8 and 9 of the nucleotide sequence 1 in the sense strand of the siRNA represented by Nu are fluoro modified nucleotides, and the nucleotides at the rest of positions in the sense strand of the siRNA are methoxy modified nucleotides; and in the direction from 5' terminal to 3' terminal, the nucleotides at positions 2, 6, 14 and 16 of the nucleotide sequence 2 in the antisense strand of the siRNA represented by Nu are fluoro modified nucleotides, and the nucleotides at the rest of positions in the antisense strand of the siRNA are methoxy modified nucleotides.

In some embodiments, the nucleotide has modifications on phosphate groups. In some embodiments, the modification on a phosphate group is a phosphorothioate modification as shown by Formula (101) below, that is, the substitution of a non-bridging oxygen atom in a phosphodiester bond with a sulfur atom so that the phosphodiester bond is changed to a phosphorothioate diester bond. This modification stabilizes the structure of the siRNA, while maintaining high specificity and high affinity for base pairing.

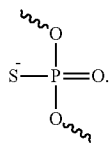

Formula (101)

In some embodiments, in the siRNA represented by Nu, a phosphorothioate linkage exists in at least one of the following positions: between the first and the second nucleotides from either terminal of the sense or antisense strand, between the second and the third nucleotides from either terminal of the sense strand or antisense strand, or any combination thereof. In some embodiments, a phosphorothioate linkage exists at all the above positions except for 5' terminal of the sense strand. In some embodiments, a phosphorothioate linkage exists at all the above positions except for 3' terminal of the sense strand. In some embodiments, a phosphorothioate linkage exists in at least one of the following positions: between the first and second nucleotides from 5' terminal of the sense strand; between the second and third nucleotides from 5' terminal of the sense strand; between the first and second nucleotides from 3' terminal of the sense strand; between the second and third nucleotides from 3' terminal of the sense strand; between the first and second nucleotides from 5' terminal of the antisense strand; between the second and third nucleotides from 5' terminal of the antisense strand; between the first and second nucleotides from 3' terminal of the antisense strand; and between the second and third nucleotides from 3' terminal of the antisense strand.

In some embodiments, the 5'-terminal nucleotide in the antisense strand sequence of the siRNA molecule represented by Nu is a 5'-phosphate nucleotide or a 5'-phosphate analogue modified nucleotide.

In some embodiments, the 5'-phosphate nucleotide or the 5'-phosphate analogue modified nucleotide is a 5'-phosphate modified nucleotide as shown by Formula (102), a nucleotide comprising an E-vinylphosphonate (E-VP) modification as shown by Formula (103), or a 5'-phosphorothioate modified nucleotide as shown by Formula (105).

The inventors of the present disclosure have surprisingly found that the second siRNA conjugate of the present disclosure exhibits a significantly improved stability in serum and lower off-target effect without significantly compromising the silencing activity against HBV mRNA, and further shows higher inhibitory effect on blood lipid. Thus, in some embodiments, the siRNAs represented by Nu in the second siRNA conjugate of the present disclosure may be those shown in Table 1:

TABLE 1

| siRNA NO. | SEQ ID NO: | Sequence direction 5'-3' |
|---|---|---|
| siHBa1 | 5 | CCUUGAGGCAUACUUCAAA |
|  | 6 | UUUGAAGUAUGCCUCAAGGUU |
| siHBa2 | 7 | GACCUUGAGGCAUACUUCAAA |
|  | 8 | UUUGAAGUAUGCCUCAAGGUCGG |
| siHBa1M1 | 9 | CmCmUmUmGmAmGfGfCfAmUmAmCmUmUmCmAmAmAm |
|  | 10 | UmUfUmGmAmAfGmUmAmUmGmCmCmUfCmAfAmGmGmUmUm |
| siHBa1M2 | 11 | CmCmUmUmGfAmGfGfCfAmUmAmCmUmUmCmAmAmAm |
|  | 12 | UmUfUmGmAmAfGmUfAfUmGmCmCmUfCmAfAmGmGmUmUm |
| siHBa2M1 | 13 | GmAmCmCmUmUmGmAmGfGfCfAmUmAmCmUmUmCmAmAmAm |
|  | 14 | UmUfUmGmAmAfGmUmAmUmGmCmCmUfCmAfAmGmGmUmCmGm Gm |
| siHBa2M2 | 15 | GmAmCmCmUmUmGfAmGfGfCfAmUmAmCmUmUmCmAmAmAm |
|  | 16 | UmUfUmGmAmAfGmUfAfUmGmCmCmUfCmAfAmGmGmUmCmGmG m |
| siHBa1M1S | 17 | CmsCmsUmUmGmAmGfGfCfAmUmAmCmUmUmCmAmAmAm |
|  | 18 | UmsUfsUmGmAmAfGmUmAmUmGmCmCmUfCmAfAmGmGmsUmsUm |
| siHBa1M2S | 19 | CmsCmsUmUmGfAmGfGfCfAmUmAmCmUmUmCmAmAmAm |
|  | 20 | UmsUfsUmGmAmAfGmUfAfUmGmCmCmUfCmAfAmGmGmsUmsUm |
| siHBa2M1S | 21 | GmsAmsCmCmUmUmGmAmGfGfCfAmUmAmCmUmUmCmAmAmAm |
|  | 22 | UmsUfsUmGmAmAfGmUmAmUmGmCmCmUfCmAfAmGmGmUmCms GmsGm |
| siHBa2M2S | 23 | GmsAmsCmCmUmUmGfAmGfGfCfAmUmAmCmUmUmCmAmAmAm |
|  | 24 | UmsUfsUmGmAmAfGmUfAfUmGmCmCmUfCmAfAmGmGmUmCmsGms Gm |

TABLE 1-continued siRNA sequences in the conjugates of the present disclosure

| siRNA NO. | SEQ ID NO: | Sequence direction 5'-3' |
|---|---|---|
| siHBa1M1P1 | 25 | CmCmUmUmGmAmGfGfCfAmUmAmCmUmUmCmAmAmAm |
| | 26 | P1-UmUfUmGmAmAfGmUmAmUmGmCmCmUfCmAfAmGmGmUmUm |
| siHBa1M2P1 | 27 | CmCmUmUmGfAmGfGfCfAmUmAmCmUmUmCmAmAmAm |
| | 28 | P1-UmUfUmGmAmAfGmUfAfUmGmCmCmUfCmAfAmGmGmUmUm |
| siHBa2M1P1 | 29 | GmAmCmCmUmUmGmAmGfGfCfAmUmAmCmUmUmCmAmAmAm |
| | 30 | P1-UmUfUmGmAmAfGmUmAmUmGmCmCmUfCmAfAmGmGmUmCmGmGm |
| siHBa2M2P1 | 31 | GmAmCmCmUmUmGfAmGfGfCfAmUmAmCmUmUmCmAmAmAm |
| | 32 | P1-UmUfUmGmAmAfGmUfAfUmGmCmCmUfCmAfAmGmGmUmCmGmGm |
| siHBa1M1SP1 | 33 | CmsCmsUmUmGmAmGfGfCfAmUmAmCmUmUmCmAmAmAm |
| | 34 | P1-UmsUfsUmGmAmAfGmUmAmUmGmCmCmUfCmAfAmGmGmsUmsUm |
| siHBa1M2SP1 | 35 | CmsCmsUmUmGfAmGfGfCfAmUmAmCmUmUmCmAmAmAm |
| | 36 | P1-UmsUfsUmGmAmAfGmUfAfUmGmCmCmUfCmAfAmGmGmsUmsUm |
| siHBa2M1SP1 | 37 | GmsAmsCmCmUmUmGmAmGfGfCfAmUmAmCmUmUmCmAmAmAm |
| | 38 | P1-UmsUfsUmGmAmAfGmUmAmUmGmCmCmUfCmAfAmGmGmUmCmsGmsGm |
| siHBa2M2SP1 | 39 | GmsAmsCmCmUmUmGfAmGfGfCfAmUmAmCmUmUmCmAmAmAm |
| | 40 | P1-UmsUfsUmGmAmAfGmUfAfUmGmCmCmUfCmAfAmGmGmUmCmsGmsGm |

In the siRNA or siRNA conjugate of the present disclosure, each pair of adjacent nucleotides are linked via a phosphodiester bond or phosphorothioate diester bond. The non-bridging oxygen or sulfur atom in the phosphodiester bond or phosphorothioate diester bond is negatively charged, and may be present in the form of hydroxy or sulfhydryl. Moreover, the hydrogen ion in the hydroxy or sulfhydryl may be partially or completely substituted with a cation. The cation may be any cation, such as a metal cation, an ammonium cation $NH_4^+$ or an organic ammonium cation. In order to increase solubility, in some embodiments, the cation is selected from one or more of an alkali metal cation, an ammonium cation formed by a tertiary amine and a quaternary ammonium cation. The alkali metal ion may be $K^+$ and/or $Na^+$, and the cation formed by a tertiary amine may be an ammonium cation formed by triethylamine and/or an ammonium cation formed by N,N-diisopropylethylamine. Thus, the siRNA or siRNA conjugate of the present disclosure may be at least partially present in the form of salt. In one embodiment, non-bridging oxygen atom or sulfur atom in the phosphodiester bond or phosphorothioate diester bond at least partly binds to sodium ion, and thus the siRNA or siRNA conjugate of the present disclosure is present or partially present in the form of sodium salt.

Those skilled in the art clearly know that a modified nucleotide may be introduced into the siRNA of the present disclosure by a nucleoside monomer with a corresponding modification. The methods for preparing a nucleoside monomer having the corresponding modification and the methods for introducing a modified nucleotide into a siRNA are also well-known to those skilled in the art. All modified nucleoside monomers may be either commercially available or prepared by known methods.

Preparation of the Second siRNA Conjugate

The second siRNA conjugate as described above may be prepared by any appropriate synthetic routes.

In some embodiments, the second siRNA conjugate of the present disclosure may be prepared by the following method, comprising: successively linking nucleoside monomers in 3' to 5' direction according to the nucleotide type and sequence in the sense strand and antisense strands of the double-stranded oligonucleotide respectively, under the condition of phosphoramidite solid phase synthesis, wherein the step of linking each nucleoside monomer includes a four-step reaction of deprotection, coupling, capping, and oxidation or sulfurization; isolating the sense strand and the antisense strand of the siRNA; and annealing; wherein each nucleotide in the siRNA is independently a modified or unmodified nucleotide. The siRNA represented by Nu comprises a sense strand and an antisense strand, wherein the sense strand comprises a nucleotide sequence 1, and the antisense strand comprises a nucleotide sequence 2; the nucleotide sequence 1 and the nucleotide sequence 2 are at least partly reverse complementary to form a double-stranded region; the nucleotide sequence 1 has the same length and no more than 3 nucleotides different from the nucleotide sequence shown in SEQ ID NO:155; and the nucleotide sequence 2 has the same length and no more than 3 nucleotides different from the nucleotide sequence shown in SEQ ID NO:156:

(SEQ ID NO: 155)
5'-CCUUGAGGCAUACUUCAAZ-3';

(SEQ ID NO: 156)
5'-Z'UUGAAGUAUGCCUCAAGG-3';

wherein,

Z is A; Z' is U;

the nucleotide sequence 1 comprises nucleotide $Z_A$ at the corresponding site to Z;

the nucleotide sequence 2 comprises nucleotide $Z'_B$ at the corresponding site to Z'; the nucleotide $Z'_B$ is the first nucleotide from 5' terminal of the antisense strand.

Moreover, the method further comprises: contacting the compound as shown by Formula (321) with a nucleoside monomer or a nucleotide sequence linked to a solid phase support under coupling reaction condition and in the presence of a coupling agent, thereby linking the compound as shown by Formula (321) to the nucleotide sequence through a coupling reaction. Hereinafter, the compound as shown by Formula (321) is also called a conjugating molecule.

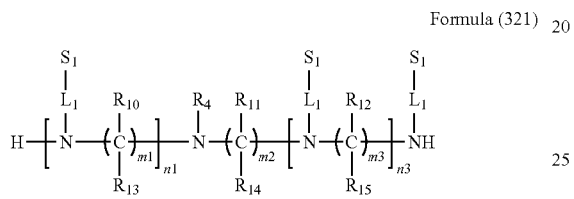

Formula (321)

wherein, $R_4$ is a moiety capable of binding to the siRNA represented by Nu. In some embodiments, $R_4$ is a moiety capable of binding to the siRNA represented by Nu via a covalent bond; in some embodiments, $R_4$ is a moiety comprising any functional group that may be conjugated to a siRNA via a phosphodiester bond by reaction;

Each $S_1$ is independently an $M_1$, which is a group formed by substituting all active hydroxyl with the group YCOO—, wherein each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl.

The definitions and options of n1, n3, m1, m2, m3, $R_{10}$, $R_{11}$, $R_{12}$, $R_{13}$, $R_{14}$, $R_{15}$, $L_1$, $M_1$ are respectively as described above.

$R_4$ is selected to achieve the linkage to the N atom on a nitrogenous backbone and to provide a suitable reaction site for synthesizing the siRNA conjugate as shown by Formula (1). In some embodiments, $R_4$ comprises a $R_2$ linking group or protected $R_2$ linking group, and can form a functional group as shown by Formula (A59) with a siRNA via reaction.

In some embodiments, $R_4$ comprises a first functional group that can react with a group on a siRNA or a nucleoside monomer to form a phosphite ester, and a second functional group that can form a covalent bond with a hydroxy group or an amino group, or comprises a solid phase support linked via the covalent bond. In some embodiments, the first functional group is a phosphoramidite, a hydroxy or a protected hydroxy. In some embodiments, the second functional group is a phosphoramidite, a carboxyl or a carboxylate salt. In some embodiments, the second functional group is a solid phase support linked to the rest of the molecule via a covalent bond which is formed by a hydroxy group or an amino group. In some embodiments, the solid phase support is linked via a phosphoester bond, a carboxyl ester bond, or an amide bond. In some embodiments, the solid phase support is a resin.

In some embodiments, the first functional group comprises hydroxy, —$OR_k$ or a group as shown by Formula (C3); the second functional group comprises a group as shown by Formula (C1), (C2), (C3), (C1'), or (C3'):

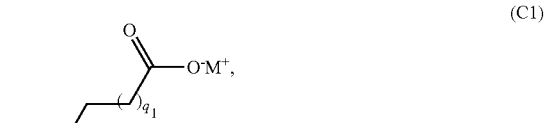

(C1)

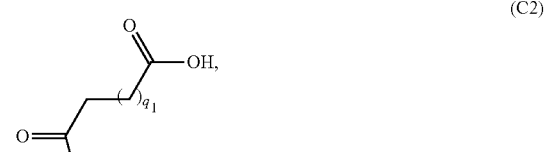

(C2)

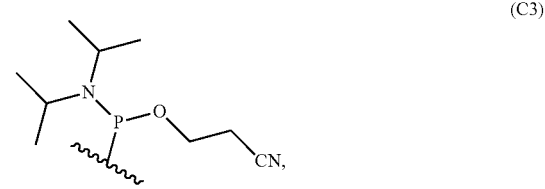

(C3)

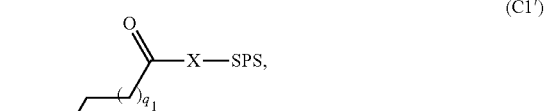

(C1')

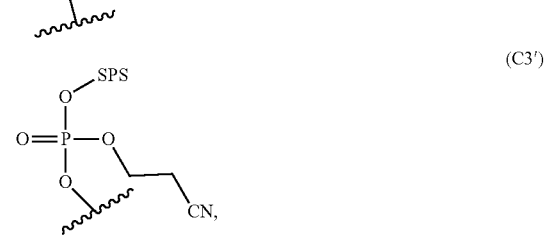

(C3')

wherein $q_1$ is an integer of 1-4, X is O or NH, $M^+$ is a cation, $R_k$ is a hydroxy protecting group, SPS represents a solid phase support, and ∿∿∿ represents the site where a group is covalently linked.

In some embodiments, the first functional group comprises a phosphoramidite functional group, such as the group as shown by Formula (C3). T The phosphoramidite group can form a phosphite ester with a hydroxy at any position on a nucleotide (such as a 2'- or 3'-hydroxy) by coupling reaction, and the phosphite ester can form a phosphodiester bond or phosphorothioate ester bond as shown by Formula (A59) via oxidation or sulfurization, so as to conjugate the conjugating molecule to a siRNA. Here, even if the second functional group does not exist, the compound as shown by Formula (321) will still be able to be conjugated to the nucleotide, without affecting the acquisition of siRNA conjugate as shown by Formula (1). Under such circumstances, after obtaining a sense or antisense strand of the siRNA by a method such as phosphoramidite solid phase synthesis, the compound as shown by Formula (321) is reacted with a hydroxy on the terminal nucleotide of the nucleotide sequence, and the resultant phosphite ester forms a phosphodiester bond or phosphorothioate bond by a subsequent oxidation or sulfurization, thereby conjugating the compound as shown by Formula (321) to a siRNA.

In some embodiments, the first functional group comprises a protected hydroxy group. In some embodiments, the second functional group comprises a group that can react with a solid phase support to provide a conjugating molecule comprising the solid phase support. In some embodiments, the second functional group comprises a carboxyl, a carboxylate or a phosphoramidite, such as the functional group as shown by Formula (C1), (C2) or (C3). When the second functional group comprises a carboxyl or a carboxylate, the compound as shown by Formula (321) can react via an esterification or an amidation reaction with a hydroxy or an amino group on a solid phase support such as a resin, to form a conjugating molecule comprising a solid phase support linked via a carboxylate ester bond or an amide bond. When the second functional group comprises a phosphoramidite functional group, the compound as shown by Formula (321) can be coupled with a hydroxy group on a universal solid phase support, such as a resin, and by oxidation, form a conjugating molecule comprising a solid phase support linked via a phosphodiester bond. Subsequently, starting from the above product linked to a solid phase support, the nucleoside monomers are linked sequentially by a phosphoramidite solid phase synthesis method, thereby obtaining a sense or antisense strand of the siRNA linked to the conjugation group. During the solid phase phosphoramidite synthesis, the first functional group is deprotected, and then coupled with a phosphoramidite group on a nucleoside monomer under coupling reaction condition.

In some embodiments, the first functional group comprises a hydroxy or a protected hydroxy group, and the second functional group comprises a solid phase support linked via a carboxylate ester bond, a amide bond or a phosphoester bond as shown by Formula (C1') or (C3'). Under such circumstances, starting from the compound as shown by Formula (321) in place of the solid phase support, the nucleoside monomers are linked sequentially by a phosphoramidite solid phase synthesis method, thereby obtaining a sense or antisense strand of the siRNA linked to a conjugation group. In some embodiments, the carboxylate may be expressed as —COO$^-$M$^+$, wherein M$^+$ is a cation such as one of a metal cation, an ammonium cation NH$_4^+$ and an organic ammonium cation. In one embodiment, the metal cation may be an alkali metal cation, such as K$^+$ or Na$^+$. In order to increase solubility and facilitate the reaction, in some embodiments, the organic ammonium cation is an ammonium cation formed by a tertiary amine, or a quaternary ammonium cation, such as an ammonium cation formed by triethylamine or N,N-diisopropylethylamine. In some embodiments, the carboxylate is a triethylamine carboxylate or an N,N-diisopropylethylamine carboxylate.

In some embodiments, R$_4$ comprises a structure as shown by Formula (B9), (B10), (B9'), (B10'), (B11), (B12), (B11') or (B12'):

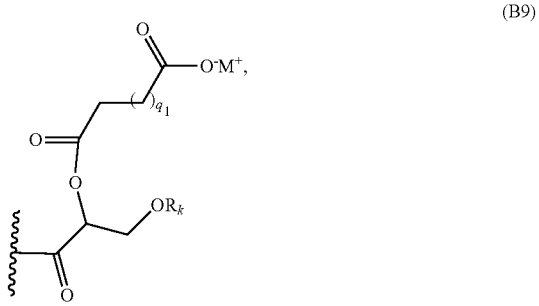
(B9)

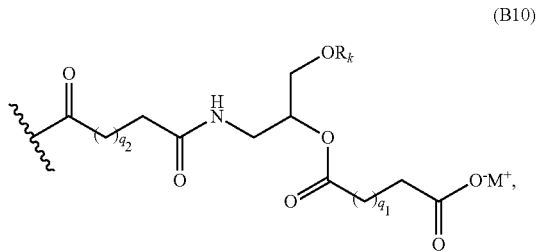
(B10)

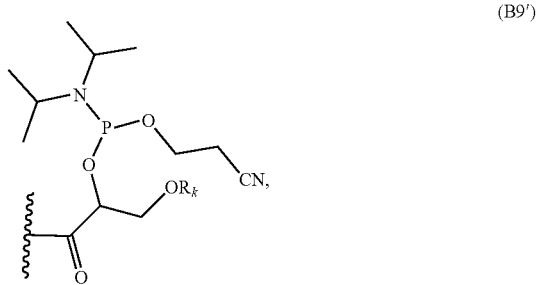
(B9')

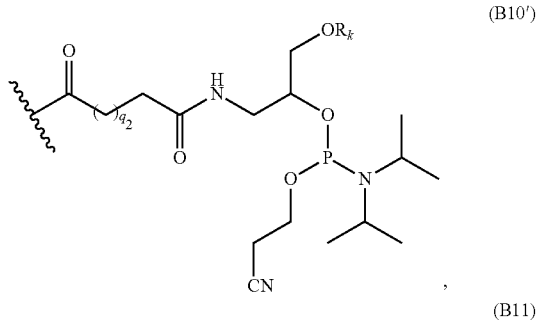
(B10')

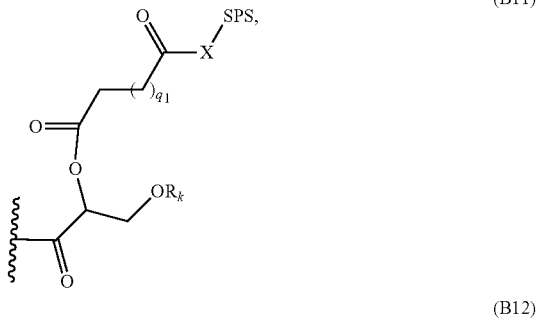
(B11)

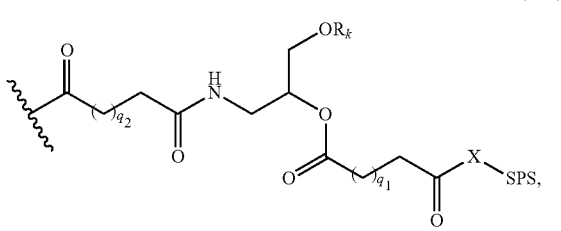
(B12)

-continued

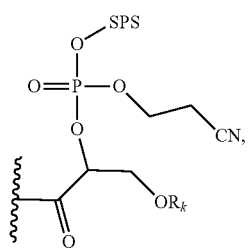
(B11')

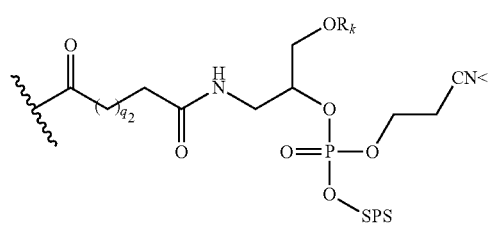
(B12')

wherein $q_1$ is an integer of 1-4, $q_2$ is an integer of 1-10, X is O or NH, $M^+$ is a cation, $R_k$ is a hydroxy protecting group, SPS represents a solid phase support, and ⌇⌇⌇ represents a site where a group is covalently linked. In some embodiments, $q_1$ is 1 or 2. In some embodiments, $q_2$ is an integer of 1-5. In some embodiments, $R_4$ comprises a structure as shown by Formula (B9) or (B10). In some embodiments, $R_4$ comprises a structure as shown by Formula (B11) or (B12).

In some embodiments, $R_k$ is one or more of Tr (trityl), MMTr (4-methoxytrityl), DMTr (4,4'-dimethoxytrityl), and TMTr (4,4',4"-trimethoxytrityl). In some embodiments, $R_k$ may be DMTr, i.e., 4,4'-dimethoxytrityl.

The definition of $L_1$ is as described above.

In some embodiments, $L_1$ is used to link the $M_1$ ligand to the N atom on the nitrogenous backbone, thereby providing liver targeting function for the oligonucleotide conjugate. In some embodiments, $L_1$ comprises any one of Formulae A1-A26, or the combination thereof.

According to the embodiments described above, those skilled in the art would easily understand that as compared with the well-known phosphoramidite solid phase synthesis methods in the art, an siRNA conjugate in which a conjugating molecule is linked to any possible position of the nucleotide sequence can be obtained through the above first functional group and an optional second functional group. For example, the conjugating molecule is linked to a terminal of the nucleotide sequence or to either terminal of the nucleotide sequence. Correspondingly, unless otherwise specified, in the following description regarding conjugate preparation, when referring to the reactions such as "deprotection", "coupling", "capping", "oxidation", "sulfurization", it will be understood that the reaction conditions and agents involved in the well-known phosphoramidite solid phase synthesis methods in the art would also apply to these reactions. Exemplary reaction conditions and agents will be described in detail hereinafter.

In some embodiments, each $S_1$ is independently an $M_1$. In some embodiments, each $S_1$ is independently a group formed by protecting at least one active hydroxyl in $M_1$ with a hydroxyl protecting group. In some embodiments, $S_1$ is independently a group formed by protecting all active hydroxyls in $M_1$ with hydroxyl protecting groups. In some embodiments, any hydroxyl protecting group known to those skilled in the art may be used to protect the active hydroxyl on $M_1$. In some embodiments, the protected hydroxy is expressed as the formula YCOO—, wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

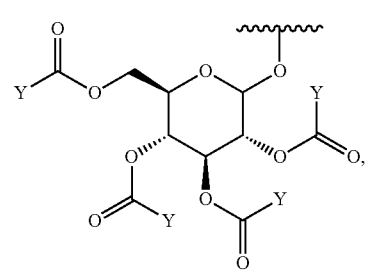
(A46)

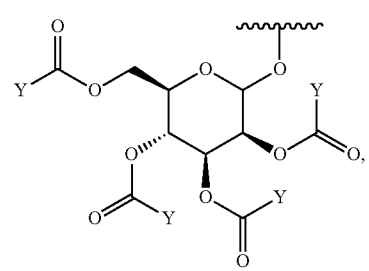
(A47)

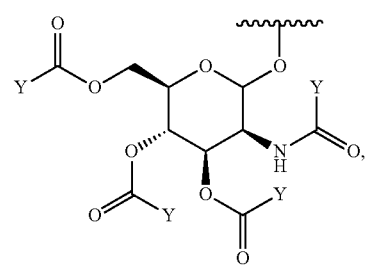
(A48)

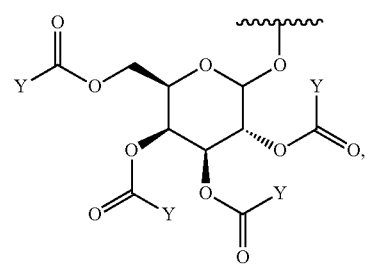
(A49)

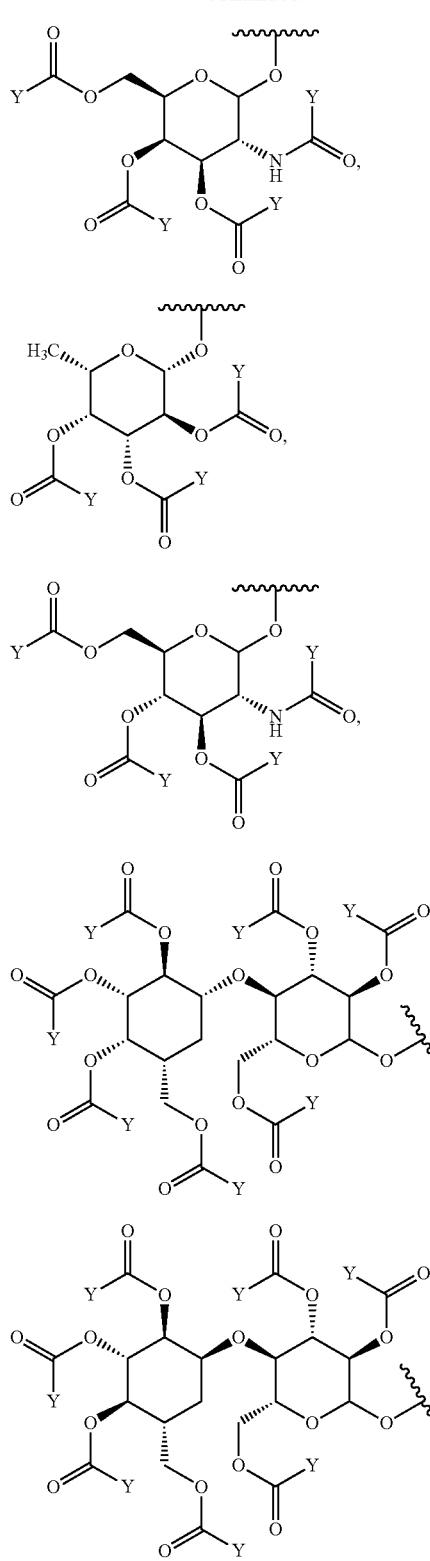

(A50)

(A51)

(A52)

(A53)

(A54)

In some embodiments, $S_1$ is Formula A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. For the purpose of simplifying the conjugating molecule of the present disclosure, in some embodiments, Y is methyl.

As mentioned previously, the method for preparing the second siRNA conjugate further comprises the following step: synthesizing the other strand of the siRNA (for example, when a sense strand of the siRNA linked to a conjugating molecule is synthesized in the above step, the method further comprises synthesizing an antisense strand of the siRNA by the solid phase synthesis method, and vice versa); isolating the sense strand and the antisense strand; and annealing. In particular, in the isolating step, the solid phase support linked to the nucleotide sequence and/or conjugating molecule is cleaved and at the same time the necessary protecting group is removed (in this case, each $S_1$ group in the compound as shown by Formula (321) is converted to the corresponding $M_1$ ligand), thereby providing a sense strand (or antisense strand) of the siRNA linked to the conjugating molecule and the corresponding antisense strand (or sense strand). The sense strand and the antisense strand are annealed to form a double-stranded RNA structure, thereby providing a siRNA conjugate as shown by Formula (1).

In some embodiments, the method for preparing the second siRNA conjugate comprises the following steps: contacting the compound as shown by Formula (321) with the first nucleoside monomer at 3' terminal of the sense or antisense strand under coupling reaction condition in the presence of a coupling agent, thereby linking the compound as shown by Formula (321) to the first nucleotide in the sequence; successively linking nucleoside monomers in 3' to 5' direction to synthesize the sense or antisense strand of the siRNA according to the desired nucleotide type and sequence of the sense or antisense strand, under the condition of phosphoramidite solid phase synthesis; wherein the compound of Formula (321) is a compound in which $R_4$ comprises a first functional group comprising a protected hydroxy and a second functional group comprising a group as shown by Formula (C1') or (C3'), and the compound of Formula (321) is deprotected before linked to the first nucleoside monomer; and the linking of each nucleoside monomer comprises a four-step reaction of deprotection, coupling, capping, and oxidation or sulfurization; thus obtaining a sense or antisense strand of nucleic acid linked to the conjugating molecule: successively linking nucleoside monomers in 3' to 5' direction to synthesize the sense or antisense strand of nucleic acid according to the nucleotide type and sequence of the sense or antisense strand, under the condition of phosphoramidite solid phase synthesis; wherein the linking of each nucleoside monomer includes a four-step reaction of deprotection, coupling, capping, and oxidation or sulfurization; removing the protecting groups and cleaving the solid phase support; isolating and purifying the sense strand and the antisense strand of nucleic acid; and annealing.

In some embodiments, the method for preparing the siRNA conjugate comprises the following steps: successively linking nucleoside monomers in 3' to 5' direction to synthesize the sense strand or the antisense strand according to the nucleotide type and sequence of the sense or antisense strand in the double-stranded oligonucleotide; wherein the linking of each nucleoside monomer comprises a four-step reaction of deprotection, coupling, capping, and oxidation or sulfurization, thus obtaining a sense strand linked to the solid phase support and an antisense strand linked to the solid phase support; contacting the compound as shown by Formula (321) with the sense strand linked to the solid phase support or the antisense strand linked to the solid phase support under coupling reaction condition in the presence of a coupling agent, thereby linking the compound as shown by Formula (321) to the sense strand or the antisense strand; wherein the compound of Formula (321) is a compound in which $R_4$ comprises a phosphoramidite group as the first functional group; removing the protecting groups and cleaving the solid phase support; respectively isolating and purifying the sense or antisense strand of the siRNA; and annealing; wherein the sense or antisense strand of the siRNA is linked to a conjugating molecule.

In some embodiments, the P atom in formula A59 is linked to the 3' terminal of the sense strand of the siRNA, and the method for preparing the siRNA conjugate of the present disclosure comprises:

(1) removing the hydroxyl protecting group $R_k$ in the compound of Formula (321) (wherein the compound of Formula (321) is a compound in which $R_4$ comprises a first functional group and a second function group, wherein the first functional group comprises a protected hydroxy $OR_k$, and the second function group has a structure as shown by Formula (C') or (C3')); contacting the deprotected product with a nucleoside monomer to obtain a nucleoside monomer linked to a solid phase support via the conjugating molecule, under a coupling reaction condition in the presence of a coupling agent;

(2) starting from the nucleoside monomer linked to a solid phase support via the conjugating molecule, synthesizing a sense strand of a sense strand of the siRNA in 3' to 5' direction by a phosphoramidite solid phase synthesis method;

(3) synthesizing an antisense strand of the siRNA by a phosphoramidite solid phase synthesis method; and (4) isolating the sense strand and the antisense strand of the siRNA and annealing the same to obtain the siRNA conjugate of the present disclosure;

wherein in step (1), the method for removing the protecting group $R_k$ in the compound of Formula (321) comprises contacting the compound of Formula (321) with a deprotection agent under deprotection condition. The deprotection condition comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, the deprotection agent is dichloroacetic acid. The molar ratio of the deprotection agent to the compound as shown by Formula (321) may be 10:1 to 1000:1, and in some embodiments, 50:1 to 500:1.

The coupling reaction condition and the coupling agent may be any conditions and agents suitable for the above coupling reaction. In some embodiments, the same condition and agent as those of the coupling reaction in the solid phase synthesis method can be used.

In some embodiments, the coupling reaction condition comprises a reaction temperature of 0-50° C., and in some embodiments, 15-35° C. The molar ratio of the compound of Formula (321) to the nucleoside monomer may be 1:1 to 1:50, and in some embodiments, 1:2 to 1:5. The molar ratio of the compound of Formula (321) to the coupling agent may be 1:1 to 1:50, and in some embodiments, 1:3 to 1:10. The reaction time may be 200-3000 seconds, and in some embodiments, 500-1500 seconds. The coupling agent may be selected from one or more of 1H-tetrazole, 5-ethylthio-1H-tetrazole and 5-benzylthio-1H-tetrazole, and in some embodiments, is 5-ethylthio-1H-tetrazole. The coupling reaction may be performed in an organic solvent. The organic solvent may be selected from one or more of anhydrous acetonitrile, anhydrous DMF and anhydrous dichloromethane, and in some embodiments, is anhydrous acetonitrile. The amount of the organic solvent may be 3-50 L/mol, and in some embodiments, 5-20 L/mol, with respect to the compound as shown by Formula (321).

In step (2), a sense strand S of the siRNA conjugate is synthesized in 3' to 5' direction by the phosphoramidite solid phase synthesis method, starting from the nucleoside monomer linked to a solid phase support via a conjugating molecule prepared in the above steps. In this case, the conjugating molecule is linked to the 3' terminal of the resultant sense strand.

Other conditions for the solid phase synthesis in steps (2) and (3), including the deprotection condition for the nucleoside monomer, the type and amount of the deprotection agent, the coupling reaction condition, the type and amount of the coupling agent, the capping reaction condition, the type and amount of the capping agent, the oxidation reaction condition, the type and amount of the oxidation agent, the sulfurization reaction condition, and the type and amount of the sulfurization agent, adopt various conventional agents, amounts, and conditions in the art.

In some embodiments, for example, the solid phase synthesis in steps (2) and (3) can use the following conditions:

The deprotection condition for the nucleoside monomer comprises a reaction temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, is dichloroacetic acid. The molar ratio of the deprotection agent to the protecting group 4,4'-dimethoxytrityl on the solid phase support is 2:1 to 100:1, and in some embodiments, is 3:1 to 50:1.

The coupling reaction condition comprises a reaction temperature of 0-50° C., and in some embodiments, 15-35° C. The molar ratio of the nucleic acid sequence linked to the solid phase support to the nucleoside monomer is 1:1 to 1:50, and in some embodiments, is 1:5 to 1:15. The molar ratio of the nucleic acid sequence linked to the solid phase support to the coupling agent is 1:1 to 1:100, and in some embodiments, is 1:50 to 1:80. The selection of the reaction time and the coupling agent can be same as above.

The capping reaction condition comprises a reaction temperature of 0-50° C., and in some embodiments, 15-35° C., and a reaction time of 5-500 seconds, and in some embodiments, 10-100 seconds. The selection of the capping agent can be same as above. The molar ratio of the total amount of the capping agent to the nucleic acid sequence linked to the solid phase support may be 1:100 to 100:1, and in some embodiments, is 1:10 to 10:1. In the case where the capping agent uses equimolar acetic anhydride and N-methylimidazole, the molar ratio of acetic anhydride, N-methylimidazole, and the nucleic acid sequence linked to the solid phase support may be 1:1:10-10:10:1, and in some embodiments, is 1:1:2-2:2:1.

The oxidation reaction condition comprises a reaction temperature of 0-50° C., and in some embodiments, 15-35° C., and a reaction time of 1-100 seconds, and in some embodiments, 5-50 seconds. In some embodiments, the oxidation agent is iodine (in some embodiments provided as iodine water). The molar ratio of the oxidation agent to the nucleic acid sequence linked to the solid phase support in the coupling step may be 1:1 to 100:1, and in some embodiments, is 5:1 to 50:1. In some embodiments, the oxidation reaction is performed in a mixed solvent in which the ratio of tetrahydrofuran:water:pyridine is 3:1:1-1:1:3. The sulfurization reaction condition comprises a reaction temperature of 0-50° C., and in some embodiments, 15-35° C., and a reaction time of 50-2000 seconds, and in some embodiments, 100-1000 seconds. In some embodiments, the sulfurization agent is xanthane hydride. The molar ratio of the sulfurization agent to the nucleic acid sequence linked to the solid phase support in the coupling step is 10:1 to 1000:1, and in some embodiments, is 10:1 to 500:1. In some embodiments, the sulfurization reaction is performed in a mixed solvent in which the ratio of acetonitrile:pyridine is 1:3-3:1.

The method further comprises isolating the sense strand and the antisense strand of the siRNA after linking all nucleoside monomers and before the annealing. Methods for isolation are well-known to those skilled in the art and generally comprise cleaving the synthesized nucleotide sequence from the solid phase support, removing protecting groups on the bases, phosphate groups and ligands, purifying and desalting.

The conventional cleavage and deprotection methods in the synthesis of siRNAs can be used to cleave the synthesized nucleotide sequence from the solid phase support, and remove the protecting groups on the bases, phosphate groups and ligands. For example, contacting the resultant nucleotide sequence linked to the solid phase support with concentrated aqueous ammonia; during deprotection, the protecting group YCOO⁻ in groups A46-A54 is converted to a hydroxyl group, and thus the $S_1$ groups are converted to corresponding $M_1$ groups, providing the conjugate as shown by Formula (1); wherein the concentrated aqueous ammonia may be aqueous ammonia of a concentration of 25-30% by weight. The amount of the concentrated aqueous ammonia may be 0.2 ml/μmol-0.8 ml/mol with respect to the target siRNA.

When there are at least some 2'-TBDMS protections on the synthesized nucleotide sequence, the method further comprises contacting the nucleotide sequence removed from the solid phase support with triethylamine trihydrofluoride to remove the 2'-TBDMS protection. Here, the resultant target siRNA sequence comprises the corresponding nucleoside having free 2'-hydroxy. The amount of pure triethylamine trihydrofluoride is 0.4 ml/mol-1.0 ml/μmol with respect to the target siRNA sequence. As such, the siRNA conjugate as shown by Formula (1) may be obtained.

Methods for purification and desalination are well-known to those skilled in the art. For example, nucleic acid purification may be performed using a preparative ion chromatography purification column with a gradient elution of NaBr or NaCl; after collection and combination of the product, the desalination may be performed using a reverse phase chromatography purification column.

The non-bridging oxygen or sulfur atom in the phosphodiester bond or phosphorothioate diester bond between the nucleotides in the resultant siRNA conjugate substantially binds to a sodium ion, and the siRNA conjugate is substantially present in the form of a sodium salt. The well-known ion-exchange methods may be used, in which the sodium ion may be replaced with hydrogen ion and/or other cations, thereby providing other forms of siRNA conjugates. The cations are as described above.

During synthesis, the purity and molecular weight of the nucleic acid sequence may be determined at any time, in order to better control the synthesis quality. Such determination methods are well-known to those skilled in the art. For example, the purity of the nucleic acid may be determined by ion exchange chromatography, and the molecular weight may be determined by liquid chromatography-mass spectrometry (LC-MS).

Methods for annealing are also well-known to those skilled in the art. For example, the synthesized sense strand (S strand) and antisense strand (AS strand) may be simply mixed in water for injection at an equimolar ratio, heated to 70-95° C., and then cooled at room temperature to form a double-stranded structure via hydrogen bond. Hence, the second siRNA conjugate of the present disclosure may be obtained.

After obtaining the conjugate, in some embodiments, the second siRNA conjugate thus synthesized can also be characterized by the means such as molecular weight detection using the methods such as LC-MS, to confirm that the synthesized siRNA conjugate is the designed second siRNA conjugate of interest, and the sequence of the synthesized siRNA is the sequence of the siRNA sequence desired to be synthesized, for example, is one of the sequences listed in Table 1 above.

The compound as shown by Formula (321) may be prepared by the following method comprising: contacting a compound as shown by Formula (313) with a cyclic anhydride in an organic solvent under esterification reaction condition in the presence of a base and an esterification catalyst; isolating the compound as shown by Formula (321) by ion exchange:

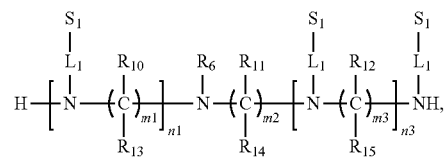

Formula (313)
wherein the definitions and options of n1, n3, m1, m2, m3, $R_{10}$, Ru, $R_{12}$, $R_{13}$, $R_{14}$, $R_{15}$, $L_1$, $S_1$ are respectively as described above;
$R_6$ is a group for providing $R_4$ of Formula (321). In some embodiments, for example, $R_6$ has a structure as shown by Formula (A61):

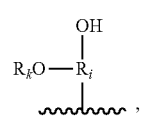

Formula (A61)

wherein,
$R_i$ is any group capable of linking to the N atom on the nitrogenous backbone, linking to $R_kO$ and linking to a free hydroxy group; $R_k$ is a hydroxy protecting group. In this case, a compound as shown by Formula (321) is obtained, wherein $R_4$ comprises a first functional group as a hydroxy protecting group and a second functional group comprising a group as shown by Formula (C1) or (C2).

The esterification reaction condition includes a reaction temperature of 0-100° C. and a reaction time of 8-48 hours.

In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol, with respect to the compound as shown by Formula (313).

In some embodiments, the cyclic anhydride is one of succinic anhydride, glutaric anhydride, adipic anhydride or pimelic anhydride, and in some embodiments, the cyclic anhydride is succinic anhydride. The molar ratio of the cyclic anhydride to the compound as shown by Formula (313) is 1:1 to 10:1, and in some embodiments, 2:1 to 5:1.

The esterification catalyst may be any catalyst capable of catalyzing esterification, such as 4-dimethylaminopyridine. The molar ratio of the catalyst to the compound as shown by Formula (313) is 1:1 to 10:1, and in some embodiments, is 2:1 to 5:1.

In some embodiments, the base may be any inorganic base, organic base or combination thereof. Considering solubility and product stability, the base is an organic base of tertiary amine. In some embodiments, the organic base of tertiary amine is triethylamine or N,N-diisopropylethylamine. The molar ratio of the organic base of tertiary amine to the compound as shown by Formula (313) is 1:1 to 20:1, and in some embodiments, is 3:1 to 10:1.

The ion exchange serves the function of converting the compound as shown by Formula (321) into a desired form of carboxylic acid or carboxylic salt and the methods of ion exchange are well-known to those skilled in the art. The above conjugating molecule in which the cation is $M^+$ may be obtained by using suitable ion exchange solution and ion exchange condition, which is not described here in detail. In some embodiments, a triethylamine phosphate solution is used in the ion exchange reaction. In some embodiments, the concentration of the triethylamine phosphate solution is 0.2-0.8 M. In some embodiments, the concentration of the triethylamine phosphate solution is 0.4-0.6 M. In some embodiments, the amount of the triethylamine phosphate solution is 3-6 L/mol, and in further embodiment, 4-5 L/mol, with respect to the compound as shown by Formula (313).

The compound as shown by Formula (321) may be isolated from the reaction mixture using any suitable isolation methods. In some embodiments, the compound as shown by Formula (321) may be isolated by removal of solvent via evaporation followed by chromatography, for example, using the following chromatographic conditions for the isolation: (1) normal phase purification: 200-300 mesh silica gel filler, gradient elution of 1 wt ‰ triethylamine in dichloromethane:methanol=100:18-100:20; or (2) reverse phase purification: C18 and C8 reverse phase filler, gradient elution of methanol:acetonitrile=0.1:1-1:0.1. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the product obtained from the above ion exchanging reaction with a solid phase support with amino or hydroxy groups in an organic solvent under condensation reaction condition in the presence of a condensing agent and an organic base of tertiary amine. In this case, a compound as shown by Formula (321) is obtained, wherein $R_4$ comprises a first functional group comprising a hydroxy protecting group and a second functional group having a structure as shown by Formula (C1').

The solid phase support is one of the supports used in solid phase synthesis of siRNA, some of which are well-known to those skilled in the art. For example, the solid phase support may be selected from the solid phase supports containing an active hydroxy or amino functional group. In some embodiments, the solid phase support is an amino or hydroxy resin. For the purpose of facilitating subsequent solid phase synthesis of nucleic acid, the amino or hydroxy resin has in some embodiments the following parameters: particle size of 100-400 mesh, and surface amino or hydroxy loading of 0.2-0.5 mmol/g. The ratio of the compound as shown by Formula (321) to the solid phase support is 10 μmol compound per gram of solid phase support (μmol/g) to 400 μmol/g. In some embodiments, the ratio of compound of Formula (321) to the solid phase support is 50 μmol/g to 200 μmol/g.

The organic solvent may be any suitable solvent or mixed solvents known to those skilled in the art. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran; the ether solvent is diethyl ether and/or methyl tertbutyl ether; the haloalkane solvent is one or more of dichloromethane, trichloromethane and 1,2-dichloroethane. In some embodiments, the organic solvent is acetonitrile. The amount of the organic solvent is 20-200 L/mol, in some embodiments, 50-100 L/mol, with respect to the compound as shown by Formula (321).

The condensing agent may be benzotriazol-1-yl-oxytripyrrolidinophosphonium hexafluorophosphate, 3-diethoxyphosphoryl-1,2,3-benzotrizin-4(3H)-one and/or O-benzotriazol-tetramethyluronium hexafluorophosphate. In some embodiments, the condensing agent is O-benzotriazol-tetramethyluronium hexafluorophosphate. The molar ratio of the condensing agent to the compound as shown by Formula (321) is 1:1 to 20:1, and in some embodiments, 1:1 to 5:1.

In some embodiments, the organic base of tertiary amine is triethylamine and/or N,N-diisopropylethylamine, and in some embodiments, N,N-diisopropylethylamine. The molar ratio of the organic base of tertiary amine to the compound as shown by Formula (321) is 1:1 to 20:1, and in some embodiments, 1:1 to 5:1.

In some embodiments, the method for preparing the compound as shown by Formula (321) further comprises: contacting the resultant condensation product with a capping agent and an acylation catalyst in an organic solvent under capping reaction condition, and isolating the compound as shown by Formula (321). The capping reaction is used to remove any active functional group that does not completely react, so as to avoid producing unnecessary by-products in subsequent reactions. The capping reaction condition comprises a reaction temperature of 0-50° C., and in some embodiments, 15-35° C., and a reaction time of 1-10 hours, and in some embodiments, 3-6 hours. The capping agent may be a capping agent used in solid phase synthesis of siRNA, which are well known to those skilled in the art.

In some embodiments, the capping agent is composed of capping agent A (capA) and capping agent B (capB). The capA is N-methylimidazole, and in some embodiments, provided as a mixed solution of N-methylimidazole in pyridine/acetonitrile, wherein the volume ratio of pyridine to acetonitrile is 1:10 to 1:1, and in some embodiments, 1:3 to 1:1. In some embodiments, the ratio of the total volume of pyridine and acetonitrile to the volume of N-methylimidazole is 1:1 to 10:1, and in some embodiments, 3:1 to 7:1. The capping reagent B acetic anhydride. In some embodiments, the capB is provided as a solution of acetic anhydride in acetonitrile, wherein the volume ratio of acetic anhydride to acetonitrile is 1:1 to 1:10, and in some embodiments, 1:2 to 1:6.

In some embodiments, the ratio of the volume of the mixed solution of N-methylimidazole in pyridine/acetonitrile to the mass of the compound of Formula (321) is 5 ml/g-50 ml/g, and in some embodiments, 15 ml/g-30 ml/g. The ratio of the volume of the solution of acetic anhydride in acetonitrile to the mass of the compound of Formula (321) is 0.5 ml/g-10 ml/g, and in some embodiments, 1 ml/g-5 ml/g.

In some embodiments, the capping agent comprises equimolar acetic anhydride and N-methylimidazole. The organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. The amount of the organic solvent is 10-50 L/mol, and in some embodiments, 5-30 L/mol, with respect to the compound as shown by Formula (321).

The acylation catalyst may be selected from any catalyst that may be used for esterification condensation or amidation condensation, such as alkaline heterocyclic compounds. In some embodiments, the acylation catalyst is 4-dimethylaminopyridine. The mass ratio of the catalyst to the compound as shown by Formula (321) may be 0.001:1 to 1:1, and in some embodiments, 0.01:1 to 0.1:1.

The compound as shown by Formula (321) may be isolated from the reaction mixture by any suitable methods. In some embodiments, the compound of Formula (321) may be obtained by thoroughly washing with an organic solvent and filtering to remove unreacted reactants, excess capping agent and other impurities, wherein the organic solvent is selected from acetonitrile, dichloromethane, or methanol. In some embodiments, the organic solvent is acetonitrile.

In some embodiments, the preparation of the conjugating molecule as shown by Formula (321) comprises contacting a compound as shown by Formula (313) with a phosphorodiamidite in an organic solvent under coupling reaction condition in the presence of a coupling agent, and isolating the compound as shown by Formula (321). In this case, a compound as shown by Formula (321) is obtained, where $R_4$ comprises a first functional group comprising a hydroxy protecting group and a second functional group having a structure as shown by Formula (C3).

In some embodiments, the coupling reaction condition comprises a reaction temperature of 0-50° C., such as 15-35° C. The molar ratio of the compound of Formula (313) to the phosphorodiamidite may be 1:1 to 1:50, such as 1:5 to 1:15. The molar ratio of the compound of Formula (313) to the coupling agent may be 1:1 to 1:100, such as 1:50 to 1:80. The reaction time may be 200-3000 seconds, such as 500-1500 seconds. The phosphorodiamidite may be, for example, bis(diisopropylamino)(2-cyanoethoxy)phosphine, which may be commercially available or synthesized according to well-known methods in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. In some embodiments, the organic solvent is selected from one or more of anhydrous acetonitrile, anhydrous DMF and anhydrous dichloromethane, such as anhydrous acetonitrile. The amount of the organic solvent may be 3-50 L/mol, such as 5-20 L/mol, with respect to the compound as shown by Formula (313). By performing the coupling reaction, the hydroxy group in the compound (313) reacts with the phosphorodiamidite to form a phosphoramidite group. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the isolated product with a solid phase support with hydroxy groups in an organic solvent under coupling reaction condition in the presence of a coupling agent, followed by capping, oxidation, and isolation, to obtain the compound as shown by Formula (321), where $R_4$ a first functional group comprising a hydroxy protecting group and a second functional group having a structure as shown by Formula (C3').

In some embodiments, the solid phase support is a well-known support in the art for solid phase synthesis of a nucleic acid, such as a deprotected commercially available universal solid phase support, such as NittoPhase®HL UnyLinker™ 300 Oligonucleotide Synthesis Support, Kinovate Life Sciences, as shown by Formula B80:

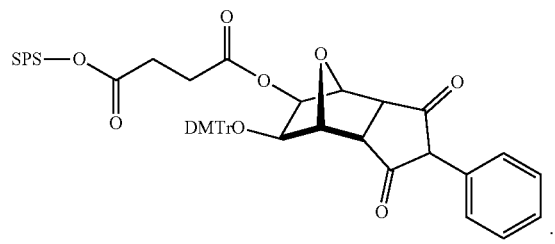

Formula (B80)

A deprotection reaction is well-known in the art. In some embodiments, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid. The molar ratio of the deprotection agent to the protecting group -DMTr (4,4'-dimethoxytrityl) on the solid phase support may be 2:1 to 100:1, such as 3:1 to 50:1. By such deprotection, reactive free hydroxy groups are obtained on the surface of the solid phase support, for facilitating the subsequent coupling reaction.

The coupling reaction condition and the coupling agent may be selected as above. By such a coupling reaction, the free hydroxy groups formed in the deprotection reaction reacts with the phosphoramidite groups, so as to form a phosphite ester linkage.

In some embodiments, the capping reaction condition comprises a temperature of 0-50° C., such as 15-35° C., and a reaction time of 5-500 seconds, such as 10-100 seconds.

The capping reaction is performed in the presence of a capping agent. The selection and amount of the capping agent are as above.

The oxidation reaction condition may comprise a temperature of 0-50° C., such as 15-35° C., and a reaction time of 1-100 seconds, such as 5-50 seconds. The oxidation agent may be, for example, iodine (in some embodiments, provided as iodine water). In some embodiments, the molar ratio of the oxidation agent to the phosphite ester group is 1:1 to 100:1, preferably 5:1 to 50:1. In some embodiments, the oxidation reaction is performed in a mixed solvent in which the ratio of tetrahydrofuran:water:pyridine is 3:1:1-1:1:3.

In some embodiments, $R_6$ is a group as shown by Formula B7 or B8:

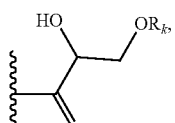

(B7)

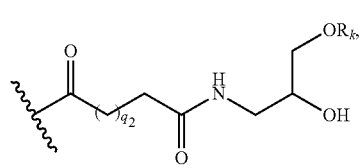

(B8)

wherein $q_2$ is as defined above.

In this case, the compound shown in the Formula (313) may be prepared by the following preparation method comprising: contacting the compound as shown by Formula (314) with a compound as shown by Formula (A-1) or (A-2) in an organic solvent under amidation reaction condition in the presence of an agent for amidation condensation and an organic base of tertiary amine, and isolating:

Formula (314)

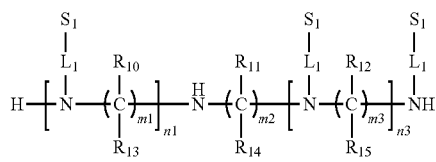

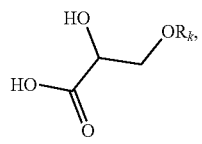

(A-1)

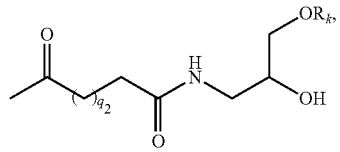

(A-2)

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively as described above.

The amidation reaction condition may comprise a reaction temperature of 0-100° C. and a reaction time of 1-48 hours.

In some embodiments, the amidation reaction condition comprises a reaction temperature of 10-40° C. and a reaction time of 2-16 hours.

In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in further embodiments, ethanol. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 3-20 L/mol, with respect to the compound as shown by Formula (314).

In some embodiments, the agent for amidation condensation is benzotriazol-1-yl-oxytripyrrolidinophosphonium hexafluorophosphate, 3-(diethoxyphosphoryloxy)-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ) or O-benzotriazol-tetramethyluronium hexafluorophosphate, and in further embodiments, 3-(diethoxyphosphoryloxy)-1,2,3-benzotrizin-4(3H)-one. The molar ratio of the agent for amidation condensation to the compound as shown by Formula (314) may be 1:1 to 10:1, and in some embodiments, 2.5:1 to 5:1.

In some embodiments, the organic base of tertiary amine is triethylamine or N,N-diisopropylethylamine, and in some embodiments, N,N-diisopropylethylamine. The molar ratio of the tertiary amine to the compound as shown by Formula (314) may be 3:1 to 20:1, and in some embodiments, 5:1 to 10:1.

The compounds of Formula (A-1) and (A-2) may be prepared by any suitable methods. For example, when $R_k$ is a DMTr group, the compound of Formula (A-1) may be prepared by reacting calcium glycerate with DMTrCl. Similarly, the compound of Formula (A-2) may be prepared by contacting 3-amino-1,2-propanediol with a cyclic anhydride and then reacting with DMTrCl, wherein the cyclic anhydride may have 4-13 carbon atoms, and in some embodiments, 4-8 carbon atoms. Those skilled in the art would readily understand that the selections of different cyclic anhydrides correspond to different values for $q_2$ in the compound of Formula (A-2). For example, when the cyclic anhydride is succinic anhydride, $q_2=1$; when the cyclic anhydride is glutaric anhydride, $q_2=2$, and so on.

In some variants, the compound of Formula (313) can also be prepared by successively reacting the compound as shown by Formula (314) with the cyclic anhydride, 3-amino-1,2-propanediol, and DMTrCl. Those skilled in the art would readily understand that these variants would not affect the structure and function of the compound of Formula (313), and these variants can be readily achieved by those skilled in the art on the basis of the above methods.

Similarly, the compound as shown by Formula (313) may be isolated from the reaction mixture by any suitable isolation methods. In some embodiments, the compound as shown by Formula (313) may be isolated by removal of solvent via evaporation followed by chromatography, for example, using the following two sets of chromatographic conditions for isolation: (1) normal phase purification: 200-300 mesh silica gel filler, gradient elution of petroleum ether:ethyl acetate:dichloromethane:N,N-dimethylformamide=1:1:1:0.5-1:1:1:0.6; and (2) reverse phase purification:

C18 and C8 reverse phase fillers, gradient elution of methanol:acetonitrile=0.1:1-1:0.1. In some embodiments, the solvent may be directly removed to obtain a crude product of the compound as shown by Formula (313), which may be directly used in subsequent reactions.

In some embodiments, the compound as shown by Formula (314) may be prepared by the following preparation method comprising contacting the compound as shown by Formula (315) with haloacetic acid in an organic solvent under deprotection reaction condition, and then isolating:

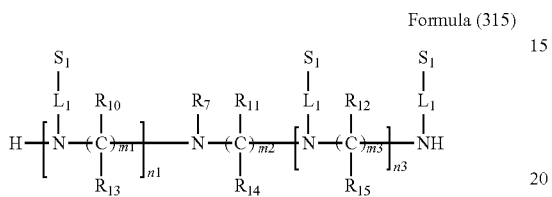

Formula (315)

wherein $R_7$ is selected from the groups as shown by Formula (330), (331), (332) and (333), and in some embodiments, $R_7$ has the structure as shown by Formula (330):

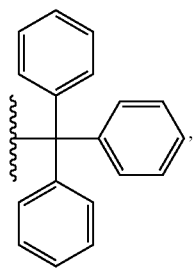

Formula (330)

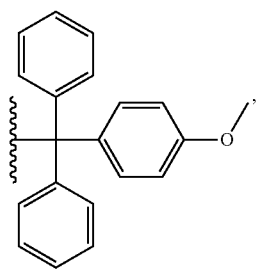

Formula (331)

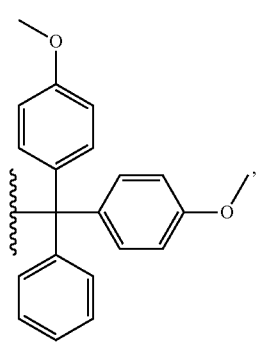

Formula (332)

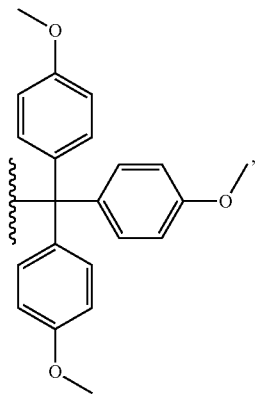

Formula (333)

wherein the definitions and options of n1, n3, m1, m2, m3, $R_{10}$, $R_{11}$, $R_{12}$, $R_{13}$, $R_{14}$, $R_{15}$, $L_1$ and $S_1$ are respectively as described above.

The haloacetic acid may be selected from one or more of dichloroacetic acid, trichloroacetic acid, monochloroacetic acid and trifluoroacetic acid, and in some embodiments, dichloroacetic acid.

The deprotection reaction condition may comprise a reaction temperature of 0-100° C. and a reaction time of 0.1-24 hours, and in some embodiments comprises a reaction temperature of 10-40° C. and a reaction time of 0.5-16 hours.

In some embodiments, the organic solvent is one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol, with respect to the compound as shown by Formula (315).

The molar ratio of the haloacetic acid to the compound as shown by Formula (315) is 5:1 to 100:1, and in some embodiments, 10:1 to 50:1.

Similarly, the compound as shown by Formula (314) may be isolated from the reaction mixture by any suitable isolation methods. In some embodiments, the compound as shown by Formula (314) may be isolated by removal of solvent via evaporation followed by chromatography, for example, using the following two sets of chromatographic conditions for isolation, (1) normal phase purification: 200-300 mesh silica gel filler, gradient elution of dichloromethane:methanol=100:30-100:40; and (2) reverse phase purification: C18 and C8 reverse phase fillers, gradient elution of methanol:acetonitrile=0.1:1-1:0.1. In some embodiments, the solvent may be directly removed to obtain a crude product of the compound as shown by Formula (314), which may be directly used in subsequent reactions.

The compound as shown by Formula (315) may be prepared by the following method comprising contacting the compound as shown by Formula (317) with the compound as shown by Formula (316) in an organic solvent under condensation reaction condition in the presence of an agent for amidation condensation and an organic base of tertiary amine, and isolating: $S_1$-$L_1$-COOH Formula (316), Formula (317)

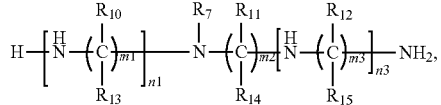

wherein the definitions and options of n1, n3, m1, m2, m3, $R_7$, $R_{10}$, $R_{11}$, $R_{12}$, $R_{13}$, $R_{14}$, $R_{15}$, $L_1$ and $S_1$ are respectively as described above.

The compound of Formula (316) can be, such as, those disclosed in J. Am. Chem. Soc. 2014, 136, 16958-16961. Alternatively, the compounds of Formula (316) may be prepared by those skilled in the art via various methods. For example, some compounds of Formula (316) may be prepared according to the methods as disclosed in Example 1 of U.S. Pat. No. 8,106,022 B2, which is incorporated herein by reference in its entirety.

In some embodiments, the condensation reaction condition comprises a reaction temperature of 0-100° C. and a reaction time of 0.1-24 hours. In some embodiments, the condensation reaction condition comprises a reaction temperature is 10-40° C. and a reaction time is 0.5-16 hours.

The molar ratio of the compound as shown by Formula (316) to the compound as shown by Formula (317) may be 2:1 to 10:1, and in some embodiments, 2.5:1 to 5:1.

In some embodiments, the organic solvent is one or more of acetonitrile, an epoxy solvent, an ether solvent, an haloalkane solvent, dimethyl sulfoxide, N,N-dimethylformamide and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is acetonitrile. The amount of the organic solvent may be 3-50 L/mol, and in some embodiments, 5-20 L/mol, with respect to the compound as shown by Formula (317).

The agent for amidation condensation is benzotriazol-1-yl-oxytripyrrolidinophosphonium hexafluorophosphate, 3-(diethoxyphosphoryloxy)-1,2,3-benzotrizin-4(3H)-one (DEPBT), O-benzotriazol-tetramethyluronium hexafluorophosphate or 4-(4,6-dimethoxytriazin-2-yl)-4-methylmorpholine hydrochloride, and in some embodiments, is 4-(4,6-dimethoxytriazin-2-yl)-4-methylmorpholine hydrochloride. The molar ratio of the agent for amidation condensation to the compound as shown by Formula (317) is 2:1 to 10:1, and in some embodiments, is 2.5:1 to 5:1.

The organic base of tertiary amine is N-methylmorpholine, triethylamine or N,N-diisopropylethylamine, and in some embodiments, N-methylmorpholine. The molar ratio of the tertiary amine to the compound as shown by Formula (317) may be 3:1 to 20:1, and in some embodiments, is 5:1 to 10:1.

Similarly, the compound as shown by Formula (315) may be isolated from the reaction mixture by any suitable isolation methods. In some embodiments, the compound as shown by Formula (315) is isolated by removal of solvent via evaporation followed by chromatography, for example, using the following two sets of chromatographic conditions for isolation, (1) normal phase purification: 200-300 mesh silica gel filler, gradient elution of dichloromethane:methanol=100:5-100:7; (2) reverse phase purification: C18 and C8 reverse phase fillers, gradient elution of methanol:acetonitrile=0.1:1-1:0.1. In some embodiments, the solvent is directly removed to obtain a crude product of the compound as shown by Formula (315), which may be directly used in subsequent reactions.

In some embodiments, the compound of Formula (317) reacts with a sufficient amount of one compound of Formula (316) in one batch to obtain the desired compound of Formula (315), wherein all $S_1$-$L_1$ moieties are identical. In some embodiments, the compound of Formula (317) reacts with different compounds of Formula (316) in batches as desired, i.e., the compounds of Formula (316) having different $L_1$ and/or $S_1$, so as to obtain the compound of Formula (315) having two or more types of $S_1$ and/or $L_1$ therein. For example, 1 eq of the compound of Formula (317) may be firstly contacted with 2 eq of a first compound of Formula (316) to attach the first $S_1$-$L_1$ moieties to the two terminal primary amine groups in the compound of Formula (317), and then contacted with the (n3+n1-1) eq of a second compound of Formula (316) to attach the second $S_1$-$L_1$ moieties to the (n3+n1-1) secondary amine groups in the compound of Formula (317), wherein the definitions and ranges of n3 and n1 are as described above.

In some embodiments, the compound as shown by Formula (317) may be prepared by the following method comprising contacting the compound as shown by Formula (318) with aqueous methylamine solution under deprotection reaction condition in the presence of an organic solvent, and isolating:

Formula (318)

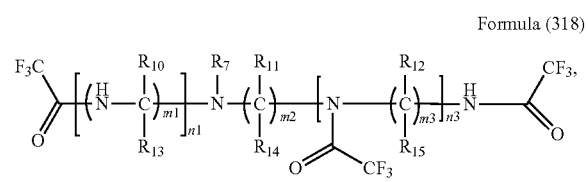

wherein the definitions and options of n1, n3, m1, m2, m3, $R_7$, $R_{10}$, $R_{11}$, $R_{12}$, $R_{13}$, $R_{14}$ and $R_{15}$ are respectively as described above.

The deprotection reaction condition comprises a reaction temperature of 0-150° C. and a reaction time of 5-72 hours, and in some embodiments comprises a reaction temperature of 20-80° C. and a reaction time of 10-30 hours.

The organic solvent is selected from alcohols, in some embodiments, is one of methanol, ethanol and isopropanol, and in some embodiments, methanol. The amount of the organic solvent may be 1-20 L/mol, and in some embodiments, is 1.5-10 L/mol, with respect to the compound as shown by Formula (318).

The concentration of the methylamine aqueous solution may be 30%-40% by mass, and the molar ratio of methylamine to the compound as shown by Formula (318) may be 10:1 to 500:1, and in some embodiments, 50:1 to 200:1.

Similarly, the compound as shown by Formula (317) may be isolated from the reaction mixture using any suitable isolation methods. In some embodiments, the compound as shown by Formula (317) may be isolated by removal of solvent via evaporation followed by chromatography, for example, using the following two sets of chromatographic conditions for isolation, (1) normal phase purification: 200-300 mesh silica gel filler, gradient elution of dichloromethane:methanol:aqueous ammonia (25 wt %)=1:1:0.05-1:1:0.25; and (2) reverse phase purification: C18 and C8 reverse phase fillers, gradient elution of methanol:acetonitrile=0.1:

1-1:0.1. In some embodiments, the solvent may be directly removed to obtain a crude product of the compound as shown by Formula (317), which may be directly used in subsequent reactions.

The compound as shown by Formula (318) may be prepared by the following method comprising contacting the compound as shown by Formula (319) with triphenylchloromethane (TrCl), diphenylethylphenylchloromethane, phenyldiethylphenylchloromethane or triethylphenylchloromethane (in some embodiments, with triphenylchloromethane (TrCl)) under substitution reaction condition in the presence of an organic solvent, and isolating:

Formula (319)

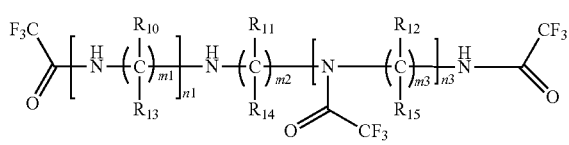

wherein the definitions and options of n1, n3, m1, m2, m3, $R_{10}$, $R_{11}$, $R_{12}$, $R_{13}$, $R_{14}$ and $R_{15}$ are respectively as described above.

The substitution reaction condition may comprise a reaction temperature of 0-100° C. and a reaction time of 5-72 hours, and in some embodiments comprises a reaction temperature of 10-40° C. and a reaction time of 10-30 hours.

Triphenylchloromethane (TrCl), diphenylethylphenylchloromethane, phenyldiethylphenylchloromethane or triethylphenylchloromethane are commercially available. The molar ratio of triphenylchloromethane (TrCl), diphenylethylphenylchloromethane, phenyldiethylphenylchloromethane or triethylphenylchloromethane to the compound as shown by Formula (319) may be 1:1 to 10:1, and in some embodiments, 1:1 to 3:1.

The organic solvent may be one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent may be 3-50 L/mol, and in some embodiments, 5-20 L/mol, with respect to the compound as shown by Formula (319).

Similarly, the compound as shown by Formula (318) may be isolated from the reaction mixture by any suitable isolation methods. In some embodiments, the compound as shown by Formula (318) may be isolated by removal of solvent via evaporation followed by chromatography, for example, using the following two sets of chromatographic conditions for isolation, (1) normal phase purification: 200-300 mesh silica gel filler, gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, gradient elution of methanol:acetonitrile=0.1:1-1:0.1. In some embodiments, the solvent may be directly removed to obtain a crude product of the compound as shown by Formula (318), which may be directly used in subsequent reactions.

In some embodiments, the compound as shown by Formula (319) may be prepared by the following method comprising contacting the compound as shown by Formula (320) with ethyl trifluoroacetate in an organic solvent under substitution reaction condition, and isolating:

Formula (320)

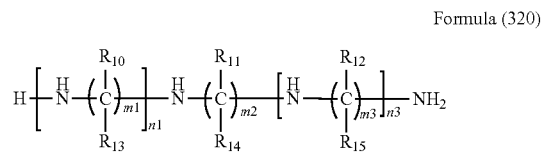

wherein the definitions and options of n1, n3, m1, m2, m3, $R_{10}$, $R_{11}$, $R_{12}$, $R_3$, $R_{14}$ and $R_{15}$ are respectively as described above.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is acetonitrile. The amount of the organic solvent is 1-50 L/mol, and in some embodiments, 1-20 L/mol, with respect to the compound as shown by Formula (320).

The substitution reaction condition may comprise a reaction temperature of 0-100° C. and a reaction time of 5-72 hours, and in some embodiments comprises a reaction temperature of 10-40° C. and a reaction time of 10-30 hours.

The compound as shown by Formula (320) may be commercially available, or obtained by those skilled in the art via the known methods. For example, in the case that m1=m2=m3=3, n1=1, n3=2, and $R_{10}$, $R_{11}$, $R_{12}$, $R_{13}$, $R_{14}$ and $R_{15}$ are all H, the compound as shown by Formula (320) is commercially available from Alfa Aesar Inc.

The molar ratio of ethyl trifluoroacetate to the compound as shown by Formula (320) may be 2:1 to 10:1, and in some embodiments, 3:1 to 5:1.

Similarly, the compound as shown by Formula (319) may be isolated from the reaction mixture using any suitable isolation methods. In some embodiments, the compound as shown by Formula (319) may be isolated by removal of solvent via evaporation followed by chromatography, for example, using the following two sets of chromatographic conditions for isolation: (1) normal phase purification: 200-300 mesh silica gel filler, gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, gradient elution of methanol:acetonitrile=0.1:1-1:0.1. In some embodiments, the solvent may be directly removed to obtain a crude product of the compound as shown by Formula (319), which may be directly used in subsequent reactions.

The first or second siRNA conjugate of the present disclosure may also be used in combination with other pharmaceutically acceptable excipients, which may be one or more of the various conventional formulations or compounds in the art. For details, please refer to the above description of the pharmaceutical compositions of the present disclosure.

Use of the Modified siRNA, the Pharmaceutical Composition, the First siRNA Conjugate and the Second siRNA Conjugate of the Present Disclosure In some embodiments, provided herein is use of the siRNA, the pharmaceutical composition, the first siRNA conjugate and/or the second siRNA conjugate of the present disclosure in the manufacture of a medicament for treating and/or preventing pathological conditions or diseases caused by hepatitis B virus (HBV) infection.

According to some embodiments, provided herein is a method for treating pathological conditions or diseases caused by hepatitis B virus (HBV) infection, comprising administering an effective amount of the siRNA, the pharmaceutical composition, the first siRNA conjugate and/or the second siRNA conjugate of the present disclosure to a patient.

According to other embodiments, provided herein is a method for inhibiting the expression of HBV genes in hepatitis cells infected with chronic HBV, comprising contacting the siRNA, the pharmaceutical composition, the first siRNA conjugate and/or the second siRNA conjugate of the present disclosure with the hepatitis cells infected with chronic HBV.

The pathological condition or disease caused by hepatitis B virus (HBV) infection is selected from chronic liver diseases, inflammation, fibrotic diseases, and proliferative diseases.

It is possible to achieve the purpose of treating hepatitis B based on the mechanism of RNA interference (RNAi) by administering the siRNA and/or the pharmaceutical composition, the first siRNA conjugate and/or the second siRNA conjugate of the present invention to a patient in need thereof. Thus, the siRNA and/or the pharmaceutical composition and the siRNA conjugates of the present disclosure may be used for preventing and/or treating hepatitis B, or for preparing a medicament for preventing and/or treating hepatitis B.

As used herein, the term "administration/administer" refers to the delivery of the modified siRNA, the pharmaceutical composition, the first siRNA conjugate and/or the second siRNA conjugate of the present disclosure into a subject's body by a method or a route that at least partly locates the modified siRNA, the pharmaceutical composition, the first siRNA conjugate and/or the second siRNA conjugate of the present disclosure at a desired site to produce a desired effect. Suitable administration routes for the methods of the present disclosure include topical administration and systemic administration. In general, topical administration results in the delivery of more modified siRNA, pharmaceutical composition, first siRNA conjugate and/or second siRNA conjugate to a particular site compared with the whole body of the subject; whereas systemic administration results in the delivery of the modified siRNA, pharmaceutical composition, first siRNA conjugate and/or second siRNA conjugate to substantially the whole body of the subject. Considering that the present invention is intended to provide a means for the prevention and/or treatment of dyslipidemia, in some embodiments, an administration mode capable of delivering drugs to liver is used.

The administration to a subject may be achieved by any suitable routes known in the art, including but not limited to, oral or parenteral route, such as intravenous administration, intramuscular administration, subcutaneous administration, transdermal administration, intratracheal administration (aerosol), pulmonary administration, nasal administration, rectal administration and topical administration (including buccal administration and sublingual administration). The administration frequency may be once or more times daily, weekly, biweekly, triweekly, monthly, or yearly.

The dose of the siRNA, the pharmaceutical composition, the first siRNA conjugate and/or the second siRNA conjugate of the present disclosure may be a conventional dose in the art, which may be determined according to various parameters, especially age, weight and gender of a subject. Toxicity and efficacy may be measured in cell cultures or experimental animals by standard pharmaceutical procedures, for example, by determining LD50 (the lethal dose that causes 50% population death) and ED50 (the dose that can cause 50% of the maximum response intensity in a quantitative response, and that causes 50% of the experimental subjects to have a positive response in a qualitative response). The dose range for human may be derived based on the data obtained from cell culture assays and animal studies.

When administrating the pharmaceutical composition or the siRNA conjugate of the present invention, for example, to male or female C57BL/6J or C3H/HeNCrlVr mice of 6-12 weeks old and 18-25 g body weight, and calculating based on the amount of the siRNA in the pharmaceutical composition or the siRNA conjugate: (i) for the first siRNA conjugate and/or the second siRNA conjugate, the dosage of siRNA thereof may be 0.001-100 mg/kg body weight, and in further embodiments is 0.01-50 mg/kg body weight, and in still further embodiments is 0.05-20 mg/kg body weight, and in still yet further embodiments is 0.1-10 mg/kg body weight; (ii) for a pharmaceutical composition formed by a siRNA and a pharmaceutically acceptable carrier, the dosage of siRNA thereof may be 0.001-50 mg/kg body weight, and in further embodiments is 0.01-10 mg/kg body weight, and in still further embodiments is 0.05-5 mg/kg body weight, and in still yet further embodiments is 0.1-3 mg/kg body weight.

Furthermore, by introducing the siRNA and/or the pharmaceutical composition and/or the siRNA conjugates of the present invention into hepatitis cells infected with chronic HBV, the purpose of inhibiting the expression of HBV gene in the hepatitis cells infected with chronic HBV may also be achieved by the mechanism of RNA interference. In some preferred embodiments, the cells are HepG2.2.15 cells.

In the case where the expression of HBV genes in cells is inhibited by using the method provided by the present invention, the amount of siRNA in the siRNA, pharmaceutical composition, first siRNA conjugate and/or second siRNA conjugate provided is typically an amount sufficient to reduce the expression of the target gene and result in an extracellular concentration of 1 pM to 1 µM, or 0.01 nM to 100 nM, or 0.05 nM to 50 nM or 0.05 nM to about 5 nM on the surface of the target cells. The amount required to achieve this local concentration will vary with various factors, including the delivery method, the delivery site, the number of cell layers between the delivery site and the target cells or tissues, the delivery route (topical or systemic), etc. The concentration at the delivery site may be significantly higher than that on the surface of the target cells or tissues.

Kit

Provided herein is a kit comprising an effective amount of at least one of the modified siRNA, the pharmaceutical composition, the first siRNA conjugate and/or the second siRNA conjugate.

In some embodiments, the kits disclosed herein provide modified siRNA in one container. In some embodiments, the kit of the present disclosure comprises a container comprising pharmaceutically acceptable excipients. In some embodiments, the kis of the present disclosure further comprises additional ingredients, such as stabilizers or preservatives. In some embodiments, the kit comprises at least one additional therapeutic agent in other container than the container comprising the modified siRNA of the present disclosure. In some embodiments, the kit comprises an instruction for mixing the modified siRNA with pharmaceutically acceptable carriers and/or adjuvants or other ingredients (if any).

In the kits of the present disclosure, the modified siRNA and pharmaceutically acceptable carriers and/or adjuvants as well as the modified siRNA, pharmaceutical composition, first siRNA conjugate and/or second siRNA conjugate and/or conjugate, and/or pharmaceutically acceptable adjuvants may be provided in any form, e.g., in a liquid form, a dry form, or a lyophilized form. In some embodiments, the modified siRNA and pharmaceutically acceptable carriers and/or adjuvants as well as the pharmaceutical composition and/conjugate and optional pharmaceutically acceptable adjuvants are substantially pure and/or sterile. In some embodiments, sterile water may be provided in the kits of the present disclosure.

Advantageous Effects

In some embodiments, the siRNA, siRNA composition or siRNA conjugate provided herein can have higher stability, lower toxicity, and/or higher activity in vivo. In some embodiments, the siRNA, siRNA composition or siRNA conjugate of the present disclosure exhibits an inhibition percentage of HBV gene expression of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of HBV gene expression in liver of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of HBV gene expression in liver in animal models of at least 20%, 30%, 40%, 50%, 60%, 70%, 80%, 90%, or 95% in vivo. In some embodiments, the siRNA, siRNA composition or siRNA conjugate of the present disclosure exhibits an inhibition percentage of HBV surface antigen expression of at least 20%, 30%, 40%, 50%, 60%, 70%, 80%, 90%, or 95% in vivo. In some embodiments, the double-stranded oligonucleotide, composition or oligonucleotide conjugate of the present disclosure exhibits no significant off-target effect. An off-target effect may be for example inhibition of normal expression of a gene which is not the target gene. It is considered that if the binding/inhibition of the expression of an off-target gene is 50%, 40%, 30%, 20%, or 10% lower than that of the target activity, then the off-target effect is not significant.

In some embodiments, the siRNA conjugates provided herein has lower toxicity at animal level.

In some embodiments, the siRNA conjugates provided herein can remain undegraded in up to 72 hours in human plasma, showing excellent stability in human plasma.

In some embodiments, the siRNA conjugates provided herein can remain undegraded in up to 72 hours in cynomolgus monkey plasma, showing excellent stability in monkey plasma.

In some embodiments, the siRNA conjugates provided herein can remain undegraded for at least 24 hours either in human- and rat-originated lysosome lysate, showing satisfactory stability.

In some embodiments, the siRNA conjugates provided herein can be specifically and significantly enriched in liver and remain stable, showing a high degree of targeting.

In some embodiments, in several experiments with different testing time points the siRNA conjugates provided herein show high inhibitory activity against the expression of HBV mRNA in mice in vivo.

In some embodiments, the siRNA conjugates provided herein exhibit prolonged and efficient inhibitory efficiency on serum HBsAg in various animal models, showing regular dose dependency.

In some embodiments, the siRNA conjugates provided herein not only have higher activity in intro, but also show low off-target effects.

Hereinafter, the present disclosure will be further described by preparation examples and experimental examples, but is not limited thereto in any respect.

EXAMPLES

Hereinafter, the present disclosure will be described in detail with reference to the examples. Unless otherwise specified, the agents and culture media used in following examples are all commercially available, and the procedures used such as nucleic acid electrophoresis and real-time PCR are all performed according to methods described in Molecular Cloning (Cold Spring Harbor Laboratory Press (1989)).

Unless otherwise specified, ratios of reagents provided below are all calculated by volume ratio (v/v).

HBV transgenic mice C57BL/6J-Tg (Alb1HBV) 44Bri/J: purchased from Department of Laboratory Animal Science, Peking University Health Science Center. Mice with S/COV>10 are selected before experiments; hereinafter sometimes also referred to as 44Bri model mice;

HBV transgenic mice: named M-Tg HBV, purchased from Department of Animal, Shanghai Public Health Center. The preparation methods of transgenic mice were described as Ren J. et al., in J. Medical Virology. 2006, 78:551-560; hereinafter sometimes also referred to as M-Tg model;

AAV-HBV transgenic mice: prepared according to the literature method (Xiaoyan Dong et al., Chin J Biotech 2010, May 25; 26(5): 679-686) by using rAAV8-1.3HBV, D type (ayw) virus (purchased from Beijing FivePlus Molecular Medicine Institute Co. Ltd., $1\times10^{12}$ viral genome (v.g.)/mL, Lot number 2016123011). The rAAV8-1.3HBV was diluted to $5\times10^{11}$ v.g./mL with sterile PBS. 200 µL of the diluted rAAV8-1.3HBV was injected into each mouse, i.e., $1\times10^{11}$ v.g. per mouse. The orbital blood (about 100 µL) was taken from all mice on day 28 after injection of the virus to collect serum for detection of HBsAg and HBV DNA; hereinafter also referred to as AAV-HBV model mice;

Low-concentration AAV-HBV transgenic mice: using substantially the same modeling method as described above, the difference was that the virus was diluted to $1\times10^{11}$ v.g./mL with sterile PBS before the experiment. 100 µL virus was injected into each mouse, i.e., $1\times10^{10}$ v.g. per mouse; hereinafter sometimes also referred to as AAV-HBV low-concentration mouse model;

HBV transgenic mice: C57BL/6-HBV, Strain name: B6-Tg HBV/Vst (1.28 copy, genotype A), purchased from Beijing Vitalstar Biotechnology Co., Ltd. Mice with COI>$10^4$ are selected before experiments; hereinafter sometimes also referred to as 1.28 copy model.

Preparation Example 1 Preparation of Conjugates 1-11

In this preparation example, Conjugate 1 (hereinafter also referred to as L10-siHBa1M1SVP conjugate), Conjugate 2

(hereinafter also referred to as L10-siHBa1M1SP conjugate), Conjugate 3 (hereinafter also referred to as L10-siHBa1M1SPsT conjugate), Conjugate 4 (hereinafter also referred to as L10-siHBa1M1SPs conjugate), Conjugate 5 (hereinafter also referred to as L10-siHBa1M2S), Conjugate 6 (hereinafter also referred to as L10-siHBa1M2S), Conjugate 7 (hereinafter also referred to as L10-siHBa2M1S), Conjugate 8 (hereinafter also referred to as L10-siHBa1M1S), Conjugate 9 (hereinafter also referred to as L10-siHBa1M2S), Conjugate 10 (hereinafter also referred to as L10-siHBa2M2S), and Conjugate 11 (hereinafter also referred to as L10-siHBa2M1S) were synthesized. The conjugates were those formed by conjugating L-9 Conjugating Molecule respectively with the siRNA numbered as L10-siHBa1M1SVP, L10-siHBa1M1SP, L10-siHBa1M1SPsT, L10-siHBa1M1SPs, L10-siHBa1M2S, L10-siHBa1M2S, L10-siHBa2M1S, L10-siHBa1M1S, L10-siHBa1M2S), L10-siHBa2M2S, or L10-siHBa2M1S. The conjugated siRNA sequences in the conjugates were shown in Table 3.

(1-1) Synthesis of Compound L-10

A Compound L-10 was synthesized according to the following method:

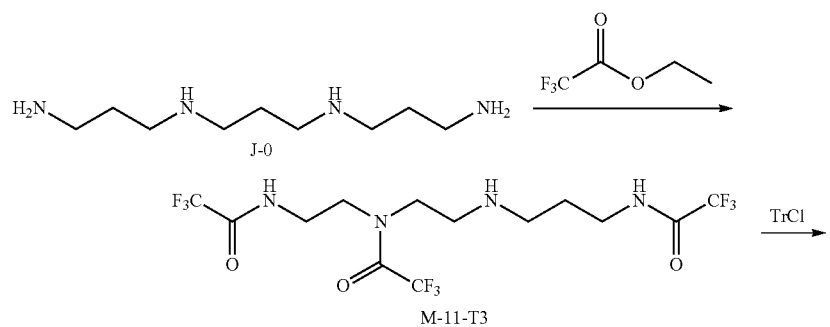

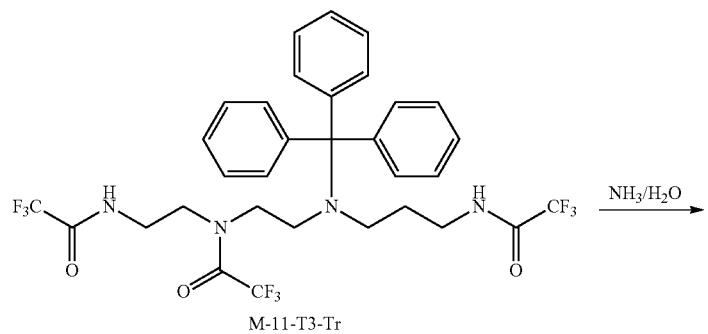

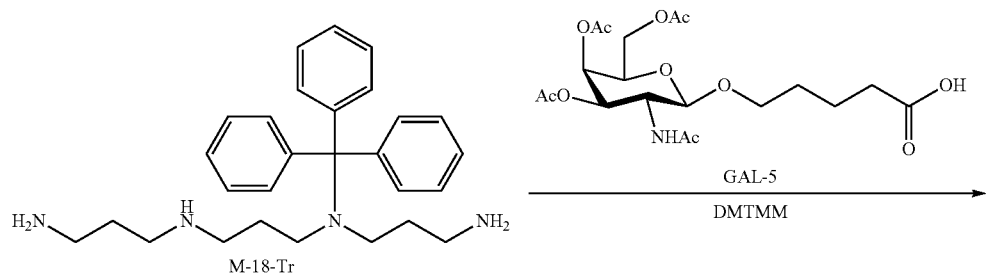

-continued
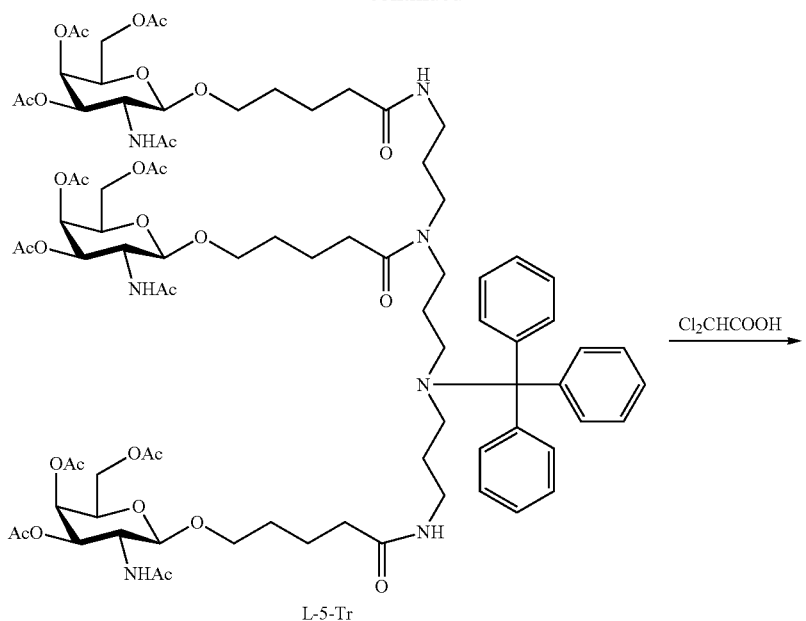
L-5-Tr
$\xrightarrow{Cl_2CHCOOH}$
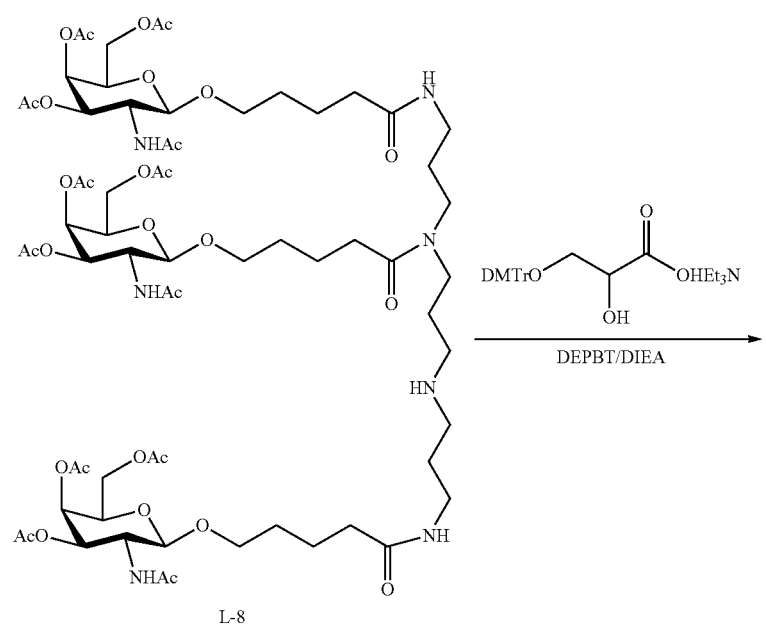
L-8
$\xrightarrow{\text{DEPBT/DIEA}}$ -continued
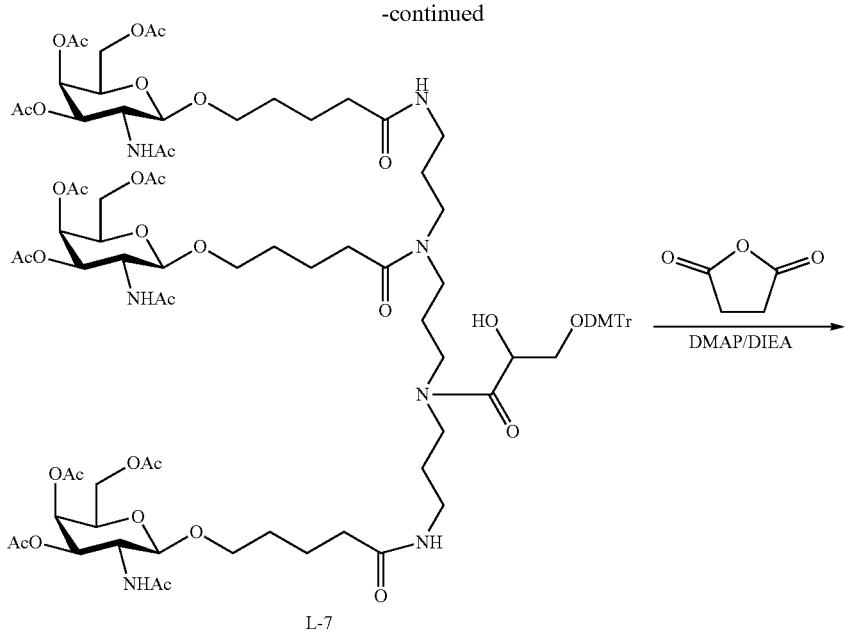
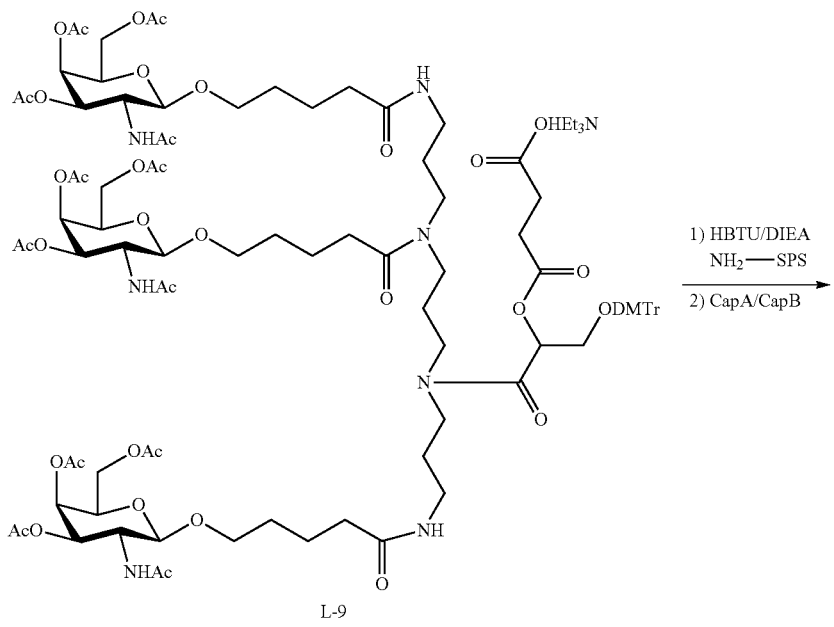

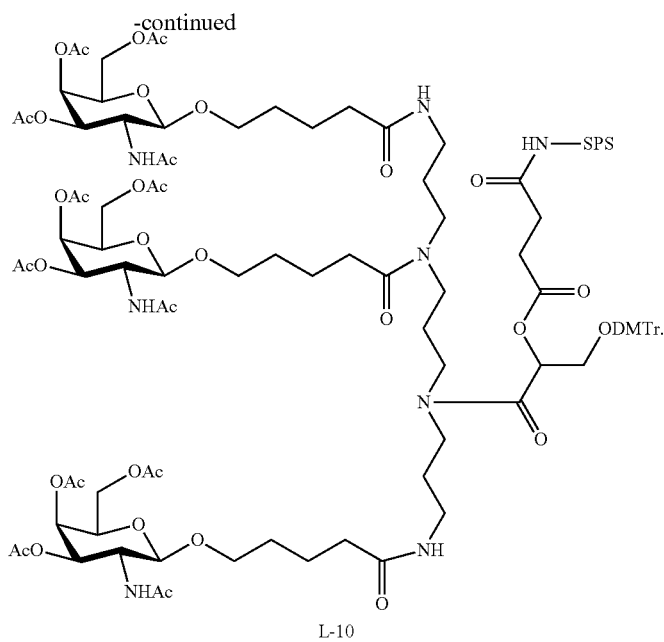
L-10
(1-1-1) Synthesis of GAL-5 (a Terminal Segment of the Conjugating Molecule)
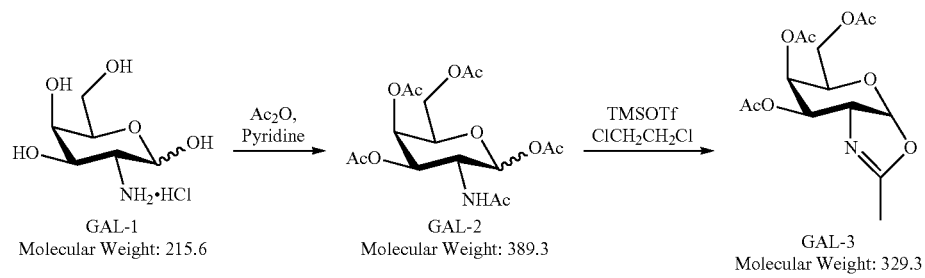
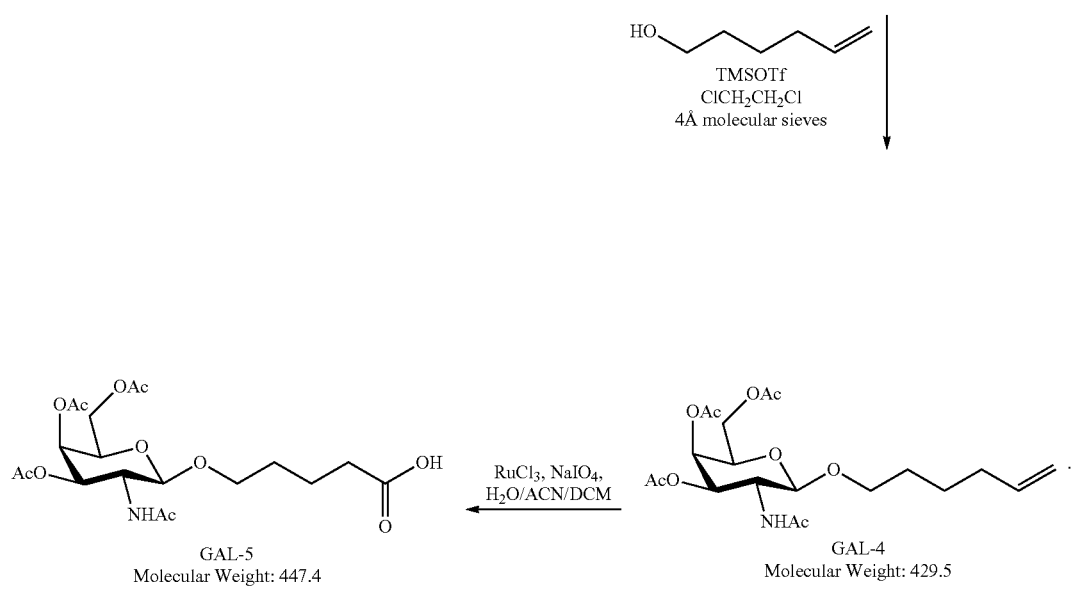

(1-1-1a) Synthesis of GAL-2

100.0 g of GAL-1 (N-acetyl-D-galactosamine hydrochloride, CAS No.: 1772-03-8, purchased from Ningbo Hongxiang Bio-Chem Co., Ltd., 463.8 mmol) was dissolved in 1000 mL of anhydrous pyridine, to which 540 mL of acetic anhydride (purchased from Enox Inc., 5565.6 mmol) was added in an ice water bath to react under stirring at room temperature for 1.5 hours. The resultant reaction solution was poured into 10 L of ice water and subjected to suction filtration under reduced pressure. The residue was washed with 2 L of ice water, and then added with a mixed solvent of acetonitrile/toluene (v/v ratio=1:1) until completely dissolved. The solvent was removed by evaporation to give 130.0 g of product GAL-2 as a white solid.

(1-1-1b) Synthesis of GAL-3

GAL-2 (35.1 g, 90.0 mmol) obtained in step (1-1-1a) was dissolved in 213 mL of anhydrous 1,2-dichloroethane, to which 24.0 g of TMSOTf (CAS No.: 27607-77-8, purchased from Macklin Inc., 108.0 mmol) was added under an ice water bath and nitrogen atmosphere to react at room temperature overnight.

400 mL dichloromethane was added to the reaction solution for dilution, filtered with diatomite, and then added with 1L saturated aqueous sodium bicarbonate solution and stirred evenly. An organic phase was isolated. The aqueous phase remained was extracted twice, each with 300 ml of dichloroethane, and all organic phases were combined and washed with 300 ml of saturated aqueous sodium bicarbonate solution and 300 ml of saturated brine, respectively. The organic phase resulted from washing was isolated and dried with anhydrous sodium sulfate. The solvent was removed by evaporation under reduced pressure to give 26.9 g of product GAL-3 as a light yellow viscous syrup.

(1-1-1c) Synthesis of GAL-4

GAL-3 (26.9 g, 81.7 mmol) obtained in step (1-1-1b) was dissolved in 136 ml of anhydrous 1,2-dichloroethane, added with 30 g of dry 4 Å molecular sieve powder followed by 9.0 g of 5-hexen-1-ol (CAS No.: 821-41-0, purchased from Adamas-beta Inc., 89.9 mmol), and stirred at room temperature for 30 minutes. 9.08 ml of TMSOTf (40.9 mmol) was added in an ice bath and nitrogen atmosphere to react under stirring at room temperature overnight. The 4 Å molecular sieve powder was removed by filtration. The filtrate was added with 300 ml dichloroethane for dilution, filtered with diatomite, and then added with 500 ml of saturated aqueous sodium bicarbonate solution and stirred for 10 minutes for washing. An organic phase was isolated. The aqueous phase was extracted once with 300 ml of dichloroethane. All organic phases were combined and washed with 300 ml of saturated aqueous sodium bicarbonate solution and 300 ml of saturated brine respectively. The organic phase resulted from the washing was isolated and dried with anhydrous sodium sulfate. The solvent was removed by evaporation under reduced pressure to give 41.3 g of product GAL-4 as a yellow syrup, which was directly used in the next oxidation reaction without purification.

(1-1-1d) Synthesis of GAL-5

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react at room temperature overnight. The resultant reaction solution was diluted by adding 300 ml of water under stirring, and adjusted to a pH of about 7.5 by adding saturated sodium bicarbonate. The organic phase was isolated and discarded. The aqueous phase was extracted three times, each with 200 ml of dichloromethane, and the organic phase resulted from the extraction was discarded. The aqueous phase resulted from the extraction was adjusted to a pH of about 3 with citric acid solids and extracted three times, each with 200 ml of dichloromethane, and the resultant organic phases were combined and dried with anhydrous sodium sulfate. The solvent is removed by evaporation under reduced pressure to give 6.5 g of product GAL-5 as a white foamy solid. $^1$H NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of M-11-T3

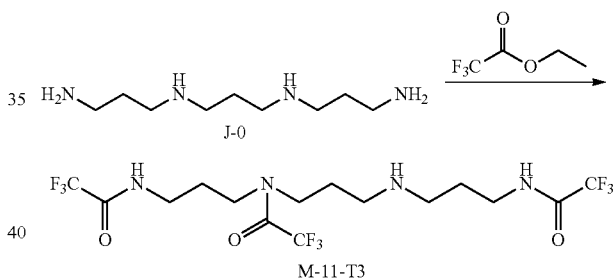

J-0 (1.883 g, 10 mmol, purchased from Alfa Aesar) was dissolved in 25 ml of acetonitrile, added with triethylamine (4.048 g, 40 mmol), and cooled to 0° C. in an ice water bath. Ethyl trifluoroacetate (5.683 g, 40 mmol) was added to react at room temperature for 22 hours. The solvent was removed by evaporation under reduced pressure, and the residue was foam-dried in a vacuum oil pump for 18 hours to give 5.342 g of crude solid product M-11-T3, which was directly used in subsequent reaction without further purification. MS m/z: C15H22F9N4O3, [M+H]+, calcd: 477.35, measured: 477.65.

(1-1-3) Synthesis of M-11-T3-Tr

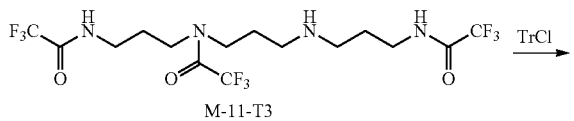

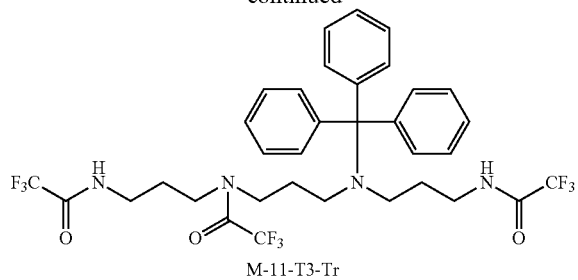

M-11-T3-Tr

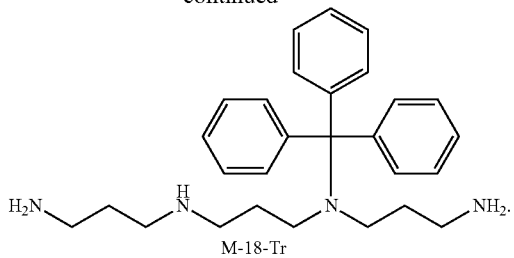

M-18-Tr

The crude product M-11-T3 (5.342 g, 10 mmol) was dissolved in 50 ml of dichloromethane. The resultant reaction solution was added with TrCl (3.345 g, 12 mmol) and triethylamine (1.518 g, 15 mmol) to react under stirring at room temperature for 20 hours. The reaction solution was washed twice, each with 20 ml of saturated sodium bicarbonate and once with 20 ml of saturated brine. The resultant organic phase was dried with anhydrous sodium sulfate and filtered. The organic solvent was removed by evaporation under reduced pressure, and the residue was foam-dried in a vacuum oil pump overnight to give 7.763 g of crude solid product M-11-T3-Tr. MS m/z: C34H36F9N4O3, [M+Na]+, calcd: 741.25, measured: 741.53. The crude solid product M-11-T3-Tr was then used in the next step for synthesis of M-18-Tr without purification.

(1-1-4) Synthesis of M-18-Tr

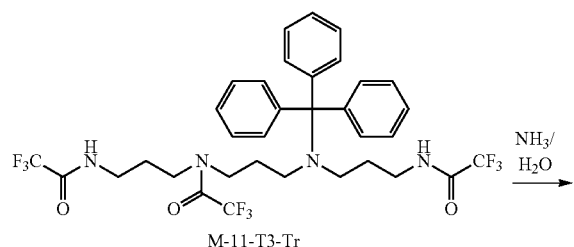

M-11-T3-Tr

The crude product M-11-T3-Tr (7.763 g, 10 mmol) obtained in step (1-1-3) was dissolved in 100 ml of methanol, and added with 100 ml of aqueous methylamine solution (40 mass %) to react under stirring at 50° C. for 23 hours. Insoluble particles were removed by filtration. The solvent was evaporated under reduced pressure, and to the residue was added 200 ml of mixed solvent of DCM:methanol in a volume ratio of 1:1, washed with 50 ml of saturated sodium bicarbonate. The aqueous phase was extracted three times, each with 50 ml of dichloromethane. All organic phases were combined, dried with anhydrous sodium sulfate and filtered. The solvent was removed by evaporation under reduced pressure, and the residue was foam-dried in a vacuum oil pump overnight, and purified by using a normal phase silica gel column (200-300 mesh). The column was packed with petroleum ether and added with 1 wt % triethylamine for neutralizing the acidity of silica gel, and eluted with a gradient elution of dichloromethane:methanol:aqueous ammonia (25 wt %)=1:1:0.05-1:1:0.25. The eluate was collected, the solvent was removed by evaporation under reduced pressure, and the residue was foam-dried in a vacuum oil pump to give 2.887 g of pure product M-18-Tr. $^1$H NMR (400 MHz, DMSO) δ7.47-7.39 (m, 6H), 7.32-7.24 (m, 6H), 7.19-7.12 (m, 3H), 2.60-2.47 (m, 4H), 2.46-2.19 (m, 13H), 1.70-1.55 (m, 4H), 1.40 (p, J=6.8 Hz, 2H). MS m/z: C28H39N4, [M+H]+, calcd: 431.65, measured: 432.61.

(1-1-5) Synthesis of L-5-Tr

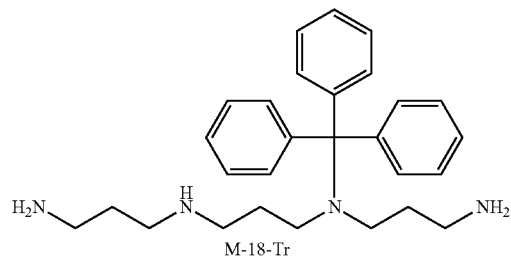

M-18-Tr

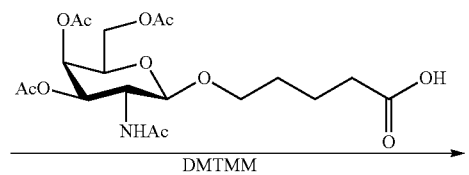

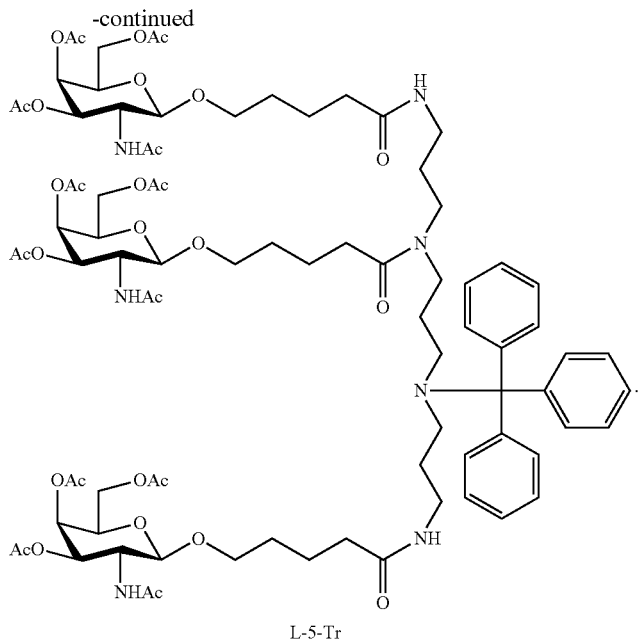

L-5-Tr

M-18-Tr (2.02 g, 4.69 mmol) obtained in step (1-1-4) and GAL-5 (6.93 g, 15.48 mmol) obtained in step (1-1-1) were mixed and dissolved in 47 ml of acetonitrile, and added with N-methylmorpholine (3.13 g, 30.96 mmol) and 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 200 ml of dichloromethane. The organic phase was washed with 100 ml of a saturated sodium bicarbonate solution and 100 ml of saturated brine, dried with anhydrous sodium sulfate, and filtered. Then the solvent was removed by evaporation under reduced pressure to give a crude product. The crude product was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and evaporated to dryness under reduced pressure to give 7.49 g of pure product L-5-Tr. $^1$H NMR (400 MHz, DMSO) δ7.83-7.10 (m, 4H), 7.67-7.60 (m, 1H), 7.44-7.34 (m, 6H), 7.33-7.24 (m, 6H), 7.20-7.15 (m, 3H), 5.22 (s, 3H), 4.97 (d, J=11.3 Hz, 3H), 4.49 (d, J=8.4 Hz, 3H), 4.06-3.07 (m, 9H), 3.95-3.83 (m, 3H), 3.77-3.64 (m, 3H), 3.45-3.35 (m, 3H), 3.12-2.87 (m, 8H), 2.30-2.15 (m, 3H), 2.11-1.98 (m, 22H), 1.95-1.84 (m, 11H), 1.81-1.61 (m, 14H), 1.54-1.36 (m, 14H).MS m/z: C85H119N7O30, [M+H]+, calcd: 1718.81, measured: 1718.03.

(1-1-6) Synthesis of L-8

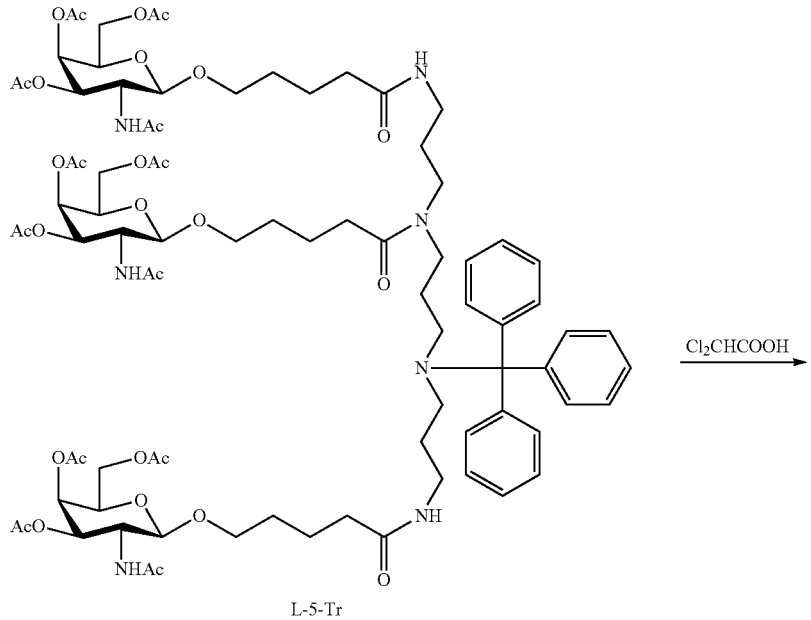

L-5-Tr → Cl$_2$CHCOOH

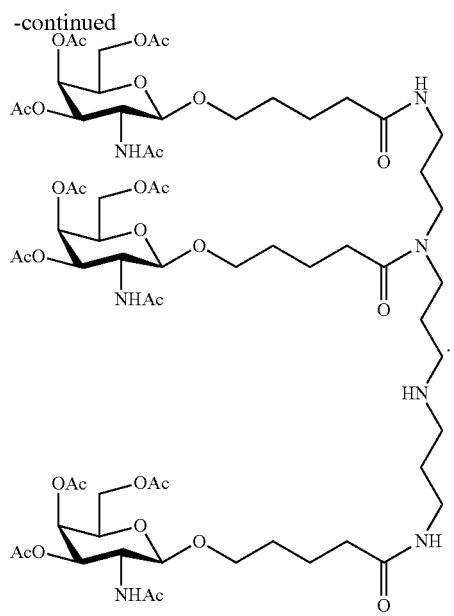

L-8

L-5-Tr (5.94 g, 3.456 mmol) obtained in step (1-1-5) was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjusted to pH 7-8 with saturated sodium bicarbonate solution. The aqueous phase isolated was extracted six times, each with 30 ml of dichloromethane. All organic phases were combined, dried with anhydrous sodium sulfate, and filtered. Then the solvent was removed by evaporation under reduced pressure to give a crude product. The crude product was purified by using a normal phase silica gel column (200-300 mesh). The column was added with 10 wt % triethylamine for neutralizing the acidity of silica gel and equilibrated with 1 wt ‰ triethylamine, and eluted with a gradient elution of dichloromethane:methanol=100:30-100:40. The eluate was collected, and the solvent was removed by evaporation under reduced pressure to give 4.26 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H).MS m/z: C85H119N7O30, [M+H]+, calcd: 1477.59, measured: 1477.23.

(1-1-7a) Synthesis of A-1

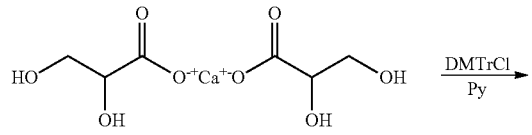

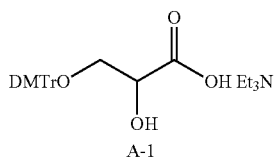

A-1

DMTrCl (4,4'-dimethoxytrityl chloride, 38.12 g, 112.5 mmol) was dissolved in 450 ml of anhydrous pyridine, and added with calcium DL-glycerate hydrate (12.88 g, 45.0 mmol) to react at 45° C. for 22 hours. The reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). The aqueous phase isolated was extracted twice, each with 200 ml of dichloromethane. All organic phases were combined, dried with anhydrous sodium sulfate, and filtered. The solvent was removed by evaporation under reduced pressure, and the residue was purified by using a normal phase silica gel column (200-300 mesh) which was eluted with a gradient elution of petroleum ether:ethyl acetate:dichloromethane:methanol=1:1:1:0.35-1:1:1:0.55. The eluate was collected, and the solvent was removed by evaporation under reduced pressure. The residue was redissolved in 500 ml of dichloromethane, and washed once with 200 ml of 0.5 M triethylamine phosphate. The aqueous phase isolated was extracted twice, each with 200 ml of dichloromethane. All organic phases were combined, dried with anhydrous sodium sulfate, and filtered. The solvent was removed by evaporation under reduced pressure (reduced pressure in a vacuum oil pump) to dryness overnight to give 20.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: C24H23O6, [M−H]⁻, calcd: 407.15, measured: 406.92.

(1-1-7b) Synthesis of L-7

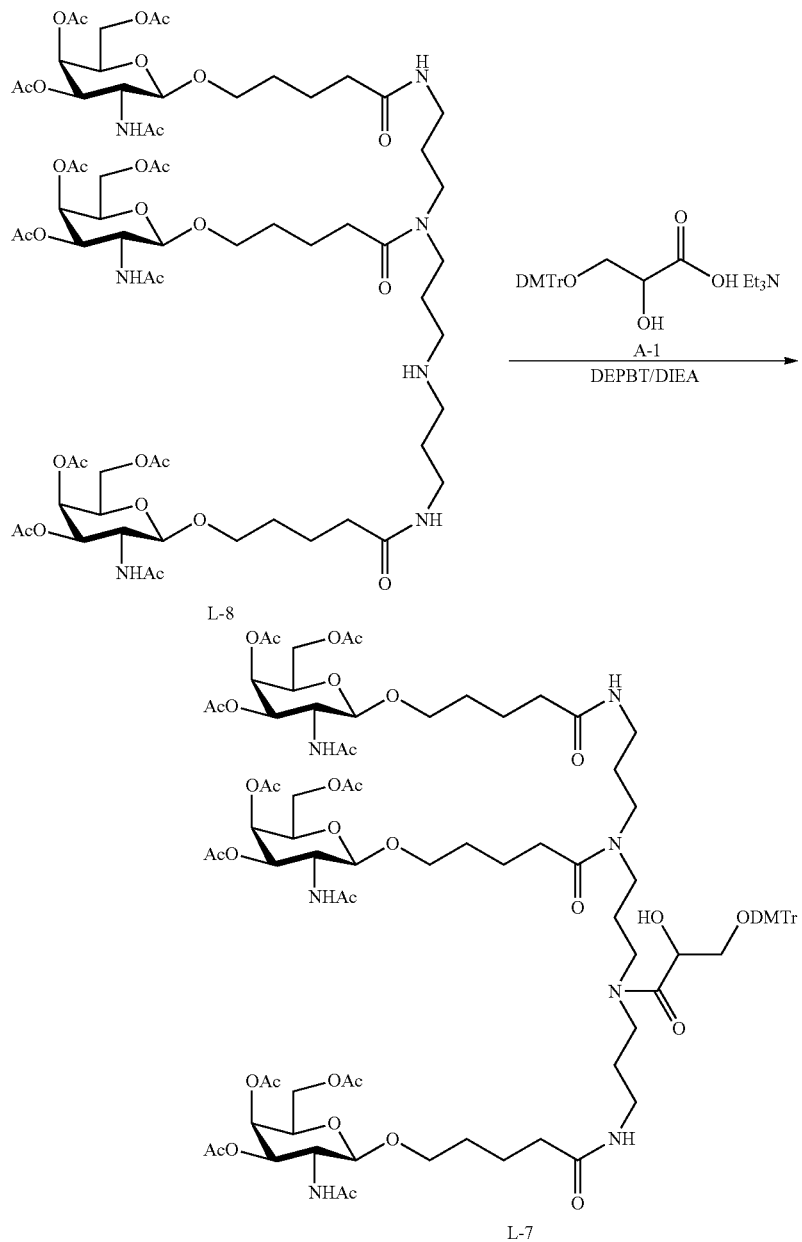

L-8 (2.262 g, 1.532 mmol) obtained in step (1-1-6) and A-1 (2.342 g, 4.596 mmol) obtained in step (1-1-7a) were mixed and dissolved in 16 ml of dichloromethane, added with 3-(diethoxyphosphoryloxy)-1,2,3-benzotrizin-4(3H)-one (DEPBT, 1.375 g, 4.596 mmol), and further added with diisopropylethylamine (1.188 g, 9.191 mmol) to react under stirring at 25° C. for 2 hours. The organic phase was washed with 10 ml of saturated sodium bicarbonate. The aqueous phase isolated was extracted three times, each with 10 ml of dichloromethane. All organic phases were combined and washed with 10 ml of saturated brine, and the aqueous phase isolated was extracted twice, each with 10 ml of dichloromethane, and the obtained organic phases were combined, dried with anhydrous sodium sulfate and filtered. The solvent was removed by evaporation under reduced pressure, and the residue was foam-dried in a vacuum oil pump overnight to give 4.900 g of crude product. The crude product was subjected to a column purification. The column was filled with 120 g normal phase silica gel (200-300 mesh), added with 20 mL triethylamine for neutralizing the acidity of silica gel, equilibrated with petroleum ether containing 1 wt % triethylamine, and eluted with a gradient elution of petroleum ether:ethyl acetate:dichloromethane:N,N-dimethylformamide=1:1:1:0.5-1:1:1:0.6. The eluate was collected, and the solvent was removed by evaporation under reduced pressure to give 2.336 g of pure product L-7. ¹H NMR (400 MHz, DMSO) 57.90-7.78 (m, 4H), 7.75-7.64 (m, 1H), 7.38-7.18 (m, 9H), 6.91-6.83 (m, 4H), 5.25-5.10

(m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 3H), 1.80-1.40 (m, 28H).MS m/z: C90H128N7O35, [M-DMTr]+, calcd: 1564.65, measured: 1564.88.

(1-1-8) Synthesis of L-9 Conjugating Molecule

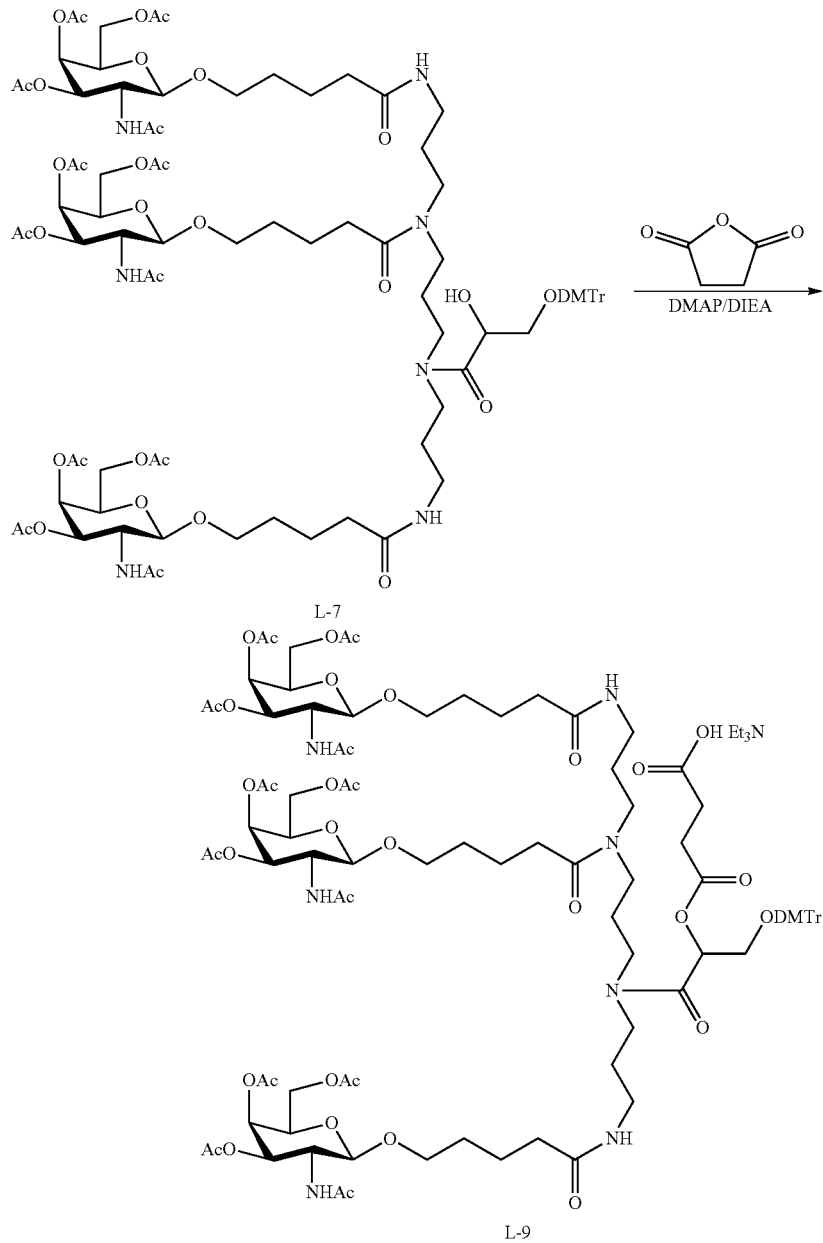

L-7 (2.300 g, 1.26 mmol) obtained in step (1-1-7b), succinic anhydride (0.378 g, 3.78 mmol) and 4-dimethylaminopyridine (DMAP, 0.462 g, 3.78 mmol) were mixed and dissolved in 13 ml of dichloromethane, further added with DIPEA (0.814 g, 6.30 mmol), and stirred at 25° C. for 24 hours. The reaction solution was washed with 5 ml of 0.5 M triethylamine phosphate. The aqueous phase was extracted three times, each with 5 ml of dichloromethane. All organic phases were combined, and the solvent was evaporated under reduced pressure to give 2.774 g of a crude product. The crude product was subjected to a column purification. The column was filled with 60 g normal phase silica gel (200-300 mesh), added with 1 wt % triethylamine for neutralizing the acidity of silica gel, equilibrated with dichloromethane and eluted with a gradient elution of 1 wt ‰ triethylamine-containing dichloromethane:methanol=100:18-100:20. The eluate was collected, and the solvent was evaporated under reduced pressure to give 1.874 g of pure product of L-9 Conjugating Molecule. $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88

(dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: C94H132N7O38, [M-DMTr]+, calcd: 1664.72, measured: 1665.03.

(1-1-9) Synthesis of Compound L-10

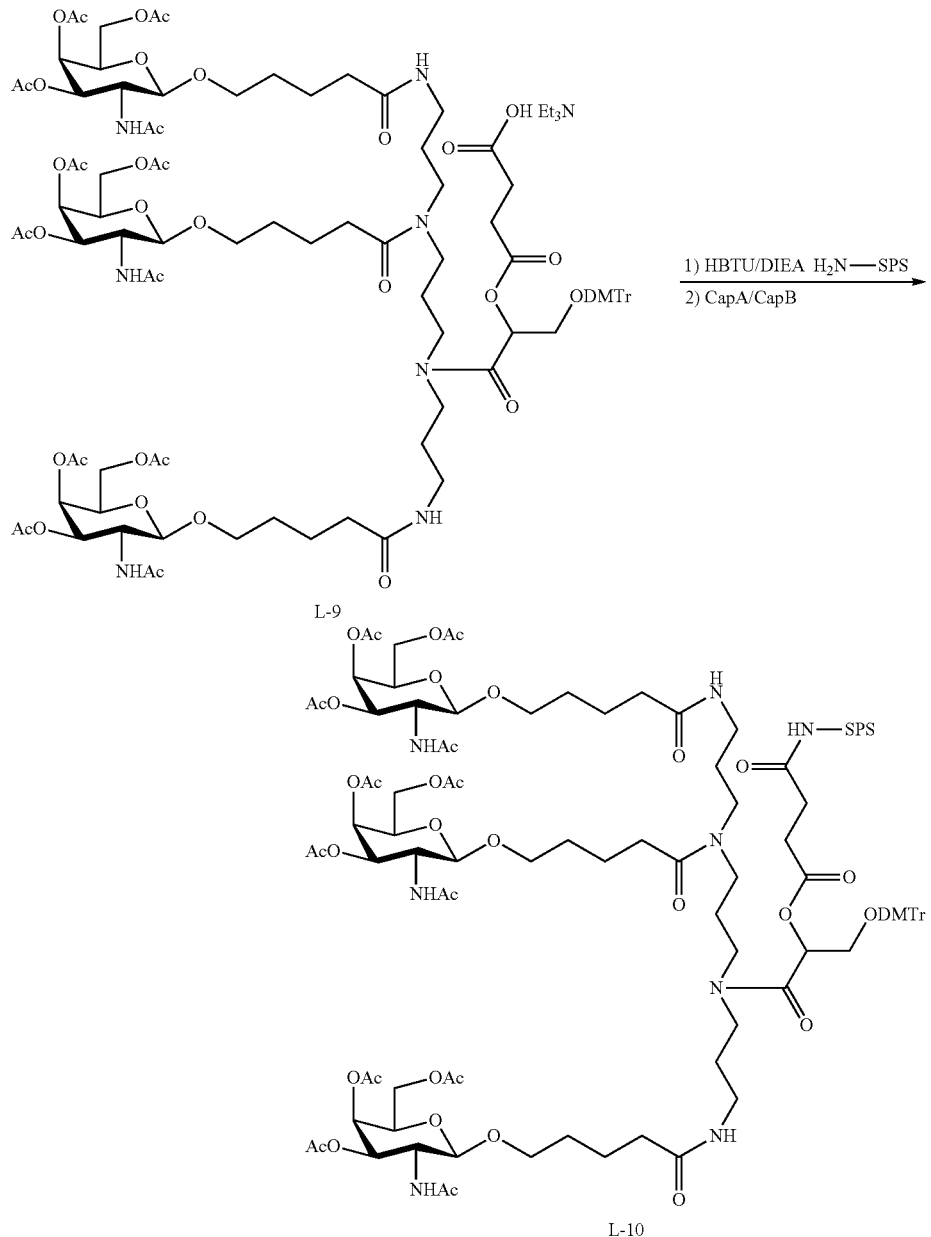

In this step, a compound L-10 was prepared by linking the L-9 conjugating molecule to a solid phase support.

The L-9 Conjugating Molecule (0.233 g, 0.1126 mmol) obtained in step (1-1-8), 0-benzotriazol-tetramethyluronium hexafluorophosphate (HBTU, 0.064 g, 0.1689 mmol) and diisopropylethylamine (DIEA, 0.029 g, 0.2252 mmol) were mixed and dissolved in 19 ml of acetonitrile, and stirred at room temperature for 5 minutes. Aminomethyl resin (0.901 g, 100-200 mesh, amino loading: 400 μmol/g, purchased from Tianjin Nankai HECHENG S&T Co., Ltd.) was added into the reaction liquid. A reaction was performed on a shaker at 25° C. and 220 rpm/min for 15 hours, followed by filtration. The residue was rinsed twice, each with 30 ml of DCM, three times, each with 30 ml of acetonitrile, and once with 30 ml of ethyl ether, and dried for 2 hours with a vacuum oil pump. Then a capping reaction was performed by adding starting materials (CapA, CapB, 4-dimethylaminopyridine (DMAP) and acetonitrile) according to the charge ratio shown in Table 2. A reaction was performed on a shaker at 25° C. and 200 rpm/min for 5 hours. The reaction liquid was filtrated. The residue was rinsed three times, each with 30 ml of acetonitrile, the solvent was evaporated to dryness, and the mixture was dried overnight under a reduced pressure with a vacuum oil pump to give 1.100 g of compound L-10 (i.e., L-9 Conjugating Molecule linked to a solid phase support), with a loading of 90.8 μmol/g.

TABLE 2

The charge ratio of capping reaction

| Starting Materials | Amount | Level | Lot No. | Manufacturer |
|---|---|---|---|---|
| CapA | 20 ml | — | — | — |
| CapB | 2.3 ml | — | — | — |
| DMAP | 0.01 g | analytical pure | I1422139 | Aladdin |
| acetonitrile | 2.3 ml | spectroscopic pure | O15161001 | CINC (Shanghai) Co., Ltd |

In the above table, CapA and CapB are solutions of capping agents. CapA is a solution of 20% by volume of N-methylimidazole in a mixture of pyridine/acetonitrile, wherein the volume ratio of pyridine to acetonitrile is 3:5. CapB is a solution of 20% by volume of acetic anhydride in acetonitrile.

(1-2) Synthesis of Sense Strands of Conjugates 1-11

Nucleoside monomers were linked one by one in 3' to 5' direction according to the arrangement sequence of nucleotides in the sense strand by the phosphoramidite solid phase synthesis method, starting the cycles from the Compound L-10 prepared in the above step. The linking of each nucleoside monomer included a four-step reaction of deprotection, coupling, capping, and oxidation or sulfurization. Therein, when two nucleotides is linked via a phosphoester linkage, a four-step reaction of deprotection, coupling, capping, and oxidation was included during linking of the later nucleoside monomer; and when two nucleotides is linked via a phosphorothioate linkage, a four-step reaction of deprotection, coupling, capping, and sulfurization was included during linking of the later nucleoside monomer. The synthesis condition was given as follows.

The nucleoside monomers are provided in a 0.1 M acetonitrile solution. The condition for deprotection reaction in each step is identical, i.e., a temperature of 25° C., a reaction time of 70 seconds, a solution of dichloroacetic acid in dichloromethane (3% v/v) as a deprotection agent, and a molar ratio of dichloroacetic acid to the protecting group on the solid phase support of 4,4'-dimethoxytrityl of 5:1.

The condition for coupling reaction in each step is identical, including a temperature of 25° C., a molar ratio of the nucleic acid sequence linked to the solid phase support to nucleoside monomers of 1:10, a molar ratio of the nucleic acid sequence linked to the solid phase support to a coupling agent of 1:65, a reaction time of 600 seconds, and 0.5 M acetonitrile solution of 5-ethylthio-1H-tetrazole as a coupling agent.

The condition for capping reaction in each step is identical, including a temperature of 25° C. and a reaction time of 15 seconds, a mixed solution of Cap A and Cap B in a molar ratio of 1:1 as a capping agent, and a molar ratio of the capping agent to the nucleic acid sequence linked to the solid phase support of 1:1:1 (anhydride:N-methylimidazole: the nucleic acid sequence linked to the solid phase support).

The condition for oxidation reaction in each step is identical, including a temperature of 25° C., a reaction time of 15 seconds, and 0.05 M iodine water as an oxidation agent; and a molar ratio of iodine to the nucleic acid sequence linked to the solid phase support in the coupling step of 30:1. The reaction is carried out in a mixed solvent in which the ratio of tetrahydrofuran:water:pyridine is 3:1:1.

The condition for sulfurization reaction in each step is identical, including a temperature of 25° C., a reaction time of 300 seconds, and xanthane hydride as a sulfurization agent; a molar ratio of the sulfurization agent to the nucleic acid sequence linked to the solid phase support in the coupling step of 120:1. The reaction is carried out in a mixed solvent in which the ratio of acetonitrile:pyridine is 1:1.

The conditions for cleavage and deprotection are as follows: adding the synthesized nucleotide sequence linked to the support into 25 wt % aqueous ammonia to react for 16 hours at 55° C., and the aqueous ammonia is in an amount of 0.5 ml/μmol. The liquid is removed, and the residue is concentrated in vacuum to dryness.

Purification and desalination: purification of the nucleic acid is achieved by using a preparative ion chromatography column (Source 15Q) with a gradient elution of NaCl.

Specifically, eluent A: 20 mM sodium phosphate (pH 8.1), solvent:water/acetonitrile=9:1 (v/v); eluent B: 1.5 M sodium chloride, 20 mM sodium phosphate (pH 8.1), solvent:water/acetonitrile=9:1 (v/v); elution gradient:eluent A:eluent B=100:0-50:50. The eluate is collected, combined and desalted by using a reverse phase chromatography column. The specific conditions include using a Sephadex column (filler: Sephadex-G25) for desalination and deionized water for eluting.

Detection: the purity was determined by ion exchange chromatography (IEX-HPLC); and the molecular weight was analyzed by Liquid Chromatography-Mass Spectrometry (LC-MS).

(1-3) Synthesis of Antisense Strands of Conjugates 1-11

(1-3A) Preparation of an Antisense Strand of Conjugates 1, 6 and 11

An antisense strands (AS) of Conjugates 1 and 2 were synthesized by starting the cycles using a universal solid phase support (UnyLinker™ loaded NittoPhase®HL Solid Supports, Kinovate Life Sciences Inc.) according to the solid phase phosphoramidite synthesis. The deprotection, coupling, capping, oxidation or sulfurization, cleavage, deprotection, purification and desalting reaction in the solid phase synthesis method were conducted under the same conditions as those in the synthesis of the sense strand.

Therein, the vinyl phosphate and 2'-methoxy modified uridine monomer (VP-Um) is synthesized according to the following method:

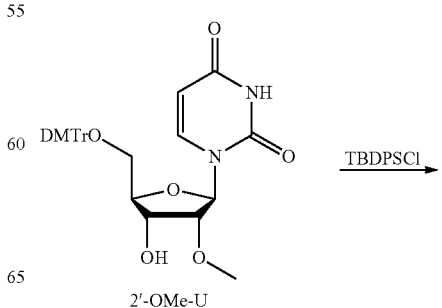

2'-OMe-U

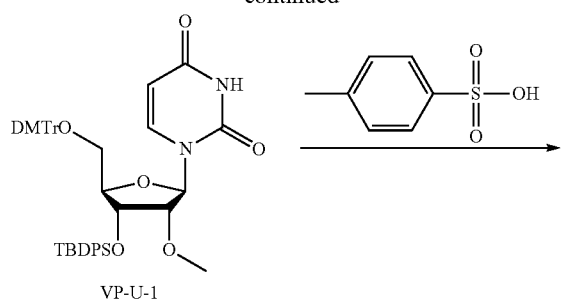

VP-U-1

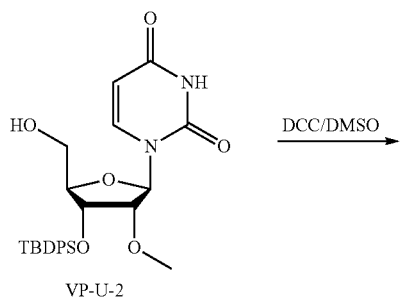

VP-U-2

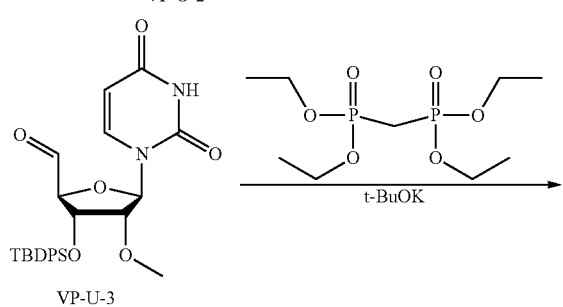

VP-U-3

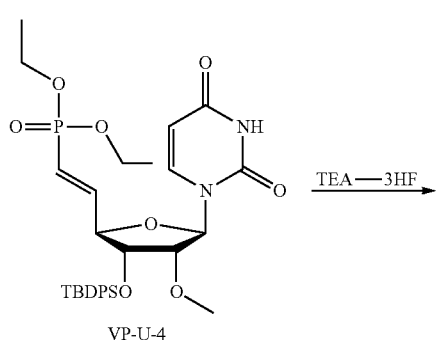

VP-U-4

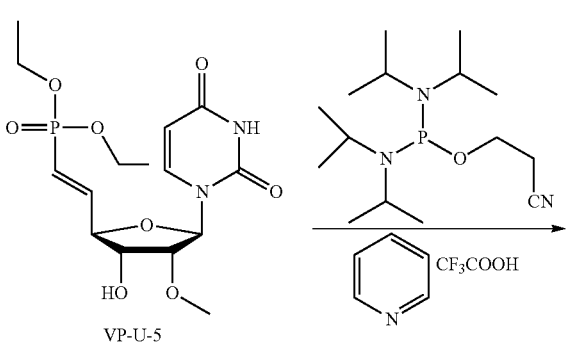

VP-U-5

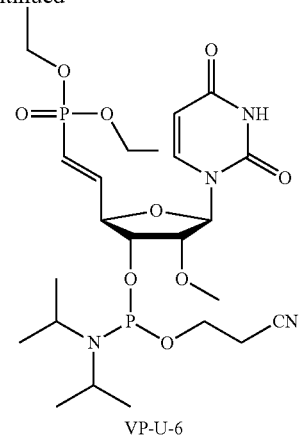

VP-U-6

(1-3-1) Synthesis of VP-U-2

VP-U-2 molecule was synthesized according to the following method:

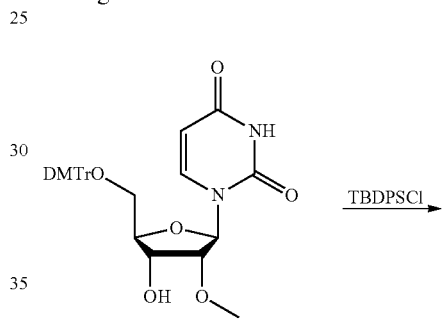

2'-OMe-U

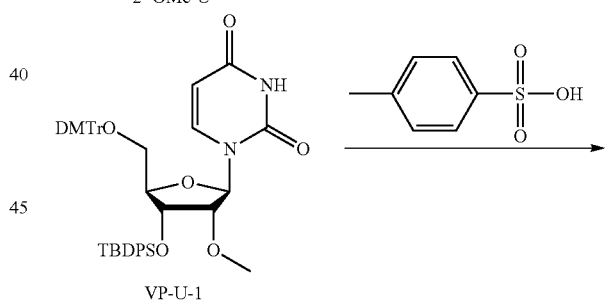

VP-U-1

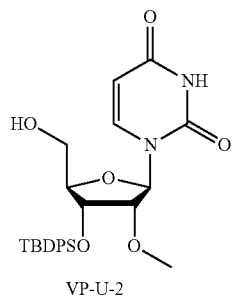

VP-U-2

A 2'-methoxy modified uracil nucleoside (2'-OMe-U, 51.30 g, 91.6 mmol), tertbutyl diphenylchlorosilane (TBDP-SCl, 50.35 g, 183.2 mmol), and imidazole (12.47 g, 183.2 mmol) were mixed and dissolved in 450 ml of N,N-dimethylformamide (DMF) to react under stirring at room temperature for 20 hours. DMF was removed by evaporation, and the residue was dissolved in 600 ml of dichloromethane and washed with 300 ml of saturated sodium bicarbonate. The aqueous phase isolated was extracted three times, each with 300 ml of dichloromethane. All organic phases were combined, washed with 5% oxalic acid until the pH of the aqueous phase is <5. The solvent was evaporated to dryness to give a crude product of VP-U-1, which was directly used in the subsequent synthesis of VP-U-2.

The crude product VP-U-1 was dissolved in 100 ml of dichloromethane, and then stirred for 10 minutes in an ice bath. 450 ml of 2% p-toluenesulfonic acid solution (with a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase obtained was washed by addition of saturated sodium bicarbonate solution to pH=8. Aqueous phases were combined and extracted twice, each with 200 ml of dichloromethane. All organic phases were combined and washed once with 200 ml of saturated brine. The solvent was removed by evaporation, and the residue was purified by using a normal phase silica gel column (200-300 mesh). The column was packed with petroleum ether and eluted with a gradient elution of petroleum ether:ethyl acetate:dichloromethane:methanol=1:1:1:0.05-1:1:1:0.25. The eluate was collected, the solvent was removed by evaporation under reduced pressure, and the residue was foam-dried in a vacuum oil pump to give a total of 40.00 g of pure product VP-U-2. 1H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: C26H33N2O6Si, [M+H]+, calcd: 497.21, Measured: 497.45.

(1-3-2) Synthesis of VP-U-4

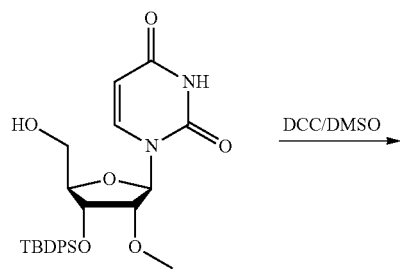

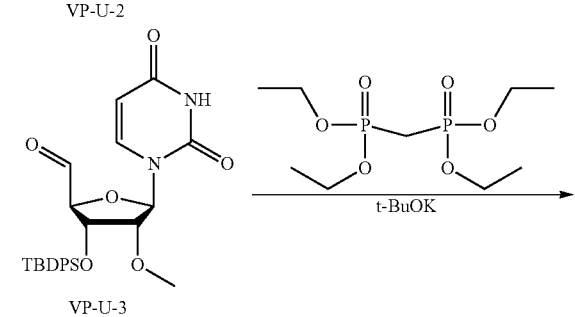

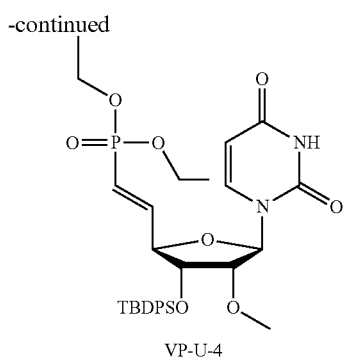

VP-U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react under stirring at room temperature for 20 hours. Separately, tetraethyl methylenediphosphate (21.44 g, 74.4 mmol) was dissolved in 120 ml of THF, cooled in an ice bath, added with t-BuOK (11.36 g, 101.2 mmol) at a temperature of the ice bath to react for 10 min, warmed to room temperature to react for 0.5 h and added into the above reaction solution over about 1 h. The reaction was carried out at a temperature of the ice bath for 1 h and then warmed to room temperature to react for 18 h. The reaction was quenched by addition of water. The aqueous phase isolated was extracted three times, each with 200 ml of dichloromethane. All organic phases were combined and washed once with 200 ml of saturated brine. The solvent was evaporated to dryness, and the residue was purified by using a normal phase silica gel column (200-300 mesh). The column was packed with petroleum ether and eluted with a gradient elution of petroleum ether:ethyl acetate=1:1-1:4. The eluate was collected, the solvent was removed by evaporation under reduced pressure, and the residue was foam-dried in a vacuum oil pump to give a total of 14.00 g of pure product VP-U-4. 1H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: C31H42N2O8PSi, [M+H]+, calcd: 629.24, measured: 629.51.

(1-3-3) Synthesis of VP-U-5

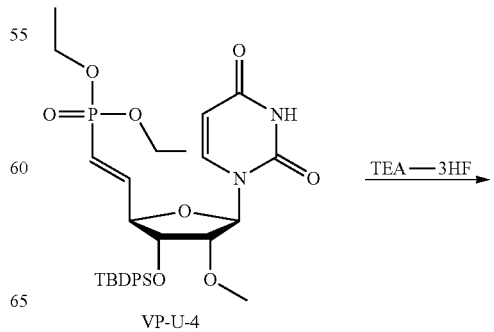

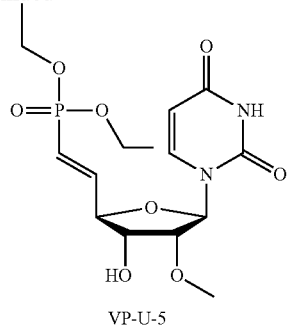

VP-U-5

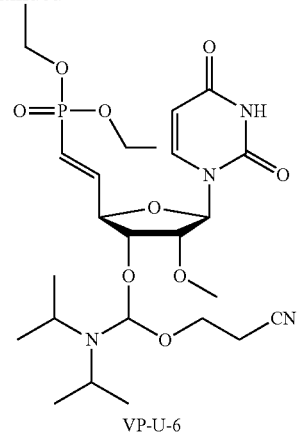

VP-U-6

VP-U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. The solvent was directly evaporated to dryness and the residue was dissolved in dichoromethane; the above evaporation and dissolution steps were additionally repeated twice, each with 50 ml of dichloromethane, to give a crude product. The crude product was purified by using a normal phase silica gel column (200-300 mesh). The column was packed with petroleum ether and eluted with a gradient elution of petroleum ether: ethyl acetate:dichloromethane:methanol=1:1:1:0.05-1:1:1: 0.25. The eluate was collected, the solvent was removed by evaporation under reduced pressure, and the residue was foam-dried in a vacuum oil pump to give a total of 6.70 g of pure product VP-U-5. 1H NMR (400 MHz, DMSO-d6) δ 7.96 (d, J=7.8 Hz, 11H), 6.77 (dd, J=15.0, 6.2 Hz, 1H), 5.99-5.82 (m, 2H), 5.73 (d, J=7.6 Hz, 11H), 5.27 (d, J=5.1 Hz, 1H), 5.10 (dd, J=5.3, 4.7 Hz, 11H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: C15H24N2O8P, [M+H]+, calcd: 391.13, measured: 391.38.

(1-3-4) Synthesis of VP-U-6

VP-U-5 (391 mg, 1.0 mmol), pyridine trifluoroacetate (0.232 g, 1.2 mmol), N-methylimidazole (0.099 g, 1.2 mmol), and bis(diisopropylamino)(2-cyanoethoxy)phosphine (0.452 g, 1.5 mmol) were added into 10 ml of anhydrous dichloromethane under argon atmosphere to react under stirring at room temperature for 5 hours. The solvent was evaporated to dryness, and then the residue was purified by column chromatography (200-300 mesh normal phase silica gel, with a gradient elution of dichloromethane:acetonitrile (containing 0.5 wt % triethylamine)=3:1-1:3). The eluate was collected and concentrated to remove the solvent to give a total of 508 mg of target product VP-U-6. 31P NMR (161 MHz, DMSO-d6) δ 150.34, 150.29, 17.07, 15.50. MS m/z: C24H41N4O9P2, [M+H]+, calcd: 591.23, measured: 591.55. It was indicated that VP-U-6 was the target product VP-Um, which involved in the synthesis of RNA strands as a nucleoside monomer.

(1-3B) Preparation of an Antisense Strand of Conjugates 2 and 10

The antisense strands of Conjugates 2 and 10 only differs from those of Conjugates 1 and 11 in the first 5'-terminal nucleotide modification. During the preparation of an antisense strand according to the method of solid phase phosphoramidite synthesis, after the linking of 2'-methoxy modified uridine monomer as the last nucleoside monomer to be linked, the monomer of Formula (CPR-I) (purchased by Suzhou GenePharma Inc. as Cat #13-2601-XX) was linked to 5' terminal of the antisense strand by a four-step reaction of deprotection, coupling, capping, and oxidation, so as to form a 5'-phosphate ester modification.

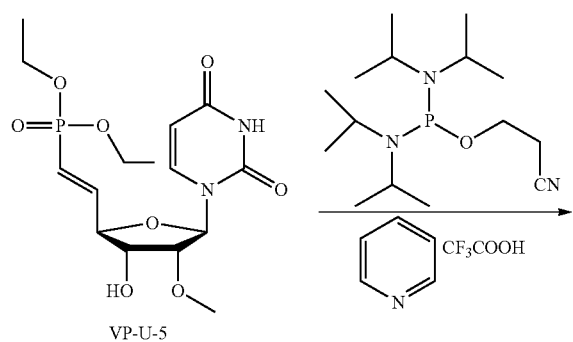

VP-U-5

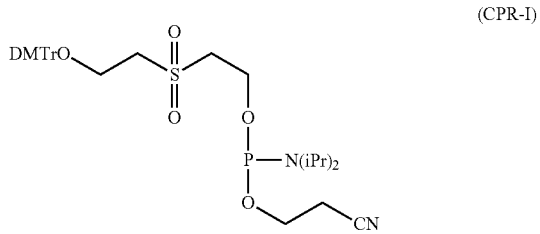

(CPR-I)

During the synthesis, the universal solid phase support to be used, the conditions of deprotection, coupling, capping, oxidation or sulfurization reaction, cleavage and deprotection, purification and desalting are the same as those used in the synthesis of the sense strand.

(1-3C) Preparation of an Antisense Strand of Conjugates 3, 4 and 9

The same synthesis procedure for synthesis of the antisense strand of Conjugates 2 and 19 was employed, except that the above oxidation reaction condition was replaced with a sulfurization reaction condition in the linking of the CPR-I monomer, thereby obtaining an antisense strand of Conjugates 3, 4 and 9 with a 5'-phosphorothioate modification.

(1-3D) Preparation of an Antisense Strand of Conjugates 5, 7 and 8

Antisense strands (AS) of Conjugates 5, 7 and 8 were synthesized by starting the cycles using a universal solid phase support (UnyLinker™ loaded NittoPhase®HL Solid Supports, Kinovate Life Sciences Inc.) according to the solid phase phosphoramidite synthesis. The deprotection, coupling, capping, oxidation or sulfurization, cleavage, deprotection, purification and desalting reaction in the solid phase synthesis method, were conducted under the same conditions as those in the synthesis of the sense strand.

(1-4) Synthesis of Conjugates 1-11

For Conjugate 1, the S strand and AS strand were respectively dissolved in water for injection to give a solution of 40 mg/m. They are mixed at an equimolar ratio, heated at 50° C. for 15 min, and then cooled at room temperature, such that they could form a double stranded structure via hydrogen bonds. The conjugate was diluted to a concentration of 0.2 mg/mL with ultra-pure water (prepared by Milli-Q ultra-pure water instrument, with resistivity of 18.2MΩ*cm (25° C.)). The molecular weight was measured by LC-MS instrument (purchased from Waters Corp., model: LCT Premier). Since the measured values were in conformity with the calculated values, it was confirmed that the synthesized Conjugate 1 was the designed double stranded nucleic acid sequence of interest with the L-9 Conjugating Molecule.

The sense strands and the corresponding antisense strands of Conjugates 2-11 as synthesized above were annealed according to the same method, to form double stranded structures; and the molecular weights of the conjugates were measured as follows:

Conjugate 2: Calculated values S: 7516.37, AS: 7065.58; Measured values: S: 7516.6, AS: 7064.5;
Conjugate 3: Calculated values S: 7504.34, AS: 7139.68; Measured values: S: 7515.6, AS: 7138.9;
Conjugate 4: Calculated values S: 7516.37, AS: 7081.64; Measured values: S: 7515.6, AS: 7080.9;
Conjugate 5: Calculated values S: 7504.34, AS: 6961.52; Measured values: S: 7503.4, AS: 6960.9;
Conjugate 6: Calculated values S: 7504.34, AS: 7037.51; Measured values: S: 7503.6, AS: 7036.9;
Conjugate 7: Calculated values S: 8218.83, AS: 7703.05; Measured values: S: 8218, AS: 7702.5;
Conjugate 8: Calculated values S: 7516.37, AS: 6985.58; Measured values: S: 7516.5, AS: 6984.9;
Conjugate 9: Calculated values S: 7504.34, AS: 7041.52; Measured values: S: 7503.6, AS: 7040.8;
Conjugate 10: Calculated values S: 7504.34, AS: 7057.58, Measured values: S: 7503.6, AS: 7057;
the measured values were in conformity with the calculated values, indicating that the synthesized conjugates were the siRNA conjugates with the target sequences.

Conjugates 1-11 have a structure as shown by Formula (3).

Preparation Example 2 Preparation of Conjugates 12-26 and Comparative Conjugate 1

It was expected that the subject conjugates can be obtained by using the same method as that in Preparation Example 1, except that: 1) the siRNAs have sequences shown in Table 1 respectively corresponding to Conjugates 12-26 and Comparative Conjugate 1; and 2) in the case where the target sequence comprises unmodified nucleotide, among the cleavage and deprotection conditions, after treatment with aqueous ammonia, the product is dissolved in N-methylpyrrolidone in an amount of 0.4 ml/μmol, followed by addition of 0.3 ml/mol of triethylamine and 0.6 ml/μmol of triethylamine trihydrofluoride, with respect to the amount of the single strand nucleic acid, thereby removing the 2'-TBDMS protection on ribose.

The conjugated siRNA sequences in the subject conjugates are shown in Table 3. Therein, the siRNA comprised in the Comparative Conjugate 1 is the negative control siRNA (hereinafter also referred to as NC) which shows no inhibitory effect against HBV gene.

TABLE 3 siRNA conjugates

| Examples | NO. | | Sequence Direction 5'-3' | SEQ ID NO |
|---|---|---|---|---|
| Conjugate 1 | L10-siHBa1M1SVP | Sense strand | CmsCmsUmUmGmAmGfGfCfAmUmAmCmUm UmCmAmAmAm | 41 |
| | | Antisense strand | VP-UmsUfsUmGmAmAfGmUmAmUmGmCmCm UfCmAfAmGmGmsUmsUm | 42 |
| Conjugate 2 | L10-siHBa1M1SP | Sense strand | CmsCmsUmUmGmAmGfGfCfAmUmAmCmUm UmCmAmAmAm | 43 |
| | | Antisense strand | P-UmsUfsUmGmAmAfGmUmAmUmGmCmCm UfCmAfAmGmGmsUmsUm | 44 |
| Conjugate 3 | L10-siHBa1M1SPsT | Sense strand | CmsCmsUmUmGmAmGfGfCfAmUmAmCmUm UmCmAmAmAm | 45 |
| | | Antisense strand | Ps-TmsUfsUmGmAmAfGmUmAmUmGmCmCm UfCmAfAmGmGmsUmsUm | 46 |

TABLE 3-continued siRNA conjugates

| Examples | NO. | | Sequence Direction 5'-3' | SEQ ID NO |
|---|---|---|---|---|
| Conjugate 4 | L10-siHBa1M1SPs | Sense strand | CmsCmsUmUmGmAmGfCfCfAmUmAmCmUm UmCmAmAmAm | 47 |
| | | Antisense strand | Ps-UmsUfsUmGmAmAfGmUmAmUmGmCmCm UfCmAfAmGmsUmsUm | 48 |
| Conjugate 5 | L10-siHBa1M2S | Sense strand | CmsCmsUmUmGfAmGfCfCfAmUmAmCmUm UmCmAmAmAm | 49 |
| | | Antisense strand | UmsUfsUmGmAmAfGmUfAfUmGmCmCmUfCm AfAmGmGmsUmsUm | 50 |
| Conjugate 6 | L10-siHBa1M2SVP | Sense strand | CmsCmsUmUmGfAmGfCfCfAmUmAmCmUm UmCmAmAmAm | 51 |
| | | Antisense strand | VP-UmsUfsUmGmAmAfGmUfAfUmGmCmCm UfCmAfAmGmsUmsUm | 52 |
| Conjugate 7 | L10-siHBa2M1S | Sense strand | GmsAmsCmCmUmUmGmAmGfGfCfAmUmAm CmUmUmCmAmAmAm | 53 |
| | | Antisense strand | UmsUfsUmGmAmAfGmUmAmUmGmCmCmUf CmAfAmGmGmUmCmsGmsGm | 54 |
| Conjugate 8 | L10-siHBa1M1S | Sense strand | CmsCmsUmUmGmAmGfCfCfAmUmAmCmUm UmCmAmAmAm | 55 |
| | | Antisense strand | UmsUfsUmGmAmAfGmUmAmUmGmCmCmUf CmAfAmGmGmsUmsUm | 56 |
| Conjugate 9 | L10-siHBa1M2SPs | Sense strand | CmCmUmUmGfAmGfCfCfAmUmAmCmUmUm CmAmAmAm | 57 |
| | | Antisense strand | Ps-UmUfUmGmAmAfGmUfAfUmGmCmCmUf CmAfAmGmGmUmUm | 58 |
| Conjugate 10 | L10-siHBa2M2SP | Sense strand | GmAmCmCmUmUmGfAmGfGfCfAmUmAmCm UmUmCmAmAmAm | 59 |
| | | Antisense strand | P-UmUfUmGmAmAfGmUfAfUmGmCmCmUf CmAfAmGmGmUmCmGmGm | 60 |
| Conjugate 11 | L10-siHBa2M1SVP | Sense strand | GmsAmsCmCmUmUmGmAmGfGfCfAmUmAm CmUmUmCmAmAmAm | 61 |
| | | Antisense strand | VP-UmsUfsUmGmAmAfGmUmAmUmGmCmCm UfCmAfAmGmGmUmCmsGmsGm | 62 |
| Conjugate 12 | L10-siHBa1 | Sense strand | CCUUGAGGCAUACUUCAAA | 63 |
| | | Antisense strand | UUUGAAGUAUGCCUCAAGGUU | 64 |
| Conjugate 13 | L10-siHBa2 | Sense strand | GACCUUGAGGCAUACUUCAAA | 65 |
| | | Antisense strand | UUUGAAGUAUGCCUCAAGGUCGG | 66 |
| Conjugate 14 | L10-siHBa1M1 | Sense strand | CmCmUmUmGmAmGfCfCfAmUmAmCmUm UmCmAmAmAm | 67 |
| | | Antisense strand | UmUfUmGmAmAfGmUmAmUmGmCmCmUf CmAfAmGmGmUmUm | 68 |
| Conjugate 15 | L10-siHBa1M2 | Sense strand | CmCmUmUmGfAmGfCfCfAmUmAmCmUmUm CmAmAmAm | 69 |
| | | Antisense strand | UmUfUmGmAmAfGmUfAfUmGmCmCmUfCm AfAmGmGmUmUm | 70 |
| Conjugate 16 | L10-siHBa2M1 | Sense strand | GmAmCmCmUmUmGmAmGfGfCfAmUmAm CmUmUmCmAmAmAm | 71 |
| | | Antisense strand | UmUfUmGmAmAfGmUmAmUmGmCmCmUf CmAfAmGmGmUmCmGmGm | 72 |
| Conjugate 17 | L10-siHBa2M2 | Sense strand | GmAmCmCmUmUmGfAmGfGfCfAmUmAmCm UmUmCmAmAmAm | 73 |
| | | Antisense strand | UmUfUmGmAmAfGmUfAfUmGmCmCmUfCm AfAmGmGmUmCmGmGm | 74 |
| Conjugate 18 | L10-siHBa2M2S | Sense strand | GmsAmsCmCmUmUmGfAmGfGfCfAmUmAm CmUmUmCmAmAmAm | 75 |
| | | Antisense strand | UmsUfsUmGmGmAmAfGmUfAfUmGmCmCmUfCm AfAmGmGmUmCmsGmsGm | 76 |

TABLE 3-continued siRNA conjugates

| Examples | NO. | | Sequence Direction 5'-3' | SEQ ID NO |
|---|---|---|---|---|
| Conjugate 19 | L10-siHBa1M1VP | Sense strand | CmCmUmUmGmAmGfGfCfAmUmAmCmUm UmCmAmAm | 77 |
| | | Antisense strand | VP-UmUfUmGmAmAfGmUmAmUmGmCmCm UfCmAfAmGmGmUmUm | 78 |
| Conjugate 20 | L10-siHBa1M2VP | Sense strand | CmCmUmUmGfAmGfGfCfAmUmAmCmUmUm CmAmAmAm | 79 |
| | | Antisense strand | VP-UmUfUmGmAmAfGmUfAfUmGmCmCmUf CmAfAmGmGmUmUm | 80 |
| Conjugate 21 | L10-siHBa2M1VP | Sense strand | GmAmCmCmUmUmGmAmGfGfCfAmUmAm CmUmUmCmAmAmAm | 81 |
| | | Antisense strand | VP-UmUfUmGmAmAfGmUmAmUmGmCmCm UfCmAfAmGmGmUmCmGmGm | 82 |
| Conjugate 22 | L10-siHBa2M2VP | Sense strand | GmAmCmCmUmUmGfAmGfGfCfAmUmAmCm UmUmCmAmAmAm | 83 |
| | | Antisense strand | VP-UmUfUmGmAmAfGmUfAfUmGmCmCmUf CmAfAmGmGmUmCmGmGm | 84 |
| Conjugate 23 | L10-siHBa2M2SVP | Sense strand | GmsAmsCmCmUmUmGfAmGfGfCfAmUmAm CmUmUmCmAmAmAm | 85 |
| | | Antisense strand | VP-UmsUfsUmGmAmAfGmUfAfUmGmCmCm UfCmAfAmGmGmUmCmsGmsGm | 86 |
| Conjugate 24 | L10-siHBa1M5SVP | Sense strand | CmsCmsUmUmGfAmGfGfCfAmUmAmCmUm UmCmAmAmAm | 87 |
| | | Antisense strand | VP-UmsUfsUmGmAmAfGmUmAmUmGmCmCm UfCmAfAmGmGmsUmsUm | 88 |
| Conjugate 25 | L10-siHBa1M3SVP | Sense strand | CmsCmsUmUmGmAmGfGmCfAmUfAmCmUm UmCmAmAmAm | 89 |
| | | Antisense strand | VP-UmsUfsUmGmAmAfGmUmAmUmGmCmCm UfCmAfAmGmGmsUmsUm | 90 |
| Conjugate 26 | L10-siHBa1M4SVP | Sense strand | CmsCmsUmUmGmAmGfGmCfAmUmAmCmUm UmCmAmAmAm | 91 |
| | | Antisense strand | VP-UmsUfsUmGmAmAfGmUfAmUmGmCmCm UfCmAfAmGmGmsUmsUm | 92 |
| Conjugate 27 | P10-siHBa1M1SVP | Sense strand | CmsCmsUmUmGmAmGfGfCfAmUmAmCmUm UmCmAmAmAm | 93 |
| | | Antisense strand | VP-UmsUfsUmGmAmAfGmUfAfUmGmCmCm UfCmAfAmGmGmsUmsUm | 94 |
| Conjugate 28 | R5-siHBa1M1SVP | Sense strand | CmCmUmUmGfAmGfGfCfAmUmAmCmUmUm CmAmAmAm | 95 |
| | | Antisense strand | VP-UmUfUmGmAmAfGmUfAfUmGmCmCmUf CmAfAmGmGmUmUm | 96 |
| Conjugate 29 | LA5-siHBa1M1SVP | Sense strand | CmsCmsUmUmGmAmGfGfCfAmUmAmCmUm UmCmAmAmAm | 97 |
| | | Antisense strand | VP-UmsUfsUmGmAmAfGmUfAmUmGmCmCm UfCmAfAmGmGmsUmsUm | 98 |
| Conjugate 30 | LB5-siHBa1M1SVP | Sense strand | CmCmUmUmGfAmGfGfCfAmUmAmCmUmUm CmAmAmAm | 99 |
| | | Antisense strand | VP-UmUfUmGmAmAfGmUfAfUmGmCmCmUf CmAfAmGmGmUmUm | 100 |
| Conjugate 31 | V8-siHBa1M1SVP | Sense strand | CmCmUmUmGfAmGfGfCfAmUmAmCmUmUm CmAmAmAm | 101 |
| | | Antisense strand | VP-UmUfUmGmAmAfGmUfAfUmGmCmCmUf CmAfAmGmGmUmUm | 102 |
| Conjugate 32 | W8-siHBa1M1SVP | Sense strand | CmCmUmUmGfAmGfGfCfAmUmAmCmUmUm CmAmAmAm | 103 |
| | | Antisense strand | VP-UmUfUmGmAmAfGmUfAfUmGmCmCmUf CmAfAmGmGmUmUm | 104 |
| Conjugate 33 | X8-siHBa1M1SVP | Sense strand | CmCmUmUmGfAmGfGfCfAmUmAmCmUmUm CmAmAmAm | 105 |
| | | Antisense strand | VP-UmUfUmGmAmAfGmUfAfUmGmCmCmUf CmAfAmGmGmUmUm | 106 |

TABLE 3-continued siRNA conjugates

| Examples | NO. | | Sequence Direction 5'-3' | SEQ ID NO |
|---|---|---|---|---|
| Conjugate 34 | Z5-siHBa1M1SVP | Sense strand | CmCmUmUmGfAmGfGfCfAmUmAmCmUmUm CmAmAmAm | 107 |
| | | Antisense strand | VP-UmUfUmGmAmAfGmUfAfUmGmCmCmUf CmAfAmGmUmUm | 108 |
| Conjugate 35 | FIN-siHBa2 | Sense strand | GACCUUGAGGCAUACUUCAAA | 109 |
| | | Antisense strand | UUUGAAGUAUGCCUCAAGGUCGG | 110 |
| Conjugate 36 | FIN-siHBa2M5SVP | Sense strand | GmsAmsCmCmUmUmGfAmGfGfCfAmUmAm CmUmCmAmAmAm | 111 |
| | | Antisense strand | VP-UmsUfsUmGmAmAfGmUmAmUmGmCmCm UfCmAfAmGmGmUmCmsGmsGm | 112 |
| Conjugate 37 | FIN-siHBa2M3SVP | Sense strand | GmsAmsCmCmUmUmGfAmGfGmCfAmUmAm CmUmCmAmAmAm | 113 |
| | | Antisense strand | VP-UmsUfsUmGmAmAfGmUmAmUmGmCmCm UfCmAfAmGmGmUmCmsGmsGm | 114 |
| Conjugate 38 | FIN-siHBa2M4SVP | Sense strand | GmsAmsCmCmUmUmGmAmGfGfCfAmUmAm CmUmCmAmAmAm | 115 |
| | | Antisense strand | VP-UmsUfsUmGmAmAfGmUfAmUmGmCmCm UfCmAfAmGmGmUmCmsGmsGm | 116 |
| Conjugate 39 | FIN-siHBa2M1SVP | Sense strand | GmsAmsCmCmUmUmGmAmGfGfCfAmUmAm CmUmCmAmAmAm | 117 |
| | | Antisense strand | VP-UmsUfsUmGmAmAfGmUmAmUmGmCmCm UfCmAfAmGmGmUmCmsGmsGm | 118 |
| Conjugate 40 | FIN-siHBa2M2SVP | Sense strand | GmsAmsCmCmUmUmGfAmGfGfCfAmUmAm CmUmCmAmAmAm | 119 |
| | | Antisense strand | VP-UmsUfsUmGmAmAfGmUfAfUmGmCmCm UfCmAfAmGmGmUmCmsGmsGm | 120 |
| Conjugate 41 | FIN-siHBa3M2SVP | Sense strand | CmsCmsUmUmGfAmGfGfCfAmUmAmCmUm UmCmAmAmAm | 121 |
| | | Antisense strand | VP-UmsUfsUmGmAmAfGmUfAfUmGmCmCm UfCmAfAmGmGmsUmsCm | 122 |
| Conjugate 42 | FIN-siHBa3M2S | Sense strand | CmsCmsUmUmGfAmGfGfCfAmUmAmCmUm UmCmAmAmAm | 123 |
| | | Antisense strand | UmsUfsUmGmAmAfGmUfAfUmGmCmCmUfCm AfAmGmGmsUmsCm | 124 |
| Conjugate 43 | FIN-siHBa1 | Sense strand | CCUUGAGGCAUACUUCAAA | 125 |
| | | Antisense strand | UUUGAAGUAUGCCUCAAGGUU | 126 |
| Conjugate 44 | FIN-siHBa1M2SVP | Sense strand | CmsCmsUmUmGfAmGfGfCfAmUmAmCmUm UmCmAmAmAm | 127 |
| | | Antisense strand | VP-UmsUfsUmGmAmAfGmUfAfUmGmCmCm UfCmAfAmGmGmsUmsUm | 128 |
| Conjugate 45 | FIN-siHBa1M2S | Sense strand | CmsCmsUmUmGfAmGfGfCfAmUmAmCmUm UmCmAmAmAm | 129 |
| | | Antisense strand | UmsUfsUmGmAmAfGmUfAfUmGmCmCmUfCm AfAmGmGmsUmsUm | 130 |
| Conjugate 46 | FIN-siHBa1M1SVP | Sense strand | CmsCmsUmUmGmAmGfGfCfAmUmAmCmUm UmCmAmAmAm | 131 |
| | | Antisense strand | VP-UmsUfsUmGmAmAfGmUmAmUmGmCmCm UfCmAfAmGmGmsUmsUm | 132 |
| Conjugate 47 | FIN-siHBa2M1S | Sense strand | GmsAmsCmCmUmUmGmAmGfGfCfAmUmAm CmUmCmAmAmAm | 133 |
| | | Antisense strand | UmsUfsUmGmAmAfGmUmAmUmGmCmCmUf CmAfAmGmGmUmCmsGmsGm | 134 |
| Conjugate 48 | FIN-siHBa1M1S | Sense strand | CmsCmsUmUmGmAmGfGfCfAmUmAmCmUm UmCmAmAmAm | 135 |
| | | Antisense strand | UmsUfsUmGmAmAfGmUmAmUmGmCmCmUf CmAfAmGmGmsUmsUm | 136 |

TABLE 3-continued siRNA conjugates

| Examples | NO. | | Sequence Direction 5'-3' | SEQ ID NO |
|---|---|---|---|---|
| Conjugate 49 | FIN-X2M2 | Sense strand | CmCmUmUmGAGGCmAUmACmUmUmCmA AAdT-S-dT | 137 |
| | | Antisense strand | UfUmUfGAAGUfAUGCCUfCAAGGdT-S-dT | 138 |
| Comp. Conjugate 1 | L10-NC | Sense strand | UUCUCCGAACGUGUCACGU | 139 |
| | | Antisense strand | ACGUGACACGUUCGGAGAAUU | 140 |
| Comp. Conjugate 2 | AD-66810 | Sense strand | GmsUmsGmUmGfCmAfCfUfUmCmGmCmUm UmCmAmCmAm | 141 |
| | | Antisense strand | UmsGfsUmGmAmAfGmCfGfAmAmGmUmGf CmAfCmAmCmsUmsUm | 142 |

Preparation Example 3 Preparation of P10-siHBa1M1SVP (Conjugate 27)

(3-1) Synthesis of P-10 Compounds

P-10 Compounds were synthesized according to the following process:

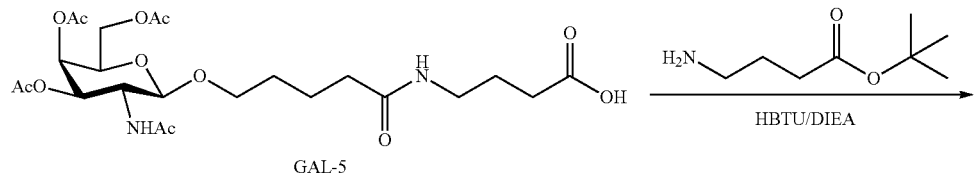

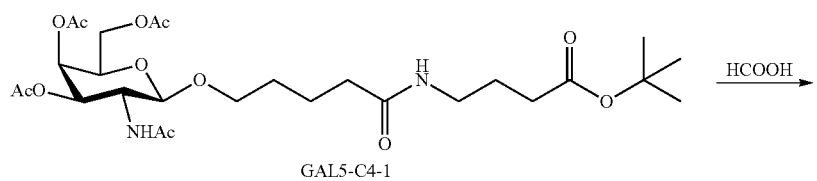

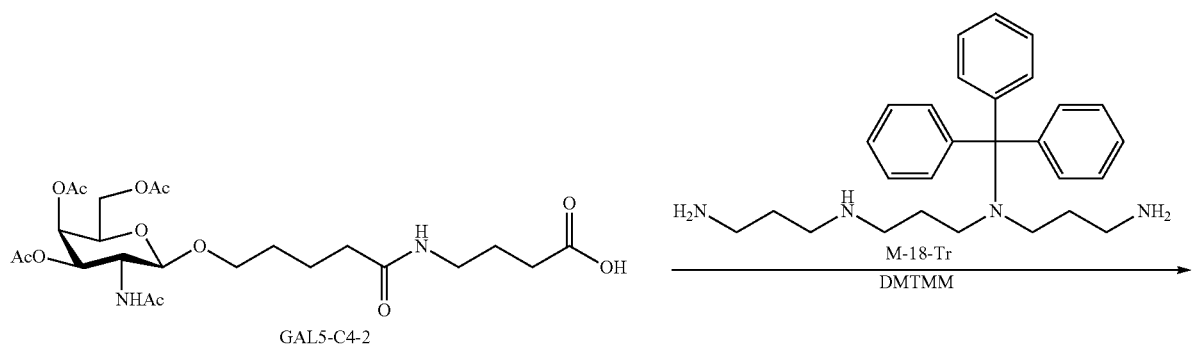

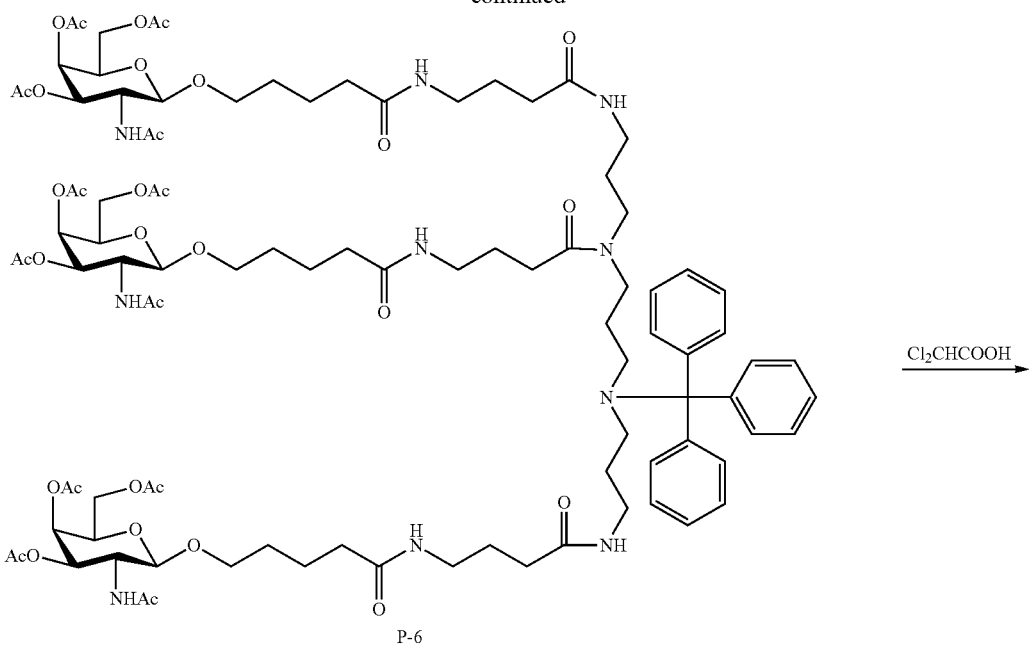
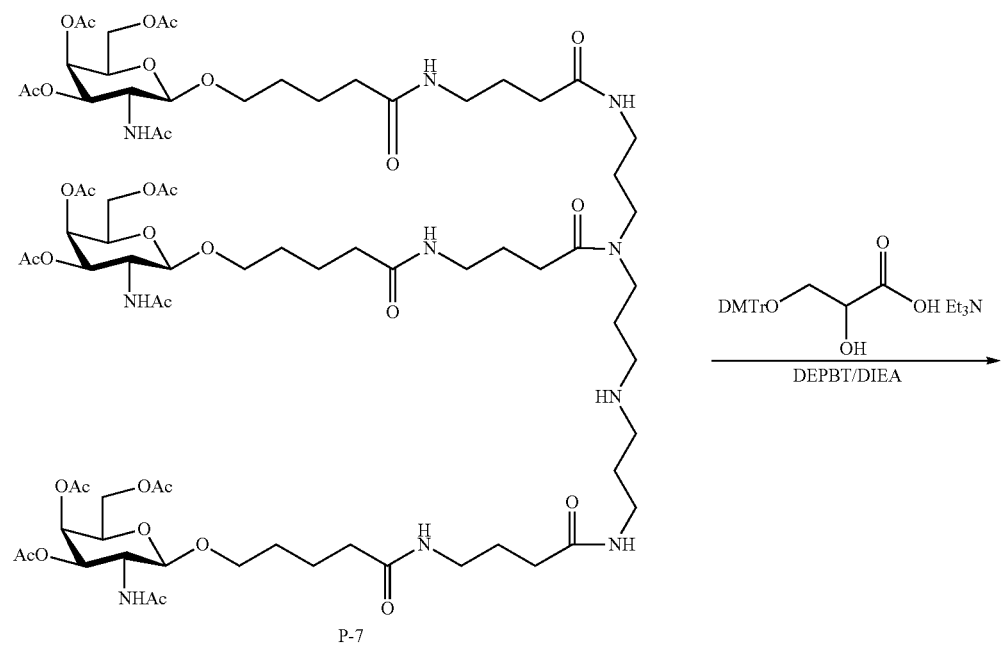

-continued
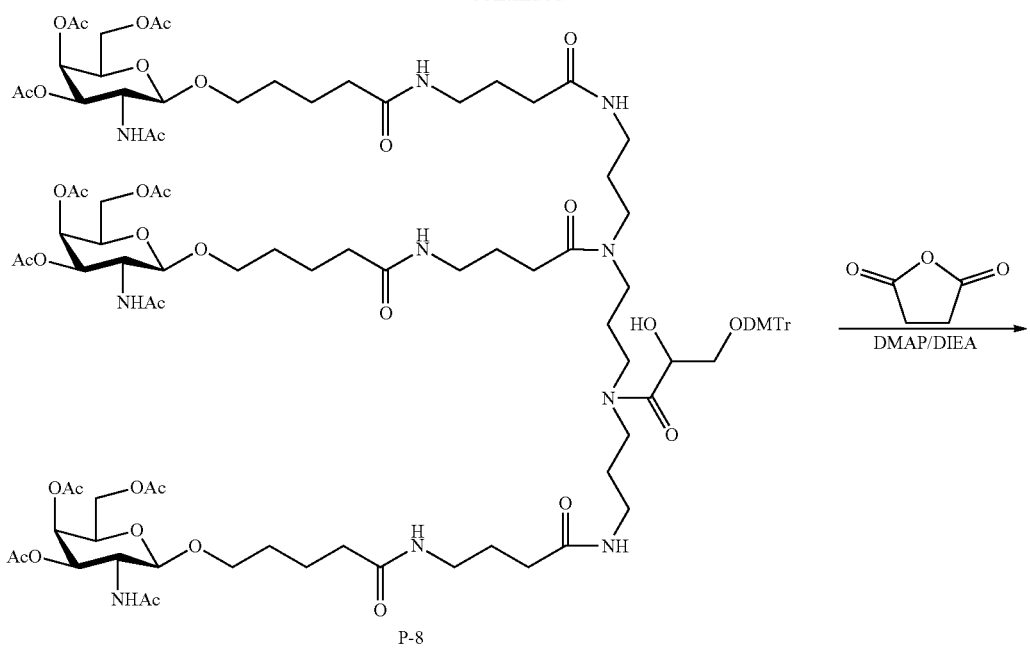
P-8
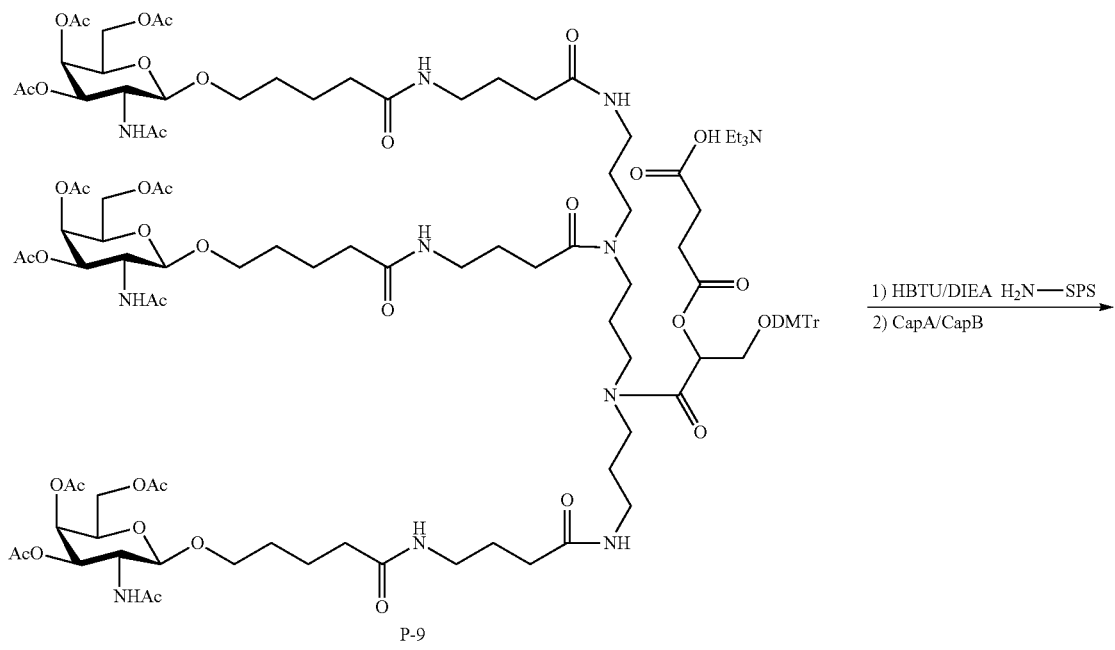
P-9

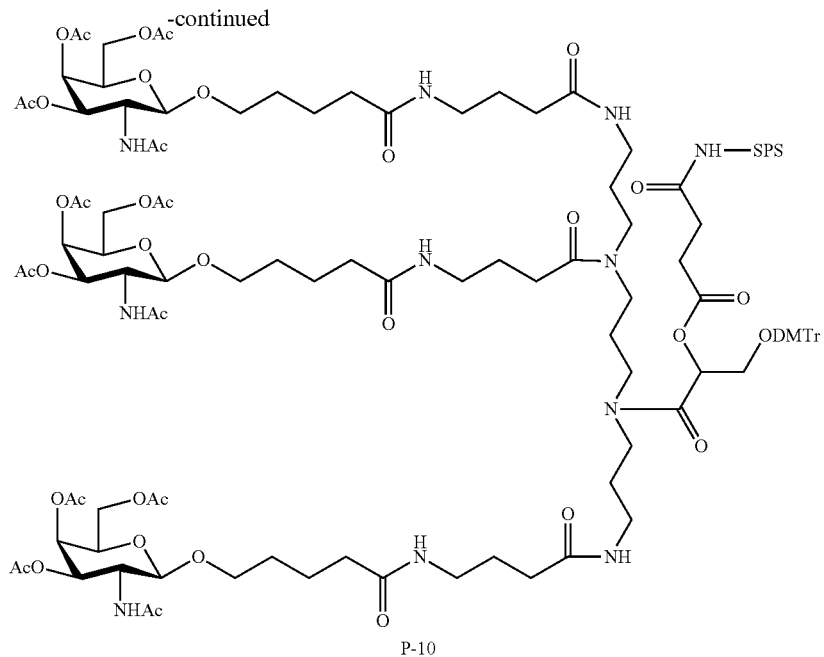

P-10

(3-1-1) Synthesis of GAL5-C4-1

GAL-5 (13.43 g, 30.0 mmol) obtained according to the method described in step (1-1-1) above, t-butyl 4-aminobutyrate hydrochloride (5.87 g, 30.0 mmol), O-benzotriazol-tetramethyluronium hexafluorophosphate (13.65 g, 36.0 mmol) and diisopropylethylamine (11.63 g, 90.0 mmol) were added into 40 ml of N,N-dimethylformamide, dissolved homogeneously and then stirred at room temperature to react for 5 hours. The resultant reaction solution was added with 300 ml of saturated aqueous sodium bicarbonate solution, extracted three times, each with 200 ml of ethyl acetate. All organic phases were combined and washed once with 200 ml of saturated brine. The organic phase was isolated and dried with anhydrous sodium sulfate. The solvent was removed by evaporation under reduced pressure to dryness to give 30.3 g of crude product GAL5-C4-1 as oil, which was directly used in the next reaction.

(3-1-2) Synthesis of GAL5-C4-2

The crude product GAL5-C4-1 (30.3 g, 30 mmol) obtained in step (3-1-1) was dissolved in 180 ml of formic acid and stirred at room temperature to react for 16 hours. The solvent was evaporated to dryness. The residue was purified by column chromatography (200-300 mesh normal phase silica gel, with a gradient elution of dichloromethane:methanol=100:18-100:20). The eluate was collected and concentrated to remove the solvents to give a total of 14.84 g of the target product GAL5-C4-2.

(3-1-3) Synthesis of P-6

M-18-Tr (2.02 g, 4.69 mmol) obtained according to the method described in step (1-1-4) and GAL5-C4-2 (8.24 g, 15.48 mmol) obtained in step (3-1-2) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 20 ml of dichloromethane. The resultant organic phase was washed with 10 ml of saturated sodium bicarbonate solution and 10 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and the solvent was removed by evaporation under reduced pressure to give a total of 8.27 g of pure product P-6.

(3-1-4) Synthesis of P-7

P-6 (6.82 g, 3.456 mmol) obtained in step (3-1-3) above was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjusted to pH 7-8 with saturated sodium bicarbonate solution. The aqueous phase isolated was extracted six times, each with 30 ml of dichloromethane. All organic phases were combined, dried with anhydrous sodium sulfate, and filtered. Then the solvent was removed by evaporation under reduced pressure to give a crude product. The crude product was purified by using a normal phase silica gel column (200-300 mesh). The column was added with 10 wt % triethylamine for neutralizing the acidity of silica gel, equilibrated with 1 wt ‰ triethylamine and eluted with a gradient elution of dichloromethane:methanol=100:30-100:40. The eluate was collected, and the solvent was removed by evaporation under reduced pressure to give a total of 4.82 g of P-7. MS m/z: C78H127N10O33, [M+H]+, calculated: 1732.91, measured: 1735.73.

(3-1-5) Synthesis of P-8

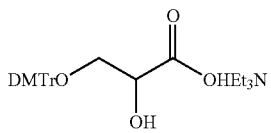

(A-1)

P-7 (2.653 g, 1.532 mmol) and A-1 (2.342 g, 4.596 mmol) were mixed and dissolved in 16 ml of dichloromethane, and added with 3-diethoxyphosphoryl-1,2,3-benzotrizin 4(3H)-one (DEPBT) (1.375 g, 4.596 mmol) followed by diisopropylethylamine (1.188 g, 9.191 mmol) to react under stirring at 25° C. for 2 hours. The organic phase was washed with 10 ml of saturated sodium bicarbonate. The aqueous phase isolated was extracted three times, each with 10 ml of dichloromethane. All organic phases were combined and washed with 10 ml of saturated brine. The aqueous phase isolated was extracted twice, each with 10 ml of dichloromethane, and the obtained organic phases were combined, dried with anhydrous sodium sulfate and filtered. The solvent was removed by evaporation under reduced pressure, and foam-dried in a vacuum oil pump overnight to give a crude product. The crude product was subjected to a column purification. The column was filled with 120 g normal phase silica gel (200-300 mesh), added with 20 ml triethylamine for neutralizing the acidity of silica gel, equilibrated with petroleum ether containing 1 wt % triethylamine and eluted with a gradient elution of petroleum ether:ethyl acetate:dichloromethane:N,N-dimethylformamide=1:1:1:0.5-1:1:1:0.6. The eluate was collected, and the solvent was removed by evaporation under reduced pressure to give a total of 2.793 g of pure product P-8.

(3-1-6) Synthesis of P-9

P-8 (490 mg, 0.231 mmol), succinic anhydride (69 mg, 0.693 mmol) and 4-dimethylaminopyridine (DMAP, 68 mg, 0.554 mmol) were mixed and dissolved in 2.3 ml of dichloromethane, and added with diisopropylethylamine (DIEA, 149 mg, 1.155 mmol) to react under stirring at 25° C. for 21 hours. The resultant reaction solution was added with 50 ml dichloromethane for dilution and then washed with 100 ml of 0.5 M triethylamine phosphate. The aqueous phase isolated was extracted three times, each with 10 ml of dichloromethane. All organic phases were combined, and the solvent was removed by evaporation under reduced pressure to give a crude product. The crude product was subjected to a column purification. The column was filled with 80 g normal phase silica gel (200-300 mesh), added with 1 wt % triethylamine for neutralizing the acidity of silica gel and equilibrated with dichloromethane, and eluted with a gradient elution of dichloromethane containing 1 wt ‰ triethylamine:methanol=100:18-100:20. The eluate was collected, and the solvent was removed by evaporation under reduced pressure to give a total of 200 mg of pure product P-9 conjugating molecule. MS m/z: C106H153N10O41, [M-DMTr]+, calculated: 1921.05, measured: 1920.97.

(3-1-7) Synthesis of P-10

P-10 was prepared by using the same method as in step (1-1-9) of Preparation Example 1, except that: P-9 conjugating molecule was used to replace L-9 conjugating molecule, thereby obtaining P-9 conjugating molecule linked to a solid phase support.

(3-2) Synthesis of P10-siHBa1M1SVP Conjugate

Conjugate 27 was prepared by using the same method as in steps (1-2), (1-3A) and (1-4) of Preparation Example 1, except that P-10 Compound was used to replace L-10 Compound to start the synthesis of a sense strand. It was expected that P10-siHBa1M1SVP conjugate with a structure as shown by Formula (4) can be obtained.

Preparation Example 4 Preparation of R5-siHBa1M1SVP Conjugate (Conjugate 28)

(4-1) Synthesis of R-5 Compound

R-5 Compound was synthesized by the following method:

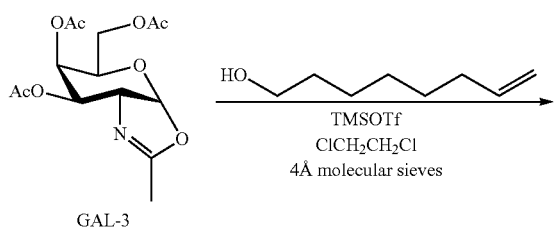

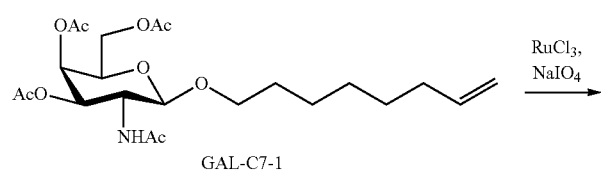

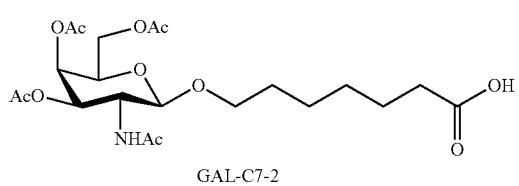

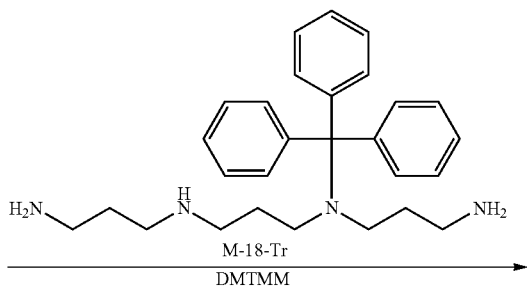

151
152
-continued
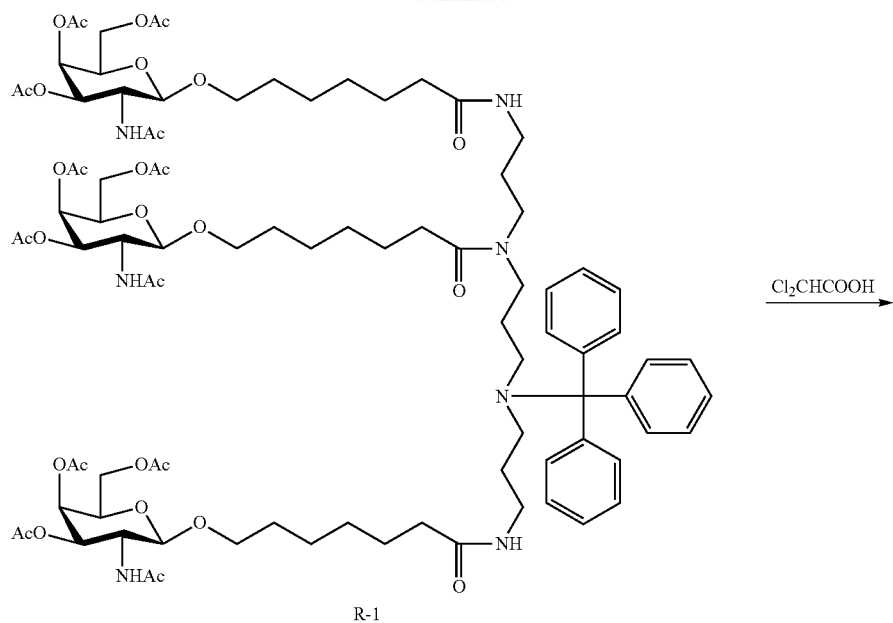
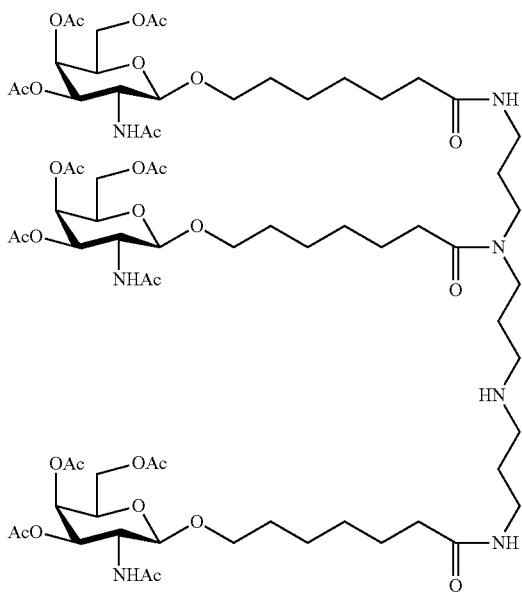
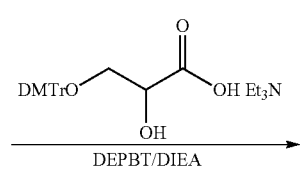

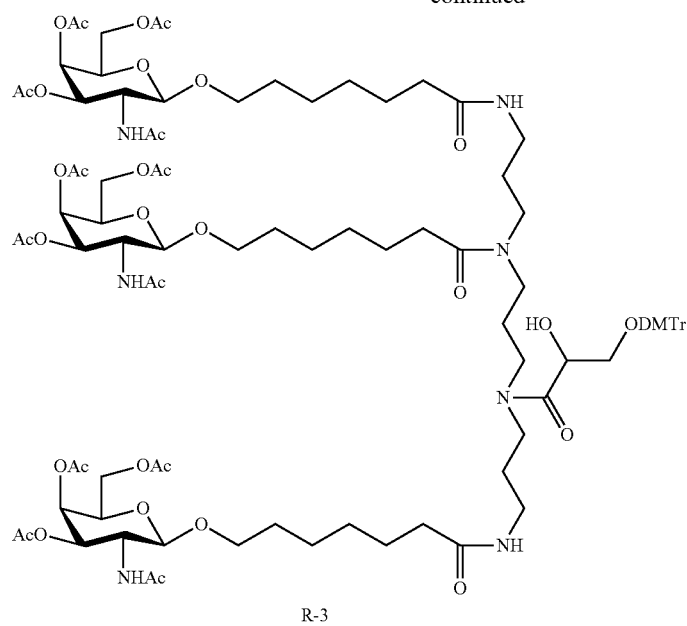
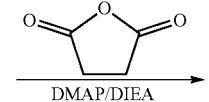
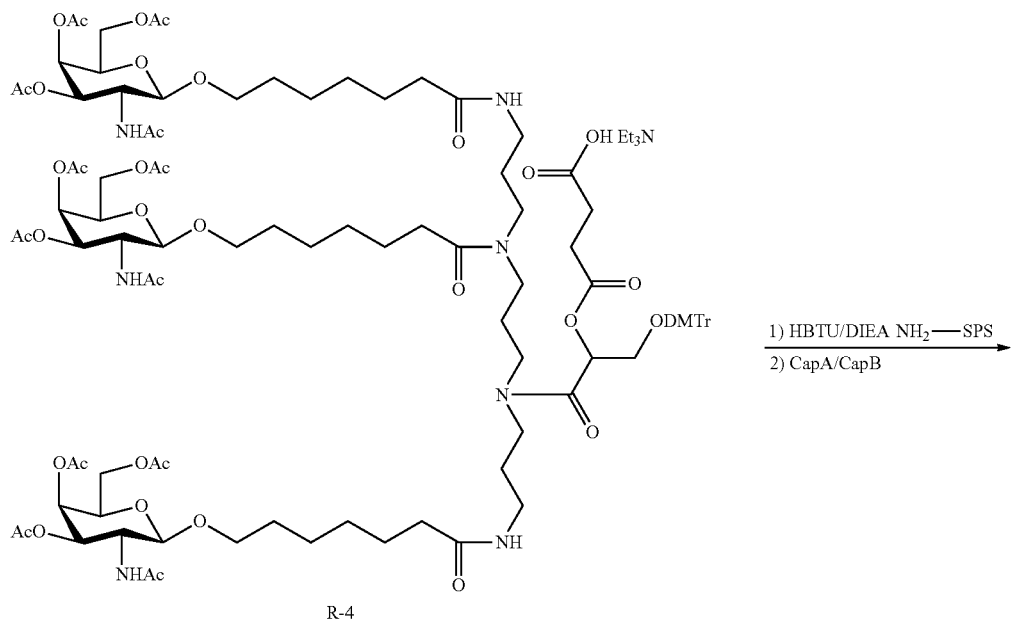

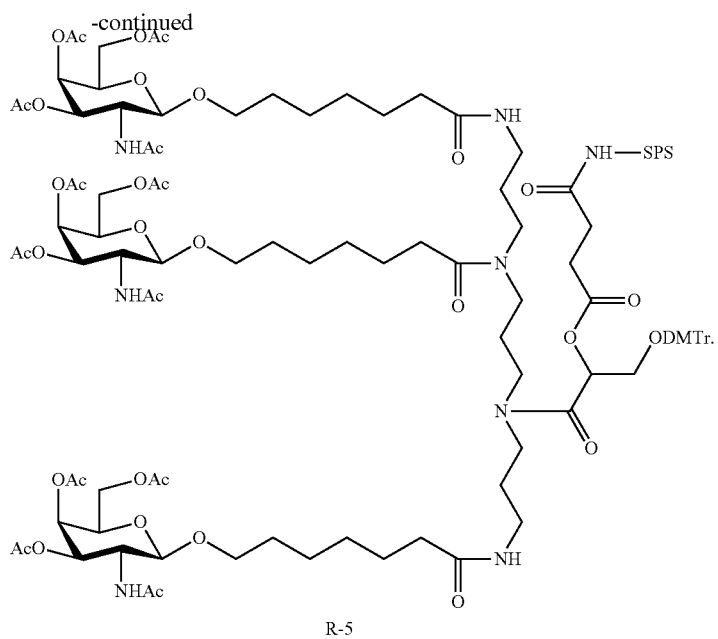

R-5

(4-1-1) Synthesis of GAL-C7-1

GAL-3 (26.4 g, 80.2 mmol) obtained according to the method described in step (1-1-1b) was dissolved in 134 ml of anhydrous 1,2-dichloroethane, and added with 60 g of 4 Å molecular sieve powder followed by 7-octen-1-ol (11.3 g, 88.2 mmol) to react under stirring at room temperature for 10 minutes. Trimethylsilyl trifluoromethanesulphonate (8.9 g, 40.1 mmol) was added in an ice bath and nitrogen atmosphere to react under stirring at room temperature for 24 hours. The 4 Å molecular sieve powder was removed by filtration. 500 ml of saturated aqueous sodium bicarbonate solution was added to the filtrate for washing. An organic phase was isolated. The aqueous phase was extracted once with 100 ml of dichloromethane. All organic phases were combined and washed once with 250 ml of saturated brine. The organic phase was isolated and dried with anhydrous sodium sulfate. The solvent was removed by evaporation under reduced pressure to dryness to give 33.3 g of product GAL-C7-1 as a yellow syrup, which was directly used in the next oxidation reaction without purification.

(4-1-2) Synthesis of GAL-C7-2

GAL-C7-1 (33.3 g, 72.8 mmol) obtained in step (4-1-1) was dissolved in a mixed solvent of 160 ml of dichloromethane and 160 ml of acetonitrile, added with 216 ml of water and solid sodium periodate (62.3 g, 291.2 mmol) respectively, stirred in an ice water bath for 10 minutes, and added with a catalyst ruthenium trichloride (498 mg, 2.4 mmol). The reaction was naturally warmed to room temperature and stirred for 23 hours. The resultant reaction solution was diluted by adding 200 ml of water under stirring, and adjusted to pH 7.5 by adding saturated sodium bicarbonate. The organic phase was isolated and discarded. The aqueous phase was extracted three times, each with dichloromethane. The organic phases resulted from the extraction were discarded. The aqueous phase resulted from the extraction was adjusted to a pH of about 3 with citric acid solid and extracted three times, each with 200 ml of dichloromethane, and the resultant organic phases were combined and dried with anhydrous sodium sulfate. The solvent was removed by evaporation under reduced pressure, and then the residue was purified by column chromatography (200-300 mesh normal phase silica gel, with a gradient elution of dichloromethane:methanol=100:18-100:20) to give 22.4 g of product GAL-C7-2 as a white foamy solid. MS m/z: C21H32NO 1, [M+H]+, calculated: 476.50, measured: 475.94.

(4-1-3) Synthesis of R-1

M-18-Tr (2.02 g, 4.69 mmol) obtained according to the method described in step (1-1-4) and GAL-C7-2 (7.36 g, 15.48 mmol) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react under stirring at room temperature for 2 hours. The resultant reaction solution was diluted with 200 ml of dichloromethane. The organic phase was washed with 100 ml of saturated sodium bicarbonate solution and 100 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected and the solvent was removed by evaporation under reduced pressure to give 7.82 g of pure product R-1.

(4-1-4) Synthesis of R-2

R-1 (6.23 g, 3.456 mmol) was dissolved in 69 ml of dichloromethane, and added with dichloroacetic acid (13.367 g, 103.67 mmol) to react at room temperature for 2 hours. The resultant reaction solution was diluted by adding 100 ml of dichloromethane, washed and adjust to pH 7-8 with saturated sodium bicarbonate solution. The aqueous phase isolated was extracted six times, each with 30 ml of dichloromethane. All organic phases were combined, dried with anhydrous sodium sulfate, and filtered. Then the solvent was removed by evaporation under reduced pressure to give a crude product. The crude product was purified by using a normal phase silica gel column (200-300 mesh). The column was added with 10 wt % triethylamine for neutralizing the acidity of silica gel and equilibrated with 1 wt ‰ triethylamine, and eluted with a gradient elution of dichloromethane:methanol=100:30-100:40. The solvent was removed by evaporation under reduced pressure to give 4.49 g of pure product R-2.

(4-1-5) Synthesis of R-3

R-2 (2.391 g, 1.532 mmol) and A-1 (2.342 g, 4.596 mmol) were mixed and dissolved in 16 ml of dichloromethane, and added with 3-(diethoxyphosphoryloxy)-1,2,3-benzotrizin-4 (3H)-one (DEPBT, 1.375 g, 4.596 mmol) followed by diisopropylethylamine (1.188 g, 9.191 mmol) to react under stirring at 25° C. for 2 hours The organic phase was washed with 10 ml of saturated sodium bicarbonate. The aqueous phase isolated was extracted three times, each with 10 ml of dichloromethane. The organic phase was washed with 10 ml of saturated brine. The aqueous phase isolated was extracted twice, each with 10 ml of dichloromethane, and the obtained organic phases were combined, dried with anhydrous sodium sulfate and filtered. The solvent was removed by evaporation under reduced pressure, and the residue was foam-dried in a vacuum oil pump overnight to give a crude product. The crude product was subjected to a column purification. The column was filled with 120 g normal phase silica gel (200-300 mesh), added with 20 ml triethylamine for neutralizing the acidity of silica gel and equilibrated with petroleum ether containing 1 wt % triethylamine, and eluted with a gradient elution of petroleum ether:ethyl acetate: dichloromethane:N,N-dimethylformamide=1:1:1:0.5-1:1:1: 0.6. The solvent was removed by evaporation under reduced pressure to give 2.642 g of pure product R-3.

(4-1-6) Synthesis of R-4

R-3 (795 mg, 0.4074 mmol), succinic anhydride (82 mg, 0.8148 mmol) and 4-dimethylaminopyridine (DMAP, 100 mg, 0.8148 mmol) were mixed and dissolved in 4 ml of dichloromethane, and added with diisopropylethylamine (DIEA, 100 mg, 0.8148 mmol) to react under stirring at 25° C. for 18 hours. The resultant reaction solution was washed with 5 ml of 0.5 M triethylamine phosphate. The aqueous phase was extracted three times, each with 5 ml of dichloromethane. All organic phases were combined, and the solvent was removed by evaporation under reduced pressure to give a crude product. The crude product was subjected to a column purification. The column was filled with 30 g normal phase silica gel (200-300 mesh), added with 1 wt % triethylamine for neutralizing the acidity of silica gel and equilibrated with dichloromethane, and eluted with a gradient elution of dichloromethane containing 1 wt ‰ triethylamine:methanol=100:18-100:20. The eluate was collected, and the solvent was removed by evaporation under reduced pressure to give 505 mg of pure product of R-4 conjugating molecule.

(4-1-7) Synthesis of R-5

R-5 was prepared by using the same method as in step (1-1-9) of Preparation Example 1, except that: R-4 conjugating molecule was used to replace L-9 conjugating molecule, thereby obtaining R-4 conjugating molecule linked to a solid phase support.

(4-2) Synthesis of R5-siHBa1M1SVP Conjugate

Conjugate 28 was prepared by using the same method as in steps (1-2), (1-3A) and (1-4) of Preparation Example 1, except that R-5 Compound was used to replace L-10 Compound to start the synthesis of a sense strand. It was expected that $R_5$-siHBa1M1SVP conjugate with a structure as shown by Formula (7) can be obtained.

Preparation Example 5 Preparation of LA5-siHBa1M1SVP (Conjugate 29)

It was expected that LA-5 Compound can be synthesized according to the following process route:

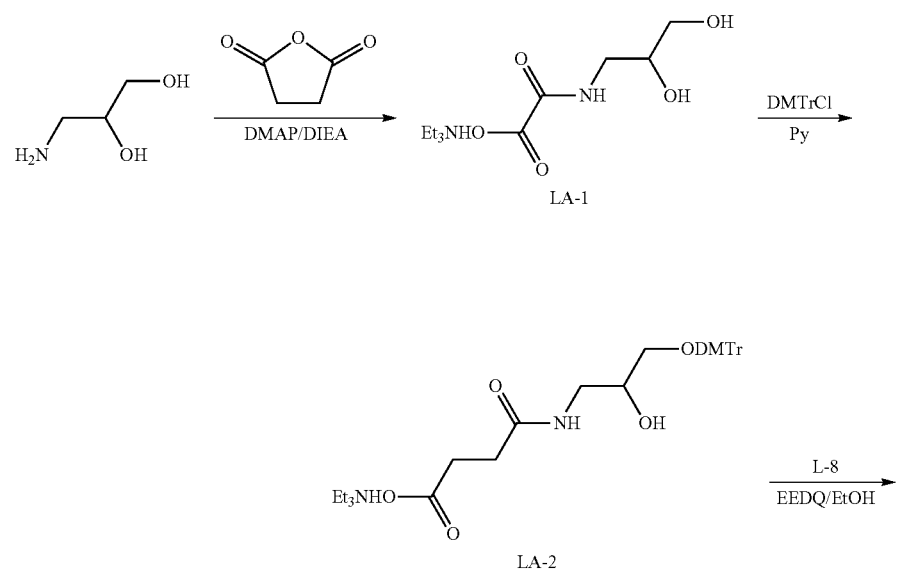

-continued
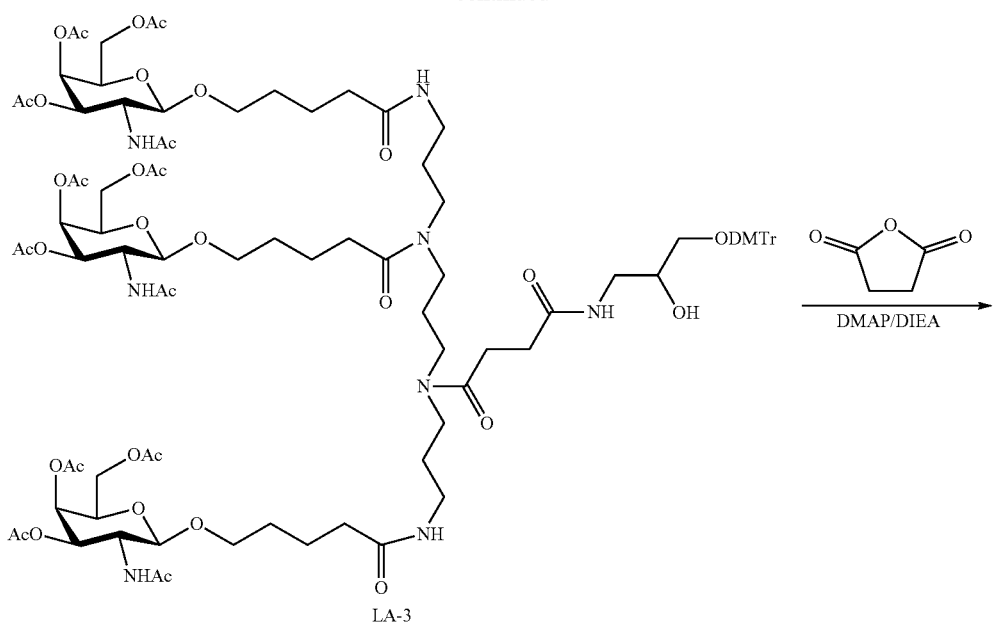
LA-3
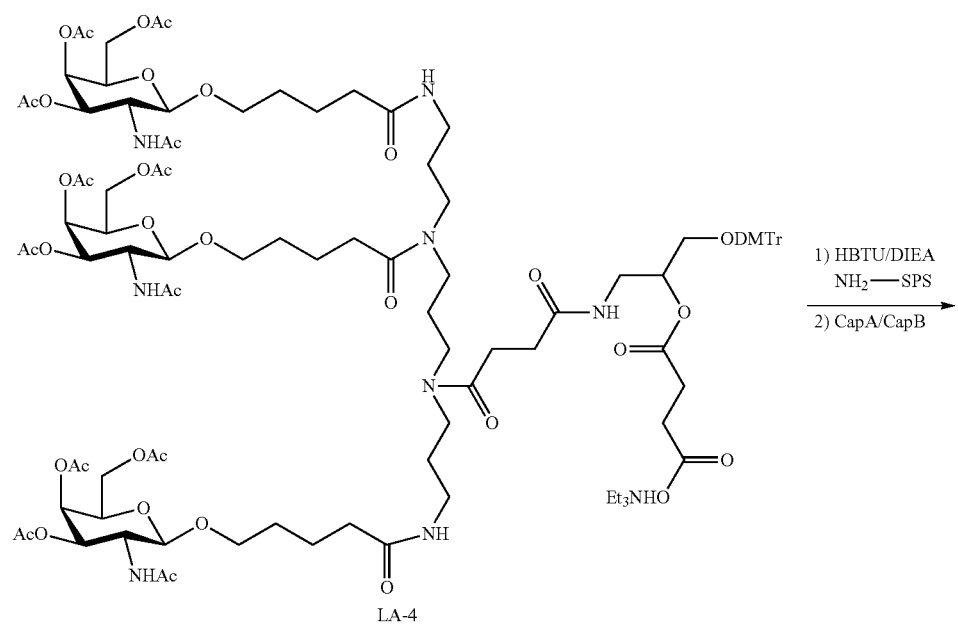
LA-4

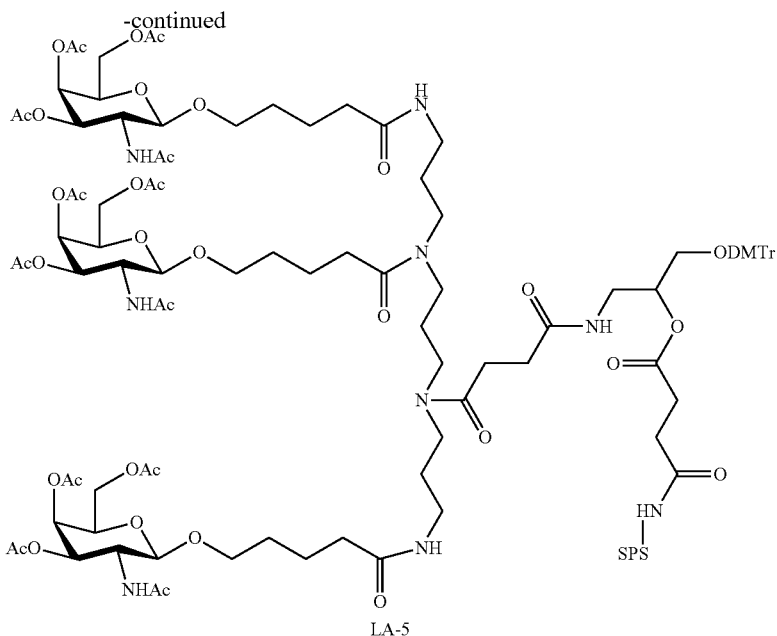

LA-5

Conjugate 29 was prepared by using the same method as in steps (1-2), (1-3A) and (1-4) of Preparation Example 1, except that LA-5 Compound was used to replace L-10 Compound to start the synthesis of a sense strand. It was expected that LA5-siHBa1M1SVP conjugate with a structure as shown by Formula (12) can be obtained.

Preparation Example 6 Preparation of LB5-siHBa1M1SVP Conjugate (Conjugate 30)

(6-1) Synthesis of LB-5 Compound

LB-5 Compound was synthesized according to the following process:

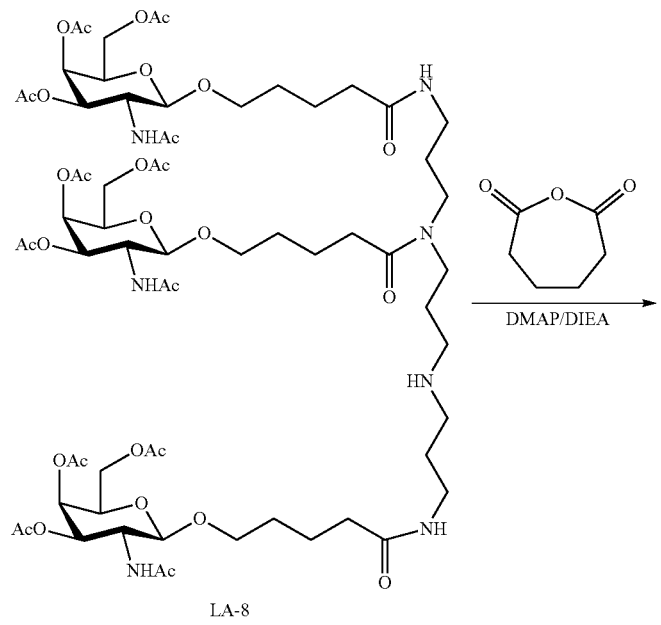

LA-8

-continued
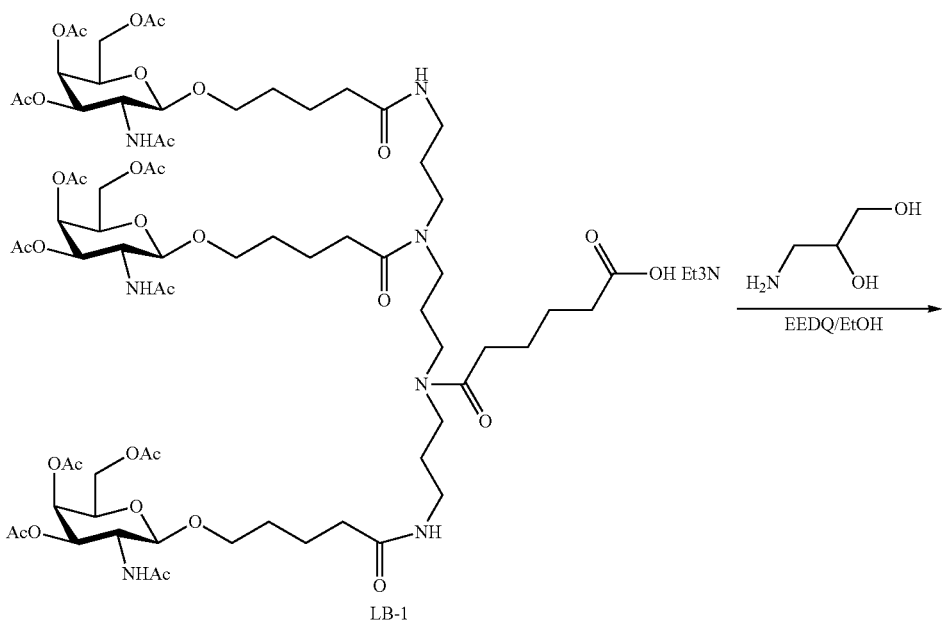
LB-1
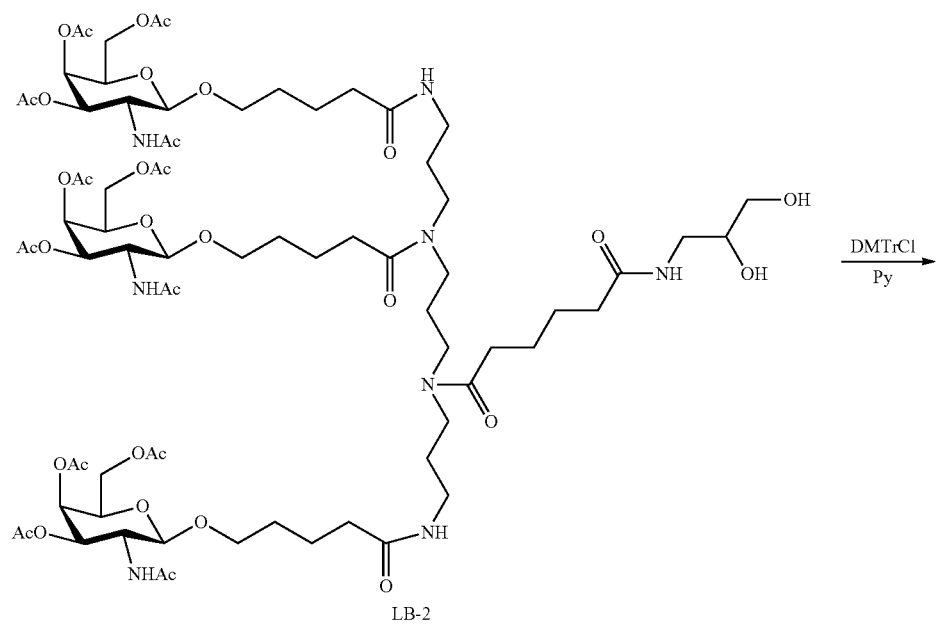
LB-2

-continued
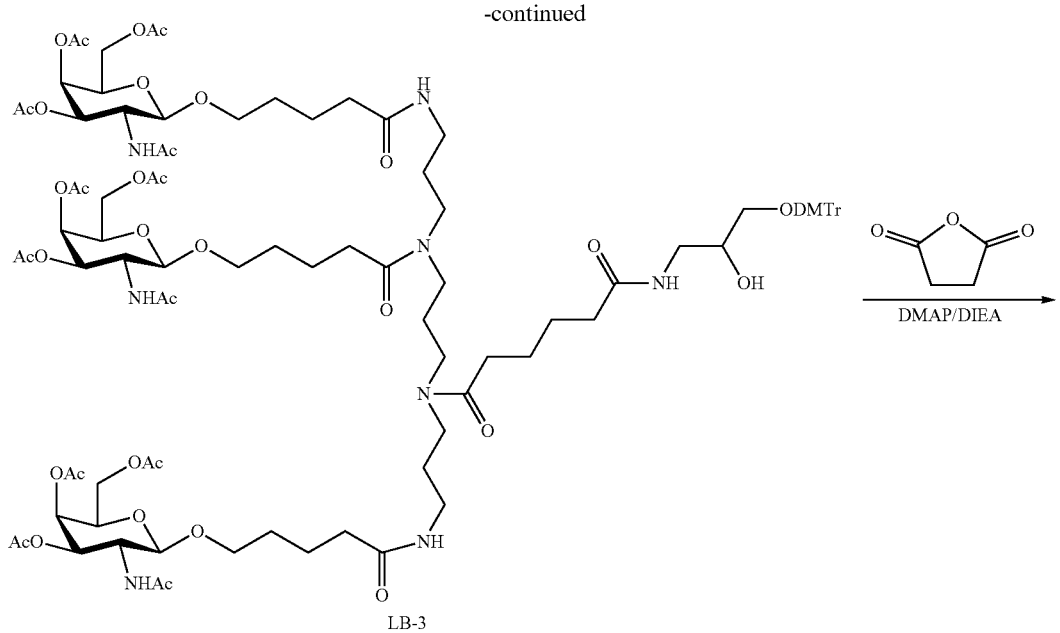
LB-3
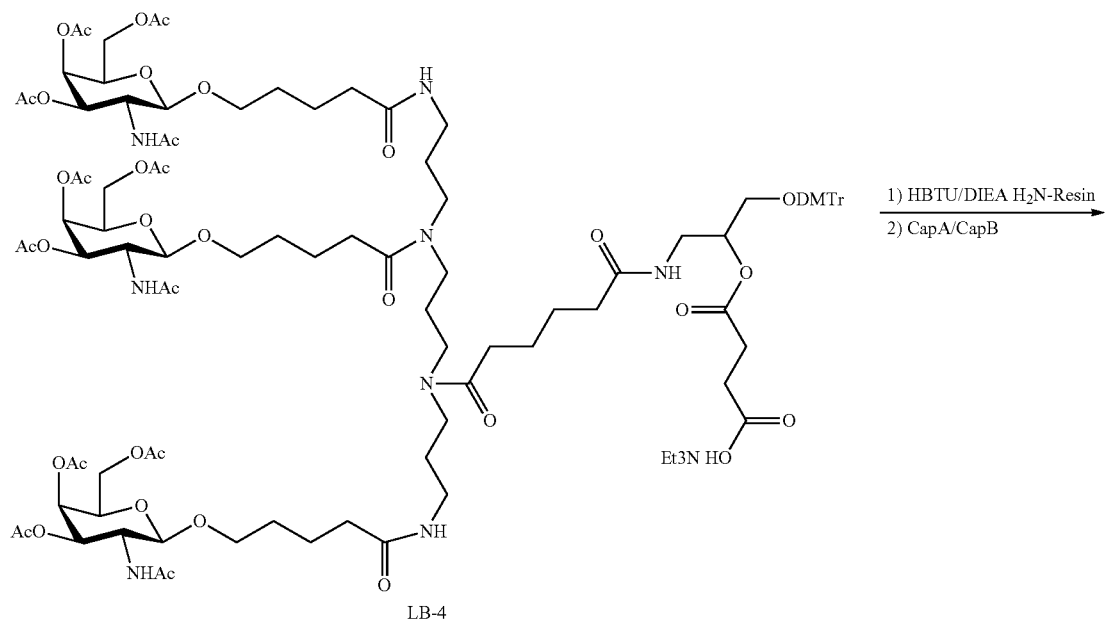
LB-4

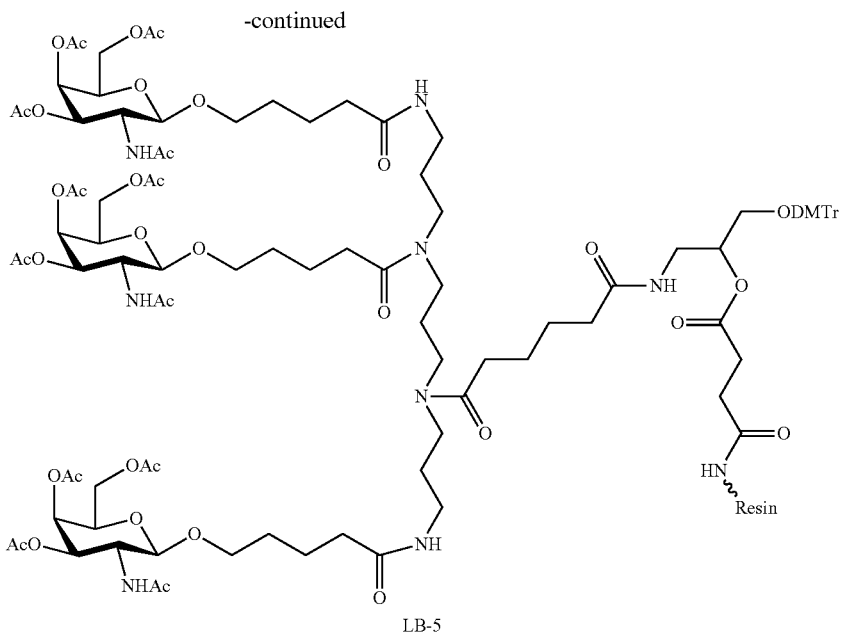

LB-5

(6-1-1) Synthesis of LB-1

L-8 (5.0 g, 3.386 mmol) obtained according to the method described in step (1-1-6), adipic anhydride (870 mg, 6.772 mmol) and 4-dimethylaminopyridine (DMAP, 827 mg, 6.772 mmol) were mixed and dissolved in 130 ml of dichloromethane, and added with diisopropylethylamine (DIEA, 2.2 g, 16.931 mmol) to react under stirring at 25° C. for 4 hours. The resultant reaction solution was added with 70 ml dichloromethane for dilution and then washed with 0.5 M triethylamine phosphate. The aqueous phase isolated was extracted four times, each with 10 ml of dichloromethane. All organic phases were combined, and the solvent was removed by evaporation under reduced pressure to give a crude product. The crude product was subjected to a column purification. The column was filled with 120 g normal phase silica gel (200-300 mesh), added with 1 wt % triethylamine for neutralizing the acidity of silica gel and equilibrated with dichloromethane, and eluted with a gradient elution of petroleum ether:ethyl acetate:dichloromethane:methanol=1:1:1:0.2-1:1:1:1. The solvent was removed by evaporation under reduced pressure to give 4.267 g of pure product LB-1.

(6-1-2) Synthesis of LB-2

LB-1 (4.697 g, 2.753 mmol, combination of 2 batches) obtained according to the method described in step (6-1-1), 3-amino-1,2-propanediol (313 mg, 3.442 mmol), 4-(4,6-dimethoxytriazin-2-yl)-4-methylmorpholine hydrochloride (DMTMM, 953 mg, 3.442 mmol) and N-methylmorpholine (700 mg, 6.884 mmol) were sequentially added to the mixture of 30 ml of acetonitrile and 3 ml of methanol to react under stirring at room temperature overnight. The solvent was evaporated to dryness, and the residue was purified by column chromatography (200-300 mesh normal phase silica gel, with a gradient elution of dichloromethane:methanol=1:0.07-1:0.5). The eluate was collected and concentrated to remove the solvents to give 3.27 g of target product LB-2.

(6-1-3) Synthesis of LB-3

LB-2 (2.27 g, 1.353 mmol) was dissolved in 14 ml of anhydrous pyridine, and added with 4,4'-dimethoxytrityl chloride (688 mg, 2.03 mmol) to react under stirring at room temperature overnight. The reaction was quenched by addition of 150 ml of methanol. The solvent was evaporated to dryness, and the residue was purified by column chromatography (200-300 mesh normal phase silica gel, with a gradient elution of dichloromethane:methanol=1:0.05-1:0.2). The eluate was collected and concentrated to remove the solvent to give 1.647 g of target product LB-3.

(6-1-4) Synthesis of LB-4

LB-3 (822 mg, 0.415 mmol), succinic anhydride (83 g, 0.83 mmol) and 4-dimethylaminopyridine (DMAP, 102 mg, 0.83 mmol) were mixed and dissolved in 4 ml of dichloromethane, added with DIEA (270 mg, 2.075 mmol), and stirred at 25° C. to react overnight. The resultant reaction solution was washed with 0.5 M triethylamine phosphate three times. The aqueous phase isolated was extracted three times, each with 2 ml of dichloromethane. All organic phases were combined, and the solvent was removed by evaporation under reduced pressure to give a crude product. The crude product was subjected to a column purification. The column was filled with normal phase silica gel (200-300 mesh), added with 5 wt % triethylamine for neutralizing the acidity of silica gel and equilibrated with petroleum ether, and eluted with a gradient elution of 1 wt ‰ triethylamine-containing dichloromethane:methanol=100:5-100:20. The solvent was removed by evaporation under reduced pressure to give 787 mg of pure product LB-4 conjugating molecule.

(6-1-5) Synthesis of LB-5

LB-5 was prepared by using the same method as in step (1-1-9) of Preparation Example 1, except that: LB-4 conjugating molecule was used to replace L-9 conjugating molecule, thereby obtaining LB-4 conjugating molecule linked to a solid phase support.

(6-2) Synthesis of LB5-siHBa1M1SVP Conjugate

Conjugate 30 was prepared by using the same method as in steps (1-2), (1-3A) and (1-4) of Preparation Example 1, except that LB-5 Compound was used to replace L-10 Compound to start the synthesis of a sense strand. It was expected that LB5-siHBa1M1SVP conjugate with a structure as shown by Formula (13) can be obtained.

Preparation Example 7 Preparation of V8-siHBa1M1SVP Conjugate (Conjugate 31)

It was expected that V-8 Compound can be synthesized according to the following process route:

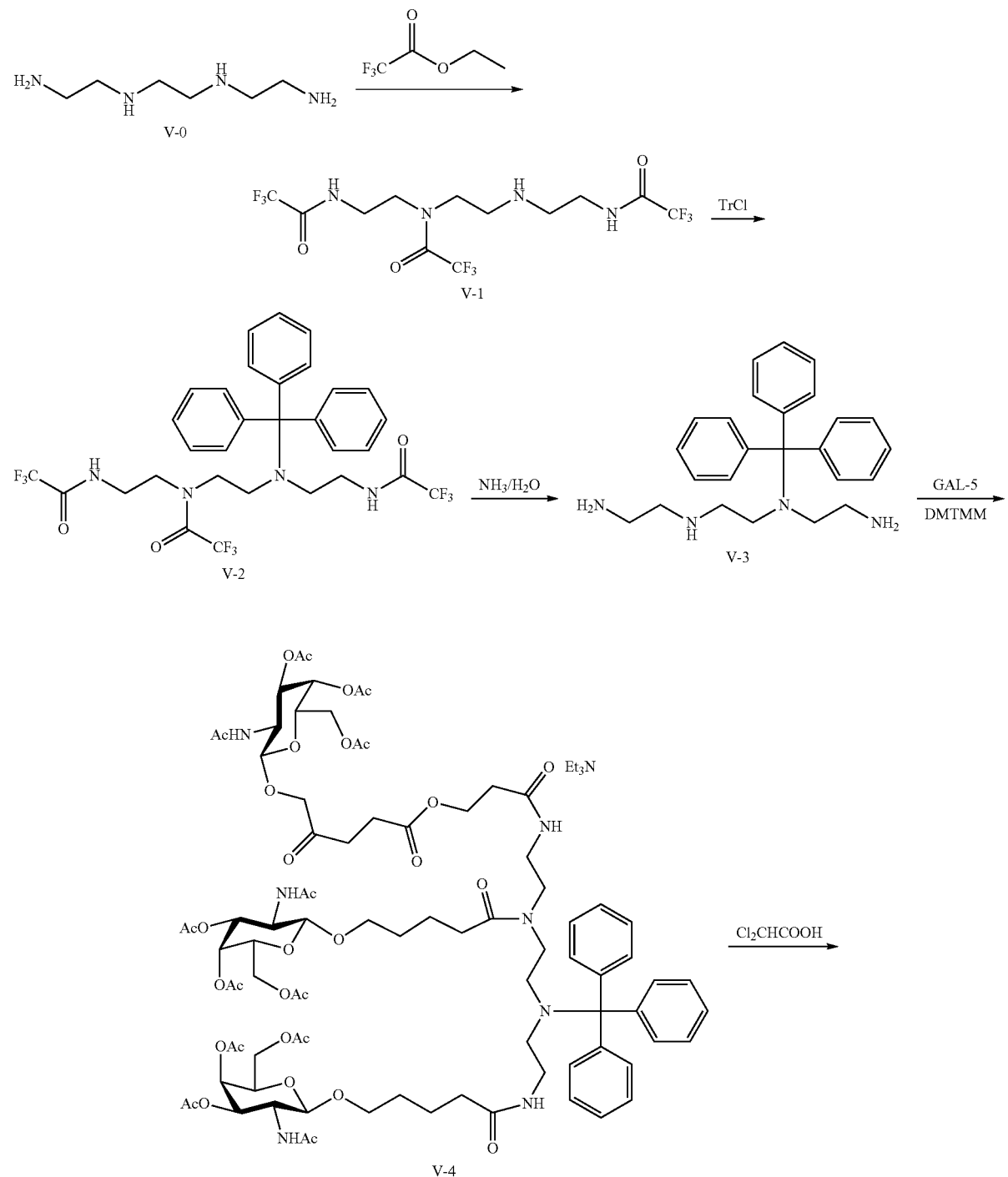

-continued
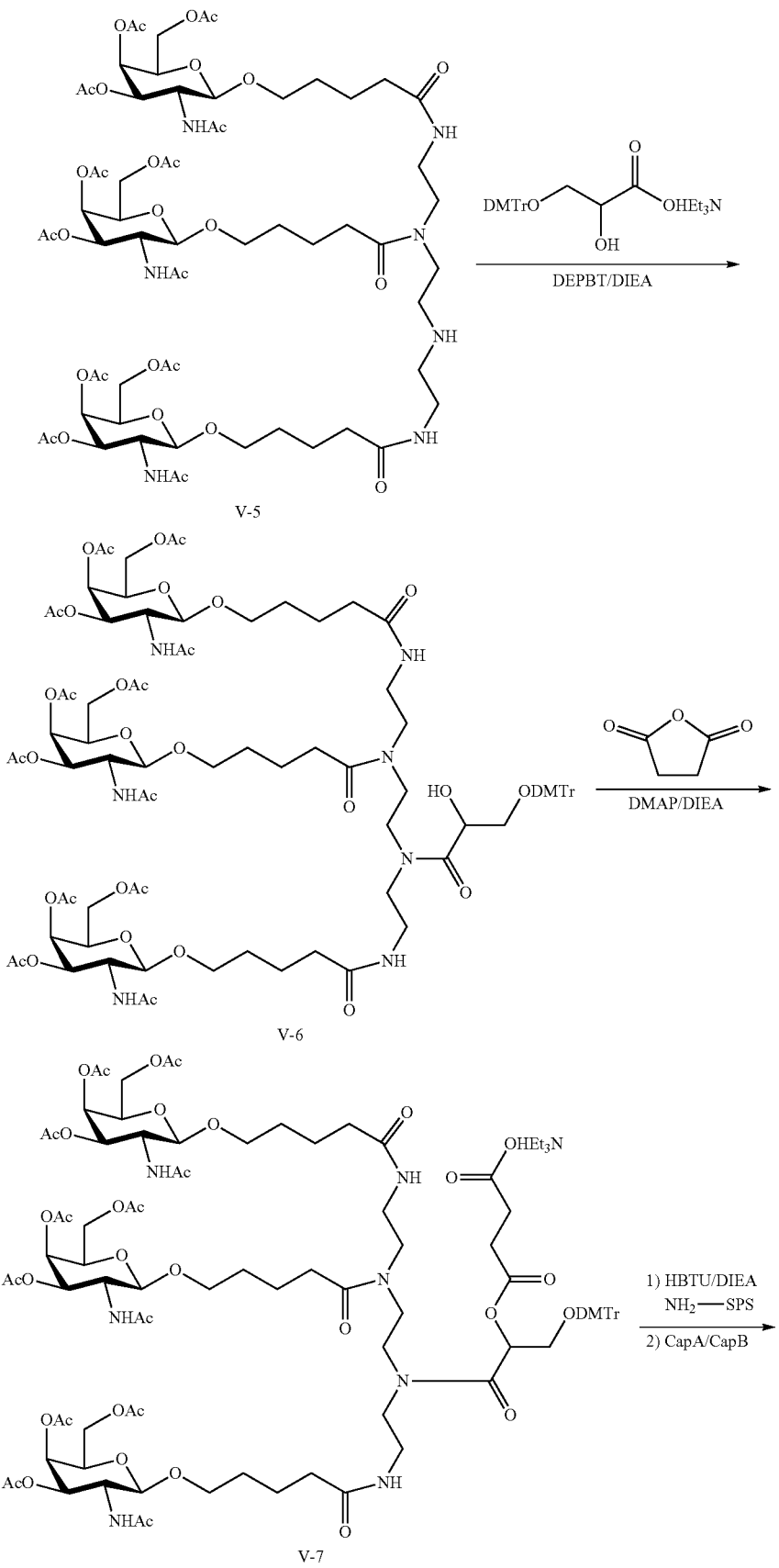

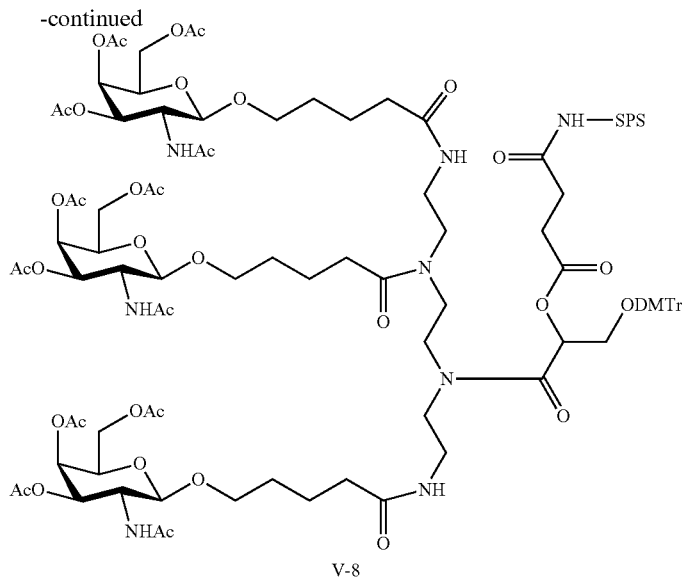

V-8

Conjugate 31 was prepared by using the same method as in steps (1-2), (1-3A) and (1-4) of Preparation Example 1, except that V-8 Compound was used to replace L-10 Compound to start the synthesis of a sense strand. It was expected that V8-siHBa1M1SVP conjugate with a structure as shown by Formula (14) can be obtained.

Preparation Example 8 Preparation of W8-siHBa1M1SVP Conjugate (Conjugate 32)

(8-1) Synthesis of W-8 Compound

W-8 Compound was synthesized according to the following process:

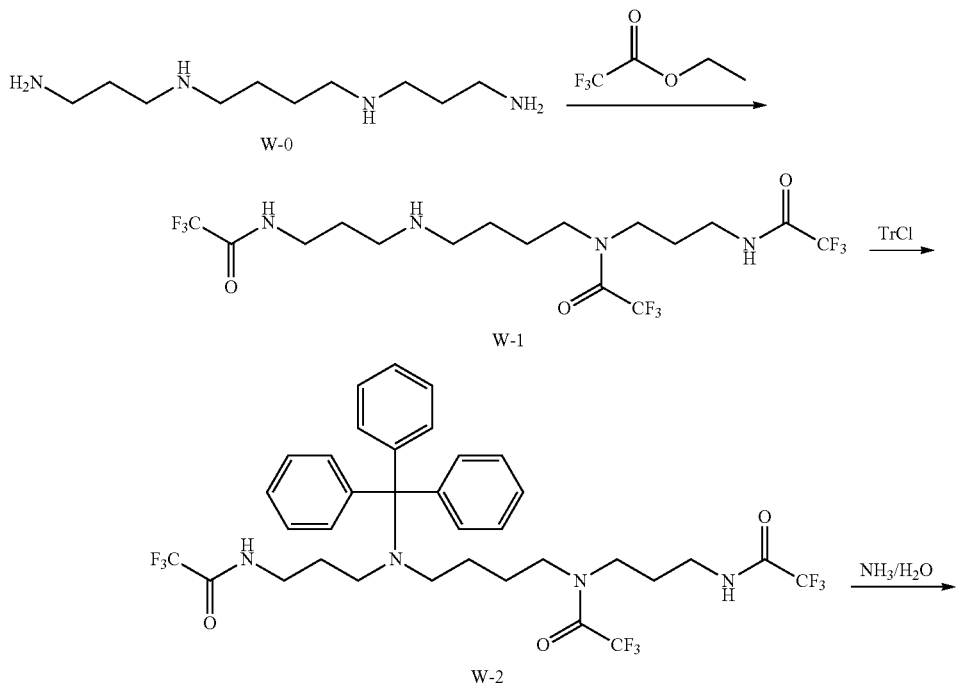

175
176
-continued
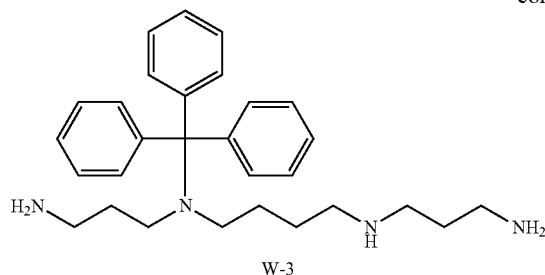
W-3
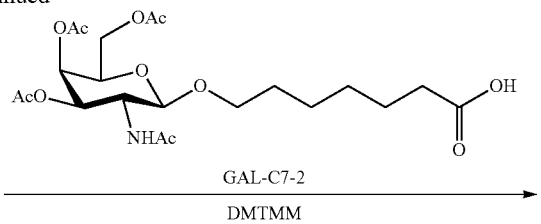
GAL-C7-2
⟶
DMTMM
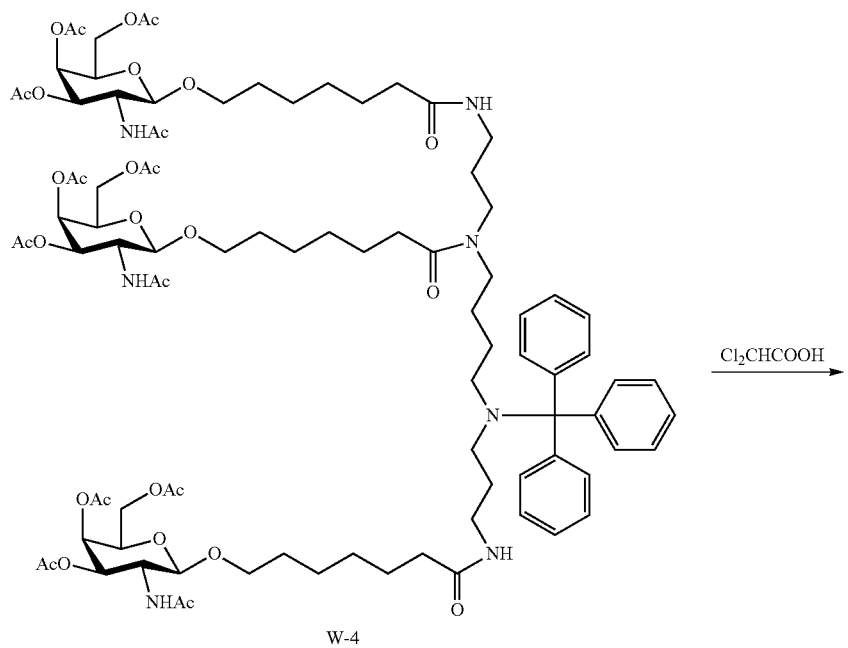
W-4
Cl$_2$CHCOOH ⟶
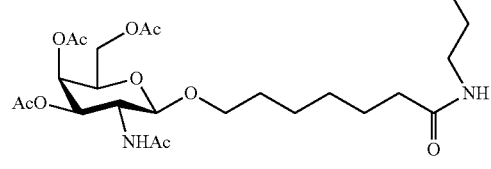
W-5
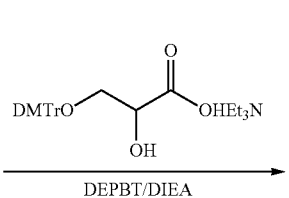
DEPBT/DIEA ⟶

-continued
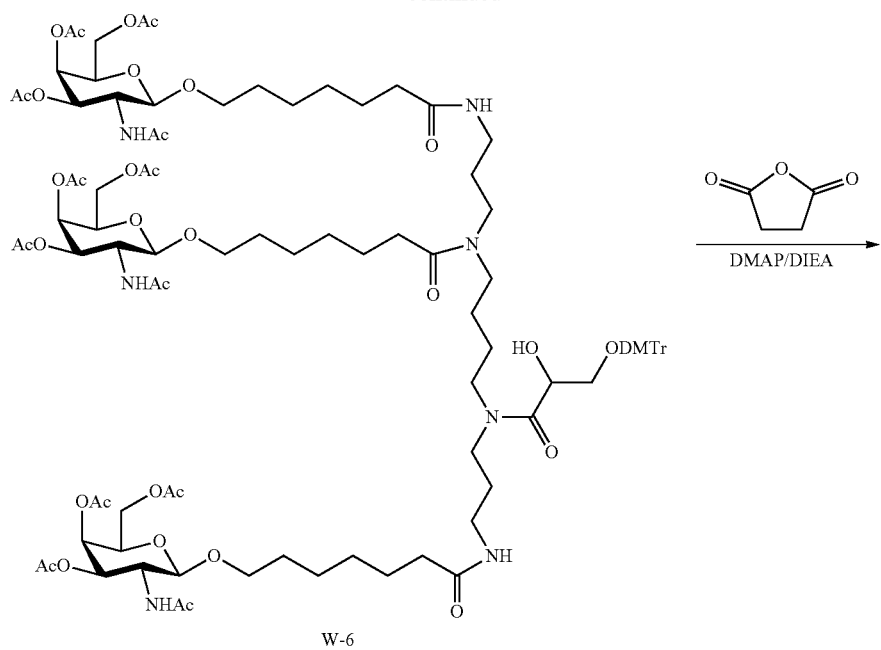
W-6
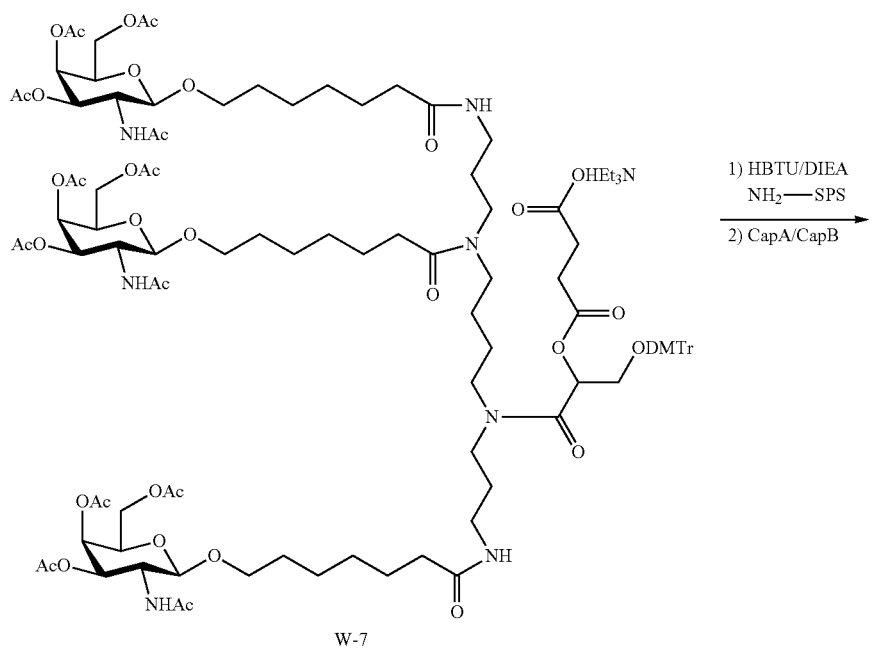
W-7

-continued

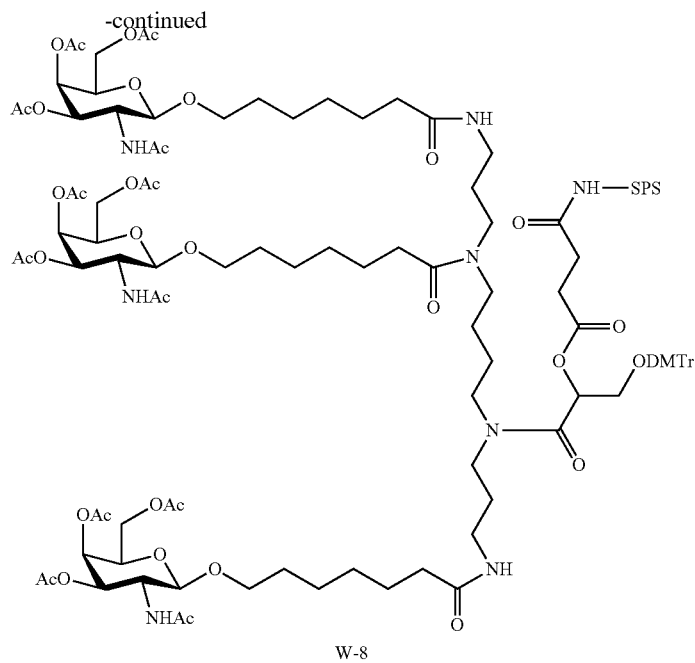

W-8

(8-1-1) Synthesis of W-1

W-0 (2.024 g, 10 mmol) was dissolved in 25 ml of acetonitrile, added with triethylamine (4.048 g, 40 mmol), and cooled to about 0° C. in an ice water bath. Ethyl trifluoroacetate (5.683 g, 40 mmol) was added to react at room temperature for 22 hours. The solvent was removed by evaporation under reduced pressure, and the residue was foam-dried in a vacuum oil pump for 18 hours to give 5.835 g of crude solid product W-1.

(8-1-2) Synthesis of W-2

The crude product W-1 (5.835 g, 10 mmol) was dissolved in 50 ml of dichloromethane. The resultant reaction solution was added with TrCl (3.345 g, 12 mmol) and triethylamine (1.518 g, 15 mmol) to react under stirring at room temperature for 20 hours. The resultant reaction solution was washed twice, each with 20 ml of saturated sodium bicarbonate and once with 20 ml of saturated brine. All organic phases were combined, dried with anhydrous sodium sulfate and filtered. The organic solvent was removed by evaporation under reduced pressure, and the residue was foam-dried in a vacuum oil pump overnight to give 8.012 g of crude solid product W-2. The crude solid product W-2 was used in the next deprotection reaction without treatment.

(8-1-3) Synthesis of W-3

The crude product W-2 (8.012 g, 10 mmol) was dissolved in 100 ml of methanol, and added with 100 ml of aqueous methylamine solution (40 wt %) to react under stirring at 50° C. for 23 hours. Insoluble particles were removed by filtration. The solvent was removed by evaporation under reduced pressure. The residue was added with 200 ml of mixed solvent of DCM:methanol in a volume ratio of 1:1, and the resultant organic phase was washed with 50 ml of saturated sodium bicarbonate. The aqueous phase isolated was extracted three times, each with 50 ml of dichloromethane. All organic phases were combined, dried with anhydrous sodium sulfate and filtered. The solvent was removed by evaporation under reduced pressure, and the residue was foam-dried in a vacuum oil pump overnight, and purified by using a normal phase silica gel column (200-300 mesh). The column was packed with petroleum ether, added with 1 wt % triethylamine for neutralizing the acidity of silica gel, and eluted with a gradient elution of dichloromethane:methanol: aqueous ammonia (25 wt %)=1:1:0.05-1:1:0.25. The eluate was collected. The solvent was removed by evaporation under reduced pressure, and the residue was foam-dried in a vacuum oil pump to give 3.062 g of pure product W-3.

(8-1-4) Synthesis of W-4

W-3 (0.675 g, 1.517 mmol) and GAL-C7-2 (2.60 g, 5.46 mmol) were mixed and dissolved in 47 ml of acetonitrile, added with diisopropylethylamine (1.57 g, 12.14 mmol) followed by 3-(diethoxyphosphoryloxy)-1,2,3-benzotrizin-4 (3H)-one (DEPBT, 1.816 g, 6.04 mmol) to react under stirring at room temperature for 2.5 hours. The resultant reaction solution was diluted with 100 ml of dichloromethane. The organic phase obtained was washed with 80 ml of saturated sodium bicarbonate solution and 80 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=100:5-100:7. The eluate was collected, and the solvent was removed by evaporation under reduced pressure to give 1.610 g of pure product W-4.

(8-1-5) Synthesis of W-5

W-4 (1.61 g, 0.886 mmol) was dissolved in 125 ml of dichloromethane, and added with dichloroacetic acid (3.5 ml, 42.43 mmol) to react at room temperature for 1 hour. The resultant reaction solution was neutralized by adding 150 ml of pyridine. The solvent was removed by evaporation under reduced pressure to give a crude product. The crude product was purified by using a normal phase silica gel column (200-300 mesh). The column was added with 10 wt % triethylamine for neutralizing the acidity of silica gel, equilibrated with 1 wt ‰ triethylamine and eluted with a gradient elution of dichloromethane:methanol=100:30-100:40. The eluate was collected, and the solvent was removed by evaporation under reduced pressure to give 1.26 g of pure product W-5.

(8-1-6) Synthesis of W-6

W-5 (1.25 g, 0.793 mmol) and A-1 (1.21 g, 2.38 mmol) obtained according to the method described in step (1-1-7a) were mixed and dissolved in 12 ml of dichloromethane, and added with 3-(diethoxyphosphoryloxy)-1,2,3-benzotrizin-4(3H)-one (DEPBT, 0.712 g, 2.38 mmol) followed by diisopropylethylamine (0.615 g, 4.76 mmol) to react under stirring at 25° C. for 3 hours. The organic phase was washed with 80 ml of saturated sodium bicarbonate. The aqueous phase isolated was extracted three times, each with 10 ml of dichloromethane. All organic phases were combined and washed with 10 ml of saturated brine. The obtained organic phases were combined, dried with anhydrous sodium sulfate and filtered. The solvent was removed by evaporation under reduced pressure, and the residue was foam-dried in a vacuum oil pump overnight to give a crude product. The crude product was subjected to a column purification. The column was filled with 185 g normal phase silica gel (200-300 mesh), added with 20 ml triethylamine for neutralizing the acidity of silica gel, equilibrated with petroleum ether containing 1 wt % triethylamine and eluted with a gradient elution of petroleum ether:ethyl acetate:dichloromethane:N,N-dimethylformamide=1:1:1:0.1-1:1:1:0.7. The eluate was collected, and the solvent was removed by evaporation under reduced pressure to give 1.57 g of pure product W-6.

(8-1-7) Synthesis of W-7

W-6 (1.238 g, 0.63 mmol), succinic anhydride (0.189 g, 1.89 mmol) and 4-dimethylaminopyridine (DMAP, 0.231 g, 1.89 mmol) were mixed and dissolved in 7 ml of dichloromethane, and added with DIEA (0.407 g, 3.15 mmol) to react under stirring at 25° C. for 24 hours. The resultant reaction solution was washed with 5 ml of 0.5 M triethylamine phosphate. The aqueous phase isolated was extracted three times, each with 5 ml of dichloromethane. All organic phases were combined, and the solvent was removed by evaporation under reduced pressure to give a crude product. The crude product was subjected to a column purification. The column was filled with 30 g normal phase silica gel (200-300 mesh), added with 1 wt % triethylamine for neutralizing the acidity of silica gel, equilibrated with dichloromethane and eluted with a gradient elution of 1 wt ‰ triethylamine-containing dichloromethane:methanol=100:18-100:20. The eluate was collected, and the solvent was removed by evaporation under reduced pressure to give 1.033 g of pure product W-7 conjugating molecule. MS m/z: C101H146N7O38, [M-DMTr]+, calculated: 1763.92, measured: 1763.21.

(8-1-8) Synthesis of W-8

W-8 was prepared by using the same method as in step (1-1-9) of Preparation Example 1, except that: W-7 conjugating molecule was used to replace L-9 conjugating molecule, thereby obtaining W-7 conjugating molecule linked to a solid phase support.

(8-2) Synthesis of W8-siHBa1M1SVP Conjugate

Conjugate 32 was prepared by using the same method as in steps (1-2), (1-3A) and (1-4) of Preparation Example 1, except that W-8 Compound was used to replace L-10 Compound to start the synthesis of a sense strand. It was expected that W8-siHBa1M1SVP conjugate with a structure as shown by Formula (15) can be obtained.

Reparation Example 9 Preparation of
X8-siHBa1M1SVP Conjugate (Conjugate 33)

It was expected that X-8 Compound can be synthesized according to the following process route:

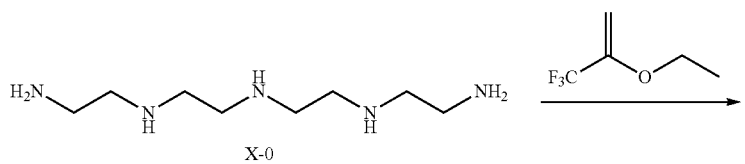

X-0

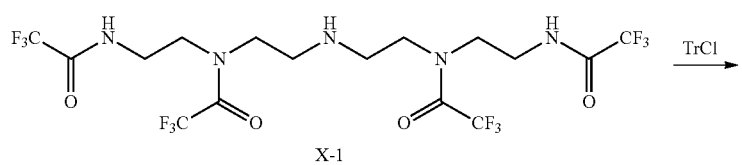

X-1

-continued
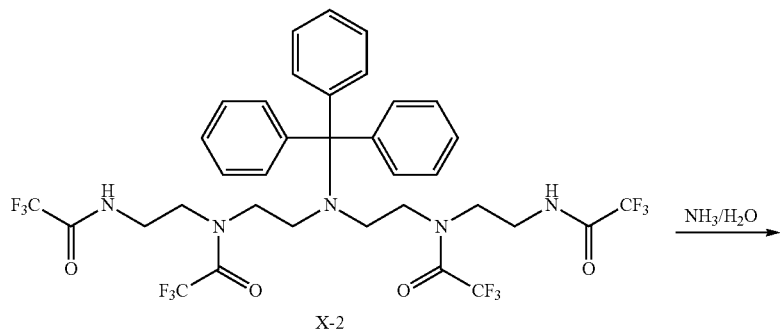
X-2 →(NH₃/H₂O)
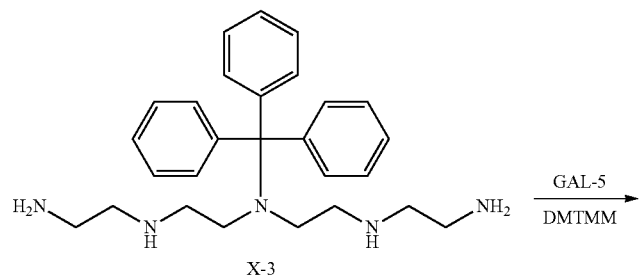
X-3 →(GAL-5, DMTMM)
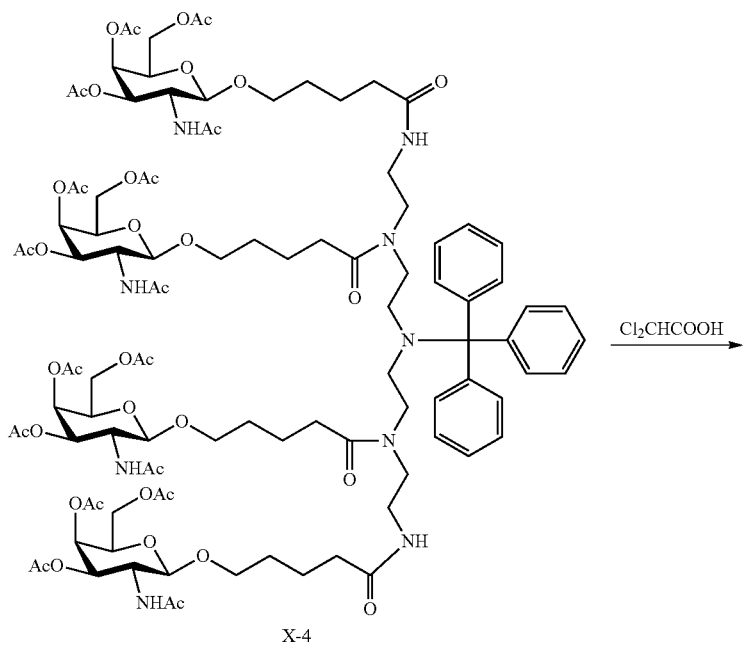
X-4 →(Cl₂CHCOOH)

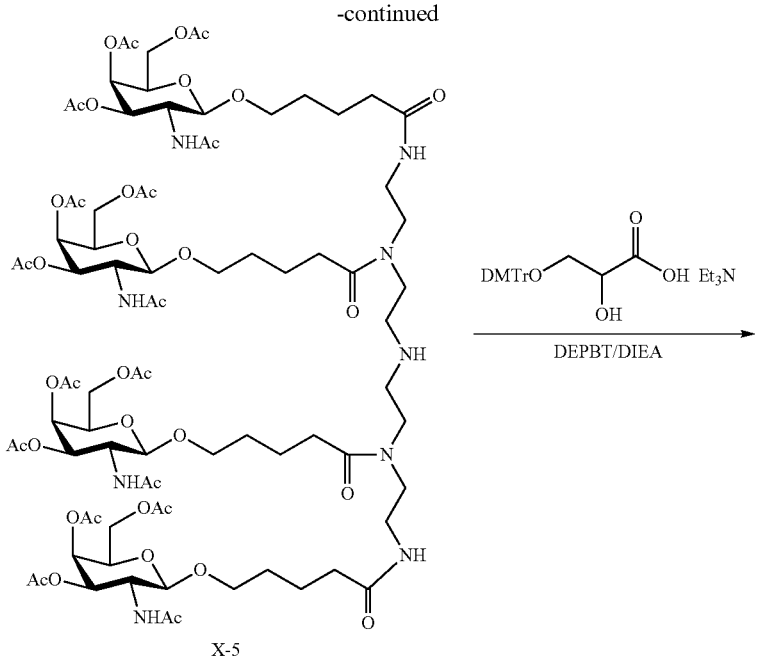
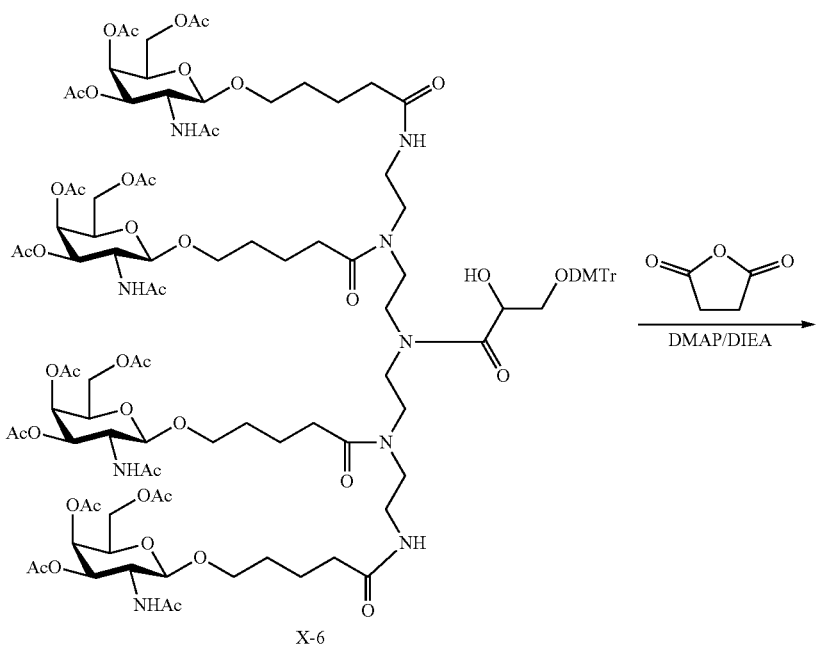

-continued
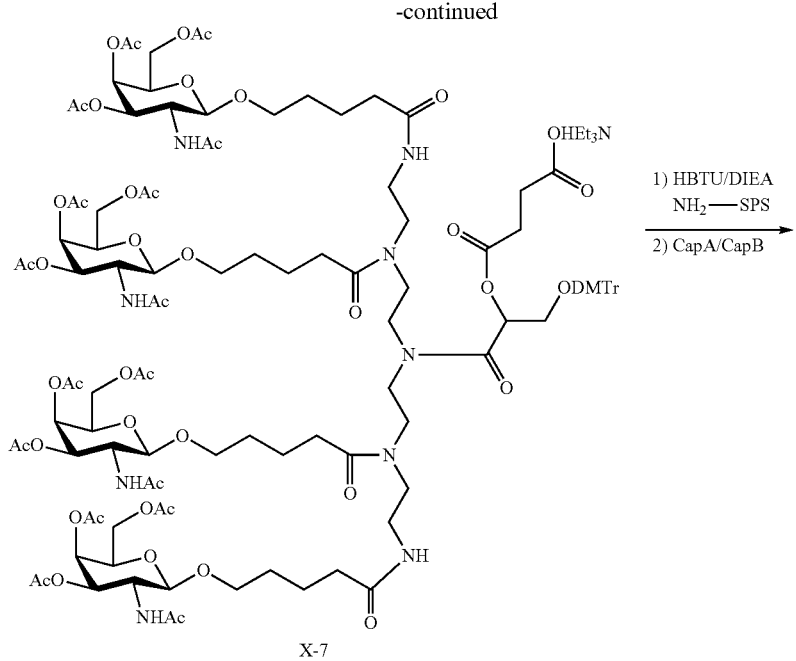
X-7
1) HBTU/DIEA
NH$_2$—SPS
———————→
2) CapA/CapB
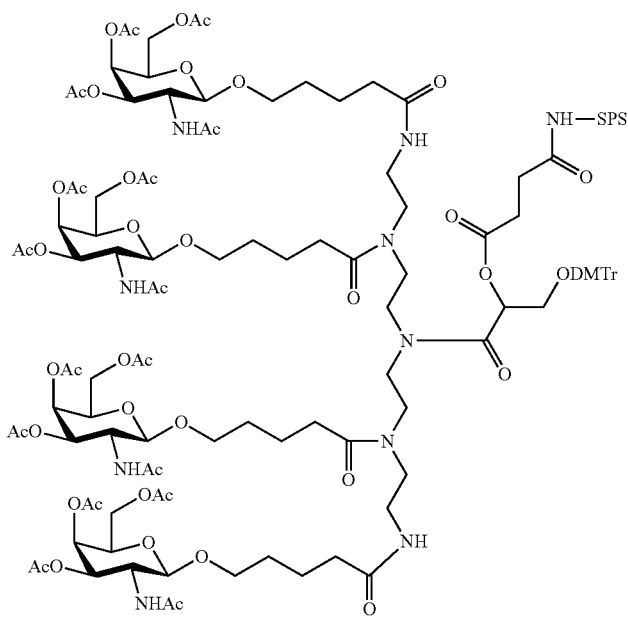
X-8

Conjugate 33 was prepared by using the same method as in steps (1-2), (1-3A) and (1-4) of Preparation Example 1, except that X-8 Compound was used to replace L-10 Compound to start the synthesis of a sense strand. It was expected that X8-siHBa1M1SVP conjugate with a structure as shown by Formula (21) can be obtained.

Preparation Example 10 Preparation of Z5-siHBa1M1SVP Conjugate (Conjugate 34)

(10-1) Synthesis of Z-5 Compound

Z-5 Compound was synthesized according to the following process:

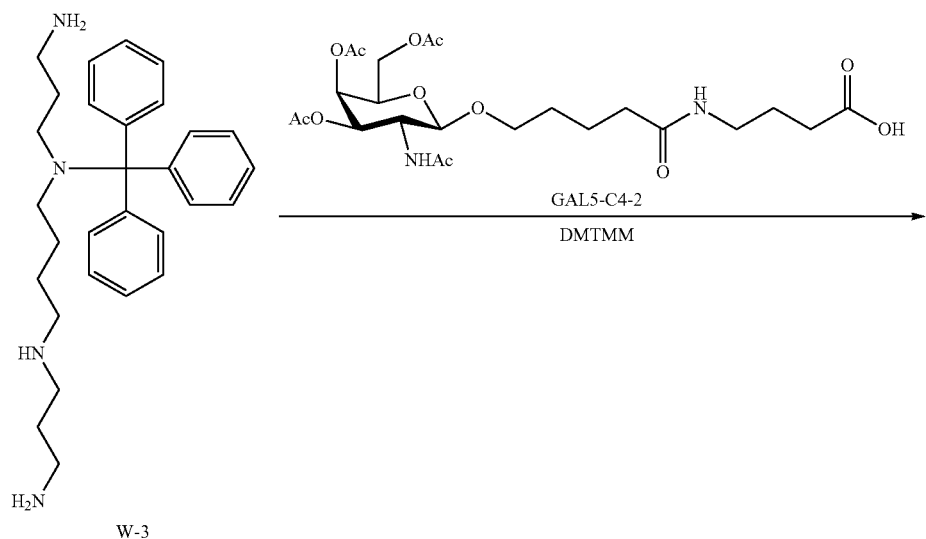

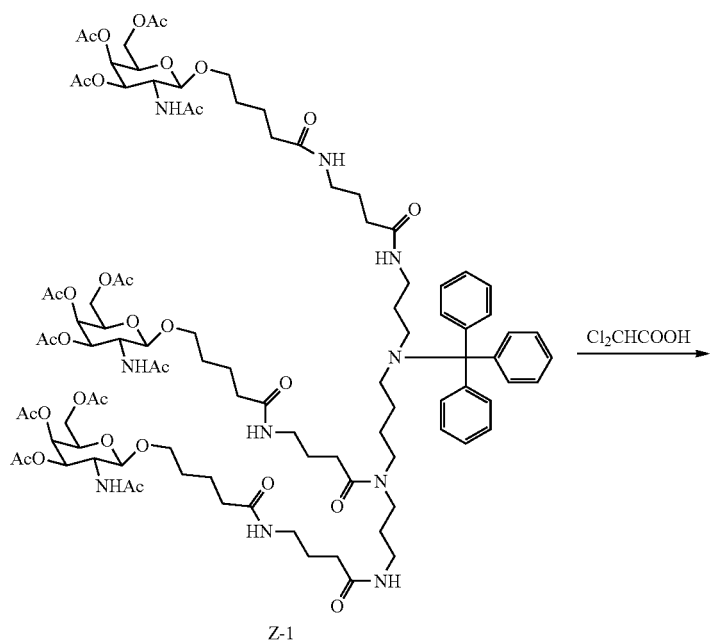

-continued
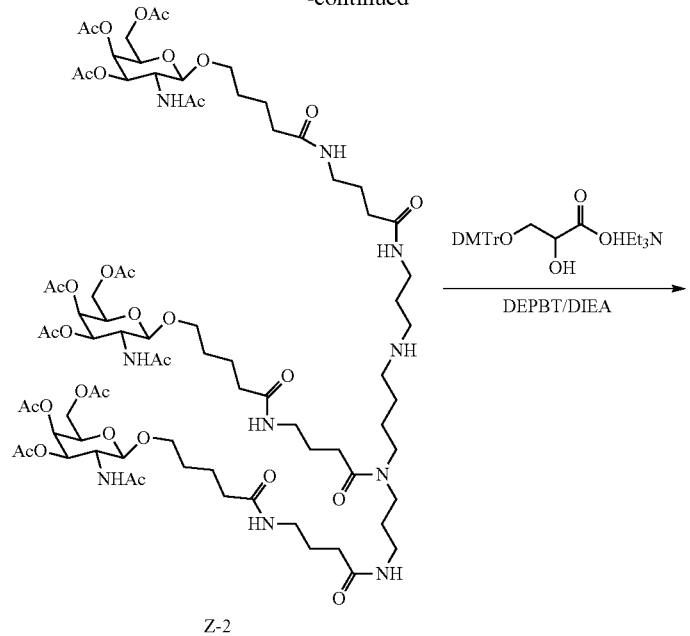
Z-2
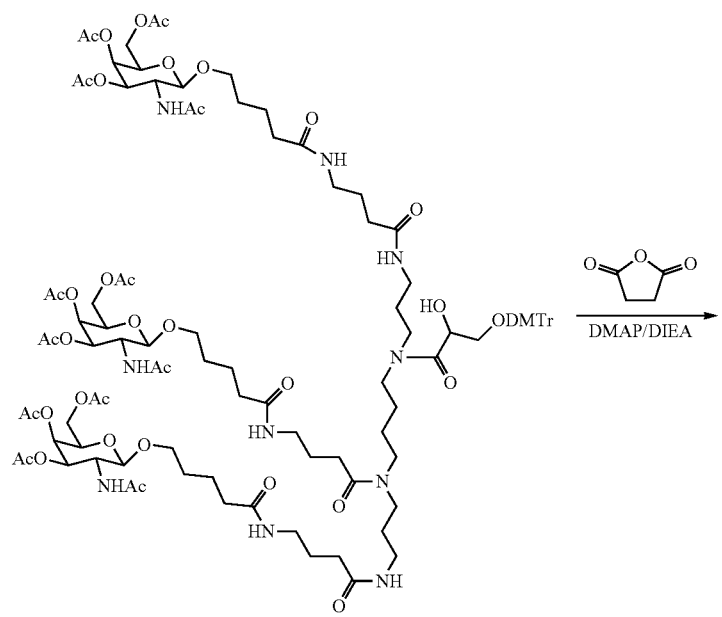
Z-3

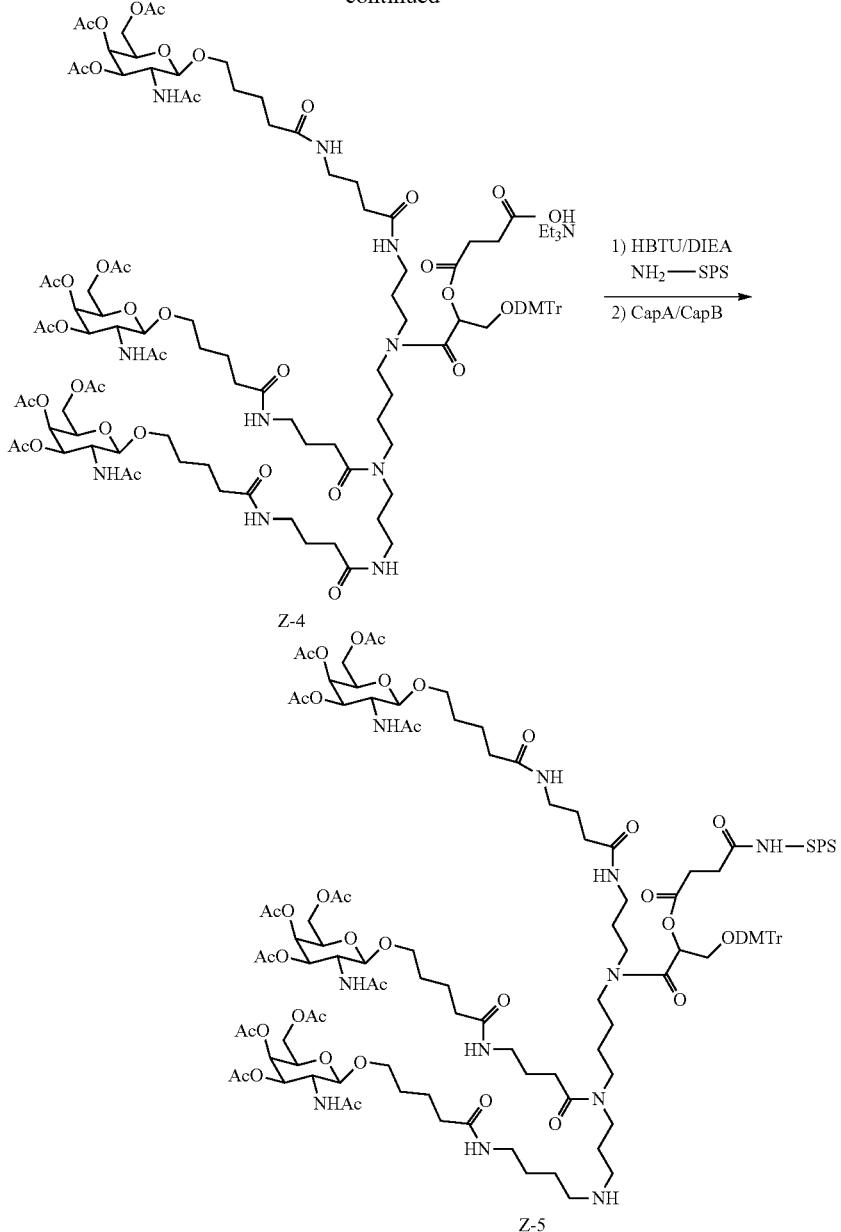

(10-1-1) Synthesis of Z-1

W-3 (1.50 g, 3.37 mmol) obtained according to the method described in step (8-1-3) and GAL5-C4-2 (7.18 g, 13.48 mmol) obtained according to the method described in step (3-1-2) were mixed and dissolved in 34 ml of dichloromethane, and added with diisopropylethylamine (3.48 g, 26.96 mmol) followed by 3-(diethoxyphosphoryloxy)-1,2,3-benzotrizin-4(3H)-one (DEPBT, 4.04 g, 13.48 mmol) to react under stirring at room temperature for 4.5 hours. The resultant liquid solution was diluted with 100 ml of dichloromethane. The organic phase was washed with 80 ml of saturated sodium bicarbonate solution and 80 ml of saturated brine, respectively. All organic phases were combined, dried with anhydrous sodium sulfate, and filtered. The solvent was removed by evaporation under reduced pressure to give a crude product, which was purified by using a normal phase silica gel column (200-300 mesh). The column was packed with petroleum ether, added with 1 wt % triethylamine for neutralizing the acidity of silica gel, and eluted with a gradient elution of dichloromethane:methanol=30:1-15:1. The eluate was collected and removed by evaporation under reduced pressure to give 3.97 g of pure product Z-1. MS m/z: C98H143N10O33, [M+H]+, calculated: 1987.98, measured: 1987.90.

(10-1-2) Synthesis of Z-2

Z-1 (3.97 g, 2.00 mmol) was dissolved in 250 ml of dichloromethane, and added with dichloroacetic acid (10.941 g, 84.85 mmol) to react at room temperature for 1 hour. Pyridine was added to neutralize the resultant reaction solution to neutral. The solvent was removed by evaporation under reduced pressure to give a crude product. The column was loaded with 220 g 200-300 mesh normal phase silica gel, and added with 10 wt % pyridine for neutralizing the acidity of silica gel, equilibrated with 1 wt ‰ pyridine and eluted with a gradient elution of dichloromethane:methanol=10:1-2:1. The eluate was collected, and the solvent was removed by evaporation under reduced pressure to give 3.49 g of pure product Z-2. MS m/z: C79H129N10O33, [M+H]+, calculated: 1746.94, measured: 1746.90.

(10-1-3) Synthesis of Z-3

Z-2 (3.49 g, 2.0 mmol) and A-1 (3.06 g, 6.0 mmol) obtained according to the method described in step (1-1-7a) were mixed and dissolved in 30 ml of dichloromethane, and added with 3-(diethoxyphosphoryloxy)-1,2,3-benzotrizin-4 (3H)-one (DEPBT, 1.80 g, 6.0 mmol) followed by diisopropylethylamine (1.55 g, 12.0 mmol) to react for 3 hours under stirring at 25° C. The resultant reaction solution was added with 100 ml dichloromethane for dilution. The organic phase was washed twice with 30 ml of saturated sodium bicarbonate. The aqueous phase was extracted with 10 ml of dichloromethane. All organic phases were combined and washed with 50 ml of saturated brine. The obtained organic phases were combined and dried with anhydrous sodium sulfate, and filtered. The solvent was removed by evaporation under reduced pressure, and the residue was foam-dried in a vacuum oil pump overnight to give a crude product. The crude product was subjected to a column purification. The column was filled with 200 g normal phase silica gel (200-300 mesh), added with 20 ml triethylamine for neutralizing the acidity of silica gel. The column was equilibrated with petroleum ether containing 1 wt % triethylamine and eluted with a gradient elution of dichloromethane:methanol=25:1-15:1. The eluate was collected, and the solvent was removed by evaporation under reduced pressure to give 2.2 g of pure product Z-3. MS m/z: C103H151N10O38, [M+H]+, calculated: 2136.02, measured: 2136.20.

(10-1-4) Synthesis of Z-4

Z-3 (2.10 g, 0.983 mmol) was dissolved in 14.8 ml of dichloromethane containing DIEA (0.635 g, 4.915 mmol), 4-dimethylaminopyridin (DMAP, 240 mg, 1.966 mmol) was added to the resultant solution and stirred until the solution is clear. Succinic anhydride (197 mg, 1.966 mmol) was added to react under stirring at 25° C. for 18 hours. The resultant reaction solution was added with 50 ml dichloromethane for dilution, and washed with 80 ml of 0.5 M triethylamine phosphate. The aqueous phase was extracted twice, each with 50 ml of dichloromethane. All organic phases were combined, and the solvent was removed by evaporation under reduced pressure to give a crude product. The crude product was subjected to a column purification. The column was filled with 188 g normal phase silica gel (200-300 mesh), added with 1 wt % triethylamine for neutralizing the acidity of silica gel, equilibrated with dichloromethane and eluted with a gradient elution of dichloromethane containing 1 wt ‰ triethylamine:methanol=10:1-3:1. The eluate was collected, and the solvent was removed by evaporation under reduced pressure to give 1.95 g of pure product Z-4 conjugating molecule. MS m/z: C107H155N10O41, [M+H]+, calculated: 1935.07, measured: 1935.29.

(10-1-5) Synthesis of Z-5

Z-5 was prepared by using the same method as in step (1-1-9) of Preparation Example 1, except that: Z-4 conjugating molecule was used to replace L-9 conjugating molecule, thereby obtaining Z-4 conjugating molecule linked to a solid phase support.

(10-2) Synthesis of Z5-siHB1M1SVP Conjugate

Conjugate 34 was prepared by using the same method as in steps (1-2), (1-3A) and (1-4) of Preparation Example 1, except that Z-5 Compound was used to replace L-10 Compound to start the synthesis of a sense strand. It was expected that Z5-siHB1M1SVP conjugate with a structure as shown by Formula (22) can be obtained.

Preparation Example 11 this Preparation Example was Used to Illustrate the Preparation of Conjugates 35-49

In this preparation example, Conjugates 35-49 were synthesized. The conjugated siRNA sequences in the conjugates are shown in Table 3.

(11-1) Synthesis of FIN-2 Conjugating Molecule

FIN-2 conjugating molecule was synthesized with reference to the preparation method described in Rajeev et al., Chem Bio Chem 2015, 16, 903-908 according to the following process route:

(11-1-1) Synthesis of PRO-10

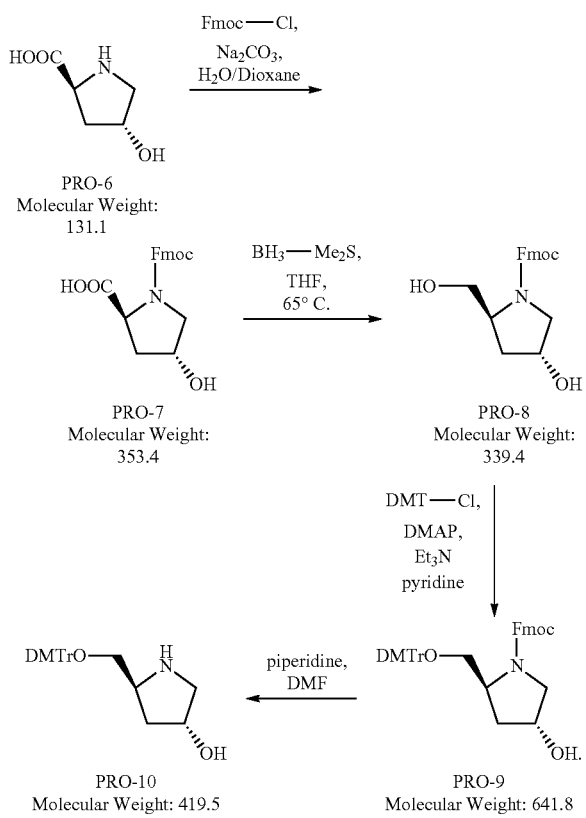

(11-1-1a) Synthesis of PRO-7

2.93 g of PRO-6 (L-hydroxyproline, CAS No.: 51-35-4, purchased from Energy Chemical, 22.4 mmol) was dissolved in 22.5 ml of 1,4-dioxane (CAS No.: 123-91-1) and added with 34 ml of 10% (w/w) aqueous $Na_2CO_3$ solution in the form of suspension. 6.95 g of Fmoc-Cl (9-fluorenyl-methyl chloroformate, CAS No.: 28920-43-6, purchased from Energy Chemical, 26.8 mmol) was dissolved in 34 ml of 1,4-dioxane, added into the above suspension in an ice bath, and naturally warmed to room temperature for reacting overnight. The reaction solution was poured into 150 ml of ice water, and extracted three times, each with 100 ml of methyl t-butyl ether, and the resultant organic phases were discarded. The aqueous phase remained was adjusted to pH≤5 with concentrated hydrochloric acid, extracted twice, each with 100 ml of ethyl acetate. The obtained organic phases were combined and dried with anhydrous sodium sulfate. The solvent was removed by evaporation under reduced pressure to give 7.83 g of product PRO-7 as a white foamy solid. $^1$H NMR (400 MHz, DMSO-d6) δ 7.91 (t, J=7.2 Hz, 2H), 7.67 (d, J=7.5 Hz, 2H), 7.48-7.39 (m, 2H), 7.38-7.27 (m, 2H), 5.17 (s, 1H), 4.27 (s, 2H), 4.23-4.11 (m, 2H), 3.55-3.41 (m, 3H), 2.31-2.10 (m, 1H), 2.08-1.88 (m, 1H). HRMS (ESI) m/z calculated. for $C_{20}H_{19}NO_5$ [M–H]- 352.1190, measured: 352.1033.

(11-1-1b) Synthesis of PRO-8

7.83 g of PRO-7 (22.2 mmol) was dissolved in 80 ml of THF (CAS No.: 109-99-9), heated to 65° C. in an oil bath, added with 36.6 ml of 2 mol/L solution of $BH_3$-$Me_2S$ in THF (CAS No. 13292-87-0, purchased from J&K Scientific Ltd., 73.2 mmol) under reflux, and refluxed continually to react for 3 hours. The reaction solution was poured out, and the remaining solid was dissolved in methanol. To the resultant reaction solution, methanol was added under stirring until no gas emits, stirred continually for 30 minutes. The solvent was removed by evaporation under reduced pressure, and then the residue was purified with petroleum ether three times to give 7.1 g of product PRO-8 as a white solid. $^1$H NMR (400 MHz, DMSO-d6) δ 7.91 (t, J=6.7 Hz, 2H), 7.67 (d, J=7.2 Hz, 2H), 7.49-7.39 (m, 2H), 7.38-7.26 (m, 2H), 5.18 (dd, J=6.1, 3.8 Hz, 1H), 4.28 (s, 2H), 4.23-4.13 (m, 2H), 3.55-3.38 (m, 2H), 2.32-2.11 (m, 1H), 2.08-1.89 (m, 1H). HRMS (ESI) m/z, calculated for $C_{20}H_{21}NO_4$ [M+Na]$^+$362.1368, measured: 362.1012.

(11-1-1c) Synthesis of PRO-9

7.1 g of PRO-8 (21 mmol) was dissolved in 100 ml of pyridine, and added with 14.2 g of DMTr-Cl (4,4'-dimethoxytrityl chloride, 42 mmol) to react under stirring at room temperature for 5 hours. The solvent was removed by evaporation under reduced pressure. The resultant crude product was dissolved in ethyl acetate and filtered to remove salt impurities. The solvent was removed by evaporation under reduced pressure, and then the residue was purified by using a silica gel column. For purification, the crude product dissolved in DCM was loaded onto the silica gel column pretreated with pyridine to alkalify the column. DMTr-Cl was eluted with DCM containing 1% (v/v) pyridine, and then the product was eluted with ethyl acetate. The eluate was collected, and the solvent was removed by evaporation under reduced pressure to give 8.2 g of product PRO-9 as a white solid. HRMS (ESI) m/z, calculated for $C_{41}H_{39}NO_6$ [M+Na]+664.2675, measured: 664.2348; C18 RP-HPLC (Lot No.: JJS160324-1); purity: 94.20%.

(11-1-1d) Synthesis of PRO-10

8.2 g of PRO-9 (12.8 mmol) was dissolved in 64 ml of DMF and added with 40 ml of piperidine (384 mmol) to react under stirring at room temperature for 30 minutes. The reaction solution was poured into 300 ml of ice water and extracted three times, each with 150 ml of ethyl acetate. The resultant organic phases were combined and washed with 200 ml of saturated brine, and the organic phase resulted from washing was dried with anhydrous sodium sulfate. The solvent was removed by evaporation under reduced pressure, and then the residue was purified by using a silica gel column. For purification, the crude product dissolved in DCM was loaded onto the silica gel column pretreated with pyridine to alkalify the column. Fmoc was eluted with DCM containing 1% (v/v) pyridine, and then the product was eluted with ethyl acetate. The eluate was collected, and the solvent was removed by evaporation under reduced pressure to give 4.65 g of product PRO-10 as a white solid. $^1$H NMR (400 MHz, DMSO-d$_6$) δ 7.40 (d, J=7.2 Hz, 2H), 7.35-7.18 (m, 7H), 6.93-6.84 (m, 4H), 4.56 (d, J=3.9 Hz, 1H), 4.12 (s, 1H), 3.74 (s, 6H), 3.46-3.37 (m, 1H), 2.88 (ddd, J=18.5, 10.0, 5.5 Hz, 2H), 2.75 (dd, J=8.7, 5.8 Hz, 1H), 2.62 (dd, J=11.0, 2.7 Hz, 1H), 1.74-1.65 (m, 1H), 1.40 (ddd, J=12.9, 8.5, 5.9 Hz, 1H); HRMS (ESI) m/z calculated for $C_{26}H_{29}NO_4$ [M+Na]$^+$ 442.1994, measured: 442.1999; C18 RP-HPLC (Lot No.: JJS160329-1), purity: 97.07%.

(11-1-2) Synthesis of FIN-1

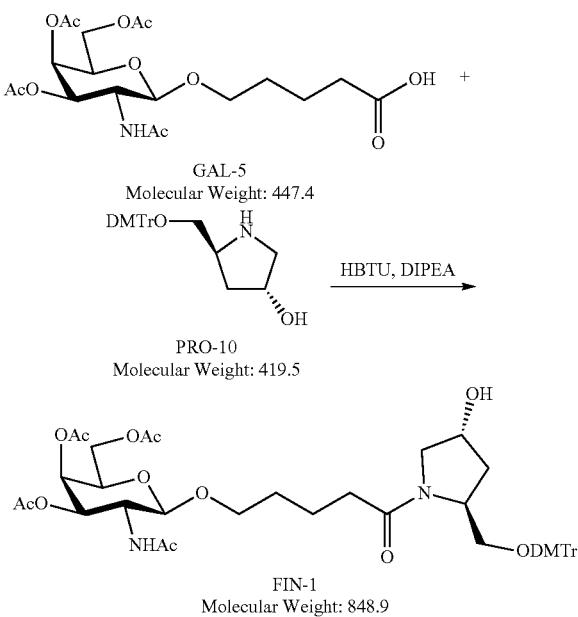

GAL-5 (4.5 g, 10 mmol) obtained according to the method described in step (1-1-1) was dissolved in 40 ml of DMF, sequentially added with 3.9 g of DIEA (N,N-diisopropylethylamine, CAS No.: 7087-68-5, purchased from Aladdin Inc., 30 mmol) and 3.8 g of HBTU (benzotriazol-N,N,N',N'-tetramethyluronium hexafluorophosphate, CAS No.: 94790-37-2, purchased from Aladdin Inc., 11 mmol), and stirred at room temperature for 10 minutes. PRO-10 (4.2 g, 10 mmol) obtained in step (11-1-1d) was dissolved in 40 ml of DMF, and then added into the above reaction solution. The resultant reaction solution was dried by addition of anhydrous sodium sulfate and stirred at room temperature for 2 hours. The reaction solution was poured into 120 ml of ice water and extracted three times, each with 60 ml of ethyl acetate. The resultant organic phases were combined, washed with 20 ml of water and 20 ml of saturated brine, respectively. The organic phase obtained from washing was isolated and dried with anhydrous sodium sulfate. The solvent was removed by evaporation under reduced pressure, and then the residue was purified by using a silica gel column. For purification, a sample was loaded onto the silica gel column pretreated with pyridine to alkalify the column, and was eluted with dichloromethane (DCM) solution containing 1% (v/v) triethylamine and 1% (v/v) methanol. The eluate was collected, and the solvent was removed by evaporation under reduced pressure to give 6.5 g of product FIN-1 as a light yellow foamy solid. $^1$H NMR (400 MHz, DMSO-$d_6$) δ 7.83 (d, J=9.2 Hz, 1H), 7.32 (t, J=6.6 Hz, 4H), 7.20 (td, J=8.9, 3.5 Hz, 5H), 6.93-6.84 (m, 4H), 5.21 (d, J=3.2 Hz, 1H), 5.04-4.90 (m, 2H), 4.49 (s, 1H), 4.40 (d, J=4.4 Hz, 0.8H), 4.31 (d, J=5.0 Hz, 0.2H), 4.15 (s, 1H), 4.03 (s, 3H), 3.93 (s, 1H), 3.74 (s, 7H), 3.59 (dt, J=12.0, 6.0 Hz, 1H), 3.50-3.40 (m, 1H), 3.39-3.25 (m, 3H), 3.13 (dd, J=8.9, 5.2 Hz, 1H), 3.00 (dq, J=9.3, 5.3, 4.3 Hz, 1H), 2.22 (s, 2H), 2.07 (s, 3H), 1.99 (s, 3H), 1.90 (s, 4H), 1.74 (s, 3H), 1.50 (s, 3H), 1.36 (s, 1H). C18 RP-HPLC (Lot Number: LJ160422), purity: 95.45%.

(11-1-3) Synthesis of FIN-2

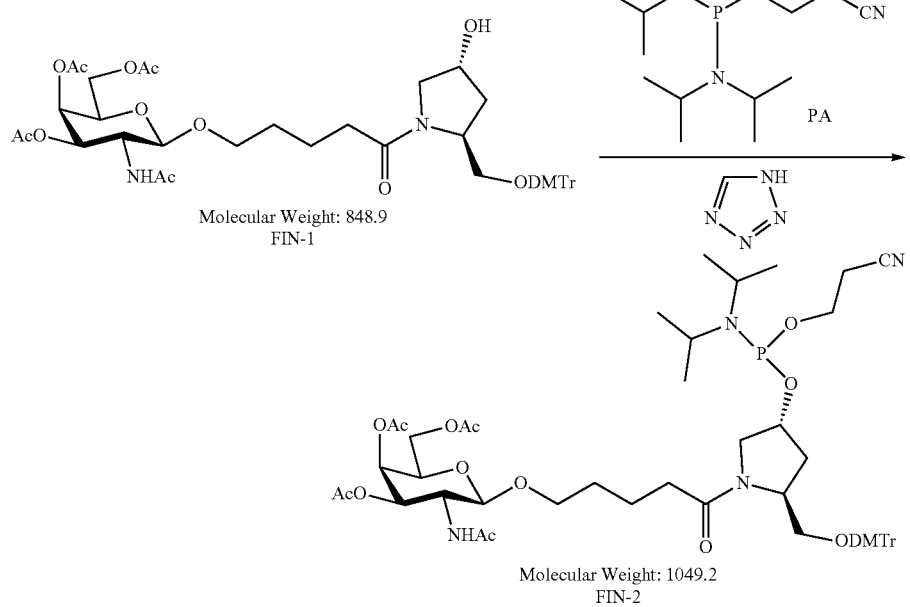

FIN-1 (3.0 g, 3.53 mmol) obtained in step (11-1-2) and acetonitrile were heated for azeotropic dehydration, subjected to suction drying under reduced pressure, dissolved in 10 ml of DMF (dried by immersing in a molecular sieve), added with 2.13 g of PA (bis(diisopropylamino)(2-cyanoethoxy)phosphine, Adamas Inc., product No. 11356B, 7.06 mmol)) and 346 mg tetrazole (CAS No.: 288-94-8, purchased from Aladdin Inc., 4.94 mmol) under nitrogen atmosphere, and stirred to reaction at room temperature. The reaction was supplemented with 10 ml of DMF and continually stirred to react for 1 hour. The solvent was removed by evaporation under reduced pressure, and then the residue was purified by silica gel column chromatography. For purification, the crude product dissolved in DCM was loaded onto the silica gel column pretreated with pyridine to alkalify the column, and eluted with ethyl acetate. The eluate was collected, and the solvent was removed by evaporation under reduced pressure to give 4.5 g of crude product as a colorless syrup. The crude product was completely dissolved in 50% (v/v) aqueous acetonitrile solution and purified by using a medium pressure column (C-18, 330 g, 300 Å) pretreated with a solution of 1% (v/v) pyridine in acetonitrile to alkalify the column. A product peak was collected by gradient elution and the solvent was removed by evaporation under reduced pressure to give 2.2 g of product FIN-2 conjugating molecule as a white powder. $^{31}$P NMR (162 MHz, CDCl$_3$) δ 148.04, 147.94, 147.62, 147.19, purity of $^{31}$P NMR: 92%; purity of C18 RP-HPLC: 90.54%.

(11-2) Linking FIN-2 Conjugating Molecule to a Solid Phase Support

The conjugating group (FIN_FIN_FIN) was linked to the 3' terminal of the sense strand of RNA by linking the FIN-2 conjugating molecule obtained in step (11-1-3) to a universal solid phase support (UnyLinker™ loaded NittoPhase®HL Solid Supports) by using the nucleic acid solid phase synthesis method through three reaction cycles.

The linking of conjugation group FIN_FIN_FIN was proformed according to the method described in Rajeev et al., Chem Bio Chem 2015, 16, 903-908. Specifically, the hydroxy protecting group was initially removed from the above-mentioned universal solid phase support and then the solid phase support, which was subsequently brought into contact and coupled with the FIN-2 conjugating molecule under coupling reaction condition in the presence of a coupling agent, and a FIN conjugating molecule linked to the solid phase support was obtained after the capping and oxidation reaction. Moreover, the hydroxy protecting group DMTr was removed from the FIN conjugating molecule linked to the solid phase support, and the solid phase support was further brought into contact and coupled with another FIN-2 conjugating molecule, followed by capping and oxidation reaction. By repeating the above steps of Deprotection-Coupling-Capping-Oxidation, a third FIN-2 conjugating molecule was linked, and thus a conjugation group (FIN_FIN_FIN) linked to the solid phase support was obtained.

In the reactions described above, the reaction conditions of the deprotection, coupling, capping and oxidation as well as the amounts of the solvents and reagents are the same as those used in the nucleic acid solid phase synthesis method described above in step (1-2).

(11-3) Synthesis of Conjugates 35-49

The subject conjugates were prepared by the same methods as in steps (1-2) to (1-4) of Preparation Example 1, except that: 1) the compound obtained in step (11-2) was used to start the synthesis of a sense strand; and 2) the conjugated siRNAs had the sequences corresponding to Conjugates 35-49 shown in Table 3.

The molecular weight was measured by LC-MS instrument (Liquid Chromatography-Mass Spectrometry, purchased from Waters Corp., Model: LCT Premier). The results showed that the measured values were in conformity with the calculated values, and thus it was confirmed that the synthesized conjugates were the designed compounds of interest, which have a structure as shown by Formula (307).

Preparation Example 12 Preparation of Comparative Conjugate 2

In this preparation example, Comparative Conjugate 2 was synthesized. The conjugated siRNA sequence in this conjugate was shown in Table 3. This conjugate has the same structure as Compound AD-66810 described in the U.S. patent application Ser. No. 15/597,225.

(12-1) Synthesis of (GalNAc)$_3$ Conjugating Molecule

Compound 30, i.e., the conjugating molecule containing the above mentioned linker -($L^A$)$_3$-trihydroxymethyl aminomethane-$L^B$- and the targeting group N-acetylgalactosamine molecule (wherein each $L^A$ can be linked to one N-acetylgalactosamine molecule such that one linker can be linked to three N-acetylgalactosamine molecules), was synthesized according to the preparation method described in WO2014025805A1. This conjugating molecule can also be referred to as (GalNAc)$_3$ conjugating molecule, and the structure of compound 30 was shown as follows:

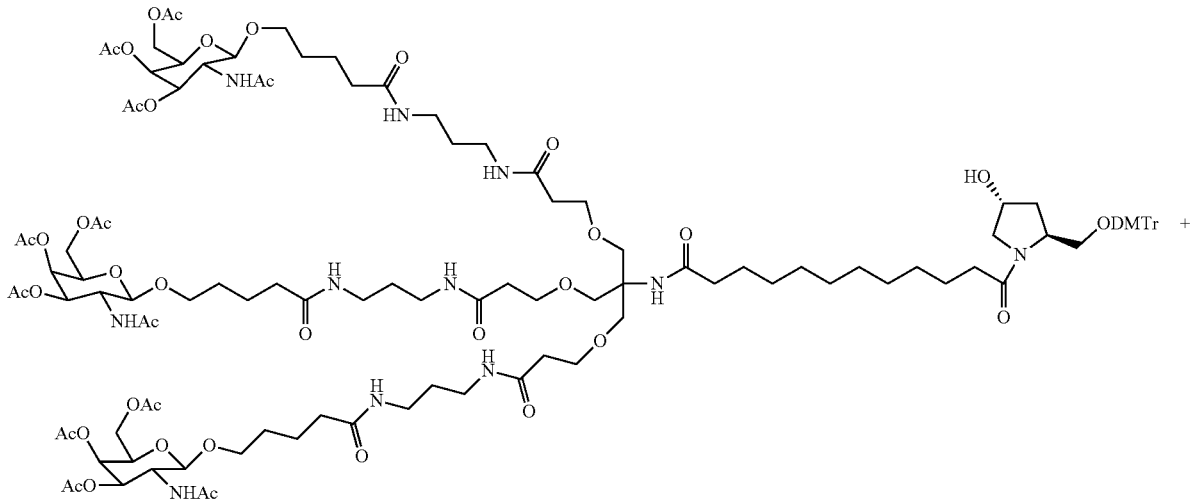

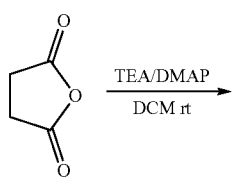

-continued

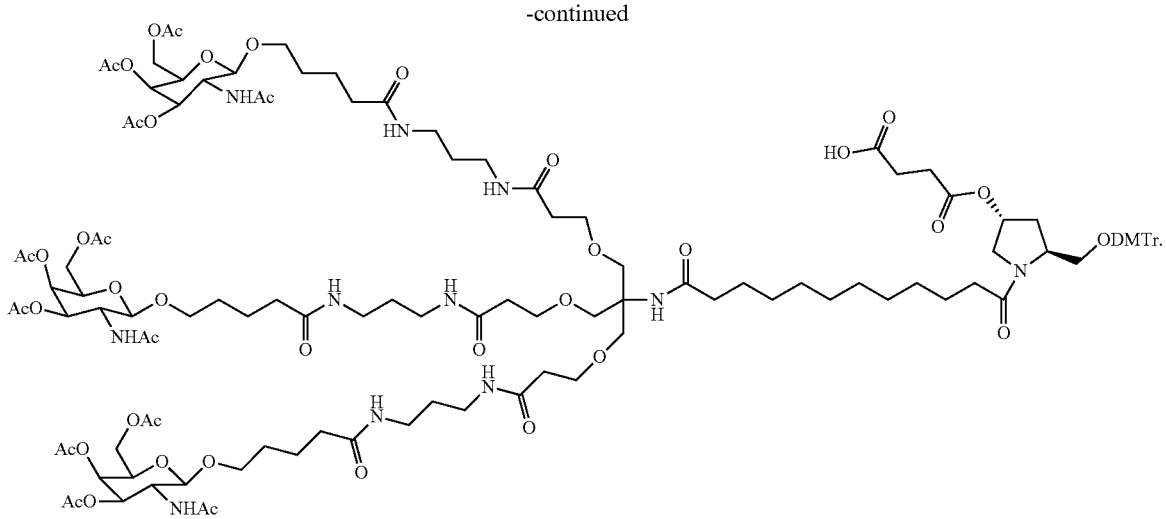

(12-2) Linking (GalNAc)₃ Conjugating Molecule to a Solid Phase Support

The (GalNAc)₃ conjugating group was linked to a solid phase support by the same method as in step (1-1-9) of Preparation Example 1, thereby obtaining (GalNAc)₃ conjugating group linked to a solid phase support.

(12-3) Synthesis of Comparative Conjugate 2

Comparative Conjugate 2 was prepared by the same method as in steps (1-2), (1-3D3) and (1-4) of Preparation Example 1, except that: 1) the compound obtained in step (12-2) was used to start the synthesis of a sense strand; and 2) the conjugated siRNA had a sequence shown under No. AD-66810 in Table 1.

The molecular weight was measured by Liquid Chromatography-Mass Spectrometry (LC-MS, purchased from Waters Corp., Model: LCT Premier). The results showed that the measured values were in conformity with the calculated values, and thus it was confirmed that the synthesized conjugate was the target designed compound, which has a structure as shown by Formula (305).

Experimental Example 1 the Toxicity of the siRNA Conjugates of the Present Disclosure In C57BL/6J mice, Conjugate 1 (0.9 wt % NaCl aqueous solution, administration volume of 10 mL/kg, concentrations of 10 mg/mL and 20 mg/mL, wherein each concentration was used for 6 mice: three male and three female) was subcutaneously administered to each mouse, with a single dose of 100 mg/kg or 200 mg/kg (based on siRNA). Continuous clinical observation was performed during treatment period, which shows no animal death and no clinical symptoms associated with adverse drug responses. 24 h after the administration, blood samples were taken for clinical pathology test and the mice were dissected. The results show that no abnormalities were found in clinical pathology test and gross anatomy. Thus, the above results indicate the conjugates of the present disclosure have a relatively low toxicity at animal level.

Experimental Example 2 this Experiment Illustrated the Stability of the siRNA Conjugates of the Present Disclosure

(Experimental Example 2-1) Stability of the siRNA Conjugates of the Present Disclosure in the Lysosome Lysate In Vitro Preparation of test samples treated with the lysosome lysate: Comparative Conjugate 2 and Conjugates 49, 36, 37, 38, 39, 43, 45 (each provided in the form of 0.9 wt % NaCl aqueous solution in which the concentration of siRNA is 20 μM, 6 μl for each group) were individually mixed well with 27.2 μL of sodium citrate aqueous solution (pH 5.0), 4.08 μL of deionized water and 2.72 μL of Tritosomes (purchased from Xenotech Inc., Cat No. R0610LT, Lot No. 1610069), and incubated at a constant temperature of 37° C. 5 μL samples were taken at each time point of 0 h, 1 h, 2 h, 4 h, 6 h, 8 h, 24 h and 48 h respectively, added to 15 μL of 9 M urea for denaturation, and added with 4 μL of 6×loading buffer (purchased from Solarbio Inc., Cat No. 20160830), then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 μL each of the conjugates above at equal moles (20 μM) was mixed well with 7.5 μL of sodium citrate aqueous solution (pH 5.0) and 1 μL of deionized water, added to 30 μL of 9 M urea solution for denaturation, and added with 8 μL of 6×loading buffer, then immediately cryopreserved in a −80° C. freezer to quench the reaction. The control sample for each conjugate is marked as Con in the electrophoretogram.

16 wt % of non-denatured polyacrylamide gel was prepared. 20 μL each of the test samples and the control samples described above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 1.

FIG. 1 shows the semiquantitative detection result of the in vitro stability of the tested siRNA conjugates in the Tritosome. The results indicate that the conjugates of the present disclosure can remain undegraded for a long time in Tritosome, showing good stability.

As can be seen from the results of FIG. 1, the siRNAs with specific modifications of the present disclosure exhibit satisfactory stability in lysosome lysate.

(Experimental Example 2-2) Stability of the siRNA Conjugates in the Lysosome Lysate In Vitro The stability was measured using the same method as in Experimental Example 2-1, except that the samples to be tested are Conjugates 1 and 6, Sequences 1 and 2, and NS negative control, and the time period of incubation with Tritosomes is 0 h, 5 min, 15 min, 30 min, 1 h, 2 h, 4 h and 8 h, respectively. Therein, the sequences of Sequences 1 and 2 are shown below and can be obtained by solid phase synthesis methods routinely used in the art:

```
Sequence 1:
Sense strand:
                                      (SEQ ID No: 143)
CCUUGAGGCAUACUUCAAA Antisense strand:
                                      (SEQ ID No: 144)
UUUGAAGUAUGCCUCAAGGUC Sequence 2:
Sense strand:
                                      (SEQ ID No: 145)
CmsCmsUmUmGfAmGfGfCfAmUmAmCmUmUmCmAmAmAm Antisense strand:
                                      (SEQ ID No: 146)
VP-UmsUfsUmGmAmAfGmUfAfUmGmCmCmUfCmAfAmGmGmsUmsCm
```

Figure 2:
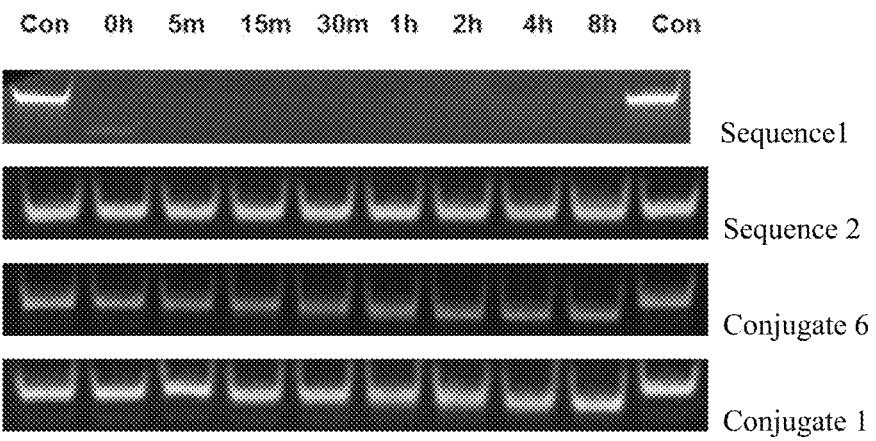
FIG. 2 shows the semiquantitative result of the stability test of the tested siRNA conjugates in the Tritosome in vitro.

The results of the electrophoresis of non-denatured polyacrylamide gel are shown in FIG. 2.

FIG. 2 shows the semiquantitative detection result of the in vitro stability of the tested siRNA conjugates in the Tritosome. The results indicate that the conjugates of the present disclosure can remain undegraded for a long time in Tritosome, showing good stability.

Experimental Example 2-3) Stability in Human Plasma

Figure 3:
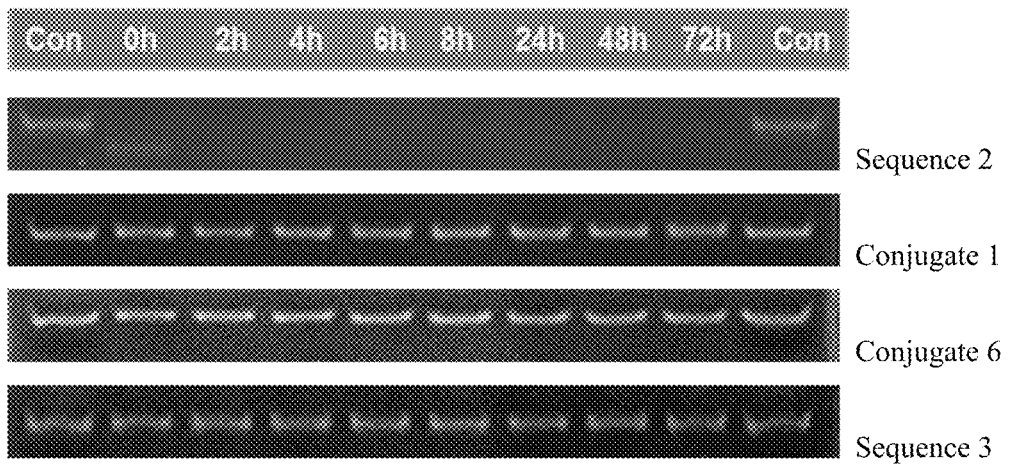
FIG. 3 shows the semiquantitative result of the stability test of the tested siRNA conjugates in the human plasma in vitro.

Conjugates 1 and 6, Sequences 2 and 3, and NS negative control (each provided in the form of 0.9 wt % NaCl aqueous solution in which the concentration of siRNA is 20 PM, 12 µl for each group) were individually mixed well with 108 µL of 90% human plasma (diluted in PBS) and incubated at a constant temperature of 37° C. 10 µL samples were taken at each time point of 0 h, 2 h, 4 h, 6 h, 8 h, 24 h, 48 h and 72 h, respectively, and immediately frozen in liquid nitrogen and cryopreserved in a −80° C. freezer. After sampling at each time point, each cryopreserved sample was diluted 5-fold with 1×PBS (pH 7.4) and then taken in a volume of 10 µL for use. Meanwhile, each of the samples to be tested was taken at equal moles (2 µM, 2 µL) and mixed well with 8 µL of 1×PBS (pH 7.4), thus obtaining 10 µL of samples untreated with human plasma (marked as Con). 20 wt % of non-denatured polyacrylamide gel was prepared. Each cryopreserved sample above was mixed with 4 µL of loading buffer (aqueous solution of 20 mM EDTA. 36 wt % glycerol, and 0.06 wt % bromophenol blue) and then loaded onto the above gel to perform electrophoresis under 80 mA constant current for 60 minutes. After finishing the electrophoresis, the gel was stained with 1×Sybr Gold dye (Invitrogen, Cat No. 11494) for 15 minutes followed by imaging. The results are shown in FIG. 3. Therein, the sequence of Sequence 3 is shown below and can be obtained by solid phase synthesis methods routinely used in the art:

```
Sequence 3:
Sense strand:
                                      (SEQ ID No: 147)
CmsCmsUmUmGfAmGfGfCfAmUmAmCmUmUmCmAmAmAm Antisense strand:
                                      (SEQ ID No: 148)
VPUmsUfsUmGmAmAfGmUfAfUmGmCmCmUfCmAfAmGmGmsUmsUm
```

FIG. 3 shows the semiquantitative detection result of the in vitro stability of the tested conjugates in human plasm.

As can be seen from the results of FIG. 3, in human plasma, the conjugates of the present disclosure remain undegraded at up to 72 hours, showing excellent stability in human plasma.

(Experimental Example 2-4) Stability of Conjugates in the Monkey Plasma

Conjugates 1 and 6, and Sequences 2 and 3 (each provided in the form of 0.9 wt % NaCl aqueous solution in which the concentration of siRNA is 20 µM, 12 µl for each group) were individually mixed well with 108 µL of 90% cynomolgus monkey plasma (Monkey plasma, purchased form HONGQUAN Bio, Cat No. HQ70082, diluted in PBS) and incubated at a constant temperature of 37° C. 10 µL samples were taken at each time point of 0 h, 2 h, 4 h, 6 h, 8 h, 24 h, 48 h and 72 h, respectively, and immediately frozen in liquid nitrogen and cryopreserved in a −80° C. freezer. After sampling at each time point, each sample was diluted 5-fold with 1×PBS (pH 7.4) and then taken in a volume of 10 µL for use. Meanwhile, each of the samples to be tested was taken at equal moles (2 µM, 2 µL) and mixed well with 8 µL of 1×PBS (pH 7.4), thus obtaining 10 µL of samples untreated with monkey plasma (marked as Con). 20 wt % of non-denatured polyacrylamide gel was prepared. Each cryopreserved sample was all mixed with 4 µL of loading buffer (aqueous solution of 20 mM EDTA, 36 wt % glycerol, and 0.06 wt % bromophenol blue) and then loaded onto the above gel to perform electrophoresis under 80 mA constant current for 60 minutes. After finishing the electrophoresis, the gel was stained with 1×Sybr Gold dye (Invitrogen, Cat No. 11494) for 15 minutes followed by imaging. The results are shown in FIG. 4.

Figure 4:
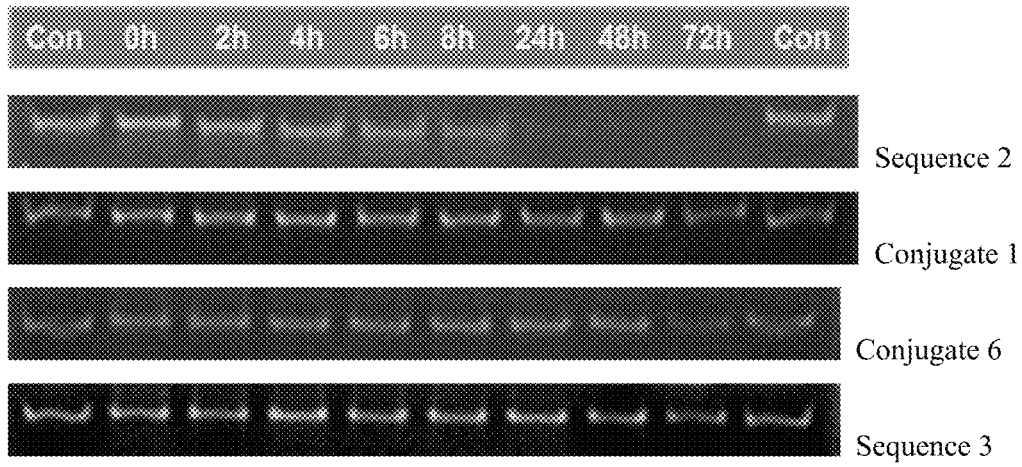
FIG. 4 shows the semiquantitative result of the stability test of the tested siRNA conjugates in the monkey plasma in vitro.

FIG. 4 shows the semiquantitative detection result of the in vitro stability of the tested siRNA in the monkey plasma.

As can be seen from the results of FIG. 4, in cynomolgus monkey plasma, the siRNA conjugates of the present disclosure remain undegraded at up to 72 hours, showing excellent stability in monkey plasma.

(Experimental Example 2-5) this Experiment Illustrated the Stability of the siRNA Conjugates of the Present Disclosure in the Lysosome Lysate In Vitro The sequence of the negative control X2M2 used in this experimental example is shown below:

```
Sense strand:
                                    (SEQ ID No: 149)
5'-CmCmUmUmGAGGCmAUmACmUmUmCmAAAdT-S-dT-3'

Antisense strand:
                                    (SEQ ID No: 150)
5'-UfUmUfGAAGUfAUGCCUfCAAGGdT-S-dT-3'.
```

This siRNA was synthesized by solid phase phosphoramidite method. The negative control and Conjugate 2 were formulated with 0.9 wt % NaCl aqueous solution respectively into aqueous solutions with a concentration of 20 µM (based on the concentration of siRNA), which were marked as X2M2 and Conjugate 2.

1) Detection of the Stability in Rat-Originated Lysosome Lysate

Preparation of test samples treated with the lysosome lysate: 6 µl for each of Conjugate 2 and X2M2 (20 µM) were individually mixed well with 27.2 µL of sodium citrate aqueous solution (pH 5.0), 4.08 µL of deionized water and 2.72 µL of murine lysosome lysate (Rat Liver Tritosomes, purchased from Xenotech Inc., Cat No. R0610.LT, Lot No. 1610069, at a final concentration of acid phosphatase of 0.2 mU/µL), and incubated at a constant temperature of 37° C. 5 µL mixed solution was taken at each time point of 0 h, 1 h, 2 h, 4 h, 6 h, and 24 h, respectively, added to 15 µL of 9 M urea solution for denaturation, and added with 4 µL of 6×loading buffer (purchased from Solarbio Inc., Cat No. 20160830), then immediately cryopreserved in a −80° C. freezer to quench the reaction. 0 h represents the moment when the sample was taken immediately after the samples to be tested are mixed well with the lysosome lysate.

Preparation of control samples untreated with the lysosome lysate: 1.5 µL for each of the Conjugate 2 and X2M2 (20 µM) at equal moles was mixed well with 7.5 µL of sodium citrate aqueous solution (pH 5.0) and 1 µL of deionized water, added to 30 µL of 9 M urea solution for denaturation, and added with 8 µL of 6×loading buffer, then immediately cryopreserved in a −80° C. freezer to quench the reaction. For each electrophoresis image, the corresponding control sample was marked as M. 16 wt % of non-denatured polyacrylamide gel was prepared. 20 µL each of the test sample and the control sample described above was loaded onto the gel to perform electrophoresis under 20 mA constant current for 10 minutes and then under 40 mA constant current for 30 minutes. After finishing the electrophoresis, the gel was placed on a shaker and stained with Gelred dye (BioTium, Cat No. 13G1203) for 10 minutes. The gel was subjected to imaging, observation and photocopying. The results are shown in FIG. 5.

2) Detection of the Stability in Human Lysosome Lysate

The stability of X2M2 and Conjugate 2 in the human lysosome lysate was measured using the same method as that in 1), except that the murine lysosome lysate was replaced with the human lysosome lysate (Human Liver Lysosomes, purchased from Xenotech Inc., Cat No. R0610.L, Lot No. 1610316). The results are shown in FIG. 6.

Figure 5:
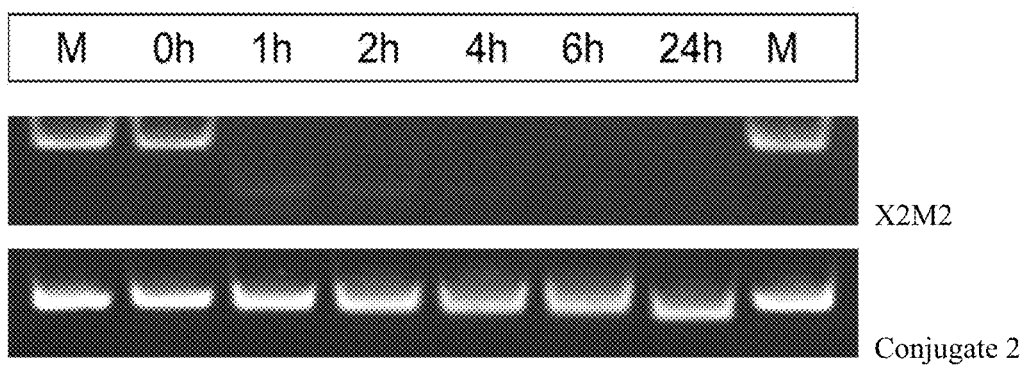
FIG. 5 shows the stability result of the tested siRNA conjugate in Rat Liver Tritosomes.
Figure 6:
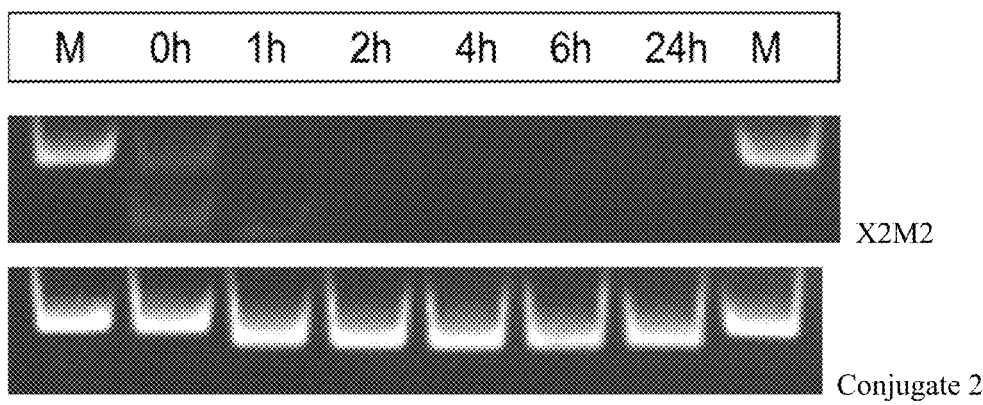
FIG. 6 shows the stability result of the tested siRNA conjugate in Human Liver Lysosomes.

The results of FIGS. 5 and 6 indicate that the siRNA conjugates of the present disclosure can remain undegraded for at least 24 hours both in human-origined lysosome lysate and in murine lysosome lysate, showing satisfactory stability.

Experimental Example 3 the Results of the Pharmacokinetic Study of Conjugates 1 and 6 in Rats In Vivo In this experimental example, Conjugates 1 and 6 was administered to rats in each experimental group (10 rats in each group, five male and five female) by subcutaneous injection, respectively, with a single dose of 10 mg/kg and 50 mg/kg. Subsequently, the drug concentration in plasma, liver and kidney tissues of rats were measured at each time point.

The SD rats used in this experimental example were provided by Beijing Vital River Laboratory Animal Technology Co., Ltd.

Firstly, SD rats were randomly divided into groups according to the body weight and gender by using the PRISTIMAdata system version 7.2.0, and then respectively administered with each group of the conjugates according to the designed dosage. The drug dosages for all animals were calculated according to the body weigh (single administration (subcutaneously), administration dosage of 10 mg/kg and 50 mg/kg, in the form of 0.9% NaCl aqueous solution containing 1 mg/ml and 5 mg/ml conjugates, and administration volume of 10 mL/kg). Rat whole blood was collected from the jugular vein before administration and at 5 minutes (±30 seconds), 30 minutes (±1 minute), 1 hour (±2 minutes), 2 hours (±2 minutes), 6 hours (±5 minutes), 24 hours (±10 minutes), 48 hours (±20 minutes), 72 hours (±20 minutes), 120 hours (±30 minutes), and 168 hours (±30 minutes) after administration. Then the whole blood samples were centrifugated at 1800×g at 2-8° C. for 10 minutes to separate plasma. About 70 µL volume of the plasma sample was placed in one tube, and the remaining of the sample was placed in another, both of which were cryopreserved at −70° C. to −86° C. for detection. Liver and kidney tissues of rats were collected at about 24, 48, 72, 120, and 168 hours after administration by the method comprising anesthetizing the rats with pentobarbital sodium according to the weight thereof (60 mg/kg, intraperitoneal injection), euthanizing the rats by blood collection from abdominal aorta, and performing gross anatomy. The liver and kidney of each rat were sampled and stored in 1 mL cryotube at below −68° C. until detection and analysis.

The concentrations of the Conjugates 24 and 25 in plasma, liver and kidney tissues of rats were measured quantitatively by High Performance Liquid Chromatography with Fluorescence Detection (HPLC-FLD) according to the following specific steps:

(1) grinding the tissue until a tissue mass of no more than 80 mg was obtained, then adding Tissue and Cell Lysis Solution (supplier: Epicentre, Cat No. MTC096H) to prepare a tissue homogenate of 66.7 mg/mL;

(2) subjecting the tissue homogenate to a sonication (150 W, 30 s) to disrupt cells;

(3) for tissue samples, adding 75 µL of tissue samples to a 96-well PCR plate, adding 5 µL of proteinase K (supplier: Invitrogen, Cat No. 25530-015) and 10 µL of mixed aqueous solution of 10 wt % acetonitrile and 0.01 wt % Tween 20; for plasma samples, adding 20 µL of plasma to a 96-well PCR plate, adding 45 µL of Tissue and Cell Lysis Solution, 5 µL of proteinase K, and 20 μL of mixed aqueous solution of 10 wt % acetonitrile and 0.01 wt % Tween 20;

(4) blocking the plates and placing them in a PCR instrument (supplier: Applied Biosystems, model: GeneAmp® PCR system 9700) and incubating at 65° C. for 45 minutes;

(5) after finishing incubation, adding 10 μl of 3 M KCl aqueous solution (supplier: Sigma-aldrich, Cat No. 60135-250ML), shaking well, and centrifuging at 3200 ref at 4° C. for 15 minutes;

(6) for tissue samples, adding 80 μL of supernatant into 120 μL of hybridization mixture solution (formula: 0.5 mL of 6 μM PNA probe (supplier: TAHE-PNA), 1 mL of 200 mM Trizma/pH=8, 5 mL of 8 M urea aqueous solution, 3.5 mL of $H_2O$, 2 mL of acetonitrile); for plasma samples, adding 40 μL of supernatant into 160 μL of hybridization mixture solution (formula: 0.5 mL of 6 μM PNA probe, 1 mL of 200 mM Trizma/pH=8, 5 mL of 8 M urea aqueous solution, 7.5 mL of $H_2O$, 2 mL of acetonitrile);

(7) blocking the plates and placing them in a PCR instrument, incubating at 95° C. for 15 minutes, then immediately placing on ice for 5 minutes;

(8) transferring the samples to new 96-well plates with conical bottom, shaking well, and centrifuging at 3200 ref for 1 minute;

(9) injecting the samples for detection and quantitatively analyzing by using HPLC-FLD (liquid-phase system supplier: Thermo Fisher, chromatography model: ultimate 3000).

Figure 7:
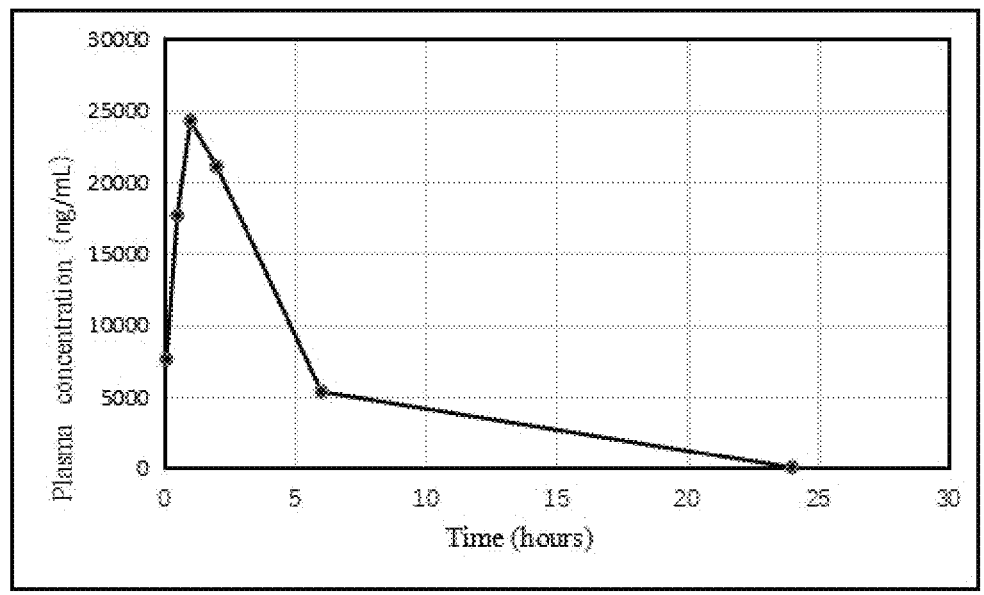
FIG. 7 is metabolic curve over time showing PK/TK plasma concentration for Conjugate 1 at a dosage of 10 mg/kg in rat plasma.

The analyzed results can be found in FIGS. 7-14, wherein FIGS. 7-10 show metabolic curves over time of PK/TK plasma concentrations in rat plasma and PK/TK tissue concentrations in rat liver and kidney for Conjugate 1 at a dosage of 10 mg/kg or 50 mg/kg, respectively; and FIGS. 11-14 show metabolic curves over time of PK/TK plasma concentrations in rat plasma and PK/TK tissue concentrations in rat liver and kidney for Conjugate 6 at a dosage of 10 mg/kg or 50 mg/kg, respectively. Specifically, FIG. 7 is a metabolic curve over time showing PK/TK plasma concentration for Conjugate 1 at a dosage of 10 mg/kg in rat plasma.

Figure 8:
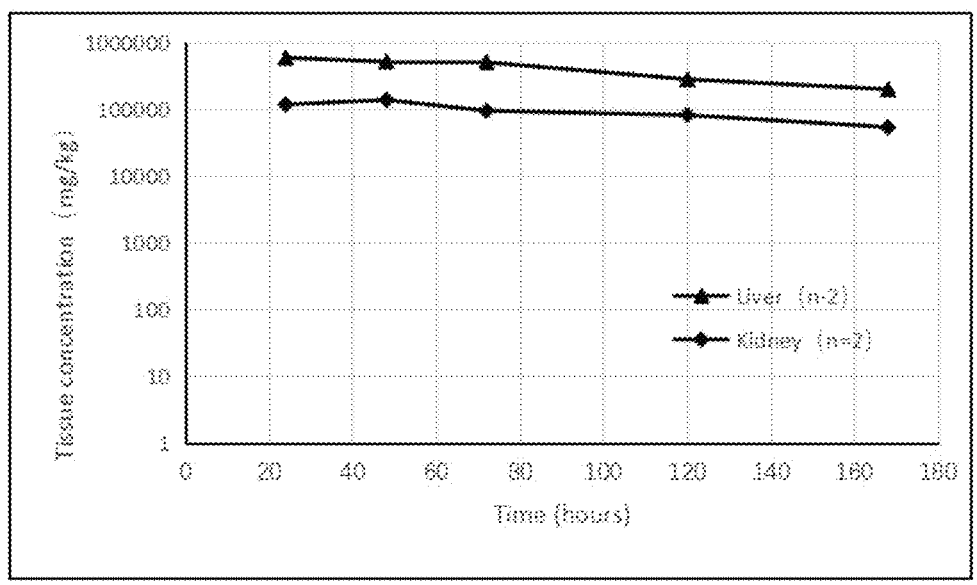
FIG. 8 is metabolic curve over time showing PK/TK tissue concentration for Conjugate 1 at a dosage of 10 mg/kg in rat liver and kidney.

FIG. 8 is a metabolic curve over time showing PK/TK tissue concentrations for Conjugate 1 at a dosage of 10 mg/kg in rat liver and kidney.

Figure 9:
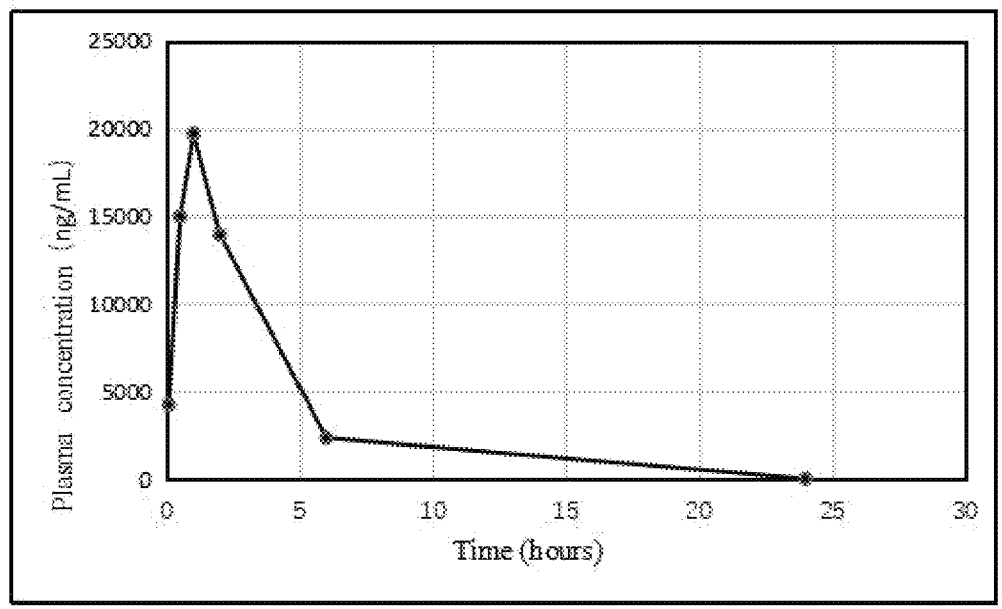
FIG. 9 is metabolic curve over time showing PK/TK plasma concentration for Conjugate 1 at a dosage of 50 mg/kg in rat plasma.

FIG. 9 is a metabolic curve over time showing PK/TK plasma concentration for Conjugate 1 at a dosage of 50 mg/kg in rat plasma.

Figure 10:
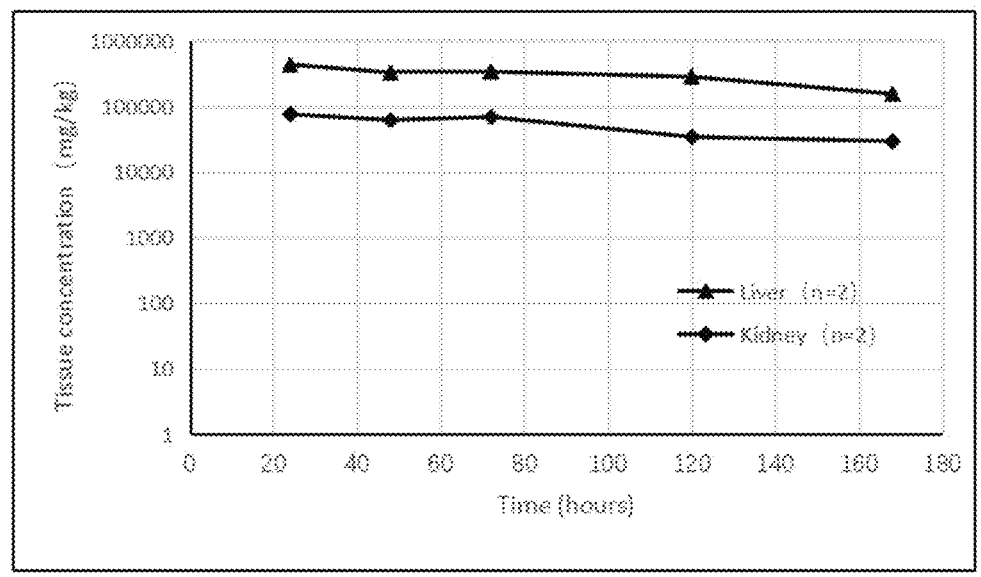
FIG. 10 is metabolic curve over time showing PK/TK tissue concentration for Conjugate 1 at a dosage of 50 mg/kg in rat liver and kidney.

FIG. 10 is a metabolic curve over time showing PK/TK tissue concentrations for Conjugate 1 at a dosage of 50 mg/kg in rat liver and kidney.

Figure 11:
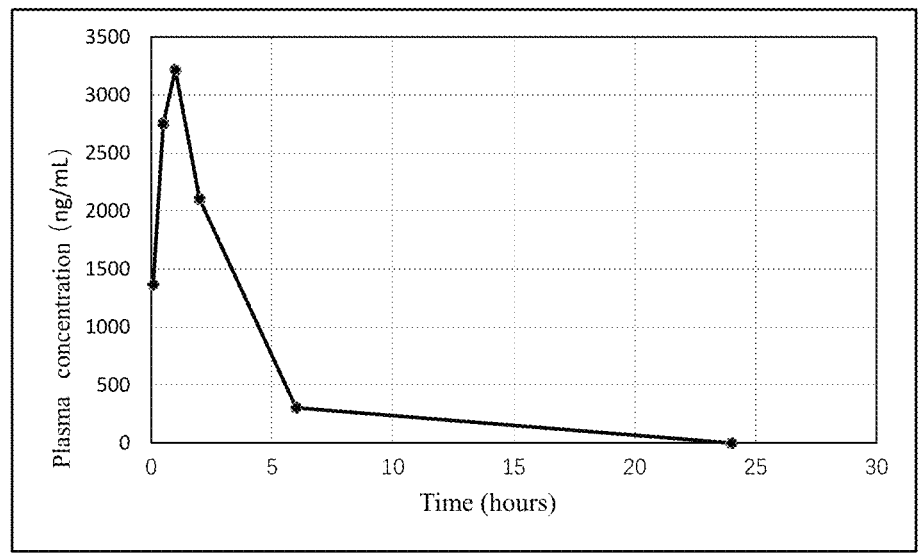
FIG. 11 is metabolic curve over time showing PK/TK plasma concentration for Conjugate 6 at a dosage of 10 mg/kg in rat plasma.

FIG. 11 is a metabolic curve over time showing PK/TK plasma concentration for Conjugate 6 at a dosage of 10 mg/kg in rat plasma.

Figure 12:
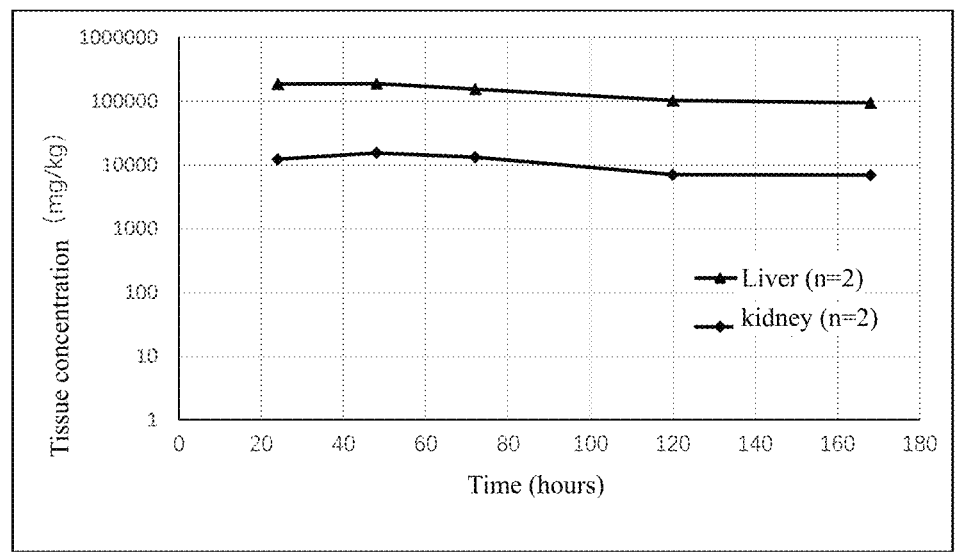
FIG. 12 is metabolic curve over time showing PK/TK tissue concentration for Conjugate 6 at a dosage of 10 mg/kg in rat liver and kidney.

FIG. 12 is a metabolic curve over time showing PK/TK tissue concentrations for Conjugate 6 at a dosage of 10 mg/kg in rat liver and kidney.

Figure 13:
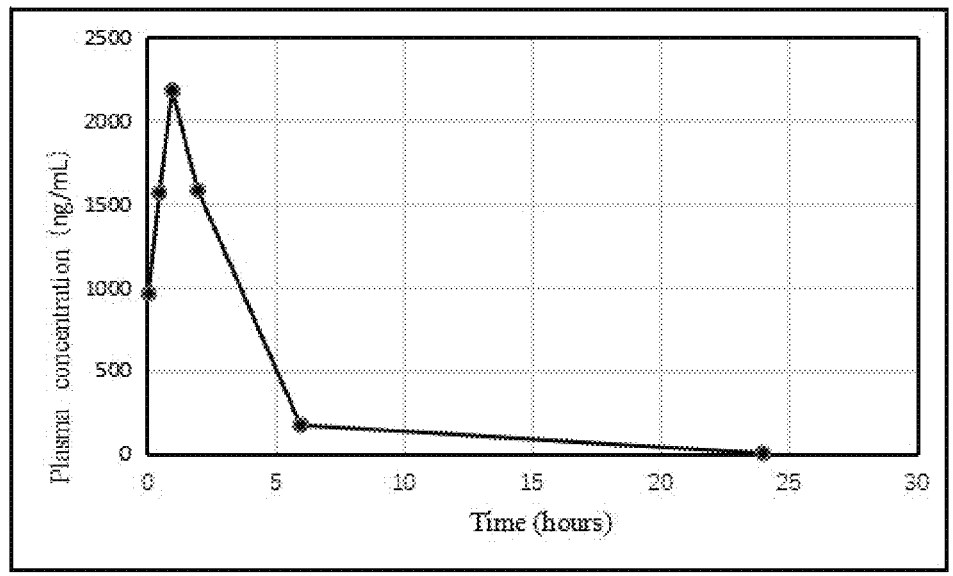
FIG. 13 is metabolic curve over time showing PK/TK plasma concentration for Conjugate 6 at a dosage of 50 mg/kg in rat plasma.

FIG. 13 is a metabolic curve over time showing PK/TK plasma concentration for Conjugate 6 at a dosage of 50 mg/kg in rat plasma.

Figure 14:
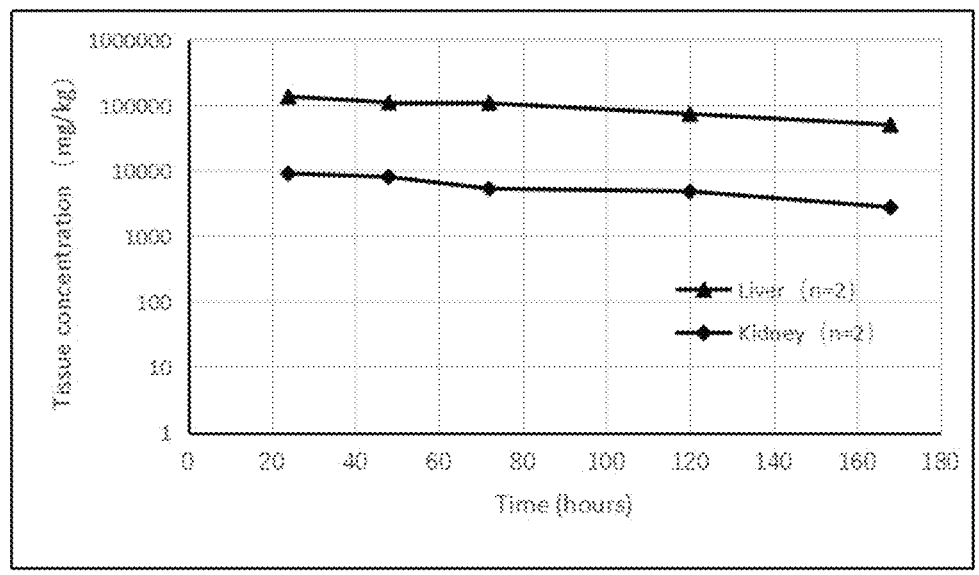
FIG. 14 is metabolic curve over time showing PK/TK tissue concentration for Conjugate 6 at a dosage of 50 mg/kg in rat liver and kidney.

FIG. 14 is a metabolic curve over time showing PK/TK tissue concentrations for Conjugate 6 at a dosage of 50 mg/kg in rat liver and kidney.

As can be seen from the results of FIGS. 7-14, the concentrations for Conjugates 1 and 6 in rat plasma were rapidly decreased below the detection limit within several hours, while the concentrations in rat liver tissue were maintained at a relatively high and stable level over at least 168 hours, either at a low dosage (10 mg/kg) or at a relatively high dosage (50 mg/kg). This shows that the siRNA conjugate of the present disclosure can be specifically and significantly enriched in liver and remain stable, showing a high degree of targeting.

Experimental Example 4—this Experiment Illustrates the Inhibitory Efficiency of the siRNA Conjugates of the Present Disclosure Against Expression of HBV mRNA In Vivo In this experimental example, the inhibition efficiency of Conjugates 5 and 7 against the expression of HBV mRNA in HBV transgenic mice C57BL/6J-Tg(Alb1HBV)44Bri/J was investigated.

HBsAg content in mouse serum was measured using Hepatitis B Virus Surface Antigen Assay Kit (Enzyme-linked Immunosorbent Assay, ELISA) (Shanghai Kehua Bio-engineering Co., Ltd.). Mice with S/COV>10 were selected and randomly divided into groups (all female, 4 mice in each group) and respectively numbered as Conjugate 5 and Conjugate 7, and a normal saline (NS) group was added as a control group. The drug dosages for all animals were calculated according to the body weight (single administration (subcutaneously), administration dosage of 1 mg/kg and 0.1 mg/kg, in the form of 0.9% NaCl aqueous solution containing 0.2 mg/ml and 0.02 mg/ml conjugates, and administration volume of 5 mL/kg). Animals were sacrificed on day 14 after administration. The liver was collected and kept with RNA later (Sigma Aldrich), and the liver tissue was homogenized with a tissue homogenizer. Then the total RNA was extracted and obtained by using Trizol according to the standard procedures for total RNA extraction.

The expression level of HBV mRNA in liver tissue was detected by real-time fluorescent qPCR. Specifically, the extracted total RNA was reverse transcribed into cDNA by using ImProm-II™ reverse transcription kit (Promega) according to the instruction, and then the inhibitory efficiency of siRNAs against the expression of HBV mRNA in liver tissue was detected by using the fluorescent qPCR kit (Beijing Cowin Biosicences Co., Ltd). In this fluorescent qPCR method, β-actin gene was used as an internal control gene, the HBV and β-actin were detected by using primers for HBV and β-actin, respectively.

Sequences of primers for detection are shown in Table 4.

TABLE 4

| Sequences of primers for detection | | |
|---|---|---|
| Genes | Upstream Primers | Downstream Primers |
| HBV | 5'-CCGTCTGTGCCTTCTC ATCT-3' (SEQ ID NO: 151) | 5'-TAATCTCCTCCCCCAACT CC-3' (SEQ ID NO: 152) |
| B-actin | 5'-AGCTTCTTTGCAGCTC CTTCGTTG-3' (SEQ ID NO: 153) | 5'- TTCTGACCCATTCCCAC CATCACA-3' (SEQ ID NO: 154) |

In this fluorescent qPCR method, the expression of HBV mRNA was expressed as the remaining expression of HBV X gene and calculated by the following equation: The remaining expression of HBV X gene=(the copy number of HBV X gene in the test group/the copy number of β-actin gene in the test group)/(the copy number of HBV gene in the control group/the copy number of β-actin gene in the control group)×100%, which is marked as HBV X/β-actin mRNA expression in the figures.

Figure 15:
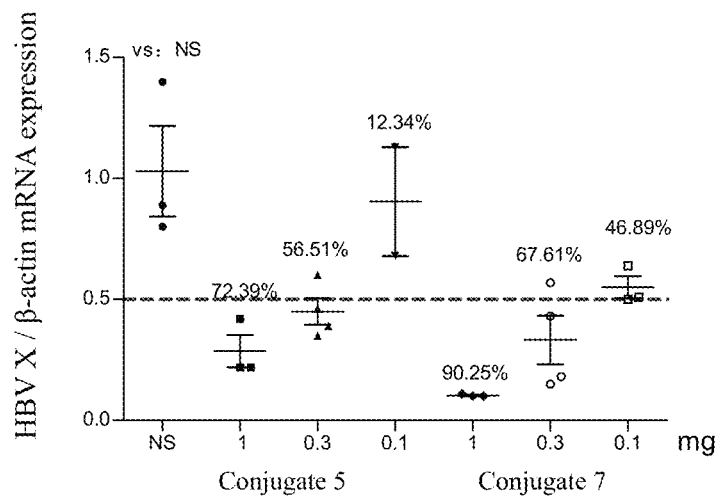
FIG. 15 shows the inhibitory efficiency of Conjugates 5 and 7 against HBV mRNA expression in 44Bri model mice.

Then, the inhibition percentage of the conjugate against mRNA was calculated according to the equation:

The inhibition percentage of the conjugate against mRNA=(1−the remaining expression of HBV X gene)×100%, wherein the control group was a group of control mice administered with NS in this experiment and each test group was a group of mice administered with different siRNA conjugates, respectively. The results are shown in FIG. 15.

Figure 16:
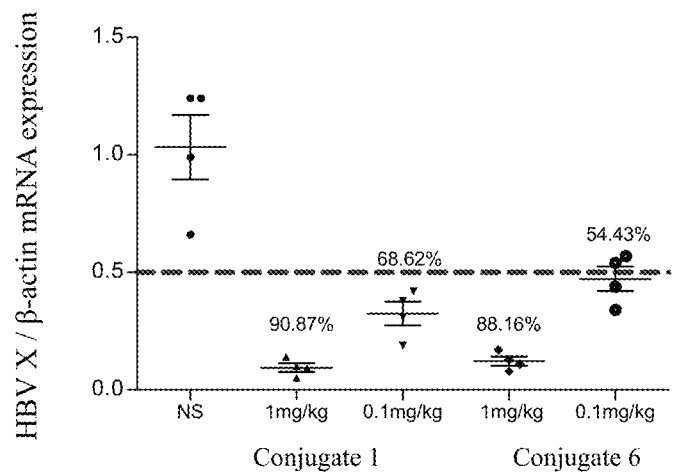
FIG. 16 shows the inhibitory efficiency of Conjugates 1 and 6 against HBV mRNA expression in 44Bri model mice.
Figure 17:
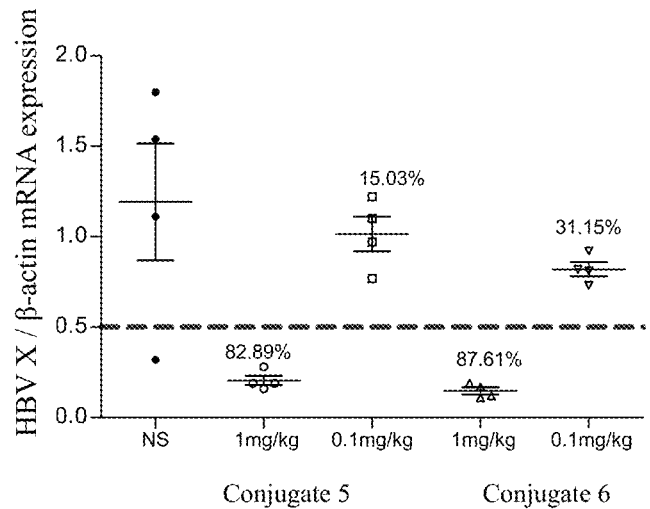
FIG. 17 shows the inhibitory efficiency of Conjugates 5 and 6 against HBV mRNA expression in 44Bri model mice.
Figure 18:
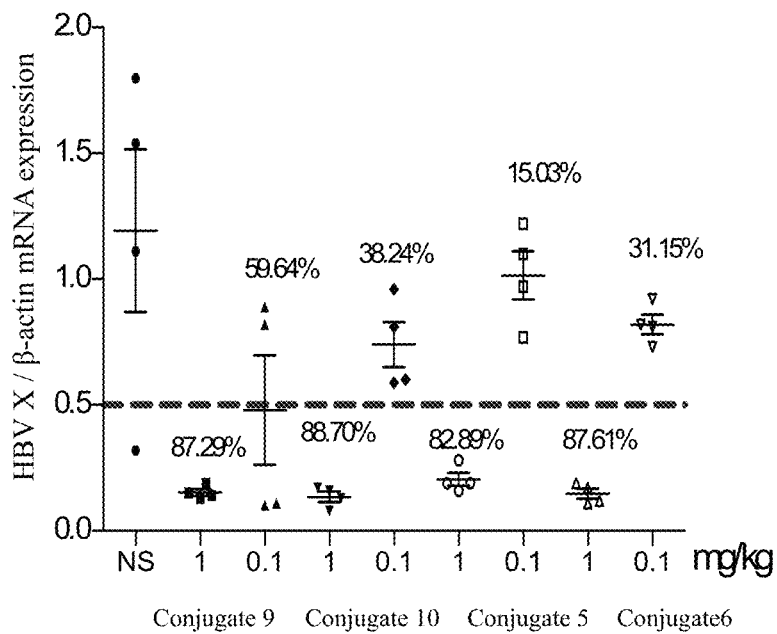
FIG. 18 shows the inhibitory efficiency of Conjugates 5, 6, 9 and 10 against HBV mRNA expression in 44Bri model mice.
Figure 19:
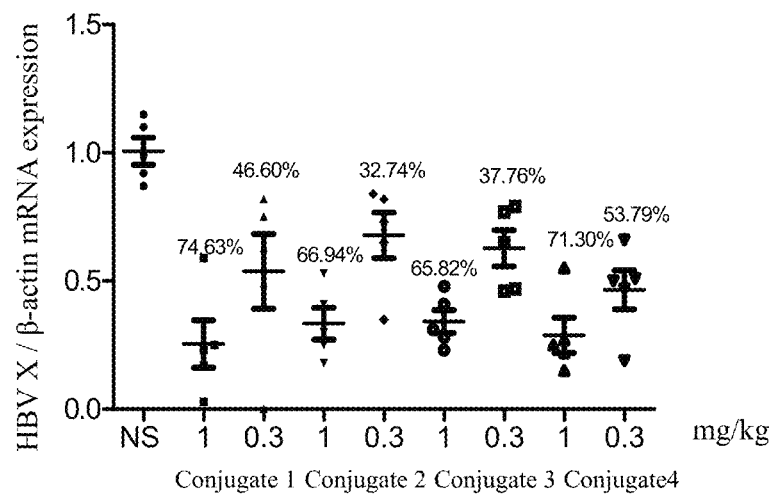
FIG. 19 shows the inhibitory efficiency of Conjugates 1, 2, 3 and 4 against HBV mRNA expression in 44Bri model mice.

In other experiments, several tests were further performed according to the following conditions:

Tests were performed by using the same method described above, except that the siRNA conjugate administered was replaced with Conjugates 1 and 6, and the data were collected on day 14. The results are shown in FIG. 16; and Tests were performed by employing the same method described above, except that the siRNA conjugates to be administered were replaced with Conjugates 5 and 6, and the data were collected on day 7. The results are shown in FIG. 17; and Tests were performed by employing the same method described above, except that the siRNA conjugates to be administered were replaced with Conjugates 9, 10, 5 and 6, and the data were collected on day 7. The results are shown in FIG. 18; and Tests were performed by employing the same method described above, except that the siRNA conjugates to be administered were replaced with Conjugates 1, 2, 3 and 4 (5 mice in each group), and the data are collected on day 28. Each conjugate was administered in the two dosages of 1 mg/kg and 0.3 mg/kg (wherein the administration volume remained the same, while the concentrations of the conjugate solutions were respectively adjusted). The results thereof are respectively shown in FIG. 19.

Figure 20:
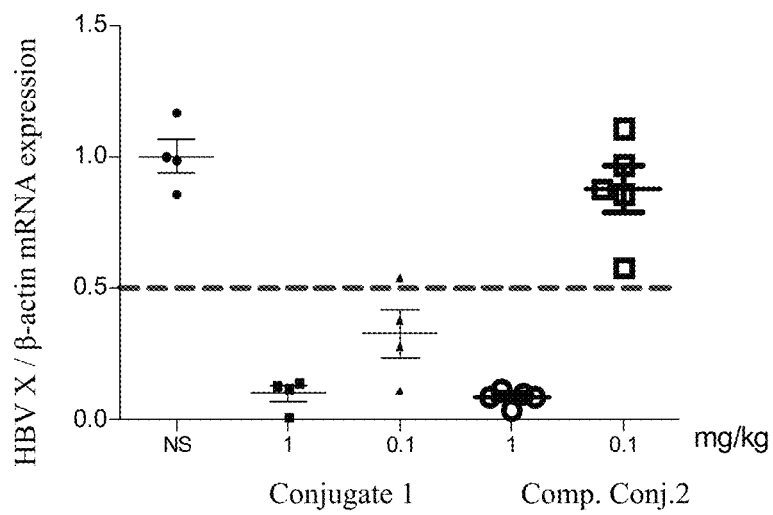
FIG. 20 shows the inhibitory efficiency of Conjugate 1 against HBV mRNA expression in 44Bri model mice.

Tests were performed by using the same method described above, except that the siRNA conjugate administered was replaced with Conjugate 1, and the data are collected on day 14. Each conjugate was administered in the two dosages of 1 mg/kg and 0.1 mg/kg (wherein the administration volume remained the same, while the concentrations of the conjugate solutions were respectively adjusted). The results are respectively shown in FIG. 20.

As can be seen from the above results, in several experiments with different testing time points, all conjugates of the present disclosure described above show high inhibitory activity against the expression of HBV mRNA in mice in vivo.

Experimental Example 5 this Experiment Illustrates a Time-Dependent Test of the Inhibitory Efficiency of the siRNA Conjugates of the Present Disclosure Against HBsAg and HBV DNA in HBV Transgenic Mice Serum An AAV-HBV model mouse was employed. After successful establishment of the animal models, these mice were randomly divided into groups based on HBsAg content in serum (5 mice in each group). Conjugates 1 and 6, Comparative Conjugate 2 and NS as a blank control were respectively administered to each group. The drug dosages for all animals were calculated according to the body weight (single administration (subcutaneously), administration dosage of 3 mg/kg and 1 mg/kg, in the form of 0.9% NaCl aqueous solution containing 0.3 mg/ml and 0.1 mg/ml conjugates, and administration volume of 5 mL/kg). The blood was taken from mouse orbital venous plexus before administration (marked as D0) and on days 7, 14, 21, 28, 56, 84, 112, 140, 154, 168 and 182 after administration, and HBsAg level in serum was measured for each time point. During the experiment, the detection of a subject is ended if the HBsAg content in serum in the test result is close to or more than the original value.

About 100 μl orbital blood was taken each time, and the serum was no less than 20 μl after centrifugation. The content of HBsAg in serum was measured by using HBsAg CLIA kit (Autobio, CL0310). The expression level of HBV DNA was measured by extraction of the DNA from the serum with reference to the instruction of QIAamp 96 DNA Blood Kit followed by qPCR.

The normalized HBsAg expression level=(the content of HBsAg after administration/the content of HBsAg before administration)×100%. The inhibition percentage against HBsAg=(1−the content of HBsAg after administration/the content of HBsAg before administration)×100%, wherein the content of HBsAg was expressed in equivalents (UI) of HBsAg per milliliter (ml) of serum.

The normalized HBV DNA expression level=(the content of HBV DNA after administration/the content of HBV DNA before administration)×100%. The inhibition percentage against HBV DNA=(1−the content of HBV DNA after administration/the content of HBV DNA before administration)×100%, wherein the content of HBV DNA was expressed in copies of HBV DNA per milliliter (ml) of serum.

Figure 21:
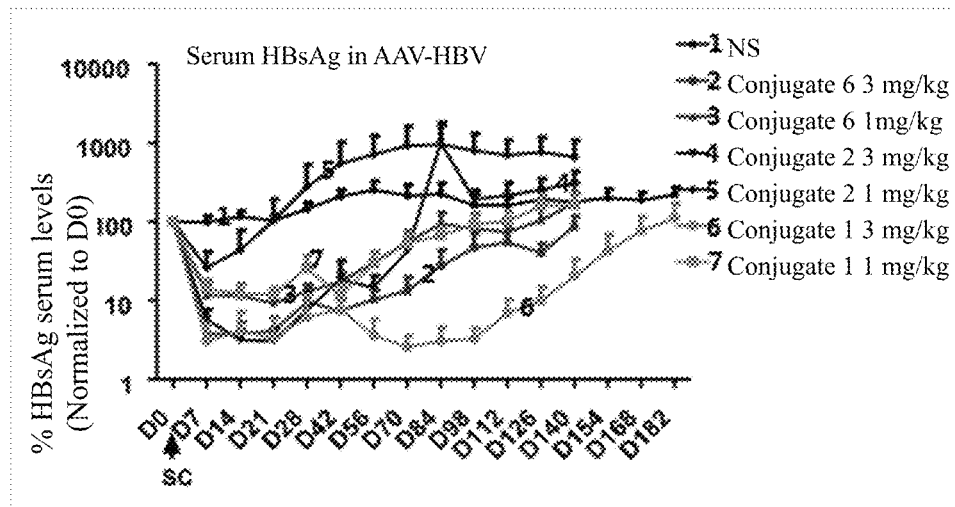
FIG. 21 shows time-dependent tests on the inhibitory efficiency of the siRNAs in the siRNA Conjugates 1 and 6 against serum HBsAg expression in AAV-HBV model mice.
Figure 22:
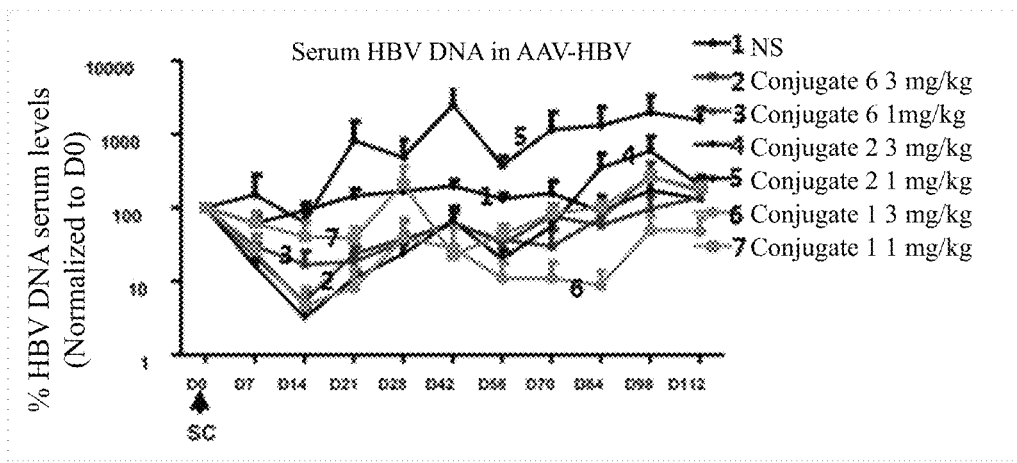
FIG. 22 shows time-dependent tests on the inhibitory efficiency of the siRNAs in the siRNA Conjugates 1 and 6 against HBV DNA in AAV-HBV model mice.

The results are shown in FIGS. 21 and 22.

As can be seen from the results of FIG. 21, the NS negative control group shows no inhibitory effect at different time points after administration; in contrast, each siRNA conjugate shows excellent inhibitory effect on HBsAg at different time points after administration. In particular, Conjugate 1 consistently showed high inhibition percentage against HBsAg in serum over a period of up to 140 days, indicating stable and effective inhibition against the expression of HBV gene over a longer time period.

As can be seen from the results of FIG. 22, the siRNA conjugate of each example also showed efficient inhibition against the expression of HBV DNA and maintained higher inhibition percentage over a period of up to 84 days.

In contrast, although Comparative Conjugate 2 achieved similar mRNA inhibitory effects to the individual conjugates in the experiments in vivo, the duration of the inhibitory effects as shown in FIGS. 21 and 22 were significantly shorter than that of Conjugates 1 and 6 at the same dose level.

Figure 23:
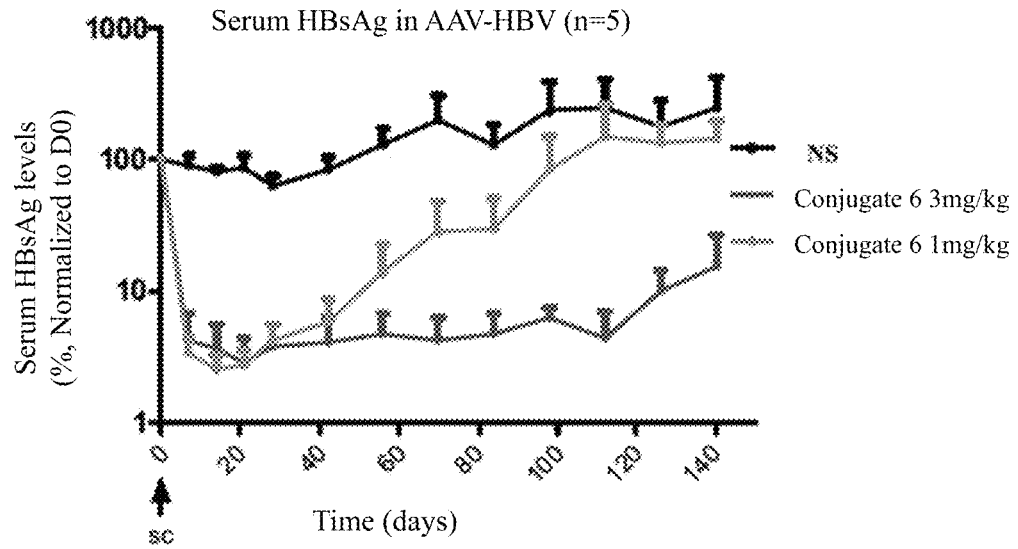
FIG. 23 shows time-dependent test on the inhibitory efficiency of Conjugate 6 against serum HBsAg expression in low-concentration AAV-HBV mouse model.
Figure 24:
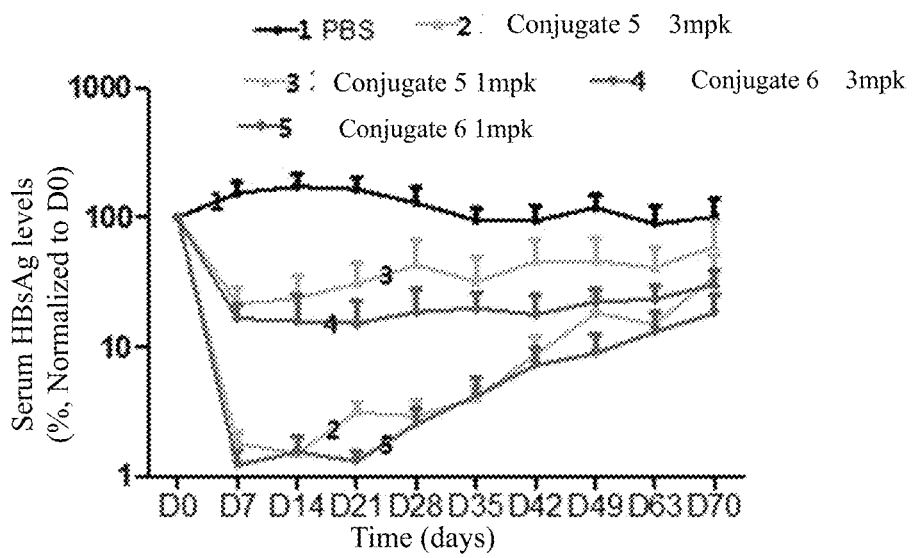
FIG. 24 shows time-dependent tests on the inhibitory efficiency of Conjugates 5 and 6 against serum HBsAg expression in M-Tg model.
Figure 25:
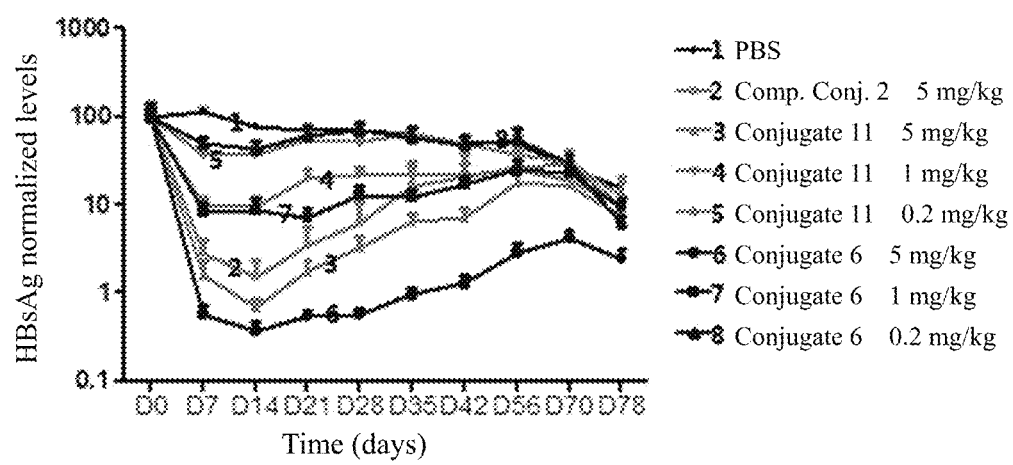
FIG. 25 shows time-dependent tests on the inhibitory efficiency of Conjugates 6 and 11 against serum HBsAg expression in M-Tg model.
Figure 26:
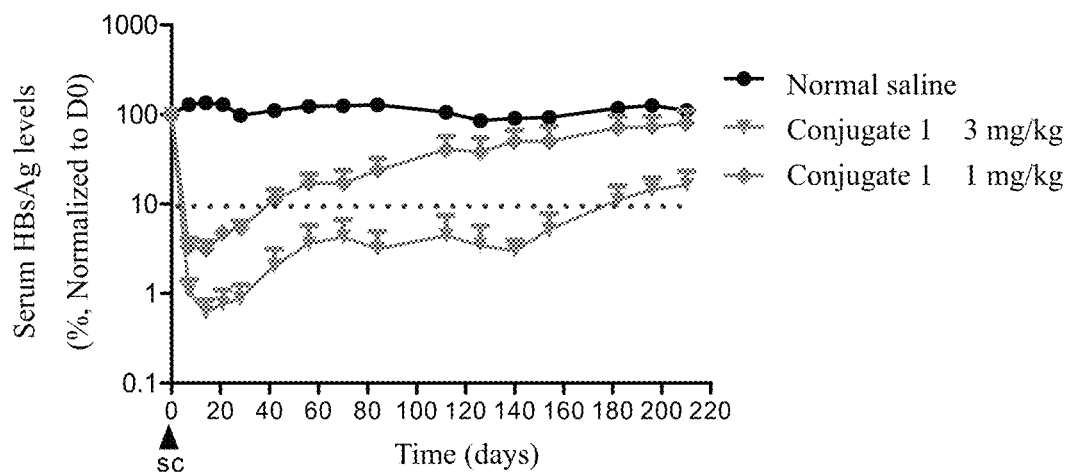
FIG. 26 shows time-dependent test on the inhibitory efficiency of Conjugate 1 against serum HBsAg expression in 1.28 copy model.
Figure 27:
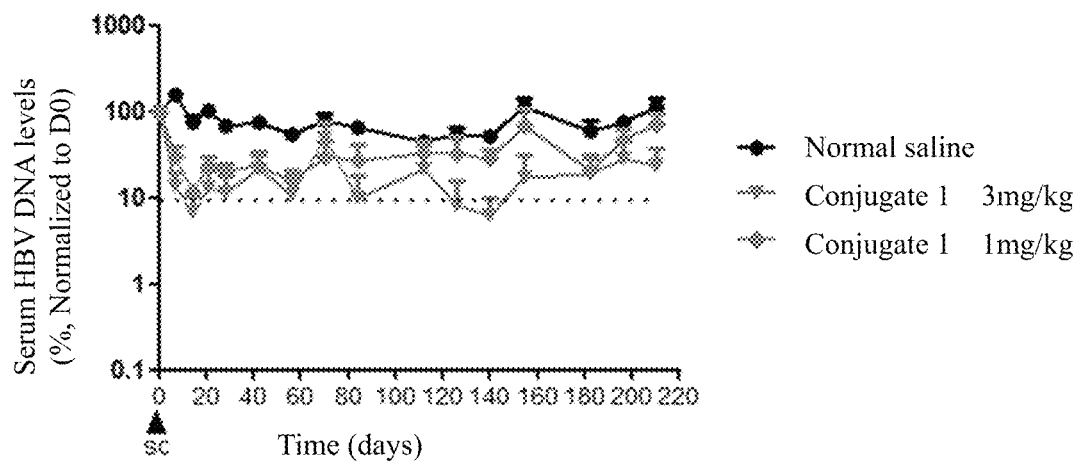
FIG. 27 shows time-dependent test on the inhibitory efficiency of Conjugate 1 against HBV DNA in 1.28 copy model.
Figure 28A:
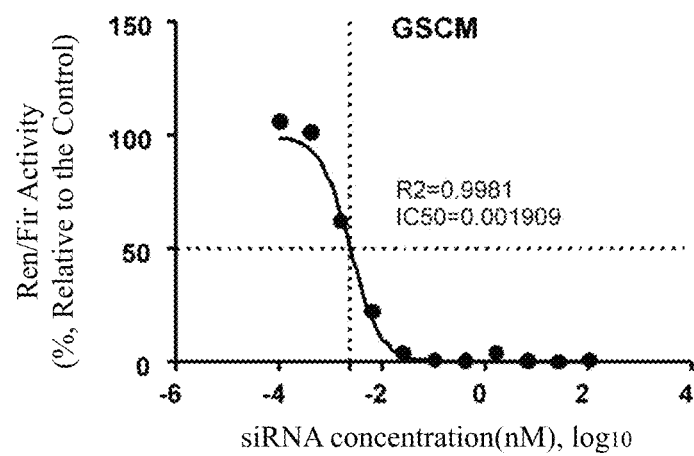
FIGS. 28A-28D show $IC_{50}$ values of Conjugate 1 when targeting GSCM, GSSM, PSCM and PSSM, respectively.
Figure 28B:
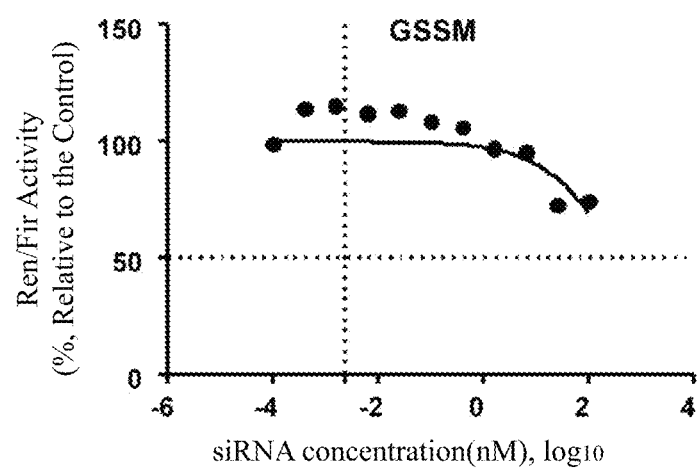
Figure 28C:
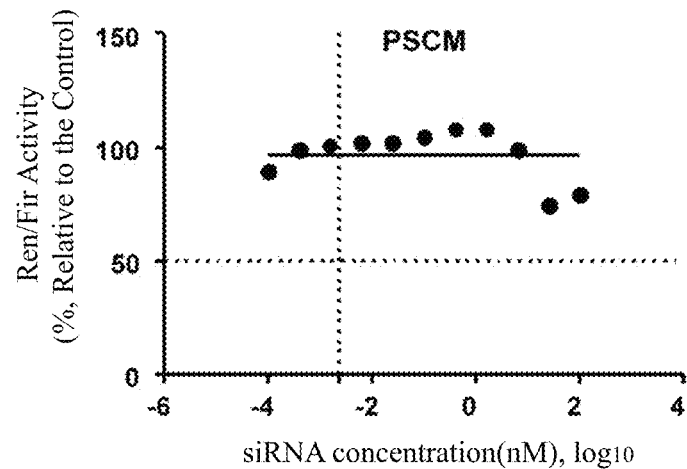
Figure 28D:
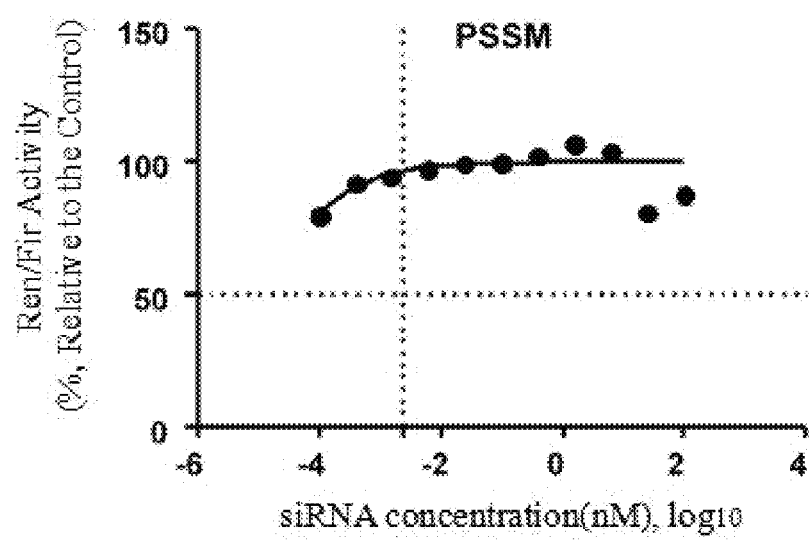

According to the same methods as described above, four more tests were further performed, wherein serum HBsAg was measured, except that:

In low-concentration AAV-HBV mouse models, 3 mg/kg and 1 mg/kg of Conjugate 6 were administered respectively; the test continued until day 140; and the results are shown in FIG. 23;

In M-Tg models, 3 mg/kg (3mpk) and 1 mg/kg (1mpk) of Conjugates 5 and 6 (PBS for the control group) were administered, respectively; the test continued until day 70; and the results are shown in FIG. 24; the mice were purchased from Department of Animal, Shanghai Public Health Center. The preparation methods of transgenic mice were described by Ren J. et al., in J. Medical Virology. 2006, 78:551-560;

In M-Tg models, 5 mg/kg, 1 mg/kg and 0.2 mg/kg of Conjugates 11 and 6 (PBS for the control group), and 5 mg/kg of Comparative Conjugate 2 were administered respectively; the test continued until day 78; and the results are shown in FIG. 25;

In 1.28 copy models, 3 mg/kg and 1 mg/kg of Conjugate 1 were administered respectively; the test continued until day 210; and the results are shown in FIGS. 26 and 27.

For the various administration doses described above, each conjugate was administered in the same administration volume, while concentration of the solution was correspondingly adjusted, so as to be administered in the corresponding dose.

From the results of FIGS. 22-27, it can be seen that the siRNA conjugates of the present disclosure showed consistent and efficient inhibitory efficiency on serum HBsAg in various animal models, and regular dose dependency.

Experimental Example 6 this Experiment Illustrates that the siRNA Conjugates of the Present Disclosure not Only have Higher Activity In Vitro, but Also Show Low Off-Target Effect (6-1) HEK293A cells used in this experimental example were provided by Nucleic Acid Technology Laboratory, Institute of Molecular Medicine, Peking University and cultured in DMEM complete media (Hyclone company) containing 20% fetal bovine serum (FBS, Hyclone company), 0.2 v % Penicillin-Streptomycin (Gibco, Invitrogen company) at 37° C. in an incubator containing 5% $CO_2$/95% air.

In this experimental example, Conjugate 1 was investigated in in vitro psiCHECK system for the on-target activity and off-target effect. Specifically, Conjugate 1 was tested for the activity of targeting completely matching target sequence (of which the nuecleotide sequence is completely complementary with the neucleotide sequence of the whole length of the sense/antisense strand of Conjugate 1) or targeting seed region matching target sequence (of which the nuecleotide sequence is complementary with the neucleotide sequence of positions 1-8 of the sense/antisense strand of Conjugate 1).

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, plasmids for detection were constructed and co-transfected with the siRNA conjugates to be detected into HEK293A cells; and the expression levels of the dual luciferase reporter gene reflect the on-target activity and off-target effect of the siRNA conjugates. Specific steps are as follows:

[1] Construction of Plasmids for Detection

Four recombinant plasmids were constructed using psi-CHECK™-2 (Promega™) plasmid, in which GSCM represents the on-target plasmid; and PSCM, GSSM and PSSM represent the off-target plasmids:

(1) GSCM, containing a target sequence, wherein the target sequence is fully complementary with all 21 nucleotide sequences of the antisense strand in the Conjugate 1.

(2) PSCM, containing a target sequence, wherein the target sequence is identical with all 21 nucleotide sequences of the antisense strand in the Conjugate 1.

(3) GSSM, containing a target sequence, wherein the target sequence is fully complementary with the nucleotide sequence at positions 1-8 from the 5' terminal of antisense strand in the Conjugate 1, while the remaining part of the target sequence corresponds to the nucleotide sequence at positions 9-21 from 5' terminal of the antisense strand in the Conjugate 1, but is completely mismatched; that is, when the nucleotide at any position in positions 9-21 from 5' terminal of the antisense strand in the Conjugate 1 is G, C, A or U, the nucleotide at the corresponding position in the target sequence is T, A, C or G.

(4) PSSM, containing a target sequence, wherein the target sequence is fully complementary with the nucleotide sequence at positions 1-8 from the 5' terminal of sense strand in the Conjugate 1, while the remaining part of the target sequence corresponds to the nucleotide sequence at positions 9-19 from 5' terminal of the sense strand in the Conjugate 1, but is completely mismatched; that is, when the nucleotide at any position in positions 9-19 from 5' terminal of the sense strand in the Conjugate 1 is G, C, A or U, the nucleotide at the corresponding position in the target sequence is T, A, C or G. In order to have the same length as the target sequence in GSSM, two CC were added at 3' terminal of the target sequence in PSSM.

The target sequence was inserted into the Xho I/Not I site of the psiCHECK™-2 plasmid.

[2] Transfection

In a 96-well plate, siRNA and each of the above plasmids were co-transfected according to the instruction of Lipofectamine™ 2000 (Invitrogen), each plasmid corresponding to several specific concentrations of Conjugate A1. Specifically, 10 ng of plasmid was transfected per well, using 0.2 µL of Lipofectamine™ 2000 per well; the final concentration (based on the concentration of siRNA) of Conjugate 1 was from 100 nM to 0.0001 nM (4-fold serial dilutions of 11 concentrations), 3 replicate wells per group.

[3] Detection 24 hours after co-transfection, the HEK293A cells were lysed by using a dual luciferase reporter gene assay kit (Promega, Cat No. E2940) according to the instruction to detect the expression level of the dual luciferase reporter gene. For the test group of each specific concentration, those untreated with the conjugate were used as control (con). The *Renilla* luciferase protein level (Ren) was normalized to the firefly luciferase protein level (Fir).

The dose-response curves were plotted by the activity results measured at different siRNA concentrations, and the curves were fitted using the function log(inhibitor) vs. response—Variable slope of Graphpad 5.0 software. The $IC_{50}$ of the siRNA targeting GSCM was calculated based on the dose-response curve with the formula below:

$$Y = Bot + \frac{\text{Top} - Bot}{1 + 10^{(LogIC50-X) \times HillSlope}}$$

wherein:

Y is the expression level of remaining mRNA,

X is the logarithm of the concentration of transfected siRNA,

Bot is the Y value at the bottom of the steady stage,

Top is the Y value at the top of the steady stage, $LogIC_{50}$ is the X value at which Y is median value between the bottom and the top of the asymptote, and HillSlope is the slope of the curve.

The $IC_{50}$ of the Conjugate 1 targeting GSCM was calculated based on the dose-effect curve. The results are shown in FIGS. 28A-28D, which indicate that the $IC_{50}$ value of Conjugate 1 corresponding to GSCM was 0.0513 nM.

Conjugate 1 corresponding to PSCM, GSSM or PSSM shows no significant inhibitory effect at each siRNA concentration, indicating that the siRNA conjugate of the present disclosure not only has higher activity in vitro, but also exhibits low off-target effect.

According to the above results, Conjugate 1 shows superior inhibitory effect on the expression of the target mRNA in the on-target plasmid with low $IC_{50}$; while shows no inhibitory effect on the expression of the three off-target plasmids. Thus, Conjugate 1 not only has superior inhibitory efficiency of the target mRNA, but also exhibits low off-target effect.

Embodiments of the present disclosure are described in detail above, but the present disclosure is not limited to the specific details of the above-described embodiments. Various simple variations of the technical solution of the present disclosure can be made within the scope of the technical concept of the present disclosure, and these simple variations are within the scope of the present disclosure.

It is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

---

What is claimed is:

1. A siRNA conjugate having a structure as shown by Formula (1):

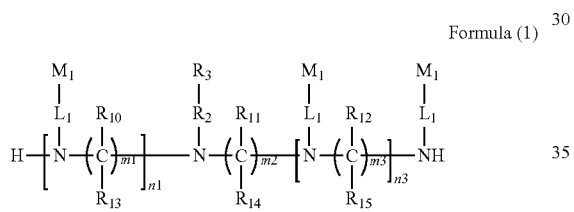

Formula (1)

wherein, n1 is an integer of 1-2 and n3 is an integer of 0-1, and n1+n3=2-3;

each of m1, m2, and m3 is independently an integer of 2-10;

each of $R_{10}$, $R_{11}$, $R_{12}$, $R_{13}$, $R_{14}$ and $R_{15}$ is independently H or selected from the group consisting of $C_1$-$C_{10}$ alkyl, $C_1$-$C_{10}$ haloalkyl and $C_1$-$C_{10}$ alkoxy;

$R_3$ is a group having a structure as shown by Formula A59:

(A59)

wherein $E_1$ is OH, SH or $BH_2$; and Nu is siRNA;

each nucleotide in the siRNA is independently a modified or unmodified nucleotide; the siRNA comprises a sense strand and an antisense strand, wherein the sense strand comprises a nucleotide sequence 1, and the antisense strand comprises a nucleotide sequence 2; the nucleotide sequence 1 and the nucleotide sequence 2 are at least partly reverse complementary to form a double-stranded region; the nucleotide sequence 1 has the same length and no more than 3 nucleotides different from the nucleotide sequence shown in SEQ ID NO:155; and the nucleotide sequence 2 has the same length and no more than 3 nucleotides different from the nucleotide sequence shown in SEQ ID NO:156:

(SEQ ID NO: 155)
5'- CCUUGAGGCAUACUUCAAZ -3';

(SEQ ID NO: 156)
5'- Z'UUGAAGUAUGCCUCAAGG -3';

wherein,

Z is A; Z' is U;

the nucleotide sequence 1 comprises nucleotide $Z_A$ at the corresponding site to Z;

the nucleotide sequence 2 comprises nucleotide $Z'_B$ at the corresponding site to Z'; the nucleotide $Z'_B$ is the first nucleotide from 5' terminal of the antisense strand;

$R_2$ is a linear alkylene of 1 to 20 carbon atoms in length, wherein one or more carbon atoms are optionally replaced with any one or more of the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O) $C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $L_1$ is independently a linear alkylene of 1 to 70 carbon atoms in length, wherein one or more carbon atoms are optionally replaced with any one or more of the group consisting of: C(O), NH, O, S, CH=N, S(O)$_2$, C$_2$-C$_{10}$ alkeylene, C$_2$-C$_{10}$ alkynylene, C$_6$-C$_{10}$ arylene, C$_3$-C$_{18}$ heterocyclylene, and C$_5$-C$_{10}$ heteroarylene, and wherein $L_1$ is optionally substituted by any one or more of the group consisting of: C$_1$-C$_{10}$ alkyl, C$_6$-C$_{10}$ aryl, C$_5$-C$_{10}$ heteroaryl, C$_1$-C$_{10}$ haloalkyl, —OC$_1$-C$_{10}$ alkyl, —OC$_1$-C$_{10}$ alkylphenyl, —C$_1$-C$_{10}$ alkyl-OH, —OC$_1$-C$_{10}$ haloalkyl, —SC$_1$-C$_{10}$ alkyl, —SC$_1$-C$_{10}$ alkylphenyl, —C$_1$-C$_{10}$ alkyl-SH, —SC$_1$-C$_{10}$ haloalkyl, halo, —OH, —SH, —NH$_2$, —C$_1$-C$_{10}$ alkyl-NH$_2$, —N(C$_1$-C$_{10}$ alkyl)(C$_1$-C$_{10}$ alkyl), —NH(C$_1$-C$_{10}$ alkyl), cyano, nitro, —CO$_2$H, —C(O)O(C$_1$-C$_{10}$ alkyl), —CON(C$_1$-C$_{10}$ alkyl)(C$_1$-C$_{10}$ alkyl), —CONH(C$_1$-C$_{10}$ alkyl), —CONH$_2$, —NHC(O)(C$_1$-C$_{10}$ alkyl), —NHC(O)(phenyl), —N(C$_1$-C$_{10}$ alkyl)C(O)(C$_1$-C$_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O)C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH(phenyl), —NHSO$_2$(C$_1$-C$_{10}$ alkyl), —NHSO$_2$(phenyl), and —NHSO$_2$(C$_1$-C$_{10}$ haloalkyl);

∿ represents a site where a group is attached to the rest of the molecule;

$M_1$ represents a targeting group.

2. The siRNA conjugate according to claim 1, wherein each $L_1$ is independently selected from the group consisting of groups A1-A26 and any connection combinations thereof:

(A1)

(A2)

(A3)

(A4)

(A5)

(A6)

(A7)

-continued (A8)

(A9)

(A10)

(A11)

(A12)

(A13)

(A14)

(A15)

(A16)

(A17)

(A18)

(A19)

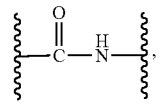
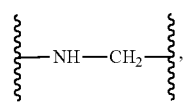
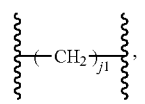
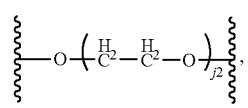
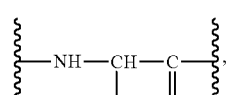
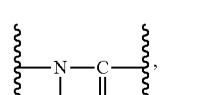
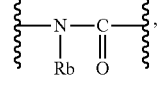
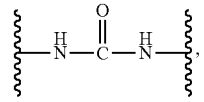
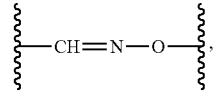
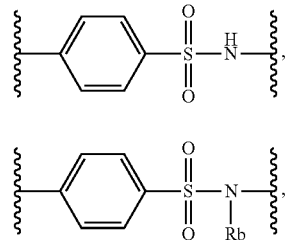
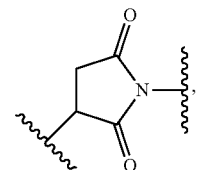
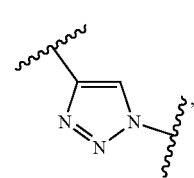
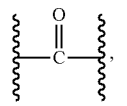
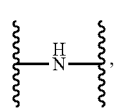
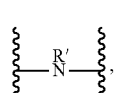
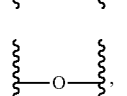
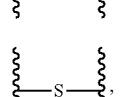
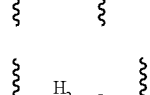
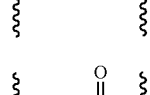

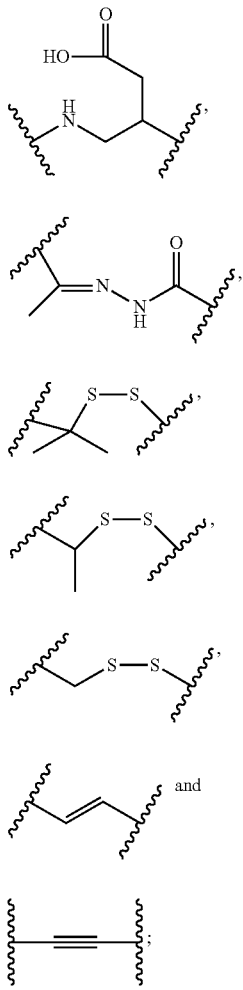
(A20)
(A21)
(A22)
(A23)
(A24)
(A25)
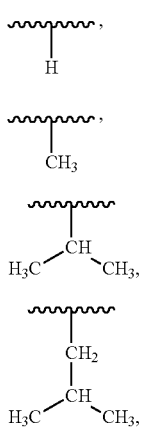
(A26)
wherein each j1 is independently an integer of 1-20;
each j2 is independently an integer of 1-20;
each R' is independently a $C_1$-$C_{10}$ alkyl;
each Ra is independently selected from the group consisting of A27-A45 and any combinations thereof:
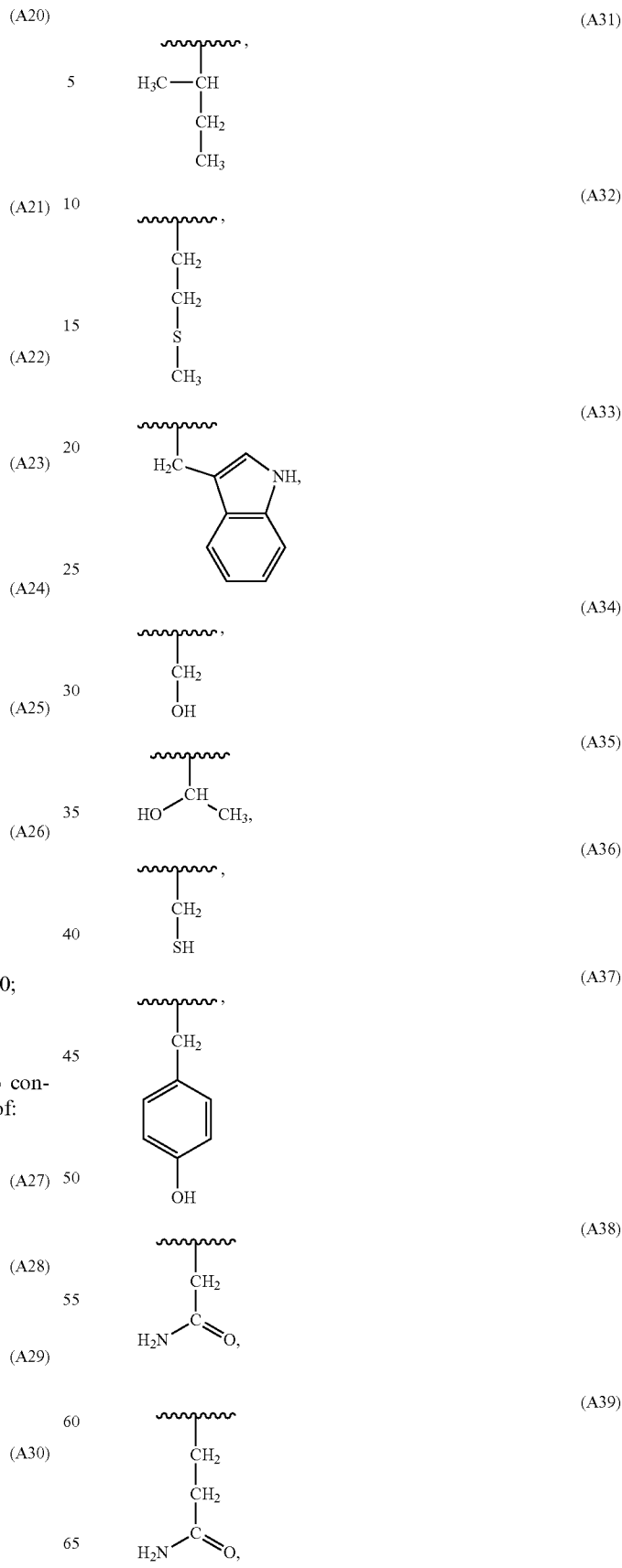
(A27)
(A28)
(A29)
(A30)
(A31)
(A32)
(A33)
(A34)
(A35)
(A36)
(A37)
(A38)
(A39)

-continued

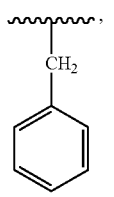 (A40)

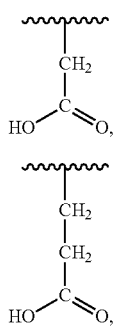 (A41)

(A42)

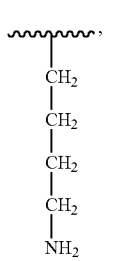 (A43)

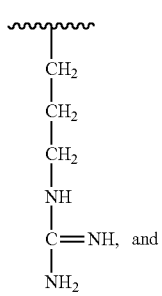 (A44)

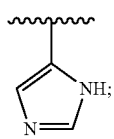 (A45)

each Rb is independently a $C_1$-$C_{10}$ alkyl.

3. The siRNA conjugate according to claim 2, wherein $L_1$ is selected from the connection combinations of one or more of A1, A4, A5, A6, A8, A10, A11, A13, and connection combinations thereof.

4. The siRNA conjugate according to claim 1, wherein the length of $L_1$ is 3 to 25 atoms.

5. The siRNA conjugate according to claim 1, wherein each of m1, m2 and m3 is independently an integer of 2-5; or wherein m1=m2=m3.

6. The siRNA conjugate according to claim 1, wherein
each $M_1$ is independently a ligand that binds to asialoglycoprotein receptors (ASGP-R) on the surface of mammalian hepatocytes; or
each $M_1$ is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O-[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose.

7. The siRNA conjugate according to claim 1, wherein $R_2$ group has both a site linking to the N atom on the nitrogenous backbone and a site linking to the P atom in $R_3$.

8. The siRNA conjugate according to claim 7, wherein $R_2$ forms an amide bond with the N atom on the nitrogenous backbone, and the site linking to the P atom in $R_3$ forms a phosphoester bond with the P atom; or wherein $R_2$ is selected from B5, B6, B5' and B6':

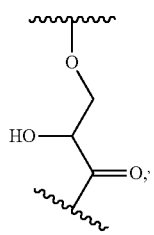 (B5)

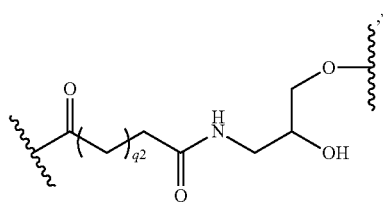 (B6)

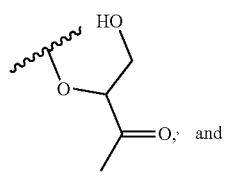 (B5')

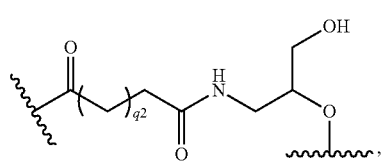
(B6')
wherein, ∼∼∼ represents the site where the groups are covalently linked; and $q_2$ is an integer of 1-10.
9. The siRNA conjugate according to claim 1, wherein the conjugate has a structure as shown by Formula (3), (4), (5), (6), (7), (8), (9), (10), (11), (12), (13), (14), (15), (16), (17), (18), (19), (20), (21) or (22):
Formula (3)
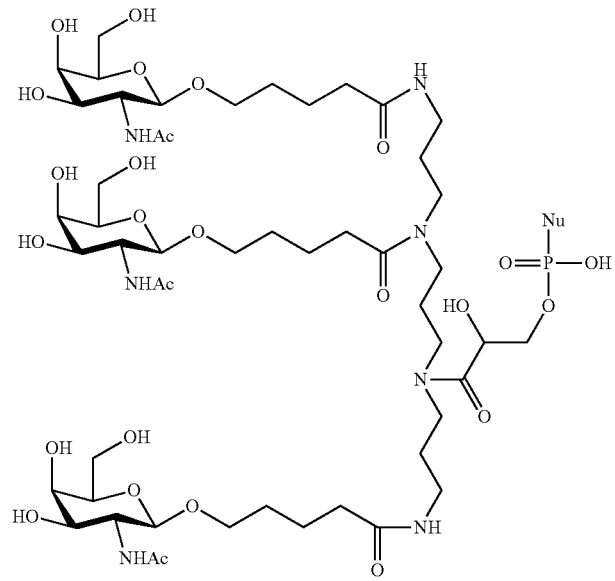
Formula (4)
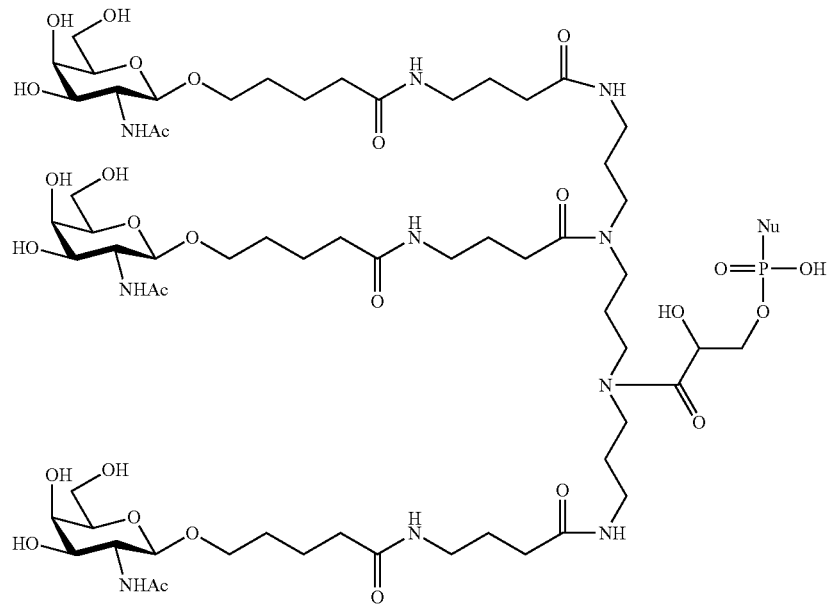

-continued
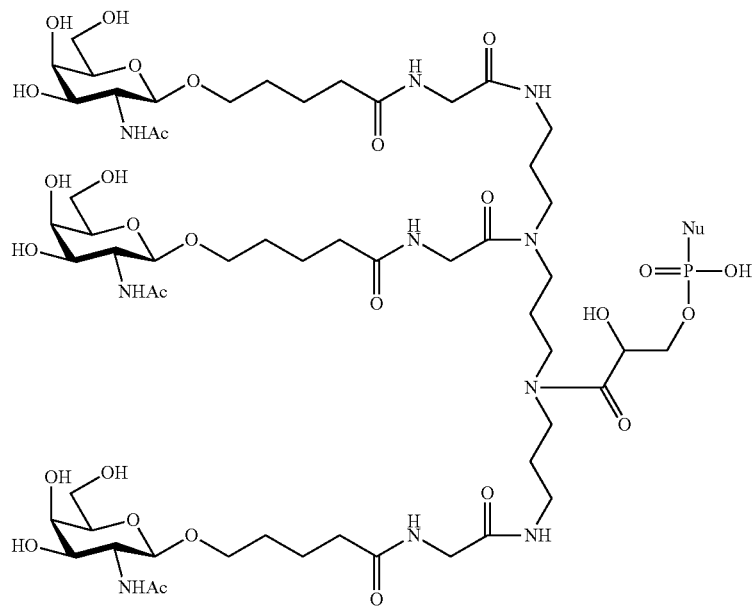
Formula (5)
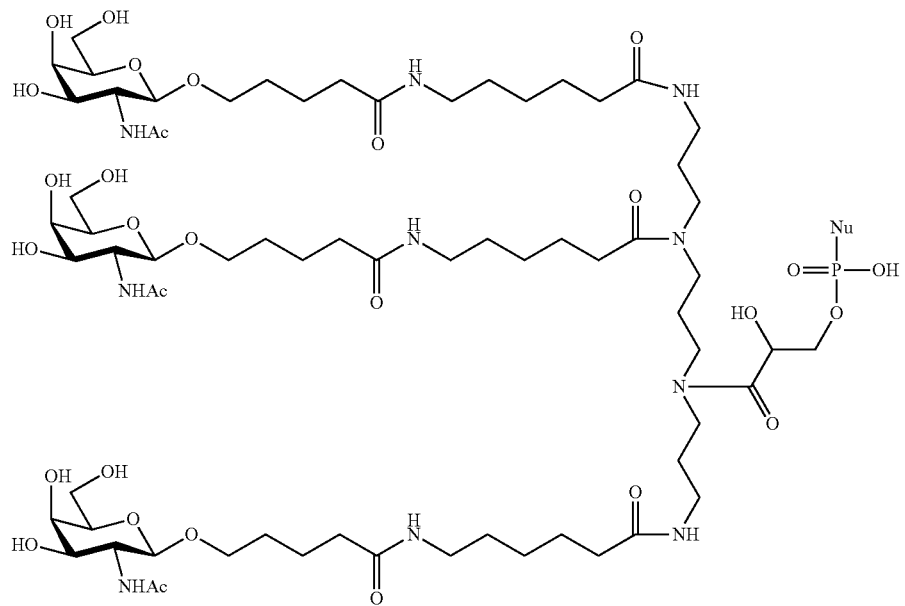
Formula (6)

-continued
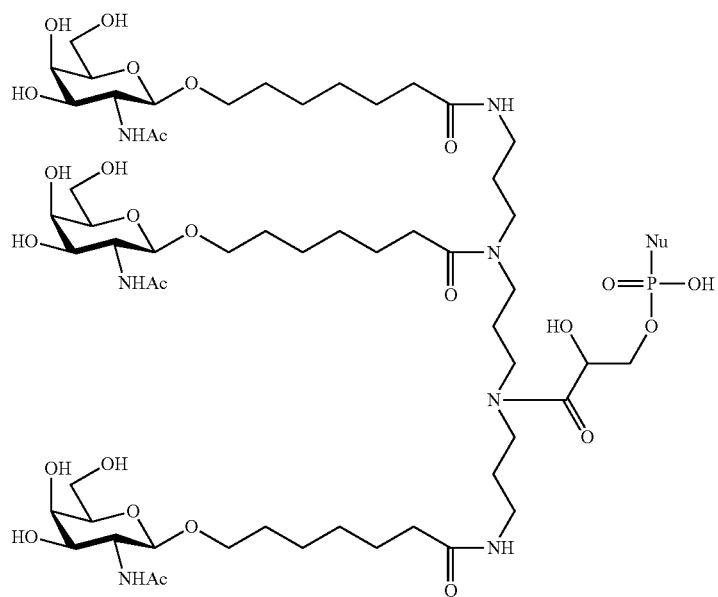
Formula (7)
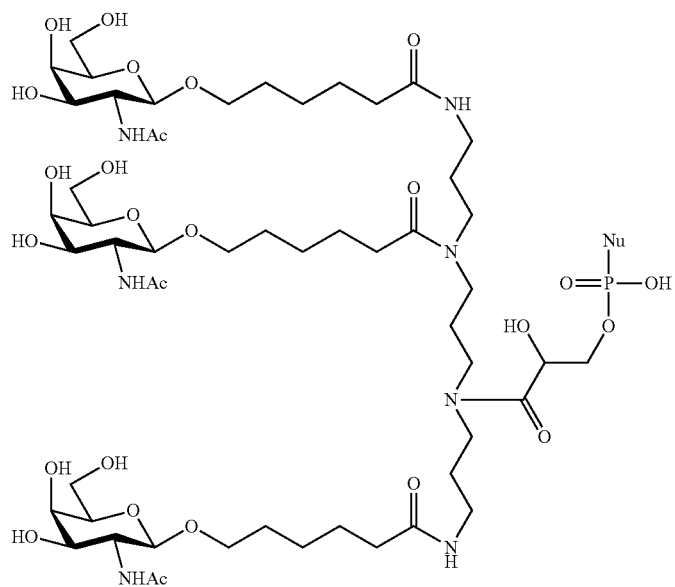
Formula (8)

Formula (9)
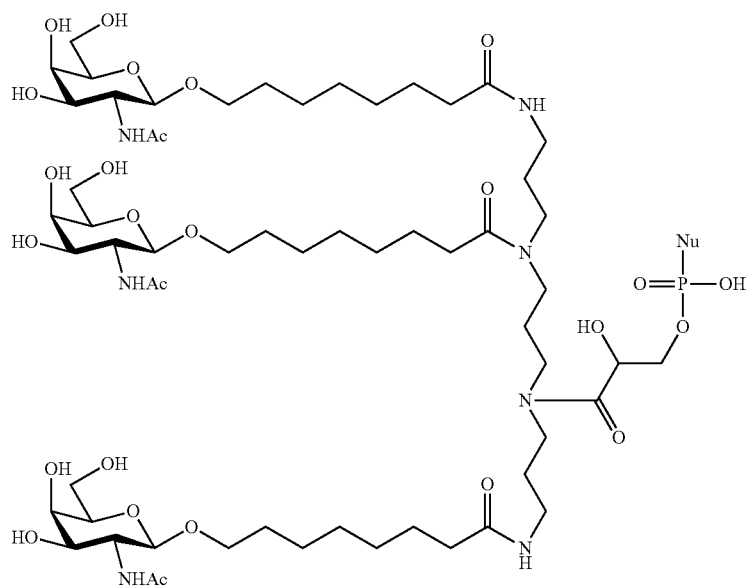
Formula (10)
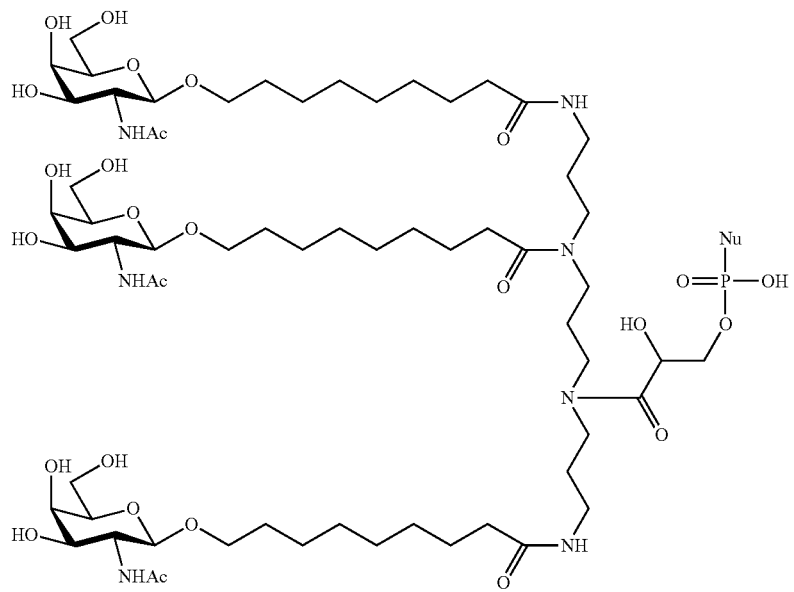

-continued
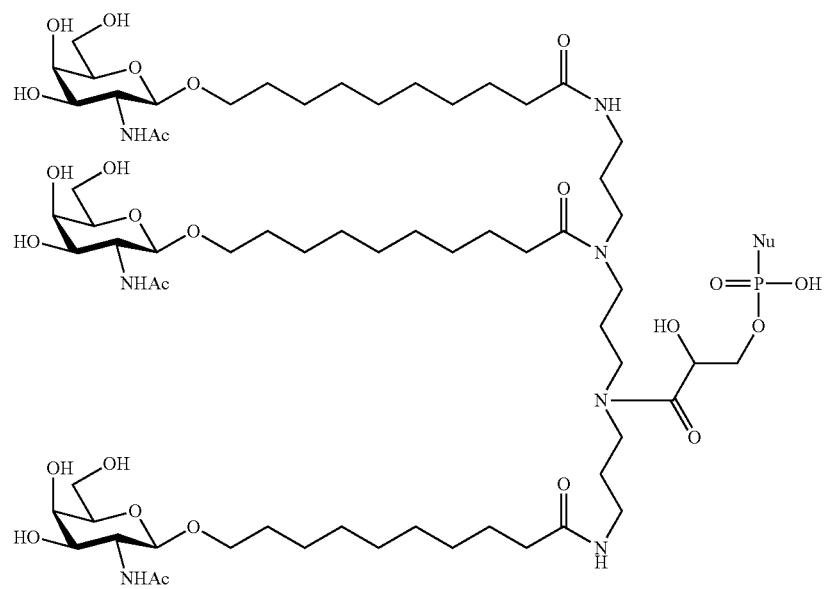
Formula (11)
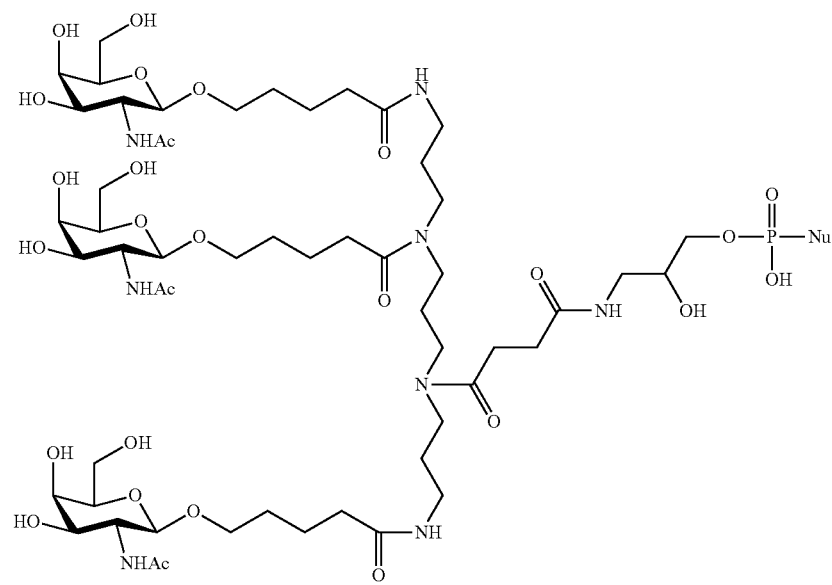
Formula (12)

Formula (13)
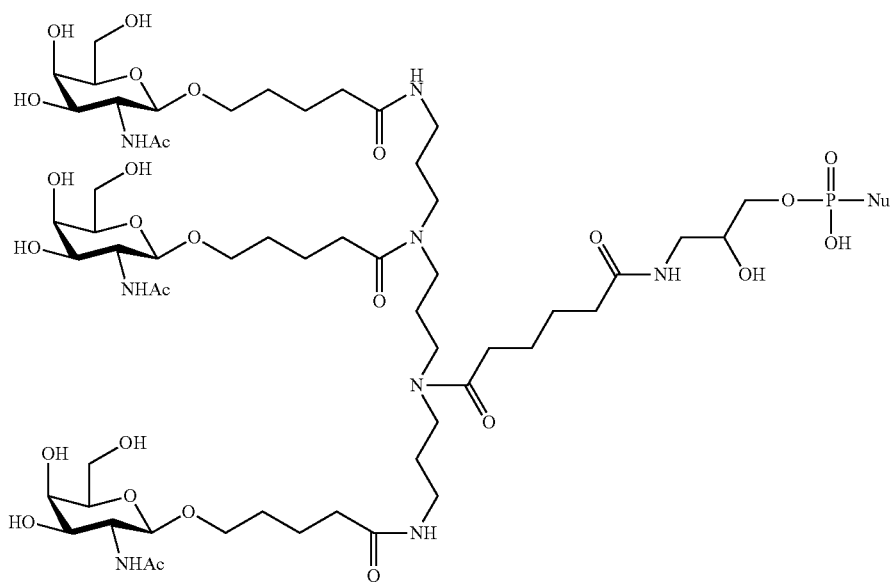
Formula (14)
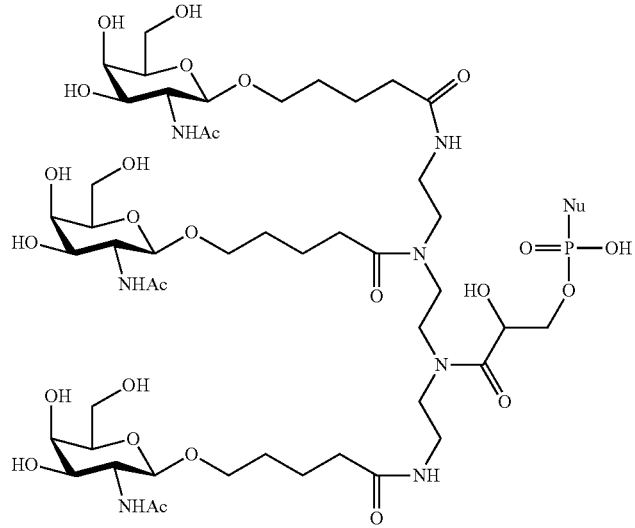

Formula (15)
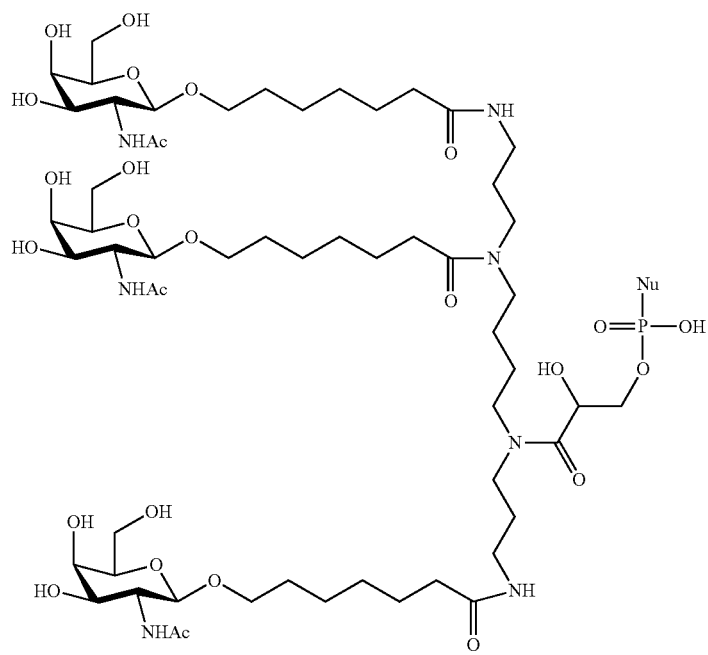
Formula (16)
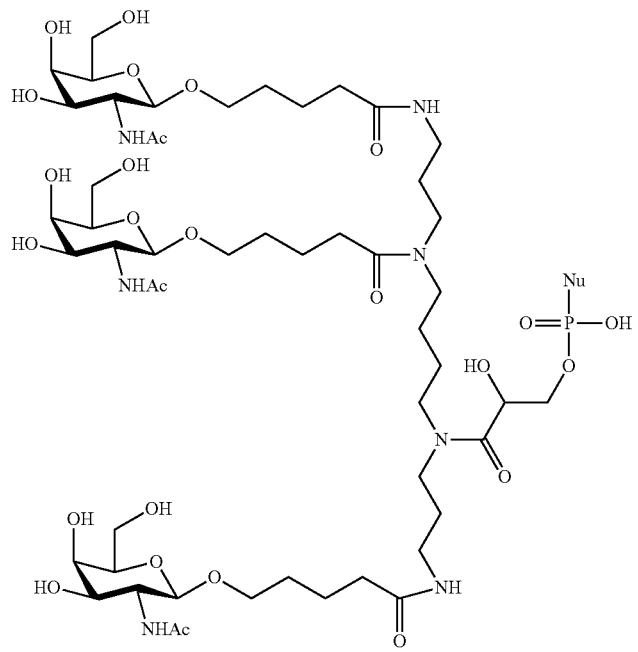

Formula (17)
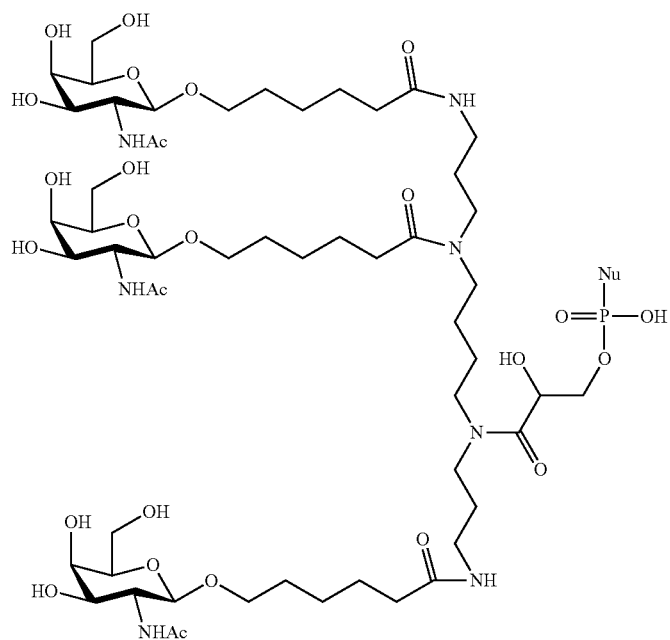
Formula (18)
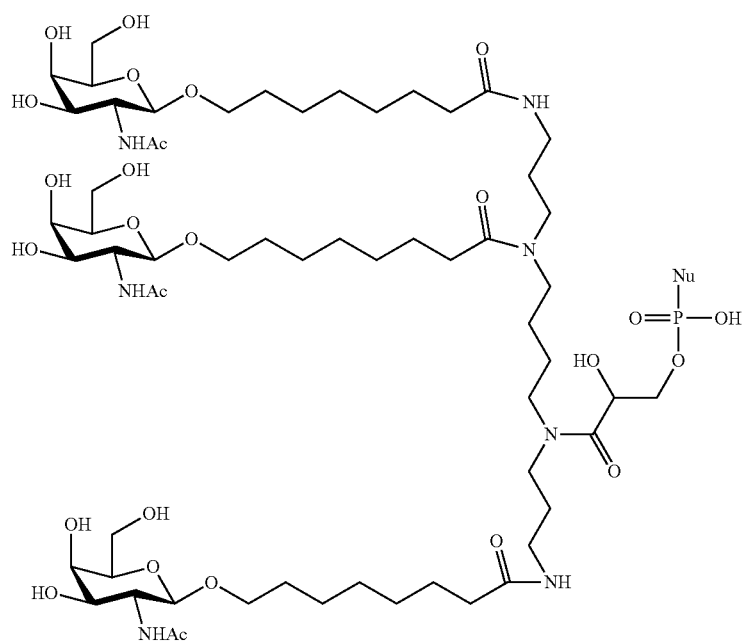

Formula (19)
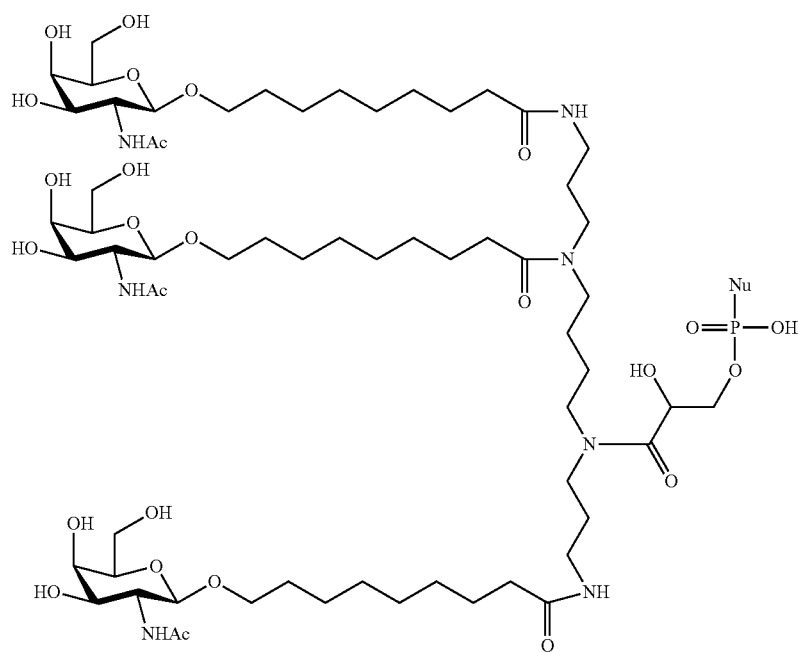
Formula (20)
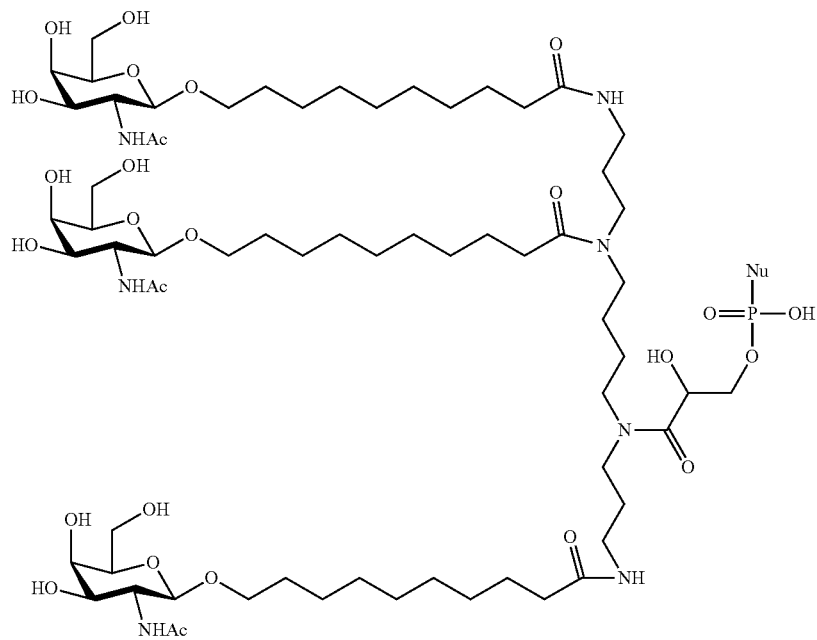

Formula (21)
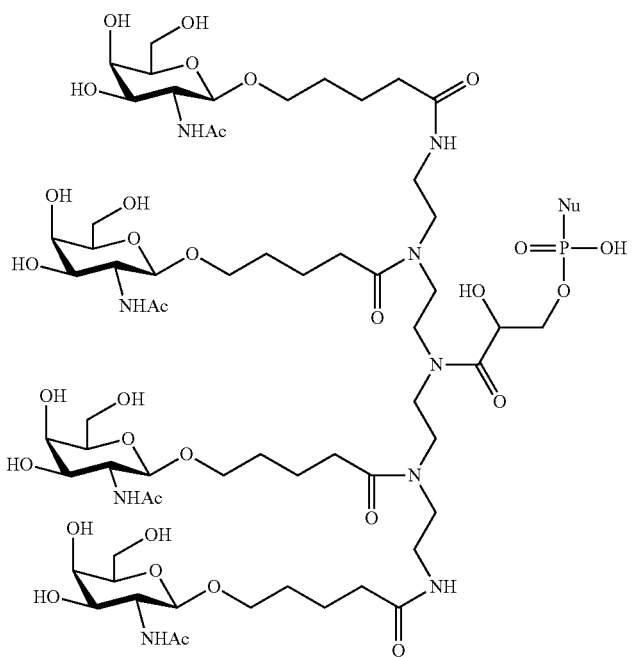
Formula (22)
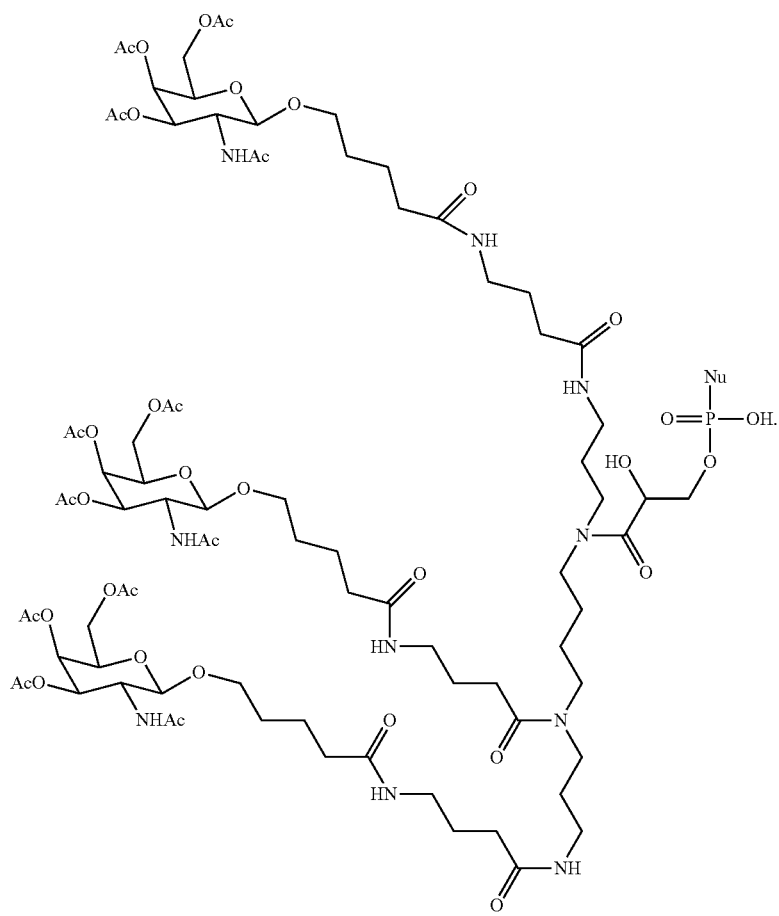

10. The siRNA conjugate according to claim 1, wherein the P atom in Formula A59 is linked to the 3' terminal of the sense strand of the siRNA.

11. The siRNA conjugate according to claim 1, wherein the nucleotide difference between the nucleotide sequence 2 and the nucleotide sequence shown in SEQ ID NO:156 includes a difference at the site of $Z'_B$, where $Z'_B$ is selected from A, C or G.

12. The siRNA conjugate according to claim 1, wherein the sense strand further comprises a nucleotide sequence 3, and the antisense strand further comprises a nucleotide sequence 4; the nucleotide sequences 3 and 4 each have a length of 1-4 nucleotides; the nucleotide sequence 3 is linked to the 5' terminal of the nucleotide sequence 1, and the nucleotide sequence 4 is linked to the 3' terminal of the nucleotide sequence 2; the nucleotide sequence 3 has the same length and is substantially reverse complementary or completely reverse complementary to the nucleotide sequence 4, the "substantially reverse complementary" refers to no more than 1 base mispairing in two nucleotide sequences:

and wherein the nucleotide sequence 3 and the nucleotide sequence 4 both have a length of 1 nucleotide, and the base of the nucleotide sequence 3 is A;

the nucleotide sequence 3 and the nucleotide sequence 4 both have a length of 2 nucleotides, and in the direction from 5' terminal to 3' terminal, the bases of the nucleotide sequence 3 are G and A in succession;

the nucleotide sequence 3 and the nucleotide sequence 4 both have a length of 3 nucleotides, and in the direction from 5' terminal to 3' terminal, the bases of the nucleotide sequence 3 are C, G and A in succession; or the nucleotide sequence 3 and the nucleotide sequence 4 both have a length of 4 nucleotides, and in the direction from 5' terminal to 3' terminal, the bases of the nucleotide sequence 3 are C, C, G and A in succession.

13. The siRNA conjugate according to claim 1, wherein the siRNA further comprises a nucleotide sequence 5, which has a length of 1-3 nucleotides and is linked to 3' terminal of the antisense strand, thereby constituting a 3' overhang of the antisense strand.

14. The siRNA conjugate according to claim 1, wherein the sense strand comprises the nucleotide sequence shown in SEQ ID NO:1, and the antisense strand comprises the nucleotide sequence shown in SEQ ID NO:3 or SEQ ID NO: 4:

```
                                          (SEQ ID NO: 1)
        5'-CCUUGAGGCAUACUUCAAZ_A-3';

(SEQ ID NO: 3)
        5'- Z'_BUUGAAGUAUGCCUCAAGGUU -3';

(SEQ ID NO: 4)
        5'- Z'_BUUGAAGUAUGCCUCAAGGUC -3';
``` wherein, the nucleotide $Z'_B$ is the first nucleotide from 5' terminal of the antisense strand; $Z_A$ is selected from A, U, G or C; and $Z'_B$ is a nucleotide complementary to $Z_A$.

15. The siRNA conjugate according to claim 1, wherein the siRNA is siHBa1 or siHBa2:

```
siHBa1
Sense strand:
                                          (SEQ ID NO: 5)
    5'-CCUUGAGGCAUACUUCAAA-3', Antisense strand:
                                          (SEQ ID NO: 6)
    5'-UUUGAAGUAUGCCUCAAGGUU-3', siHBa2
Sense strand:
                                          (SEQ ID NO: 7)
    5'-GACCUUGAGGCAUACUUCAAA-3', Antisense strand:
                                          (SEQ ID NO: 8)
    5'-UUUGAAGUAUGCCUCAAGGUCGG-3'.
```

16. The siRNA conjugate according to claim 1, wherein each nucleotide in the sense strand and the antisense strand is independently a fluoro modified nucleotide or a non-fluoro modified nucleotide;

wherein a "fluoro modified nucleotide" refers to a nucleotide formed by substituting the 2'-hydroxy of the ribose group of the nucleotide with a fluoro; a "non-fluoro modified nucleotide" refers to a nucleotide formed by substituting the 2'-hydroxy of the ribose group of the nucleotide with a group other than a fluoro, or a nucleotide analogue; and wherein in the direction from 5' terminal to 3' terminal, the nucleotides at positions 7, 8 and 9 of the nucleotide sequence 1 are fluoro modified nucleotides; and in the direction from 5' terminal to 3' terminal, the nucleotides at positions 2, 6, 14 and 16 of the nucleotide sequence 2 are fluoro modified nucleotides.

17. The siRNA conjugate according to claim 16, wherein each non-fluoro modified nucleotide is a methoxy modified nucleotide, which refers to a nucleotide formed by substituting the 2'-hydroxy of the ribose group with a methoxy group.

18. The siRNA conjugate according to claim 1, wherein, in the direction from 5' terminal to 3' terminal, the nucleotides at positions 7, 8 and 9 of the nucleotide sequence 1 in the sense strand are fluoro modified nucleotides, and the nucleotides at the rest of positions in the sense strand are methoxy modified nucleotides; and the nucleotides at positions 2, 6, 14 and 16 of the nucleotide sequence 2 in the antisense strand are fluoro modified nucleotides, and the nucleotides at the rest of positions in the antisense strand are methoxy modified nucleotides;

in the direction from 5' terminal to 3' terminal, the nucleotides at positions 5, 7, 8 and 9 of the nucleotide sequence 1 in the sense strand are fluoro modified nucleotides, and the nucleotides at the rest of positions in the sense strand are methoxy modified nucleotides; and the nucleotides at positions 2, 6, 8, 9, 14 and 16 of the nucleotide sequence 2 in the antisense strand are fluoro modified nucleotides, and the nucleotides at the rest of positions in the antisense strand are methoxy modified nucleotides; or in the direction from 5' terminal to 3' terminal, the nucleotides at positions 5, 7, 8 and 9 of the nucleotide sequence 1 in the sense strand of the siRNA are fluoro modified nucleotides, and the nucleotides at the rest of positions in the sense strand are methoxy modified nucleotides; and the nucleotides at positions 2, 6, 14 and 16 of the nucleotide sequence 2 in the antisense strand are fluoro modified nucleotides, and the nucleotides at the rest of positions in the antisense strand are methoxy modified nucleotides.

19. The siRNA conjugate according to claim 1, wherein the siRNA is siHBa1M1, siHBa1M2, siHBa2M1 or siHBa2M2:

```
siHBa1M1
Sense strand:
                                 (SEQ ID NO: 9)
5'-CmCmUmUmGmAmGfGfCfAmUmAmCmUmUmCmAmAmAm-3', Antisense strand:
                                 (SEQ ID NO: 10)
5'-UmUfUmGmAmAfGmUmAmUmGmCmCmUfCmAfAmGmGmUmUm -3', siHBa1M2
Sense strand:
                                 (SEQ ID NO: 11)
5'- CmCmUmUmGfAmGfGfCfAmUmAmCmUmUmCmAmAmAm -3', Antisense strand:
                                 (SEQ ID NO: 12)
5'-UmUfUmGmAmAfGmUfAfUmGmCmCmUfCmAfAmGmGmUmUm -3', siHBa2M1
Sense strand:
                                 (SEQ ID NO: 13)
5'-GmAmCmCmUmUmGmAmGfGfCfAmUmAmCmUmUmCmAmAmAm -3', Antisense strand:
                                 (SEQ ID NO: 14)
5'-UmUfUmGmAmAfGmUmAmUmGmCmCmUfCmAfAmGmGmUmCmGm Gm -3', siHBa2M2
Sense strand:
                                 (SEQ ID NO 15)
5'-GmAmCmCmUmUmGfAmGfGfCfAmUmAmCmUmUmCmAmAmAm -3', Antisense strand:
                                 (SEQ ID NO: 16)
5'-UmUfUmGmAmAfGmUfAfUmGmCmCmUfCmAfAmGmGmUmCmGm Gm -3',
``` wherein, C, G, U, and A indicate the base composition of the nucleotides; m indicates that the nucleotide adjacent to the left side of the letter m is a methoxy modified nucleotide; f indicates that the nucleotide adjacent to the left side of the letter f is a fluoro modified nucleotide.

20. The siRNA conjugate according to claim 1, wherein, in the siRNA, at least one phosphate group is a phosphorothioate group, and the phosphorothioate linkage exists in at least one of the following positions:

the position between the first and second nucleotides at 5' terminal of the sense strand;
the position between the second and third nucleotides at 5' terminal of the sense strand;
the position between the first and second nucleotides at 3' terminal of the sense strand;
the position between the second and third nucleotides at 3' terminal of the sense strand;
the position between the first and second nucleotides at 5' terminal of the antisense strand;
the position between the second and third nucleotides at 5' terminal of the antisense strand;
the position between the first and second nucleotides at 3' terminal of the antisense strand; and the position between the second and third nucleotides at 3' terminal of the antisense strand.

21. The siRNA conjugate according to claim 1, wherein the siRNA is siHBa1M1S, siHBa1M2S, siHBa2M1S or siHBa2M2S:

```
siHBa1M1S
Sense strand:
                                 (SEQ ID NO: 17)
5'-CmsCmsUmUmGmAmGfGfCfAmUmAmCmUmUmCmAmAmAm -3', Antisense strand:
                                 (SEQ ID NO: 18)
5'-UmsUfsUmGmAmAfGmUmAmUmGmCmCmUfCmAfAmGmGmsUms Um -3', siHBa1M2S
Sense strand:
                                 (SEQ ID NO: 19)
5'-CmsCmsUmUmGfAmGfGfCfAmUmAmCmUmUmCmAmAmAm -3', Antisense strand:
                                 (SEQ ID NO: 20)
5'-UmsUfsUmGmAmAfGmUfAfUmGmCmCmUfCmAfAmGmGmsUms Um -3', siHBa2M1S
Sense strand:
                                 (SEQ ID NO: 21)
5'-GmsAmsCmCmUmUmGmAmGfGfCfAmUmAmCmUmUmCmAmAm Am -3',
Antisense strand:
                                 (SEQ ID NO: 22)
5'-UmsUfsUmGmAmAfGmUmAmUmGmCmCmUfCmAfAmGmGmUmCms GmsGm -3', siHBa2M2S
Sense strand:
                                 (SEQ ID NO: 23)
5'-GmsAmsCmCmUmUmGfAmGfGfCfAmUmAmCmUmUmCmAmAm Am -3', Antisense strand:
                                 (SEQ ID NO: 24)
5'-UmsUfsUmGmAmAfGmUfAfUmGmCmCmUfCmAfAmGmGmUmCms GmsGm -3',
``` wherein, C, G, U, and A indicate the base composition of the nucleotides; m indicates that the nucleotide adjacent to the left side of the letter m is a methoxy modified nucleotide; f indicates that the nucleotide adjacent to the left side of the letter f is a fluoro modified nucleotide; s represents that the two nucleotides adjacent to both sides of the letter s are linked by a phosphorothioate linkage.

22. The siRNA conjugate according to claim 1, wherein the 5'-terminal nucleotide in the antisense strand is a 5'-phosphate nucleotide or a 5'-phosphate analogue modified nucleotide.

23. The siRNA conjugate according to claim 1, wherein the siRNA is any one selected from the group consisting of siHBa1M1P1, siHBa1M2P1, siHBa2M1P1, siHBa2M2P1, siHBa1M1P1, siHBa1M2P1, siHBa2M1P1, and siHBa2M2P1:

siHBa1M1P1
Sense strand:
(SEQ ID NO: 25)
5'-CmCmUmUmGmAmGfGfCfAmUmAmCmUmUmCmAmAmAm -3', Antisense strand:
(SEQ ID NO: 26)
5'-P1-UmUfUmGmAmAfGmUmAmUmGmCmCmUfCmAfAmGmGmUm Um -3', siHBa1M2P1
Sense strand:
(SEQ ID NO: 27)
5'-CmCmUmUmGfAmGfGfCfAmUmAmCmUmUmCmAmAmAm -3', Antisense strand:
(SEQ ID NO: 28)
5'-P1-UmUIUmGmAmAfGmUfAIUmGmCmCmUfCmAfAmGmGmUm Um -3', siHBa2M1P1
Sense strand:
(SEQ ID NO: 29)
5'-GmAmCmCmUmUmGmAmGfGfCfAmUmAmCmUmUmCmAmAmAm -3', Antisense strand:
(SEQ ID NO: 30)
5'- P1-UmUfUmGmAmAfGmUmAmUmGmCmCmUfCmAfAmGmGmUmCm GmGm -3', siHBa2M2P1
Sense strand:
(SEQ ID NO: 31)
5'-GmAmCmCmUmUmGfAmGfGfCfAmUmAmCmUmUmCmAmAmAm -3', Antisense strand:
(SEQ ID NO: 32)
5'-P1-UmUfUmGmAmAfGmUfAfUmGmCmCmUfCmAfAmGmGmUmCm GmGm -3', siHBa1M1SP1
Sense strand:
(SEQ ID NO: 33)
5'-CmsCmsUmUmGmAmGfGfCfAmUmAmCmUmUmCmAmAmAm -3', Antisense strand:
(SEQ ID NO: 34)
5'-P1-UmsUfsUmGmAmAfGmUmAmUmGmCmCmUfCmAfAmGmGmsUms Um -3', siHBa1M2SP1
Sense strand:
(SEQ ID NO: 35)
5'-CmsCmsUmUmGfAmGfGfCfAmUmAmCmUmUmCmAmAmAm -3', Antisense strand:
(SEQ ID NO: 36)
5'-P1-UmsUfsUmGmAmAfGmUfAfUmGmCmCmUfCmAfAmGmGmsUms Um -3', siHBa2M1SP1
Sense strand:
(SEQ ID NO: 37)
5'-GmsAmsCmCmUmUmGmAmGfGfCfAmUmAmCmUmUmCmAmAm Am -3', Antisense strand:
(SEQ ID NO: 38)
5'-P1-UmsUfsUmGmAmAfGmUmAmUmGmCmCmUfCmAfAmGmGmUm CmsGmsGm-3', siHBa2M2SP1
Sense strand:
(SEQ ID NO: 39)
5'-GmsAmsCmCmUmUmGfAmGfGfCfAmUmAmCmUmUmCmAmAm Am -3', Antisense strand:
(SEQ ID NO: 40)
5'-P1-UmsUfsUmGmAmAfGmUfAfUmGmCmCmUfCmAfAmGmGmUm CmsGmsGm -3', wherein, C, G, U, and A indicate the base composition of the nucleotides; m indicates that the nucleotide adjacent to the left side of the letter m is a methoxy modified nucleotide; f indicates that the nucleotide adjacent to the left side of the letter f is a fluoro modified nucleotide; s represents that the two nucleotides adjacent to both sides of the letter s are linked by a phosphorothioate linkage; P1 represents that the nucleotide adjacent to the right side of P1 is a 5'-phosphate nucleotide or a 5'-phosphate analog modified nucleotide.

24. A method for treating or preventing a pathological condition or disease caused by hepatitis B virus (HBV) infection, comprising administering an effective amount of the siRNA conjugate according to claim 1, to a patient in need thereof.

25. A method for inhibiting the expression of HBV genes, comprising contacting an effective amount of the siRNA conjugate according to claim 1 with hepatitis cells infected with HBV.

26. The method of claim 24, wherein the pathological condition or disease caused by hepatitis B virus (HBV) infection is selected from chronic liver diseases, hepatitis, hepatic fibrosis, and liver proliferative diseases.

* * * * *